(12) United States Patent
Wan et al.

(10) Patent No.: US 10,654,837 B2
(45) Date of Patent: May 19, 2020

(54) SULPHAMOYLARYL DERIVATIVES AND USE THEREOF AS MEDICAMENTS FOR THE TREATMENT OF LIVER FIBROSIS

(71) Applicant: Janssen Pharmaceutica NV, Beerse (BE)

(72) Inventors: Zhao-Kui Wan, Shanghai (CN); Haibing Guo, Shanghai (CN); Koen Vandyck, Paal-Beringen (BE); Pierre Jean-Marie Bernard Raboisson, Wavre (BE); Abdellah Tahri, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/484,435

(22) PCT Filed: Feb. 6, 2018

(86) PCT No.: PCT/CN2018/075362
§ 371 (c)(1),
(2) Date: Aug. 7, 2019

(87) PCT Pub. No.: WO2018/145620
PCT Pub. Date: Aug. 16, 2018

(65) Prior Publication Data
US 2019/0345145 A1  Nov. 14, 2019

(30) Foreign Application Priority Data

Feb. 7, 2017  (WO) ............... PCT/CN2017/073035
Apr. 12, 2017  (WO) ............... PCT/CN2017/080185

(51) Int. Cl.
| | | |
|---|---|---|
| *C07D 405/12* | (2006.01) | |
| *C07D 401/12* | (2006.01) | |
| *C07D 211/58* | (2006.01) | |
| *C07D 307/22* | (2006.01) | |
| *C07D 305/04* | (2006.01) | |
| *C07D 417/12* | (2006.01) | |
| *C07D 213/75* | (2006.01) | |
| *C07D 309/14* | (2006.01) | |
| *C07C 311/16* | (2006.01) | |
| *C07C 311/29* | (2006.01) | |
| *A61P 1/16* | (2006.01) | |
| *A61K 45/06* | (2006.01) | |

(52) U.S. Cl.
CPC .............. *C07D 405/12* (2013.01); *A61P 1/16* (2018.01); *C07C 311/16* (2013.01); *C07C 311/29* (2013.01); *C07D 211/58* (2013.01); *C07D 213/75* (2013.01); *C07D 305/04* (2013.01); *C07D 307/22* (2013.01); *C07D 309/14* (2013.01); *C07D 401/12* (2013.01); *C07D 417/12* (2013.01); *A61K 45/06* (2013.01); *C07B 2200/05* (2013.01)

(58) Field of Classification Search
CPC .. C07D 405/12; C07D 211/58; C07D 213/75; C07D 305/04; C07D 307/22; C07D 309/14; C07D 401/12; C07D 417/12; A61P 1/16; C07C 311/16; C07C 311/29; A61K 45/06; C07B 2200/05
USPC ...................................... 514/210.18
See application file for complete search history.

(56) References Cited

FOREIGN PATENT DOCUMENTS

| WO | 2013006394 A1 | 1/2013 |
| WO | 2013/096744 A1 | 6/2013 |
| WO | 2014106019 A2 | 7/2014 |

OTHER PUBLICATIONS

International Search Report and Written Opinion for corresponding Patent Application No. PCT/CN2018/075362, dated May 8, 2018.

*Primary Examiner* — Kristin A Vajda

(57) ABSTRACT

Potent 5-HT2B antagonist of Formula (A), including stereochemically isomeric forms, and salts, hydrates, solvates thereof and their use wherein R1 to R4 and Ar have the meaning as defined herein. The present invention also relates to processes for preparing said compounds, pharmaceutical compositions containing them, alone or in combination with other drugs, in fibrosis and/or cirrhosis prevention or therapy.

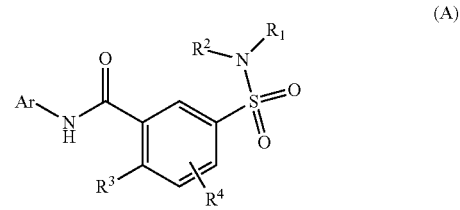

(A)

12 Claims, No Drawings

SULPHAMOYLARYL DERIVATIVES AND USE THEREOF AS MEDICAMENTS FOR THE TREATMENT OF LIVER FIBROSIS

CROSS-REFERENCE TO RELATED APPLICATIONS

This application is a national phase entry under 35 U.S.C. § 371 of International Application No. PCT/CN2018/075362, filed on Feb. 6, 2018, which claims priority to PCT/CN2017/073035, filed Feb. 7, 2017, and PCT/CN2017/080185, filed Apr. 12, 2017.

BACKGROUND ART

Liver fibrosis is a chronic disease in which the damaged parenchymal tissue fails to regenerate. This damage causes liver stellate cells to be over active and triggers the extra cellular matrix (ECM) synthesis to increase. Advanced liver fibrosis can result in cirrhosis and life-threatening live failure. Cirrhosis is a disease of the liver with as a pathological hallmark the development of scar tissue that replaces normal parenchyma. Damage to these hepatic parenchyma (due to inflammation) leads to activation of the stellate cell, which increases fibrosis through production of myofibroblasts. This process might result in the generation of fibrous tissue bands (septa), which eventually replace the entire liver architecture ending in the obstruction of blood flow.

Recently, it has become clear that 5-HT2B might play a role in the progression of liver fibrosis and/or cirrhosis. M. Ebrahimkhani et al have shown that selective antagonism of 5-HT2B enhanced hepatocyte growth in models of acute and chronic liver injury (*Nature Medicine* 17, 1668-1673 (2011)).

5-Hydroxytryptamine receptor 2B (5-HT2B) also known as serotonin receptor 2B is a protein that in humans is encoded by the HTR2B gene. 5-HT2B is a member of the 5-HT2 receptor family that binds the neurotransmitter serotonin (5-hydroxytryptamine, 5-HT).

There is a need for selective and potent 5-HT2B antagonist chemical classes, useful in the treatment or prevention of fibrosis and/or cirrhosis.

Amongst the problems which 5-HT2B antagonists may encounter are toxicity, mutagenicity, lack of selectivity, poor efficacy, poor bioavailability, low solubility and difficulty of synthesis.

There is a need for drugs to treat liver fibrosis and/or cirrhosis, more specifically 5-HT2B antagonists that may overcome at least one of these disadvantages or that have additional advantages such as increased potency or an increased safety window.

WO2013/006394, published on Jan. 10, 2013, relates to a subclass of sulphamoyl-arylamides active against Hepatitis B Virus (HBV). WO2013/096744, published on Jun. 26, 2013 also relates to sulphamoyl-arylamides active against HBV.

DESCRIPTION OF THE INVENTION

Surprisingly it was found that certain sulphamoyl-arylamides are potent 5-HT2B antagonist.

The present invention relates to a compound of Formula (I)

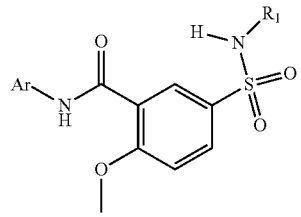

(I)

or a stereoisomer or tautomeric form thereof, wherein:
Ar represents a monocyclic or bicyclic aromatic ring, optionally containing one or more heteroatoms each independently selected from the group consisting of O, S and N, such aromatic ring optionally being substituted with one or more substituents each independently selected from the group consisting of halogen, —CN, —OR$^6$, $C_1$-$C_3$ alkyl, $C_3$-$C_7$ cycloalkyl, $CHF_2$, $CH_2F$ and $CF_3$;
R$^1$ represents a 3-7 membered saturated ring optionally containing one or more heteroatoms each independently selected from the group consisting of O, S and N, such 3-7 membered saturated ring optionally being substituted with one or more substituents each independently selected from the group consisting of fluor, —OH, oxo and $C_1$-$C_3$ alkyl optionally substituted with one or more fluor and/or OH;
R$^6$ represents hydrogen, $C_1$-$C_3$ alkyl optionally substituted with one or more fluor, or —$C_1$-$C_3$ alkyl-O(R$^5$);
R$^5$ represents hydrogen or $C_1$-$C_3$ alkyl;
or a pharmaceutically acceptable salt or a solvate thereof.

The present invention also relates to use of a compound of Formula (A)

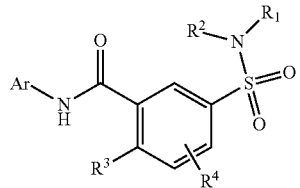

(A)

or a stereoisomer or tautomeric form, and/or a salt or solvate thereof, in the manufacture of a medicament for the prevention or treatment of fibrosis and/or cirrhosis in a mammal, wherein
Ar represents a monocyclic or bicyclic aromatic ring, optionally containing one or more heteroatoms each independently selected from the group consisting of O, S and N, such aromatic ring optionally being substituted with one or more substituents each independently selected from the group consisting of hydrogen, halogen, —CN, —OH, $C_1$-$C_3$ alkyl, $C_3$-$C_7$ cycloalkyl, —O(R$^6$), $CHF_2$, $CH_2F$ and $CF_3$;
R$^1$ represents hydrogen, a 3-7 membered saturated ring optionally containing one or more heteroatoms each independently selected from the group consisting of O, S and N, or $C_1$-$C_6$ alkyl, such 3-7 membered saturated ring or $C_1$-$C_6$ alkyl optionally being substituted with one or more substituents each independently selected from the group consisting of $C_1$-$C_3$ alkyl, halogen, $CHF_2$, $CH_2F$ and $CF_3$. —CN, —C(=O)R$^5$, oxo-C(=O) N(R$^6$)$_2$, —N(R$^6$)$_2$ and —OR$^6$;
R$^2$ represents hydrogen, or $C_1$-$C_3$ alkyl;
R$^3$ represents fluor or —O$C_1$-$C_3$ alkyl optionally substituted with one or more fluor;
R$^4$ represents hydrogen, fluor or —O$C_1$-$C_3$ alkyl;

$R^6$ represents hydrogen, $C_1$-$C_3$ alkyl optionally substituted with one or more fluor, or —$C_1$-$C_3$ alkyl-O($R^5$);

$R^5$ represents hydrogen or $C_1$-$C_3$ alkyl.

The invention further relates to the compound of Formula (I) for use as a medicament, preferably for use in the prevention or treatment of fibrosis and/or cirrhosis in a mammal.

The invention also relates to the compound of Formula (A) for use as a medicament, preferably for use in the prevention or treatment of fibrosis and/or cirrhosis in a mammal.

The invention further relates to a method for preventing or treating fibrosis and/or cirrhosis in a mammal, comprising administering the compound of Formula (I) to the subject in need thereof.

The invention also relates to a method for preventing or treating fibrosis and/or cirrhosis in a mammal, comprising administering the compound of Formula (A) to the subject in need thereof.

The invention further relates to use of the compound of Formula (I) in the manufacture of a medicament for the treatment or the prevention of liver fibrosis and/or cirrhosis.

The invention further relates to a pharmaceutical composition comprising compounds of Formula (I), and a pharmaceutically acceptable carrier.

The invention also relates to a pharmaceutical composition comprising compounds of Formula (I) and Formula (A), and a pharmaceutically acceptable carrier.

In a further aspect, the invention relates to a combination of compounds of Formula (I) and Formula (A), and another fibrosis and/or cirrhosis inhibitor.

The invention also relates to a product containing (a) a compound of Formula (I), and (b) another fibrosis and/or cirrhosis inhibitor, as a combined preparation for simultaneous, separate or sequential use in the treatment of fibrosis and/or cirrhosis.

The invention further relates to a product containing (a) compounds of Formula (I) and Formula (A), and (b) another fibrosis and/or cirrhosis inhibitor, as a combined preparation for simultaneous, separate or sequential use in the treatment of fibrosis and/or cirrhosis.

Definitions

The term "optional" or "optionally" means the event described subsequent thereto may or may not happen. This term encompasses the cases that the event may or may not happen.

The term "one or more" means one, two, three, four, five, six, seven, eight, nine or more.

The term "aryl" means a monocyclic- or polycyclic aromatic ring comprising carbon atoms, and hydrogen atoms. If indicated, such aromatic ring may include one or more heteroatoms, preferably, 1 to 3 heteroatoms, independently selected from nitrogen, oxygen, and sulfur, preferably nitrogen (heteroaryl). As is well known to those skilled in the art, heteroaryl rings have less aromatic character than their all-carbon counter parts. Thus, for the purposes of the present invention, a heteroaryl group need only have some degree of aromatic character. Illustrative examples of aryl groups are optionally substituted phenyl and naphtyl. Illustrative examples of heteroaryl groups according to the invention include optionally substituted, pyridine, pyrimidine, thiazole, indazole.

The terms "$C_{1-x}$ alkyl" and $C_1$-$C_x$ alkyl can be used interchangeably.

The term "$C_{1-3}$ alkyl" as a group or part of a group refers to a hydrocarbyl radical of Formula $C_nH_{2n+1}$ wherein n is a number ranging from 1 to 3. In case $C_{1-3}$ alkyl is coupled to a further radical, it refers to a Formula $C_nH_{2n}$. $C_{1-3}$ alkyl groups comprise from 1 to 3 carbon atoms, more preferably 1 to 2 carbon atoms. $C_{1-3}$ alkyl includes all linear, or branched alkyl groups with between 1 and 3 carbon atoms, and thus includes such as for example methyl, ethyl, n-propyl, and i-propyl. $C_{1-4}$ alkyl as a group or part of a group defines straight or branched chain saturated hydrocarbon radicals having from 1 to 4 carbon atoms such as the group defined for $C_{1-3}$alkyl and butyl and the like. $C_{1-6}$ alkyl and $C_{2-6}$ alkyl as a group or part of a group defines straight or branched chain saturated hydrocarbon radicals having from 1 to 6 carbon atoms, or from 2 to 6 carbon atoms such as the groups defined for $C_{1-4}$alkyl and pentyl, hexyl, 2-methylbutyl and the like.

The term "$C_{1-3}$ alkyloxy" as a group or part of a group refers to a radical having the Formula —$OR^c$ wherein $R^c$ is $C_{1-3}$ alkyl. Non-limiting examples of suitable $C_{1-3}$ alkyloxy include methyloxy (also methoxy), ethyloxy (also ethoxy), propyloxy and isopropyloxy.

The term oxo, C(═O), or carbonyl refers to a group composed of a carbon atom double bonded to an oxygen atom.

As used herein, the term "3-7 membered saturated ring" means saturated cyclic hydrocarbon (cycloalkyl) with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms, such that at least one carbon atom is replaced by a heteroatom selected from N, O and S, in particular from N and O. Examples include oxetane, tetrahydro-2H-pyranyl, piperidinyl, tetrahydrofuranyl, morpholinyl, thiolane 1,1-dioxide and pyrrolidinyl. Preferred are saturated cyclic hydrocarbons with 3 or 4 carbon atoms and 1 oxygen atom. Examples include oxetane, and tetrahydrofuranyl.

It should be noted that different isomers of the various heterocycles may exist within the definitions as used throughout the specification. For example, pyrrolyl may be 1H-pyrrolyl or 2H-pyrrolyl.

The term halo and halogen are generic to fluoro, chloro, bromo or iodo. Preferred halogens are bromo, fluoro and chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

Lines drawn from substituents into ring systems indicate that the bond may be attached to any of the suitable ring atoms.

When any variable (e.g. halogen or $C_{1-4}$ alkyl) occurs more than one time in any constituent, each definition is independent.

Combinations of substituents and/or variables are permissible only if such combinations result in chemically stable compounds. "Stable compound" is meant to indicate a compound that is sufficiently robust to survive isolation to a useful degree of purity from a reaction mixture, and formulation into a therapeutic agent.

For therapeutic use, the salts of the compounds of Formula (I) are those wherein the counter ion is pharmaceutically or physiologically acceptable. However, salts having a pharmaceutically unacceptable counter ion may also find use, for example, in the preparation or purification of a pharmaceutically acceptable compound of Formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms. For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The stereometric forms of Formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of Hydrogen include tritium and deuterium. Isotopes of carbon include C-13 and C-14.

DETAILED DESCRIPTION OF THE INVENTION

Whenever used hereinafter, the term "the compounds of the present invention" or "the present compounds" or similar term is meant to include all compounds of general Formula (I) and Formula (A), and compounds listed in table 1, salts, stereoisomeric forms and racemic mixtures and any subgroups thereof.

In a first aspect, the present invention provides compounds of Formula (I)

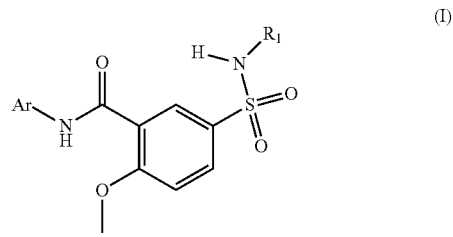

or a stereoisomer or tautomeric form thereof, wherein:

Ar represents a monocyclic or bicyclic aromatic ring, optionally containing one or more heteroatoms each independently selected from the group consisting of O, S and N, such aromatic ring optionally being substituted with one or more substituents each independently selected from the group consisting of halogen, —CN, —OR$^6$, $C_1$-$C_3$ alkyl, $C_3$-$C_7$cycloalkyl, $CHF_2$, $CH_2F$ and $CF_3$;

R$^1$ represents a 3-7 membered saturated ring optionally containing one or more heteroatoms each independently selected from the group consisting of O, S and N, such 3-7 membered saturated ring optionally being substituted with one or more substituents each independently selected from the group consisting of fluor, —OH, oxo and $C_1$-$C_3$ alkyl optionally substituted with one or more fluor and/or OH;

R$^6$ represents hydrogen, $C_1$-$C_3$ alkyl optionally substituted with one or more fluor, or —$C_1$-$C_3$ alkyl-O(R$^5$);

R$^5$ represents hydrogen or $C_1$-$C_3$ alkyl:

or a pharmaceutically acceptable salt or a solvate thereof.

In one embodiment of the present invention, Ar is phenyl, pyridine or benzimidazole optionally substituted with one or more substituents each independently selected from the group consisting of —CN, halogen, $C_1$-$C_3$ alkyl, $C_1$-$C_3$cycloalkyl, $CHF_2$, $CH_2F$ and $CF_3$.

In yet another embodiment, Ar is phenyl or pyridine, optionally substituted with one or more substituents each independently selected from halogen, —OH, $C_1$-$C_3$ alkyl, $C_1$-$C_3$cycloalkyl, $CHF_2$, $CH_2F$ and $CF_3$.

In a further embodiment, $R^1$ represents a 4-7 membered saturated ring containing carbon atoms and optionally one oxygen atom, such 4-7 membered saturated ring optionally substituted with one or more $C_1$-$C_3$ alkyl and/or OH.

In another embodiment, $R^1$ represents a 5 membered saturated ring containing carbon atoms and one oxygen atom, optionally substituted with one or more $C_1$-$C_3$ alkyl and/or OH. In a preferred embodiment, $R^1$ represents a 5 membered saturated ring containing carbon atoms and one oxygen atom.

In another aspect, the present invention provides use of compounds of Formula (A)

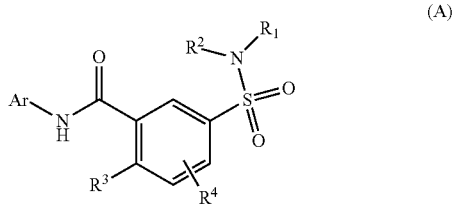

or a stereoisomer or tautomeric form, and/or a salt or solvate thereof, in the manufacture of a medicament for the prevention or treatment of fibrosis and/or cirrhosis in a mammal, wherein Ar represents a monocyclic or bicyclic aromatic ring, optionally containing one or more heteroatoms each independently selected from the group consisting of O, S and N, such aromatic ring optionally being substituted with one or more substituents each independently selected from the group consisting of hydrogen, halogen, —CN, —OH, $C_1$-$C_3$ alkyl, $C_3$-$C_7$cycloalkyl, —O($R^6$), $CHF_2$, $CH_2F$ and $CF_3$;

$R^1$ represents hydrogen, a 3-7 membered saturated ring optionally containing one or more heteroatoms each independently selected from the group consisting of O, S and N, or $C_1$-$C_6$ alkyl, such 3-7 membered saturated ring or $C_1$-$C_6$ alkyl optionally being substituted with one or more substituents each independently selected from the group consisting of $C_1$-$C_3$ alkyl, halogen, $CHF_2$, $CH_2F$ and $CF_3$, —CN, —C(=O)$R^5$, oxo, —C(=O) N($R^6$)$_2$, —N($R^6$)$_2$ and —O$R^6$;

$R^2$ represents hydrogen, or $C_1$-$C_3$ alkyl;

$R^3$ represents fluor or —O$C_1$-$C_3$ alkyl optionally substituted with one or more fluor;

$R^4$ represents hydrogen, fluor or —O$C_1$-$C_3$ alkyl;

$R^6$ represents hydrogen, $C_1$-$C_3$ alkyl optionally substituted with one or more fluor, or —$C_1$-$C_3$ alkyl-O($R^5$);

$R^5$ represents hydrogen or $C_1$-$C_3$ alkyl.

In one embodiment of the present invention, $R^3$ represents fluor or —O$C_1$-$C_3$ alkyl and $R^2$ and $R^4$ represent hydrogen.

In a further embodiment, Ar is phenyl, pyridine or benzimidazole optionally substituted with one or more substituents each independently selected from the group consisting of halogen, $C_1$-$C_3$ alkyl, $C_1$-$C_3$cycloalkyl, $CHF_2$, $CH_2F$ and $CF_3$.

In another embodiment, $R^1$ represents a 5 membered saturated ring containing carbon atoms and one oxygen atom, optionally substituted with one or more $C_1$-$C_3$ alkyl and/or OH. In a preferred embodiment, $R^1$ represents a 5 membered saturated ring containing carbon atoms and one oxygen atom.

In yet another embodiment, Ar is phenyl optionally substituted with one or more substituents each independently selected from —CN, $C_1$-$C_3$ alkyl, $C_1$-$C_3$cycloalkyl, $CHF_2$, $CH_2F$ and $CF_3$.

Further combinations of any of the embodiments as described for both Formula (I) and Formula (A) are also envisioned to be in the scope of the present invention.

Preferred compounds according to the invention are compound or a stereoisomer or tautomeric form thereof with a Formula as represented in the synthesis of compounds section and of which the activity is displayed in Table 1.

In a further aspect, the present invention concerns a pharmaceutical composition comprising a therapeutically or prophylactically effective amount of a compound of Formula (I) or Formula (A) as specified herein, and a pharmaceutically acceptable carrier. In still a further aspect, this invention relates to a process of preparing a pharmaceutical composition as specified herein, which comprises intimately mixing a pharmaceutically acceptable carrier with a therapeutically or prophylactically effective amount of a compound of Formula (I), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of Formula (I) are potent 5-HT2B antagonist.

The compounds of the present invention are potent antagonists of 5-Hydroxytryptamine receptor 2B (5-HT2B). Due to their 5-HT2B antagonist properties, the compounds of Formula (I) and Formula (A) or any subgroup thereof, are useful in the inhibition of 5-HT2B enhanced hepatocyte growth, in particular in the treatment of liver fibrosis and/or cirrhosis in warm-blooded animals, in particular humans, and for the prophylaxis of liver fibrosis and/or cirrhosis. The present invention furthermore relates to a method of treating liver fibrosis and/or cirrhosis in a warm-blooded animal, in particular human, or being at risk of infection by HBV, said method comprising the administration of a therapeutically effective amount of compounds of Formula (I) and Formula (A).

The compounds of Formula (I) and Formula (A), as specified herein, may therefore be used as a medicine, in particular as medicine to treat or prevent liver fibrosis and/or cirrhosis. Said use as a medicine or method of treatment comprises the systemic administration to subjects with liver fibrosis and/or cirrhosis or to subjects susceptible to liver fibrosis and/or cirrhosis of an amount effective to combat the conditions associated with liver fibrosis and/or cirrhosis or an amount effective to prevent liver fibrosis and/or cirrhosis.

The present invention also relates to use of the present compounds in the manufacture of a medicament for the treatment or the prevention of liver fibrosis and/or cirrhosis.

In general it is contemplated that an anti-fibrosis and/or cirrhosis effective daily amount would be from about 10 to about 200 mg/kg. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of compounds of Formula (I) and Formula (A) or any subgroup thereof, as specified herein with other agents for treating liver fibrosis and/or cirrhosis. The term "combination" may relate to a product or kit containing (a) compounds of Formula (I) and Formula (A), as specified above, and (b) at least one other compound capable of treating liver fibrosis and/or cirrhosis, as a combined preparation for simultaneous, separate or sequential use in treatment of liver fibrosis and/or cirrhosis. In an embodiment, the invention concerns combination of compounds of Formula (I) and Formula (A) or any subgroup thereof with at least one other agent for treating liver fibrosis and/or cirrhosis. In a particular embodiment, the invention concerns combination of compounds of Formula (I) and Formula (A) or any subgroup thereof with at least two other agents for treating liver fibrosis and/or cirrhosis. In a particular embodiment, the invention concerns combination of compounds of Formula (I) and Formula (A) or any subgroup thereof with at least three other agents for treating liver fibrosis and/or cirrhosis. In a particular embodiment, the invention concerns combination of compounds of Formula (I) and Formula (A) or any subgroup thereof with at least four agents for treating liver fibrosis and/or cirrhosis.

The term agent for treating liver fibrosis and/or cirrhosis also includes compounds that are therapeutic nucleic acids, antibodies or proteins either in their natural form or chemically modified and or stabilized. The term therapeutic nucleic acid includes but is not limited to nucleotides and nucleosides, oligonucleotides polynucleotides of which non limiting examples are antisense oligonucleotides, miRNA, siRNA, shRNA, therapeutic vectors and DNA/RNA editing components.

The combination of previously known agents for treating liver fibrosis and/or cirrhosis, and compounds of Formula (I) and Formula (A) or any subgroup thereof can be used as a medicine in a combination therapy.

Generic Synthesis:

The substituents (R1 and Ar) represented in this general synthesis section are meant to include any substituent or reactive aromatic amine which is suitable for transformation into any substituent according to the present invention without undue burden for the person skilled in the art.

The general synthesis of compound of Formula (IV) is described in scheme 1 and scheme 2 in four different methods (method A-D). As described in scheme 1, an 2-methoxybenzoic acid of general Formula (I) is reacted with sulfurochloridic acid to form a chlorosulfonyl methoxybenzoic acid of general formula (II), which was followed by benzoyl chloride formation and reacts with aromatic amine to transform a amide of general Formula (III). The final product was synthesized reacting with an amine to provide sulfonyl amide with general formula (IV). The detailed synthetic procedure was shown with an example of synthesis of compound 1.

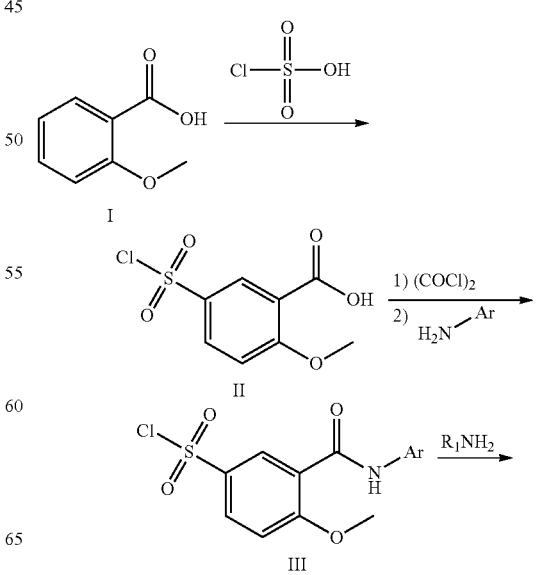

Scheme 1 (method A)

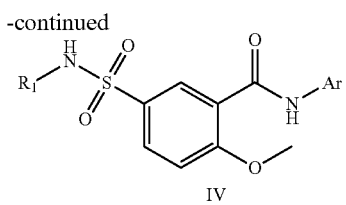

Method A (Compound 1 as Example)

Intermediate 1.2:
5-(Chlorosulfonyl)-2-methoxybenzoic acid

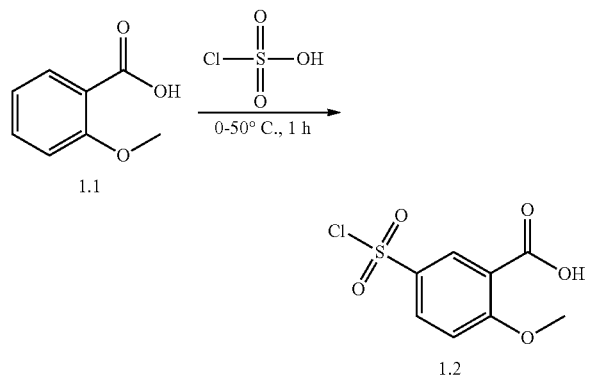

2-Methoxybenzoic acid (30.0 g, 197 mmol) was dissolved in chlorosulfonic acid (115 g, 986 mmol) at 0° C. The resultant reaction mixture was heated at 50° C. for 1 hour. After cooling to room temperature, the mixture was poured into ice water and precipitation formed. The precipitation was collected and dried to give the title compound (6.00 g, 25% yield).

$^1$H NMR (400 MHz, DMSO-d6) δ 7.85 (d, J=2.2 Hz, 1H), 7.67 (dd, J=2.3, 8.7 Hz, 1H), 7.05 (d, J=8.8 Hz, 1H), 3.79 (s, 3H).

Intermediate 1.3: 3-((4-Fluoro-3-methylphenyl)carbamoyl)-4-methoxybenzene-1-sulfonyl chloride

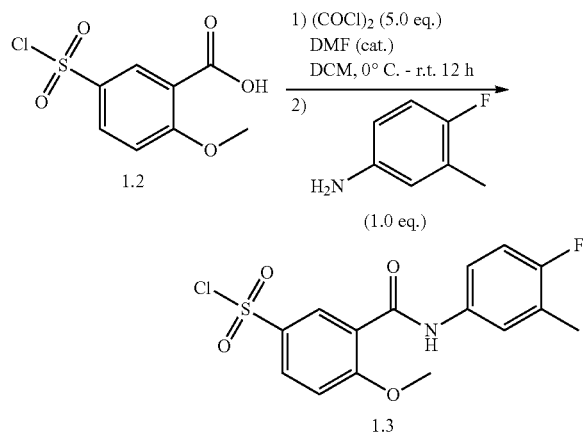

5-(Chlorosulfonyl)-2-methoxybenzoic acid (6.00 g, 22.7 mmol, purity 95%) was dissolved in a mixture of DMF (0.5 mL) and DCM (60 mL) followed by the addition of oxalyl dichloride (14.4 g, 114 mmol) at 0° C. The mixture was stirred at 20° C. for 12 hours before concentrating it to dryness. The residue was dissolved in anhydrous toluene (100 mL) and then 4-fluoro-3-methylaniline (2.79 g, 22.3 mmol) were added. The reaction was heated to reflux for 1 h and concentrated under reduced pressure. The residue was purified by column chromatography over silica gel (petroleum ether:ethyl acetate=1:1) to give the crude product which was recrystallized from ethyl acetate (20 mL) to give the title compound (4.50 g, 55% yield, purity 98%).

LCMS (ESI): $R_T$=0.81 min, mass calcd. for $C_{15}H_{13}ClFNO_4S$ 357.02, m/z found 357.8 [M+H]$^+$. $^1$H NMR (400 MHz, DMSO-d$_6$) δ 10.11 (s, 1H), 7.83 (d, J=2.0 Hz, 1H), 7.69 (dd, J=2.4, 8.7 Hz, 1H), 7.65 (dd, J=2.5, 7.0 Hz, 1H), 7.58-7.52 (m, 1H), 7.14-7.06 (m, 2H), 3.89 (s, 3H), 2.23 (d, J=1.8 Hz, 3H).

Compound 1: 5-(N-(3,3-Difluorocyclobutyl)sulfamoyl)-N-(4-fluoro-3-methylphenyl)-2-methoxybenzamide

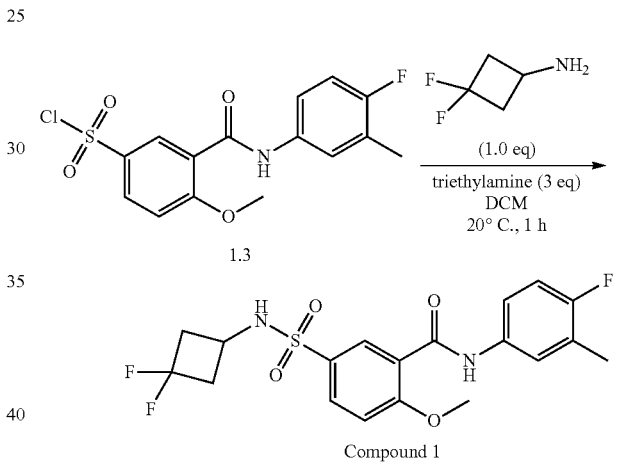

3-((4-Fluoro-3-methylphenyl)carbamoyl)-4-methoxybenzene-1-sulfonyl chloride (200 mg, 0.559 mmol) was dissolved in DCM (10 mL) followed by the addition of 3,3-difluorocyclobutanamine (65.9 mg, 0.615 mmol) and triethylamine (170 mg, 1.68 mmol) at 0° C. The mixture was stirred for 1 h at 20° C. and then concentrated to dryness under reduce pressure. The residue was purified by prep. HPLC (column: Agela DuraShell C18 150 mm×25 mm, 5 μm; mobile phase: CH$_3$CN in water (0.05% base water) from 43% to 73%, flow rate: 30 mL/min). The pure fractions were collected and the volatiles were removed under vacuum. The residue was suspended in water (5 mL). The aqueous layer was lyophilized to dryness to give the title compound as a white solid (67.9 mg, 28% yield, and purity 97.7%).

LC-MS (ESI): $R_T$=5.17 min, mass calcd. for $C_{19}H_{19}F_3N_2O_4S$ 428.10, m/z found 429.1 [M+H]$^+$. $^1$H NMR (400 MHz, DMSO-d$_6$) δ 10.21 (br.s., 1H), 8.14 (br. s., 1H), 7.97 (d, J=2.4 Hz, 1H), 7.91 (dd, J=2.4, 8.8 Hz, 1H), 7.65-7.60 (m, 1H), 7.58-7.52 (m, 1H), 7.37 (d, J=8.8 Hz, 1H), 7.13 (t, J=9.2 Hz, 1H), 3.97 (s, 3H), 3.61-3.49 (m, 1H), 2.78-2.68 (m, 2H), 2.43-2.33 (m, 2H), 2.24 (s, 3H).

The other three possible routes to compound of general Formula (IV) are described in scheme 2. The chlorosulfonylmethoxybenzoate was reacted with amine to give sulfonyl amide of general Formula (V). This sulfonyl amide benzoate was used as a reagent for the final product formation or converted to the other reagents benzoic acid and benzoic chloride by hydrolysis and chloride formation in sequence. The final compounds of general Formula (IV) were formed through method B, C and D by an amide formation with reagent V, VI, VII respectively. The detailed synthetic procedure was shown with an example of synthesis of compound 2, 3, 4.

Scheme 2 (method B, C, D)

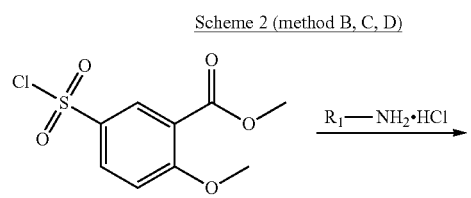

II

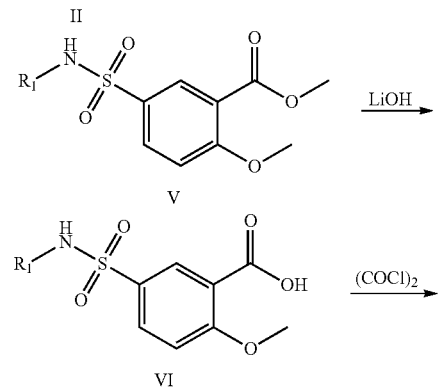

Method B:

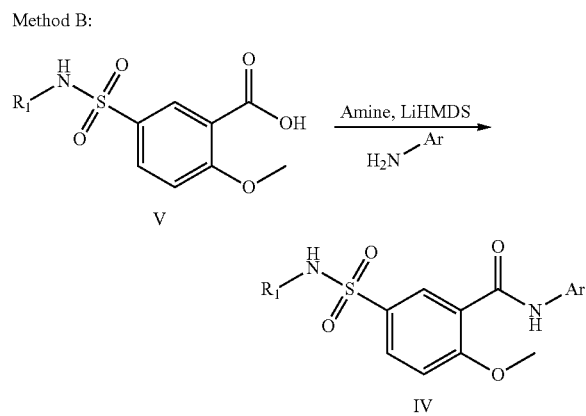

Method C:

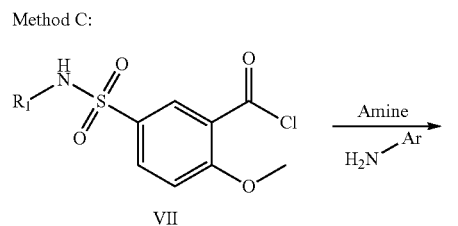

VII

-continued

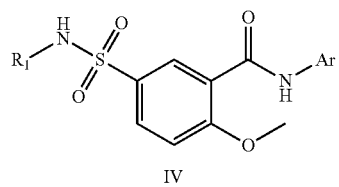

IV

Method D:

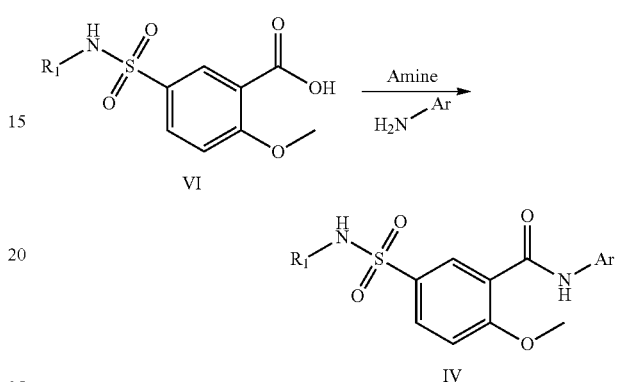

Method B (Compound 2 as Example)

Intermediate 2.2: (S)-Methyl 2-methoxy-5-(N-(tetrahydrofuran-3-yl)sulfamoyl)benzoate

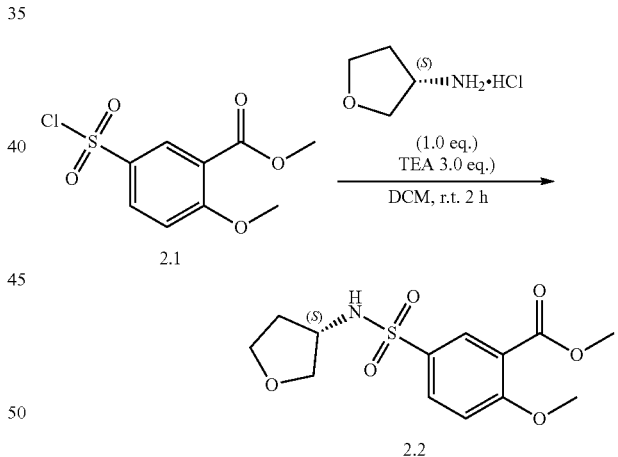

To a solution consisting of (S)-3-aminotetrahydrofuran hydrochloride (3.74 g, 30.2 mmol, Shanghai Nuohey Chemical Technology CO., LTD.), TEA (12.6 mL, 90.7 mmol) and DCM (100 mL) was added methyl 5-(chlorosulfonyl)-2-methoxybenzoate (8.00 g, 30.2 mmol). The mixture was stirred at room temperature for 2 hours and the resultant solution was concentrated under reduced pressure. Water and ethyl acetate were added. The organic layer was separated and the water phase was extracted twice with ethyl acetate. The combined organic layers were washed with brine, dried over $Na_2SO_4$ and filtered. The filtrate was concentrated under reduced pressure to give the title compound (7.50 g, 71% yield).

Compound 2: (S)—N-(5-fluoro-6-methylpyridin-2-yl-2-methoxy-5-(N-(tetrahydrofuran-3-yl) sulfamoyl)benzamide

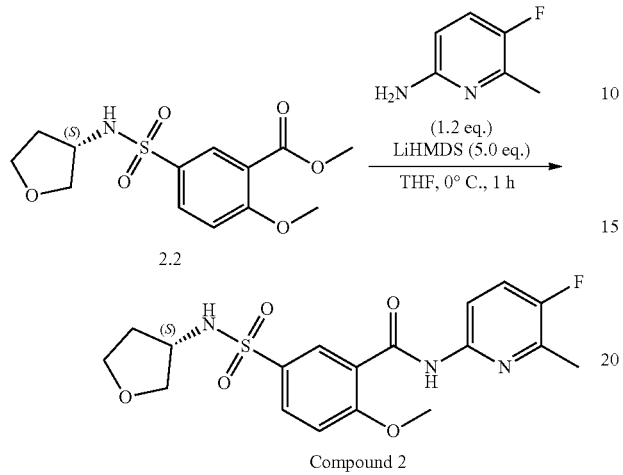

LHMDS (2.84 mL, 2.84 mmol, 1 M in THF) was added into a solution consisting of(S)-methyl 2-methoxy-5-(N-(tetrahydrofuran-3-yl)sulfamoyl)benzoate (150 mg, 0.476 mmol), oxazol-2-amine (85.7 mg, 0.680 mmol) and THF (5 mL) at 0° C. under nitrogen. The reaction mixture was stirred at 0° C. for 1 hour. The mixture was quenched with saturated NH$_4$Cl and the resulting mixture was extracted with ethyl acetate. The organic layer was washed with brine, dried over Na$_2$SO$_4$ and filtered. The filtrate was concentrated under reduced pressure to give a residue which was purified by prep.TLC to give title compound (61.9 mg, 22.27% yield, purity 99.1%). LC-MS (ESI): mass calcd. for C$_{18}$H$_{20}$FN$_3$O$_5$S 409.4, m/z found 410.1 [M+H]$^+$; $^1$H NMR (400 MHz, DMSO-d$_6$) δ 10.60 (br.s, 1H), 8.15-8.02 (m, 2H), 7.96-7.86 (m, 2H), 7.69 (t, J=8.0 Hz, 1H), 7.38 (d, J=8.0 Hz, 1H), 3.99 (s, 3H), 3.72-3.61 (m, 2H), 3.60-3.51 (m, 2H), 3.44-3.39 (m, 1H), 2.44-2.30 (m, 3H), 1.93-1.81 (m, 1H), 1.65-1.54 (m, 1H).

Method C: (Compound 3 as Example)

Intermediate 3.2: (S)-2-Methoxy-5-(N-(tetrahydrofuran-3-yl)sulfanoyl)benzoic acid

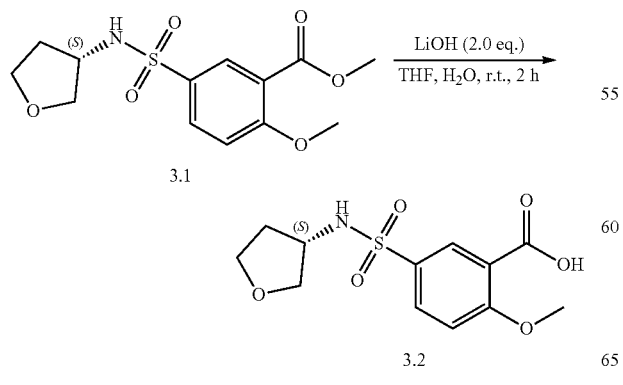

Lithium hydroxide (3.99 g, 95.1 mmol) was added into a solution consisting of (S)-methyl 2-methoxy-5-(N-(tetrahydrofuran-3-yl)sulfamoyl)benzoate (15 g, 47.6 mmol) in THF (100 mL) and H$_2$O (25 mL). The reaction mixture was stirred at room temperature for 2 hour before concentrating it under reduced pressure to remove volatiles. The resultant aqueous phase was adjust to pH=3 with aq. HCl solution and the precipitation was collected and dried to give (S)-2-methoxy-5-(N-(tetrahydrofuran-3-yl)sulfamoyl)benzoic acid (11.0 g, 69% yield).

Intermediate 3.3: (S)-2-Methoxy-5-(N-(tetrahydrofuran-3-yl)sulfamyl)benzoyl chloride

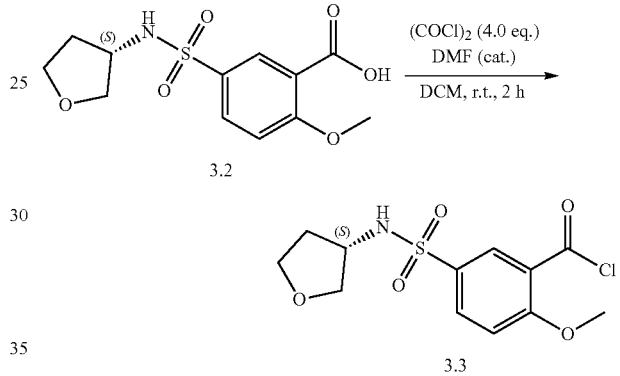

Oxalyl dichloride (8.99 mL, 106 mmol) was added into a solution consisting of(S)-2-methoxy-5-(N-(tetrahydrofuran-3-yl)sulfamoyl)benzoic acid (8.00 g, 26.6 mmol), DMF (0.5 mL) and DCM (80 mL) at 0° C. The reaction was stirred at room temperature for 2 hours. The resultant mixture was concentrated under reduced pressure to give the title compound (8.49 g, 90% yield) which was used for the next step directly.

Compound 3: (S)—N-(2-Chloro-3-fluorophenyl)-2-methoxy-5-(N-(tetrahydrofuran-3-yl)sulfamoyl) benzamide

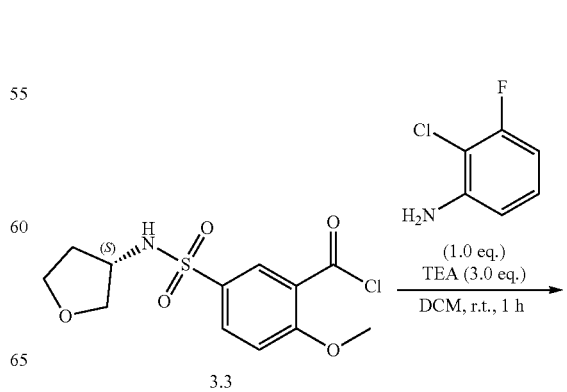

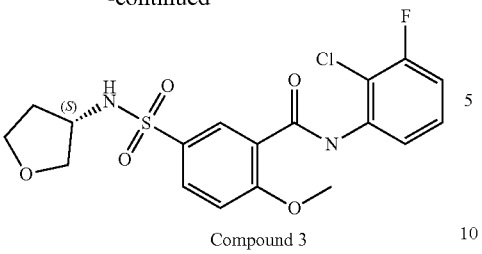

Compound 3

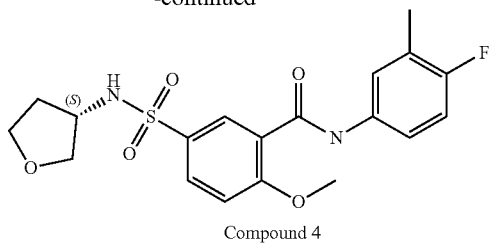

Compound 4

(S)-2-Methoxy-5-(N-(tetrahydrofuran-3-yl)sulfamoyl) benzoyl chloride (200 mg, 0.625 mmol) was dissolved in dry DCM (2 mL) and the resultant solution was added drop-wise to a well stirred solution consisting of 2-chloro-3-fluoroaniline (109 mg, 0.749 mmol), TEA (0.3 mL) and DCM (2 mL) at room temperature. The reaction mixture was stirred at room temperature for 1 hour and then diluted with DCM (15 mL). Water (10 mL) was added. The organic phase was separated, dried over $Na_2SO_4$ and filtered. The filtrate was concentrated under reduced pressure to give a residue which was purified by trituration in DCM (2~3 mL). The solid was filtered and then dried in vacuum. The resultant product was purified by prep. SFC separation (Column: ChiralPak AD 250×30 mm I.D., 10 μm, Daicel Chemical Industries, Ltd; Mobile phase: A: Supercritical $CO_2$, B: EtOH (0.1% $NH_3.H_2O$), A:B=55:45 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm). The pure fractions were collected and the volatiles were removed under vacuum. The residue was partitioned between $CH_3CN$ (1 ml) and water (5 ml). The solution was lyophilized to give title compound.

LC-MS (ESI): $R_T$=4.93 min, mass calcd. for $C_{18}H_{18}ClFN_2O_5S$ 428.06, m/z found 429.0 $[M+H]^+$. $^1H$ NMR (400 MHz, DMSO-$d_6$) δ 10.53 (br.s, 1H), 8.48-8.38 (m, 1H), 8.25-8.15 (m, 1H), 8.05-7.95 (m, 2H), 7.56-7.40 (m, 2H), 7.25 (t, J=8.8 Hz, 1H), 4.15 (s, 3H), 3.75-3.50 (m, 4H), 3.40-3.30 (m, 1H), 1.96-1.85 (m, 1H), 1.68-1.56 (m, 1H).

Method D: (Compound 4 as Example)

Compound 4: (S)—N-(4-Fluoro-3-methylphenyl)-2-methoxy-5-(N-(tetrahydrofuran-3-yl) sulfamoyl) benzamide

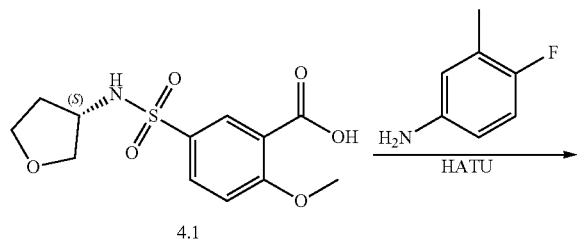

HATU (608.4 mg, 1.60 mmol) was added into a mixture consisting of (S)-2-methoxy-5-(N-(tetrahydrofuran-3-yl) sulfamoyl)benzoic acid (400.1 mg, 1.33 mmol), 4-fluoro-3-methylaniline (166.4 mg, 1.33 mmol), TEA (0.56 mL, 4.02 mmol) and DMF (5 mL). The reaction mixture was stirred at room temperature for 12 hours before pouring it into water. The aqueous layer was extracted three times with ethyl acetate (20 mL×3). The combined organic layers were washed with brine, dried over $Na_2SO_4$ and filtered. The filtrate was concentrated to dryness to give a residue which was purified by prep.HPLC (Column: Gemini 150×25 mm×5 um, Flow rate: 30 ml/min, Mobile Phase A: Base water (containing 0.05% NH3.H2O), Mobile Phase B: Acetonitrile) to give the title compound (100.7 mg, yield 18.1%).

LC-MS (ESI): mass calcd. for $C_{19}H_{21}FN_2O_5S$ 408.12, m/z found 409.1 $[M+H]^+$, $^1H$ NMR (400 MHz, DMSO-$d_6$) δ 10.21 (br.s, 1H), 8.00 (d, J=2.3 Hz, 1H), 7.96-7.876 (m, 2H), 7.63 (dd, J=7.0 Hz, J=2.3 Hz 1H), 7.58-7.53 (m, 1H), 7.38 (d, J=9.0 Hz, 1H), 7.13 (t, J=9.1 Hz, 1H), 3.97 (s, 3H), 3.74-3.65 (m, 2H), 3.64-3.55 (m, 2H), 3.38-3.35 (m, 1H), 2.24 (s, 3H), 1.96-1.85 (m, 1H), 1.67-1.57 (m, 1H).

General Procedure LCMS Analytical Methods

M 1: reverse phase LC-MS was carried out on a YMC-PACK ODS-AQ, 50×2.0 mm 5 μm column with a flow rate of 0.8 mL/min, eluting with a gradient of 0% to 60% acetonitrile containing 0.05% TFA (solvent B) and water containing 0.1% TFA (solvent A). The eluent composition was kept at 100% A for 1 minute, followed by increasing to 60% B over the course of 4 minutes. The eluent was kept at 60% B for 2.5 minutes before returning to 100% A over the course of 0.5 minutes. Total run time was 8 minutes.

M2: reverse phase LC-MS was carried out on a Agilent TC-C18, 50×2.1 mm, 5 μm column with a flow rate of 0.8 mL/min, eluting with a gradient of 0% to 85% acetonitrile containing 0.05% TFA (solvent B) and water containing 0.1% TFA (solvent A). The eluent composition was kept at 100% A for 1 minute, followed by increasing to 40% B over the course of 4 minutes. The eluent was further increased to 85% B over the course of 2.5 minutes before returning to 100% A over the course of 2 minutes. Total run time was 9.5 minutes.

M3: reverse phase LC-MS was carried out on a Agilent TC-C18, 50×2.1 mm, 5 μm column with a flow rate of 0.8 mL/min, eluting with a gradient of 10% to 80% acetonitrile containing 0.05% TFA (solvent B) and water containing 0.1% TFA (solvent A). The eluent composition was kept at 10% B for 0.8 minutes, followed by increasing to 80% B over the course of 3.7 minutes. The eluent was kept at 80% B for 3 minutes before returning to 10% B over the course of 2 minutes. Total run time was 9.5 minutes.

M4: reverse phase LC-MS was carried out on a X-Bridge Shield RP18, 50×2.1 mm 5 μm with a flow rate of 0.8 mL/min, eluting with a gradient of 0% to 95% acetonitrile (solvent B) and water with 0.05% $NH_3.H_2O$ (solvent A). The eluent composition was kept at 100% A for 1 minute, followed by increasing to 60% B over the course of 4 minutes. The eluent was increased to 95% B over the course of 2 minutes before returning to 100%/o A over the course of 2 minutes. Total run time was 9.5 minutes.

General Methods of Preparation HPLC:

$NH_3H_2O$: (Column: Agela DuraShell C18 150 mm×25 mm, 5 μm; mobile phase: $CH_3CN$ in water (0.05% $NH_3H_2O$ water) from 43% to 73%, flow rate: 30 mL/min).

$NH_4HCO_3$: (Column: Agela DuraShell C18 150 mm×25 mm, 5 μm; mobile phase: $CH_3CN$ in water (0.5% $NH_4HCO_3$ water) from 20% to 60%, flow rate: 30 mL/min).

Formic acid: (Column: Phenomenex Synergi Max-RP 250 mm×80 mm, 10 μm; mobile phase: $CH_3CN$ in water (0.225% formic acid water) from 1% to 25%, flow rate: 80 ml/min)

HCl: (Column: Gemini C18 150 mm×25 mm, 5 μm; mobile phase: $CH_3CN$ in water (0.05% HCl water) from 35% to 65%, flow rate: 25 mL/min).

TFA: (Column: Phenomenex Synergi C18 150 mm×30 mm, 4 μm (eluent: $CH_3CN/H_2O$ (0.1% TFA water) from 65% to 75%, flow rate: 30 ml/min).

General SFC Separation Methods:

Method 1: Separation condition: Column: AD 250×30 mm I.D., 5 um, Daicel Chemical Industries, Ltd; Mobile phase: A: Supercritical $CO_2$, B: MeOH (0.1% $NH_3H_2O$)

Method 2: Separation condition: Column: ChiralPak OJ-H 250×30 mm I.D., 5 um, Daicel Chemical Industries, Ltd; Mobile phase: A: Supercritical $CO_2$, B: EtOH (0.1% $NH_3H_2O$)

Method 3: Separation condition: Column: ChiralPak AD 250×30 mm I.D., 20 um, Daicel Chemical Industries, Ltd; Mobile phase: A: Supercritical $CO_2$, B: EtOH (0.1% $NH_3H_2O$)

Method 4: Separation condition: Column: ChiralPak AD, Daicel Chemical Industries, Ltd, 250×30 mm I.D., 10 μm; Mobile phase: A: Supercritical $CO_2$, B: methanol (0.1% $NH_3H_2O$)

Method 5: Separation condition: Column: AD (250 mm*30 mm, 5 um); Mobile phase: A: Supercritical $CO_2$, B: EtOH (0.1% $NH_3H_2O$);

Method 6: Separation condition: Column: ChiralPak AD 250×30 mm I.D., 10 μm, Daicel Chemical Industries, Ltd; Mobile phase: A: Supercritical $CO_2$, B: EtOH (0.1% $NH_3H_2O$)

Method 7: Column: Chiralpak AD-3 50*4.6 mm I.D., 3 um Mobile phase: 60% ethanol (0.05% DEA) in $CO_2$.

Method 8: separation condition: Column: ChiralPak OJ-H, Daicel Chemical Industries, Ltd, 250×30 mm I.D., 5 μm; Mobile phase: A: Supercritical $CO_2$, B: Methanol (0.1% $NH_3H_2O$)

TABLE 1

| # | Structure | Synthetic Method | Prep. HPLC | Prep. SFC | Analytic LC-MS |
|---|---|---|---|---|---|
| 1 | 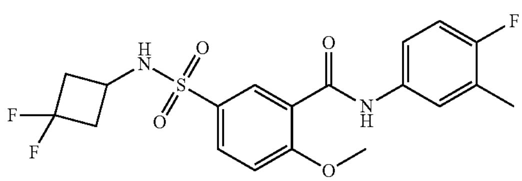 [SMILES: COc1ccc(S(=O)(=O)NC2CC(F)(F)C2)cc1C(=O)Nc1ccc(F)c(C)c1] | A | $NH_3H_2O$ | / | M2 |
| 2 | 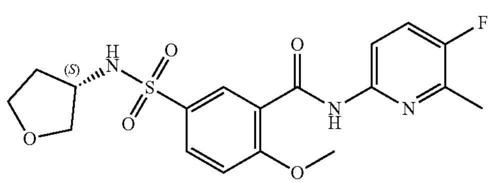 | B | / | / | M2 |
| 3 | 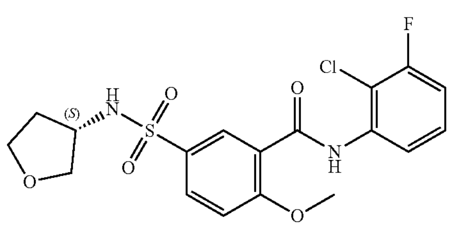 | C | / | / | M2 |
| 4 | 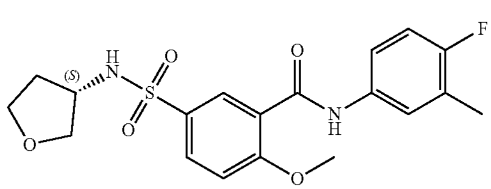 | D | $NH_3H_2O$ | / | M2 |

TABLE 1-continued

| # | Structure | Synthetic Method | Prep. HPLC | Prep. SFC | Analytic LC-MS |
|---|---|---|---|---|---|
| 5 | 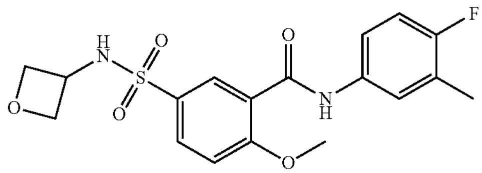 [SMILES: COc1ccc(S(=O)(=O)NC2COC2)cc1C(=O)Nc1ccc(F)c(C)c1] | A | TFA | / | M2 |
| 6a | 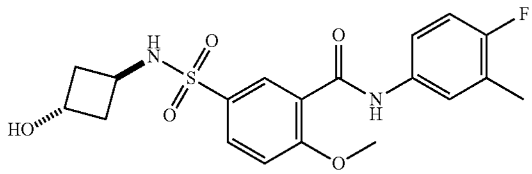 | A | NH₃H₂O | Method 1 | M2 |
| 6b | 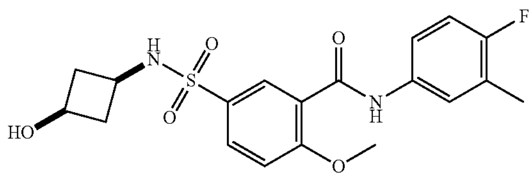 | A | NH₃H₂O | Method 1 | M2 |
| 7 | 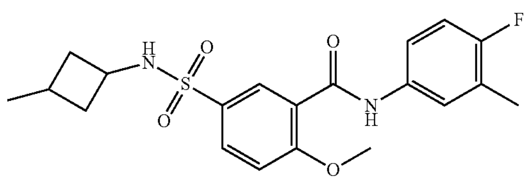 | A | / | / | M3 |
| 7a | 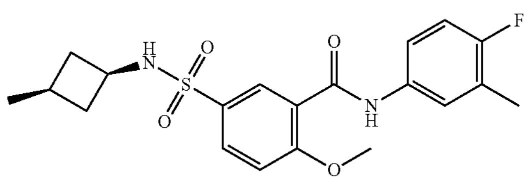 | A | / | Method 1 | M3 |
| 7b | 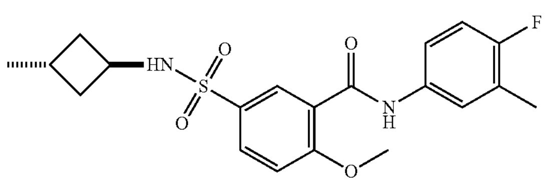 | A | / | Method 1 | M3 |
| 8 | 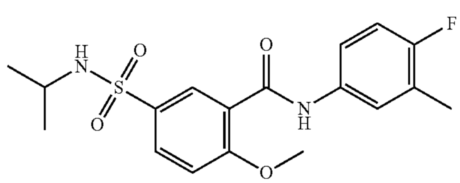 [SMILES: COc1ccc(S(=O)(=O)NC(C)C)cc1C(=O)Nc1ccc(F)c(C)c1] | A | / | / | M3 |
| 9 | 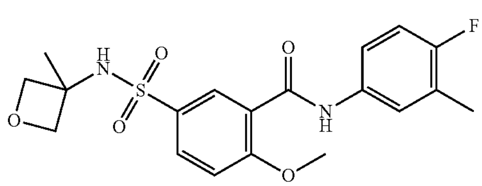 [SMILES: COc1ccc(S(=O)(=O)NC2(C)COC2)cc1C(=O)Nc1ccc(F)c(C)c1] | A | / | / | M2 |

TABLE 1-continued

| # | Structure | Synthetic Method | Prep. HPLC | Prep. SFC | Analytic LC-MS |
|---|---|---|---|---|---|
| 10 | 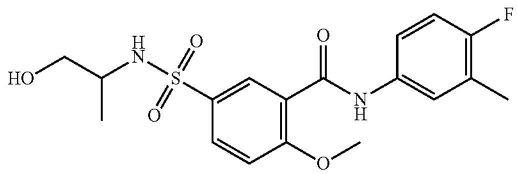 [SMILES: COc1ccc(S(=O)(=O)NC(C)CO)cc1C(=O)Nc1ccc(F)c(C)c1] | A | / | / | M2 |
| 10a | 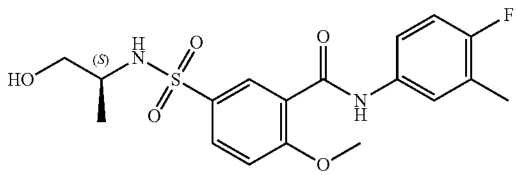 | A | / | / | M2 |
| 10b | 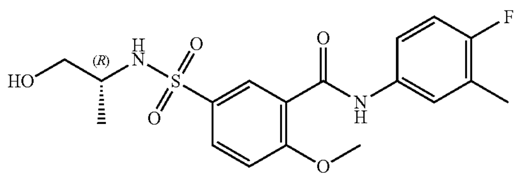 | A | / | / | M2 |
| 11a | 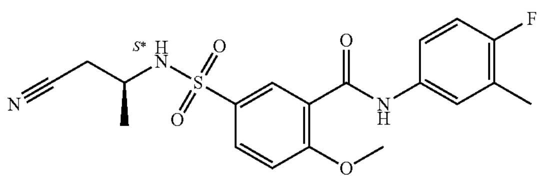 | A | / | Method 2 | M2 |
| 11b | 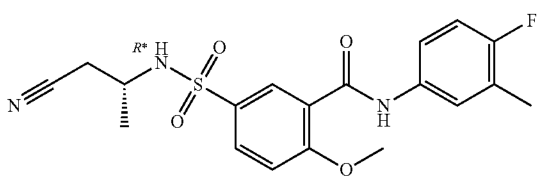 | A | / | Method 2 | M2 |
| 12 | 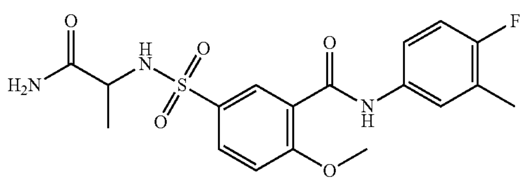 [SMILES: COc1ccc(S(=O)(=O)NC(C)C(N)=O)cc1C(=O)Nc1ccc(F)c(C)c1] | A | / | / | M2 |
| 12a | 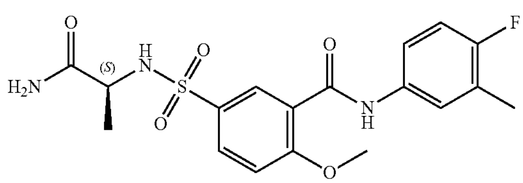 | A | / | / | M2 |
| 12b | 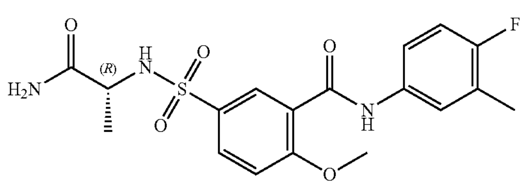 | A | NH$_4$HCO$_3$ | / | M2 |

TABLE 1-continued

| # | Structure | Synthetic Method | Prep. HPLC | Prep. SFC | Analytic LC-MS |
|---|---|---|---|---|---|
| 13 | 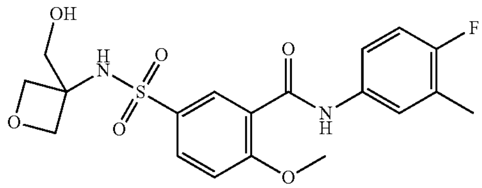 [SMILES: COc1ccc(S(=O)(=O)NC2(CO)COC2)cc1C(=O)Nc1ccc(F)c(C)c1] | A | / | / | M2 |
| 14 | 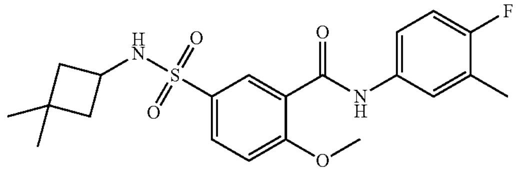 | A | / | / | M3 |
| 15a | 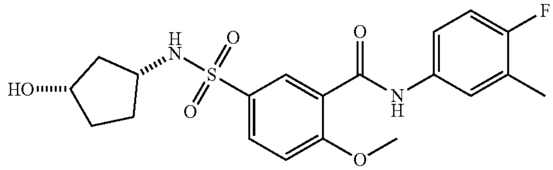 | A | NH₃H₂O | Method 3 | M4 |
| 15b | 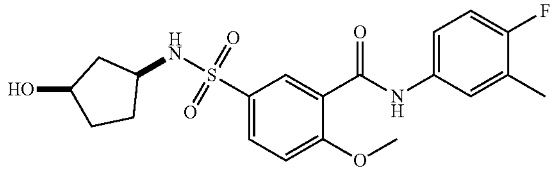 | A | / | Method 3 | M2 |
| 16a | 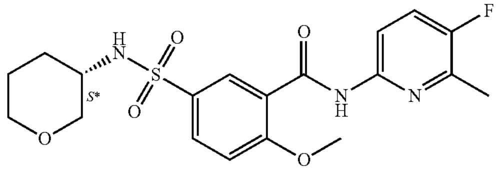 [SMILES: COc1ccc(S(=O)(=O)N[C@H]2CCCOC2)cc1C(=O)Nc1ccc(F)c(C)n1] | A | NH₃H₂O | Method 4 | M2 |
| 16b | 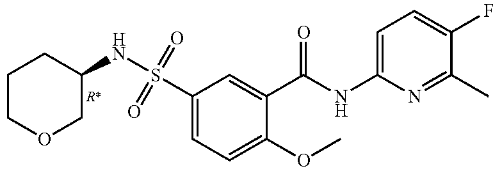 [SMILES: COc1ccc(S(=O)(=O)N[C@@H]2CCCOC2)cc1C(=O)Nc1ccc(F)c(C)n1] | A | NH₃H₂O | Method 4 | M2 |
| 17 | 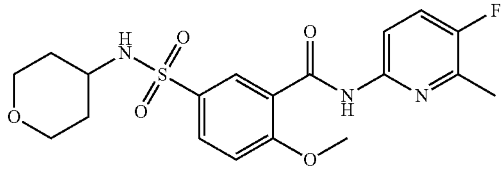 [SMILES: COc1ccc(S(=O)(=O)NC2CCOCC2)cc1C(=O)Nc1ccc(F)c(C)n1] | A | / | / | M2 |
| 18 | 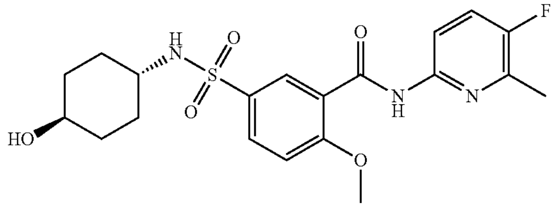 [SMILES: COc1ccc(S(=O)(=O)N[C@H]2CC[C@H](O)CC2)cc1C(=O)Nc1ccc(F)c(C)n1] | A | / | / | M2 |

TABLE 1-continued
| # | Structure | Synthetic Method | Prep. HPLC | Prep. SFC | Analytic LC-MS |
|---|---|---|---|---|---|
| 19 | 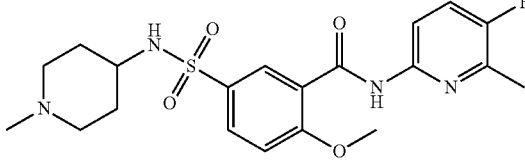 | A | / | / | M2 |
| 20 | 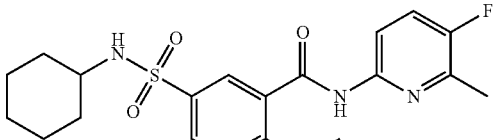 | A | NH₃H₂O | / | M2 |
| 21 | 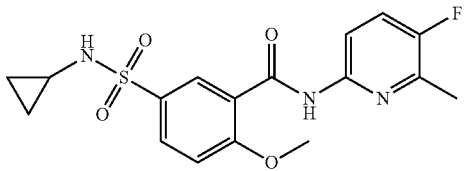 [SMILES: COc1ccc(S(=O)(=O)NC2CC2)cc1C(=O)Nc1ccc(F)c(C)n1] | A | NH₃H₂O | / | M3 |
| 22 | 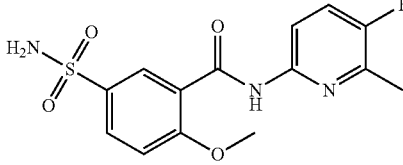 | A | NH₃H₂O | / | M4 |
| 23a | 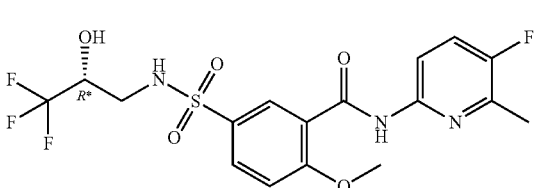 | A | NH₃H₂O | Method 4 | M2 |
| 23b | 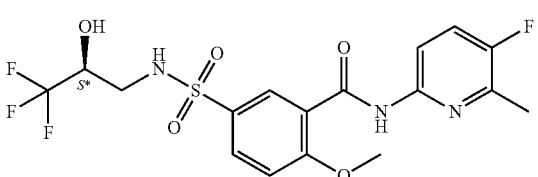 | A | NH₃H₂O | Method 4 | M2 |
| 24 | 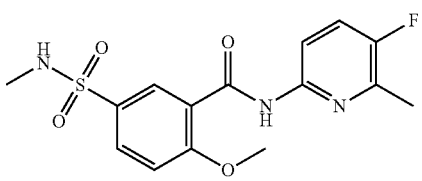 | A | NH₃H₂O | / | M2 |
| 25 | 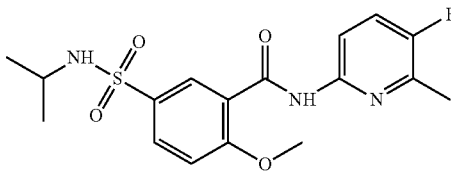 | A | NH₃H₂O | / | M4 |

TABLE 1-continued

| # | Structure | Synthetic Method | Prep. HPLC | Prep. SFC | Analytic LC-MS |
|---|---|---|---|---|---|
| 26 | 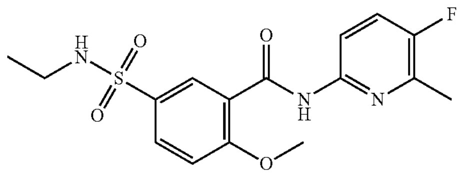 [SMILES: CCNS(=O)(=O)c1ccc(OC)c(C(=O)Nc2ccc(F)c(C)n2)c1] | A | NH$_3$H$_2$O | / | M2 |
| 27 | 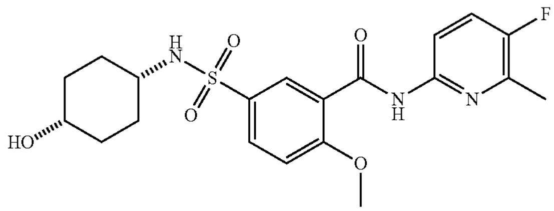 | A | NH$_3$H$_2$O | / | M2 |
| 28a | 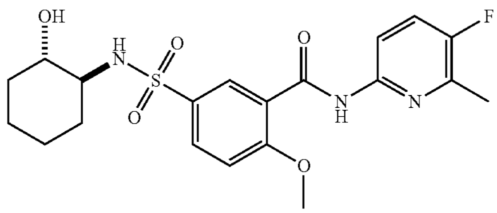 | A | NH$_3$H$_2$O | Method 4 | M2 |
| 28b | 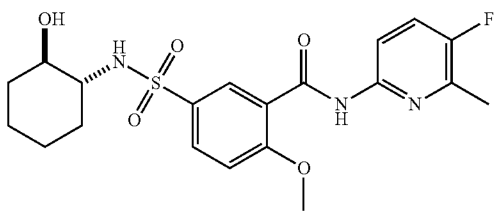 | A | NH$_3$H$_2$O | Method 4 | M2 |
| 29a | 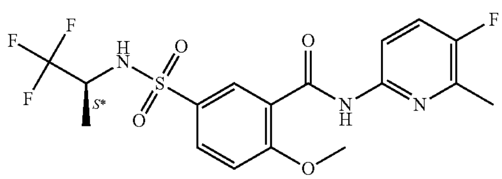 [SMILES: COc1ccc(S(=O)(=O)N[C@@H](C)C(F)(F)F)cc1C(=O)Nc1ccc(F)c(C)n1] | A | / | Method 1 | M2 |
| 29b | 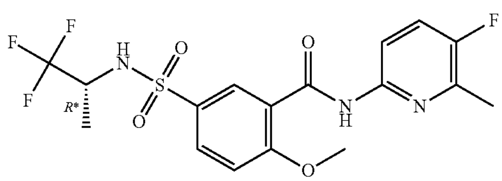 | A | / | Method 1 | M2 |
| 30 | 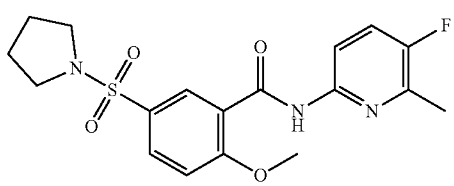 [SMILES: COc1ccc(S(=O)(=O)N2CCCC2)cc1C(=O)Nc1ccc(F)c(C)n1] | A | / | / | M2 |
| 31 | 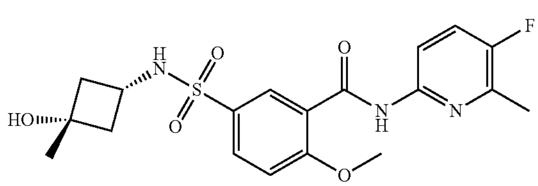 [SMILES: COc1ccc(S(=O)(=O)N[C@H]2C[C@@](C)(O)C2)cc1C(=O)Nc1ccc(F)c(C)n1] | A | / | Method 4 | M2 |

TABLE 1-continued

| # | Structure | Synthetic Method | Prep. HPLC | Prep. SFC | Analytic LC-MS |
|---|---|---|---|---|---|
| 32a | 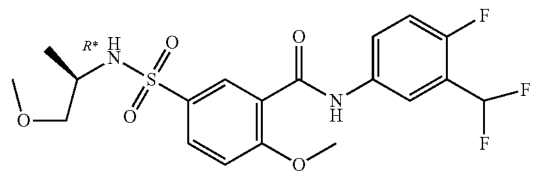 [SMILES: COC[C@@H](C)NS(=O)(=O)c1ccc(OC)c(C(=O)Nc2ccc(F)c(C(F)F)c2)c1] | A | Formic acid | Method 5 | M2 |
| 32b | 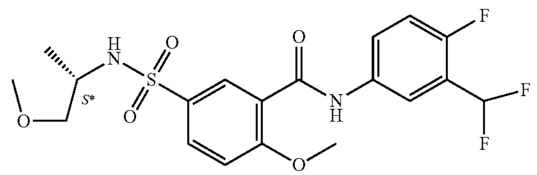 [SMILES: COC[C@H](C)NS(=O)(=O)c1ccc(OC)c(C(=O)Nc2ccc(F)c(C(F)F)c2)c1] | A | Formic acid | Method 5 | M2 |
| 33a | 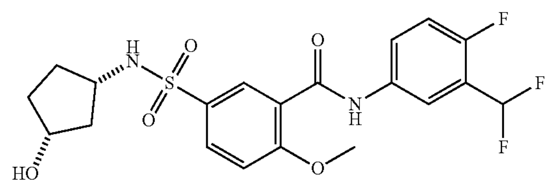 | A | Formic acid | Method 4 | M2 |
| 33b | 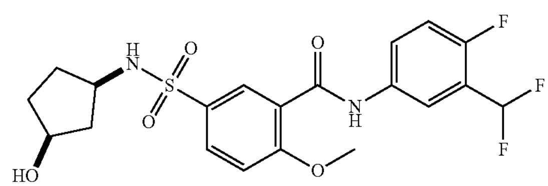 | A | Formic acid | Method 4 | M2 |
| 34a | 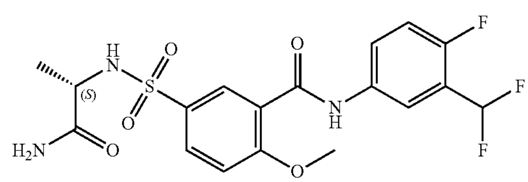 | A | / | / | M2 |
| 34b | 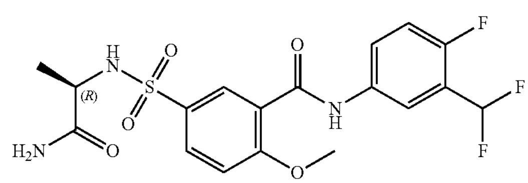 | A | / | / | M4 |
| 35a | 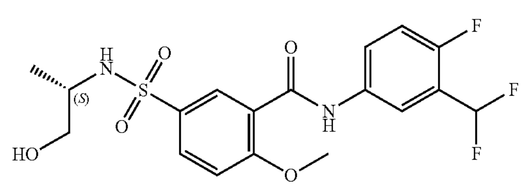 | A | / | / | M2 |
| 35b | 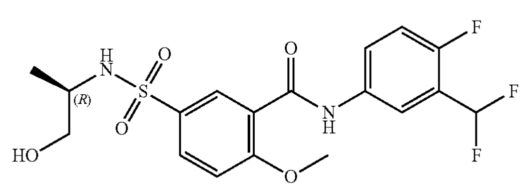 | A | / | / | M4 |

TABLE 1-continued

| # | Structure | Synthetic Method | Prep. HPLC | Prep. SFC | Analytic LC-MS |
|---|---|---|---|---|---|
| 36 | 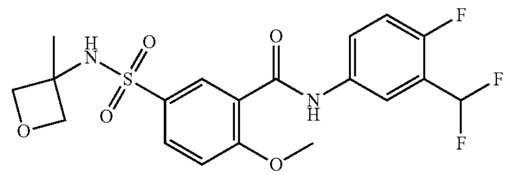 [SMILES: COc1ccc(S(=O)(=O)NC2(C)COC2)cc1C(=O)Nc1ccc(F)c(C(F)F)c1] | A | HCl | / | M2 |
| 37 | 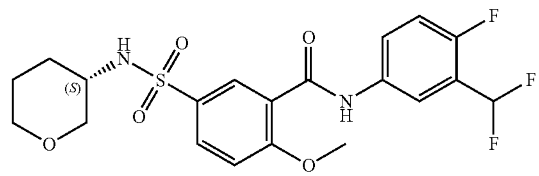 | A | HCl | / | M2 |
| 38 | 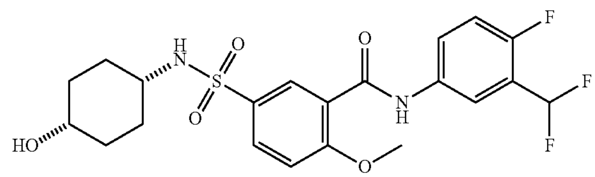 | A | HCl | / | M2 |
| 39 | 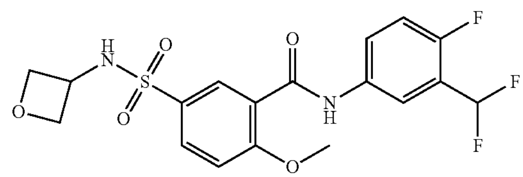 [SMILES: COc1ccc(S(=O)(=O)NC2COC2)cc1C(=O)Nc1ccc(F)c(C(F)F)c1] | A | HCl | / | M2 |
| 40a | 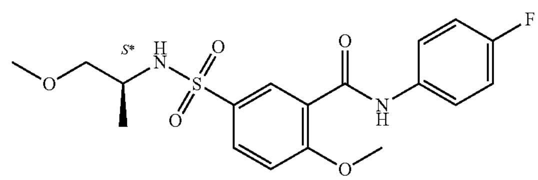 [SMILES: COC[C@H](C)NS(=O)(=O)c1ccc(OC)c(C(=O)Nc2ccc(F)cc2)c1] | A | / | Method 5 | M2 |
| 40b | 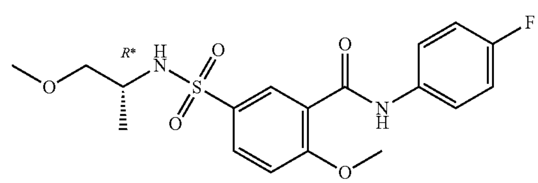 [SMILES: COC[C@@H](C)NS(=O)(=O)c1ccc(OC)c(C(=O)Nc2ccc(F)cc2)c1] | A | / | Method 5 | M2 |
| 41 | 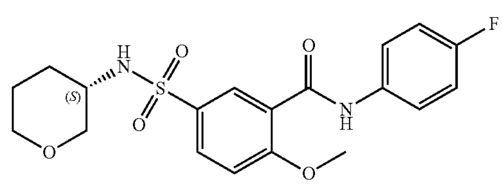 | A | NH$_4$HCO$_3$ | / | M2 |
| 42 | 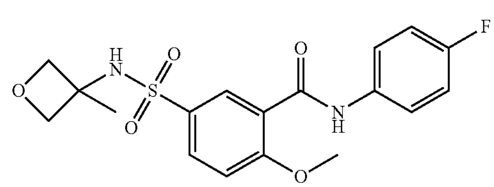 [SMILES: COc1ccc(S(=O)(=O)NC2(C)COC2)cc1C(=O)Nc1ccc(F)cc1] | A | NH$_4$HCO$_3$ | / | M2 |

TABLE 1-continued

| # | Structure | Synthetic Method | Prep. HPLC | Prep. SFC | Analytic LC-MS |
|---|---|---|---|---|---|
| 43 | 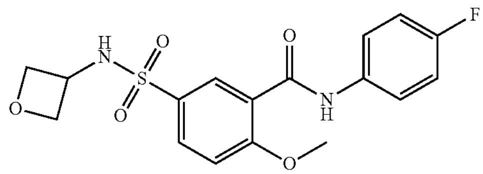 [SMILES: COc1ccc(S(=O)(=O)NC2COC2)cc1C(=O)Nc1ccc(F)cc1] | A | NH₄HCO₃ | / | M2 |
| 44a | 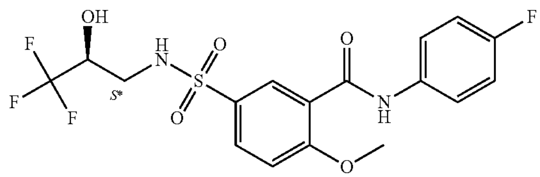 [SMILES: COc1ccc(S(=O)(=O)NC[C@H](O)C(F)(F)F)cc1C(=O)Nc1ccc(F)cc1] | A | NH₄HCO₃ | Method 5 | M2 |
| 44b | 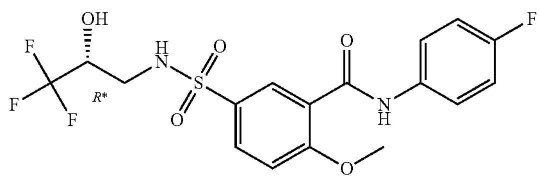 [SMILES: COc1ccc(S(=O)(=O)NC[C@@H](O)C(F)(F)F)cc1C(=O)Nc1ccc(F)cc1] | A | NH₄HCO₃ | Method 5 | M2 |
| 45a | 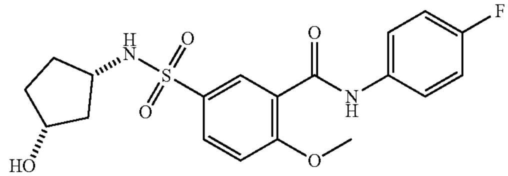 | A | / | Method 1 | M2 |
| 45b | 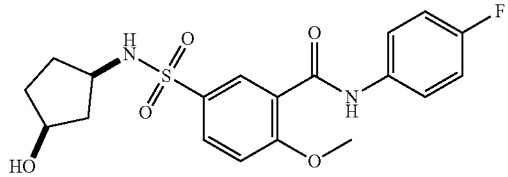 | A | / | Method 1 | M2 |
| 46a | 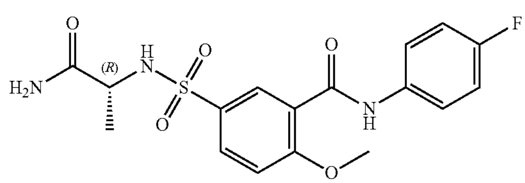 | A | / | / | M2 |
| 46b | 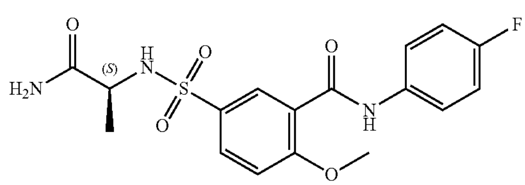 | A | HCl | / | M2 |
| 47 | 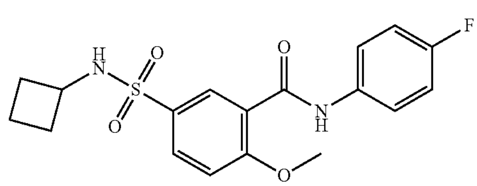 [SMILES: COc1ccc(S(=O)(=O)NC2CCC2)cc1C(=O)Nc1ccc(F)cc1] | A | HCl | / | M2 |

TABLE 1-continued

| # | Structure | Synthetic Method | Prep. HPLC | Prep. SFC | Analytic LC-MS |
|---|---|---|---|---|---|
| 48 | 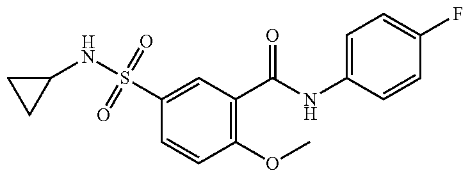 [SMILES: COc1ccc(S(=O)(=O)NC2CC2)cc1C(=O)Nc1ccc(F)cc1] | A | / | / | M2 |
| 49a | 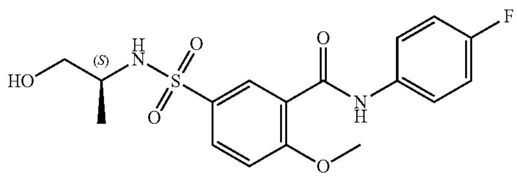 | A | / | / | M2 |
| 49b | 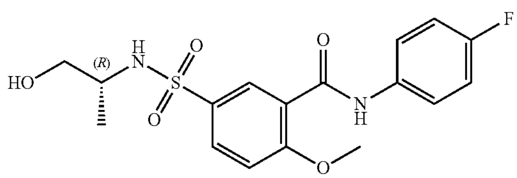 | A | / | / | M2 |
| 50 | 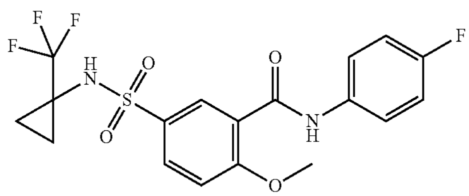 [SMILES: COc1ccc(S(=O)(=O)NC2(C(F)(F)F)CC2)cc1C(=O)Nc1ccc(F)cc1] | A | / | / | M2 |
| 51 | 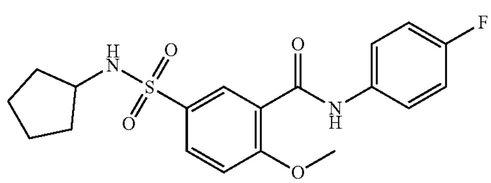 [SMILES: COc1ccc(S(=O)(=O)NC2CCCC2)cc1C(=O)Nc1ccc(F)cc1] | A | / | / | M2 |
| 52a | 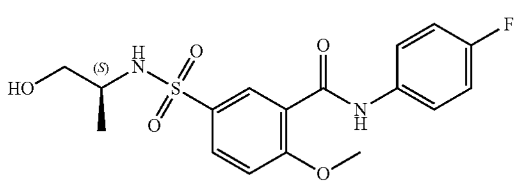 | A | / | Method 6 | M2 |
| 52b | 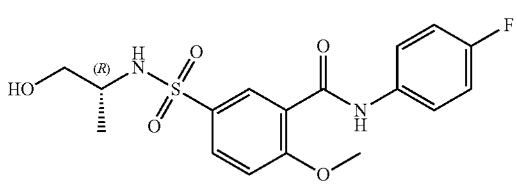 | A | / | Method 6 | M2 |
| 53 | 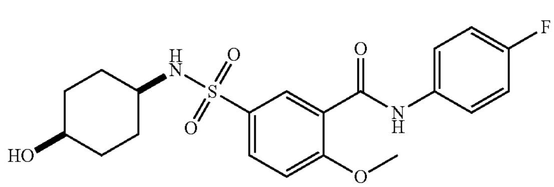 | A | / | / | M2 |

TABLE 1-continued

| # | Structure | Synthetic Method | Prep. HPLC | Prep. SFC | Analytic LC-MS |
|---|---|---|---|---|---|
| 54a | 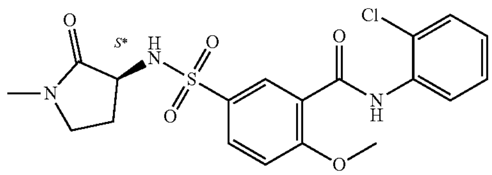 | A | / | Method 1 | M2 |
| 54b | 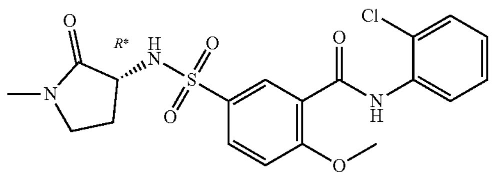 | A | / | Method 1 | M2 |
| 55a | 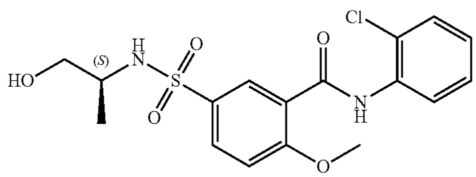 | A | / | / | M2 |
| 55b | 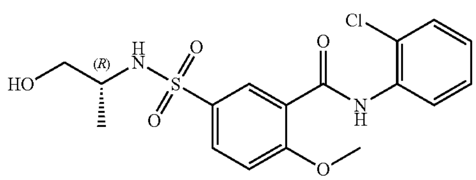 | A | / | / | M2 |
| 56a | 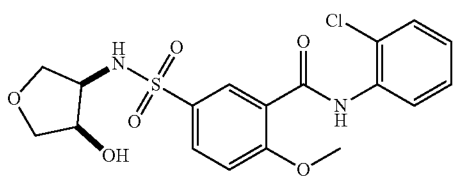 | A | NH$_3$H$_2$O | Method 5 | M2 |
| 56b | 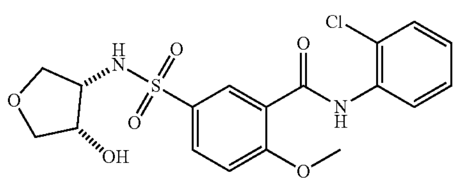 | A | NH$_3$H$_2$O | Method 5 | M2 |
| 57a | 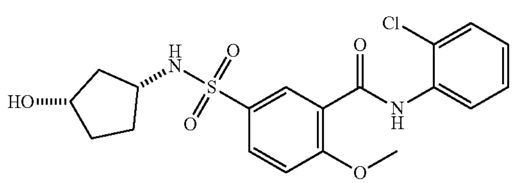 | A | / | Method 6 | M2 |
| 57b | 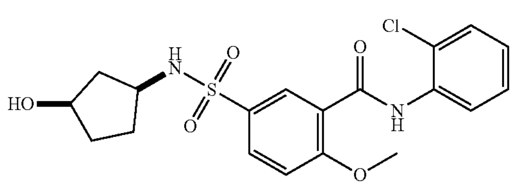 | A | / | Method 6 | M2 |

TABLE 1-continued

| # | Structure | Synthetic Method | Prep. HPLC | Prep. SFC | Analytic LC-MS |
|---|---|---|---|---|---|
| 58 | 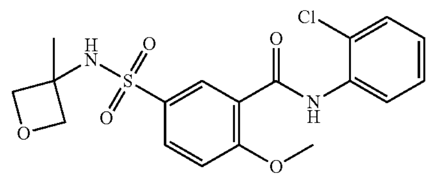 [SMILES: COc1ccc(S(=O)(=O)NC2(C)COC2)cc1C(=O)Nc1ccccc1Cl] | A | / | / | M2 |
| 59a | 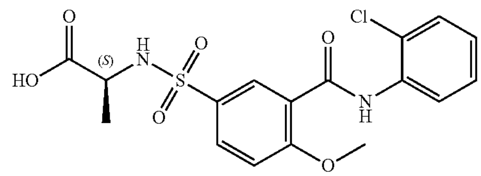 | A | / | / | M2 |
| 59b | 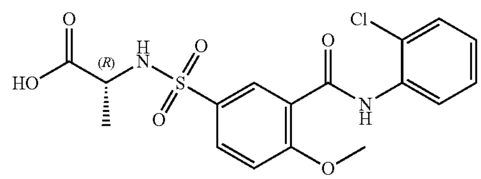 | A | / | / | M2 |
| 60a | 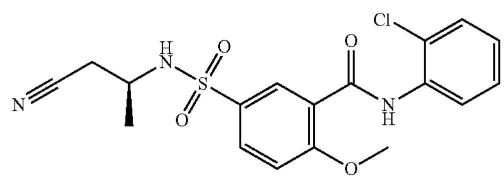 [SMILES: COc1ccc(S(=O)(=O)N[C@@H](C)CC#N)cc1C(=O)Nc1ccccc1Cl] | A | / | Method 5 | M2 |
| 60b | 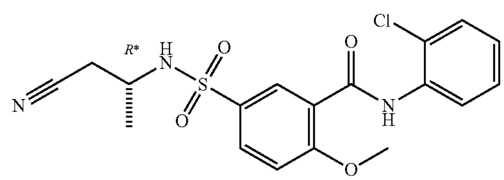 | A | / | Method 5 | M4 |
| 61a | 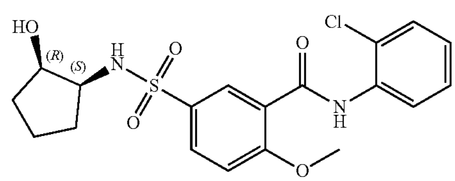 | A | NH$_3$H$_2$O | / | M2 |
| 61b | 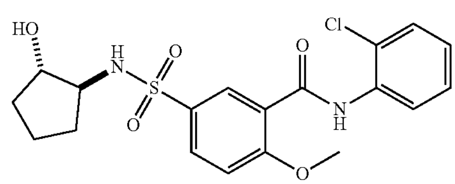 | A | NH$_3$H$_2$O | Method 7 | M4 |
| 61c | 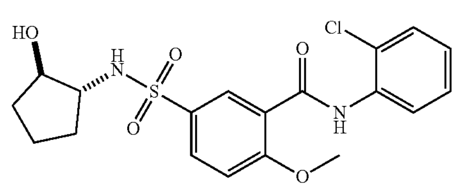 | A | NH$_3$H$_2$O | Method 7 | M4 |

TABLE 1-continued
| # | Structure | Synthetic Method | Prep. HPLC | Prep. SFC | Analytic LC-MS |
|---|---|---|---|---|---|
| 62 | 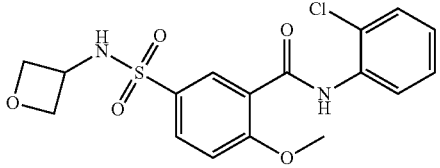 [SMILES: COc1ccc(S(=O)(=O)NC2COC2)cc1C(=O)Nc1ccccc1Cl] | A | NH₃H₂O | / | M2 |
| 63 | 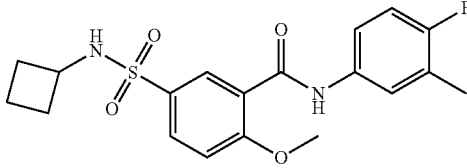 [SMILES: COc1ccc(S(=O)(=O)NC2CCC2)cc1C(=O)Nc1ccc(F)c(C)c1] | B | / | / | M2 |
| 64 | 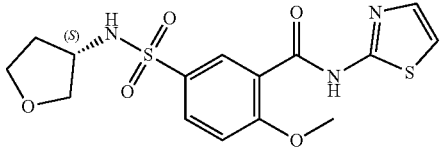 | C | NH₃H₂O | / | M2 |
| 65 | 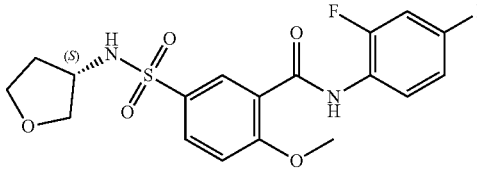 | C | / | / | M2 |
| 66 | 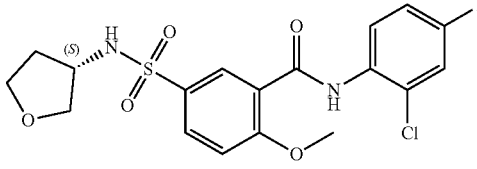 | B | / | / | M2 |
| 67 | 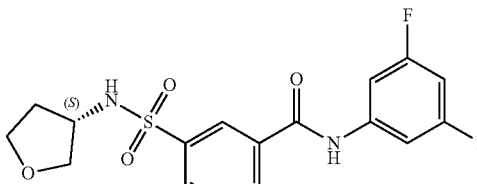 | C | / | / | M2 |
| 68 | 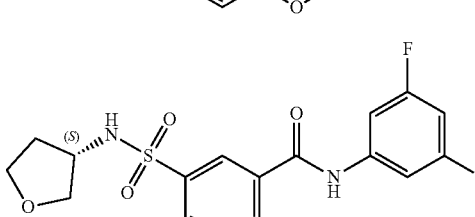 | C | / | / | M2 |
| 69 | 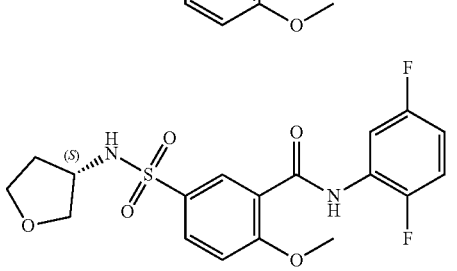 | C | / | / | M2 |

TABLE 1-continued

| # | Structure | Synthetic Method | Prep. HPLC | Prep. SFC | Analytic LC-MS |
|---|---|---|---|---|---|
| 70 | 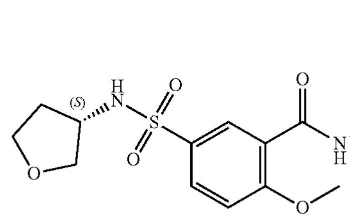 | C | / | / | M2 |
| 71 | 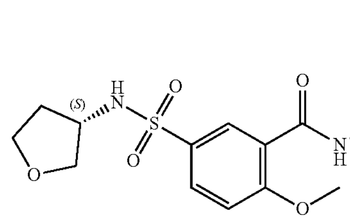 | C | / | / | M2 |
| 72 | 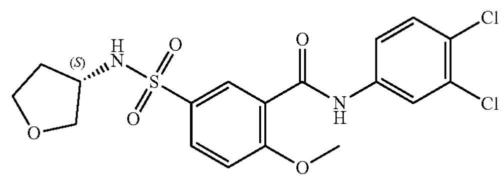 | C | / | / | M2 |
| 73 | 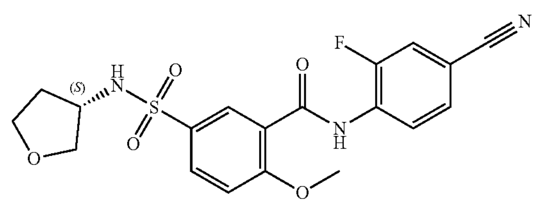 | C | / | / | M2 |
| 74 | 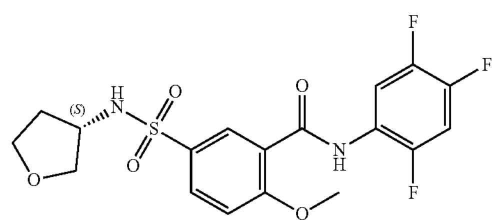 | C | / | / | M2 |
| 75 | 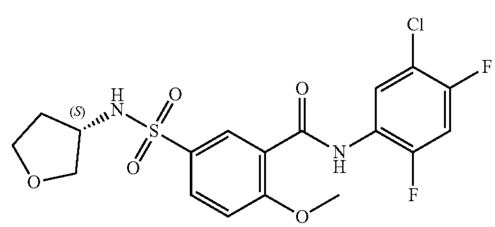 | C | / | / | M2 |
| 76 | 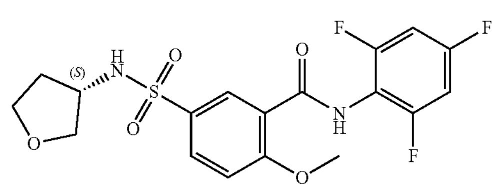 | C | / | / | M2 |

TABLE 1-continued

| # | Structure | Synthetic Method | Prep. HPLC | Prep. SFC | Analytic LC-MS |
|---|---|---|---|---|---|
| 77 | 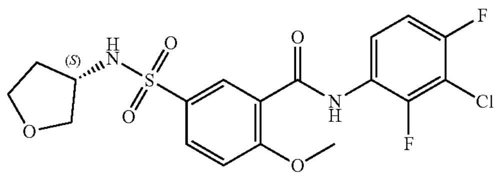 | C | / | / | M2 |
| 78 | 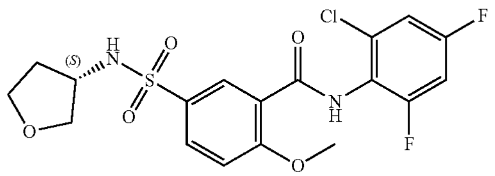 | C | / | / | M2 |
| 79 | 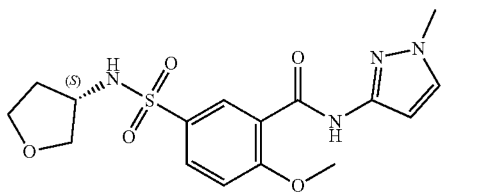 | C | / | / | M2 |
| 80 | 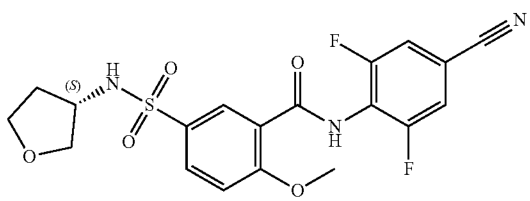 | C | / | / | M2 |
| 81 | 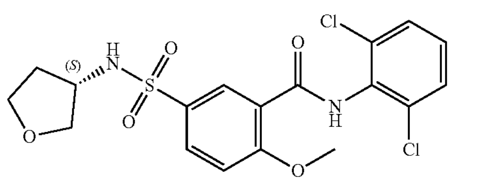 | C | NH₃H₂O | / | M2 |
| 82 | 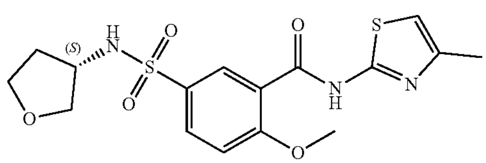 | B | / | / | M2 |
| 83 | 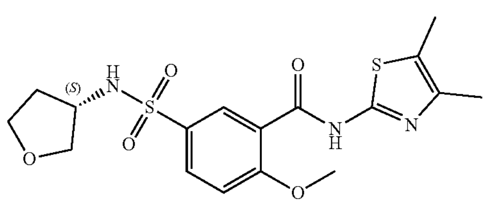 | B | / | / | M2 |
| 84 | 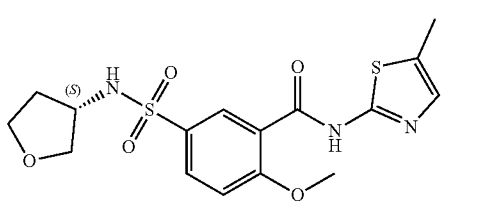 | B | / | / | M2 |

TABLE 1-continued

| # | Structure | Synthetic Method | Prep. HPLC | Prep. SFC | Analytic LC-MS |
|---|---|---|---|---|---|
| 85 | 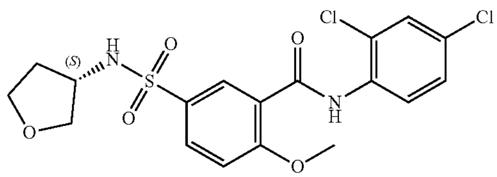 | C | / | / | M2 |
| 86 | 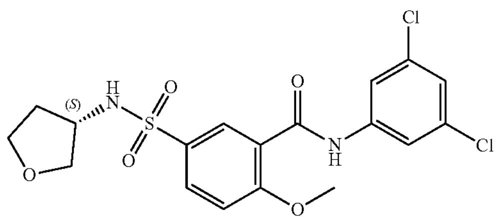 | C | / | / | M3 |
| 87 | 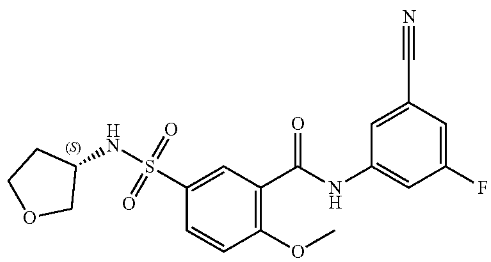 | C | / | / | M2 |
| 88 | 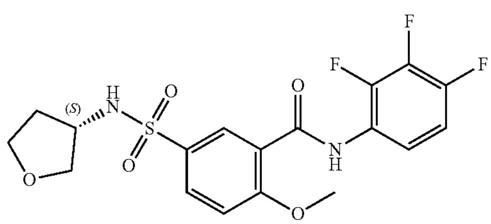 | C | / | / | M2 |
| 89 | 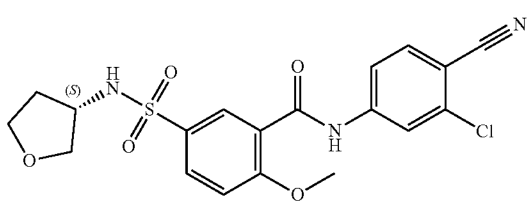 | C | / | / | M2 |
| 90 | 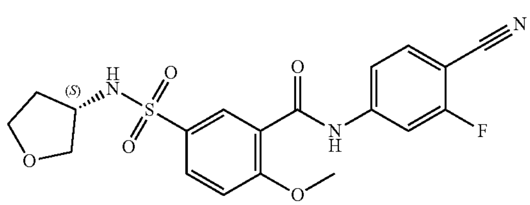 | C | / | / | M2 |
| 91 | 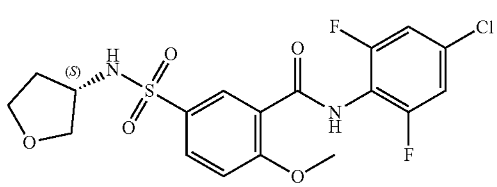 | C | NH$_3$H$_2$O | / | M2 |

US 10,654,837 B2
51      52
TABLE 1-continued
| # | Structure | Synthetic Method | Prep. HPLC | Prep. SFC | Analytic LC-MS |
|---|---|---|---|---|---|
| 92 | 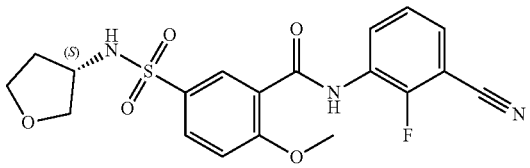 | C | / | / | M2 |
| 93 | 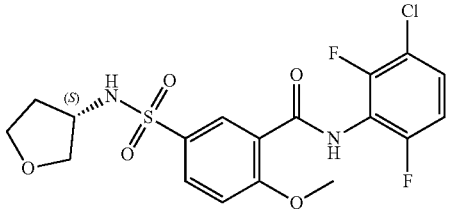 | C | / | / | M2 |
| 94 | 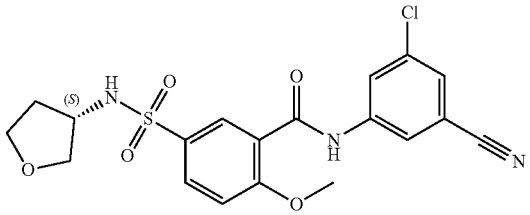 | C | / | / | M2 |
| 95 | 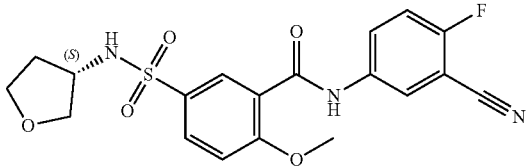 | C | / | / | M2 |
| 96 | 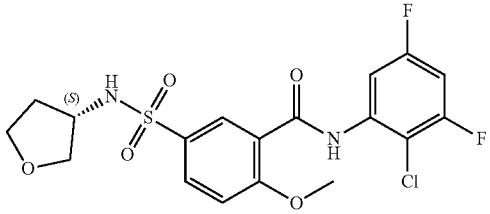 | C | / | / | M2 |
| 97 | 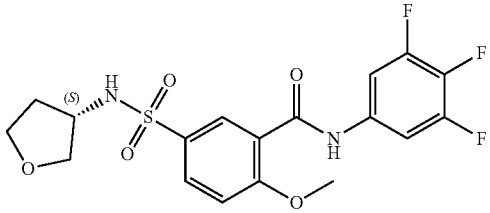 | C | / | / | M2 |
| 98 | 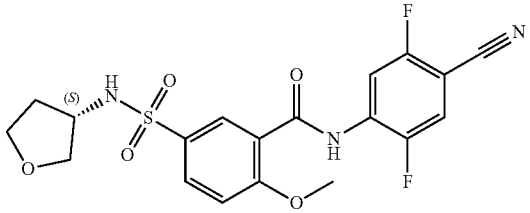 | C | / | / | M2 |

TABLE 1-continued

| # | Structure | Synthetic Method | Prep. HPLC | Prep. SFC | Analytic LC-MS |
|---|---|---|---|---|---|
| 99 | 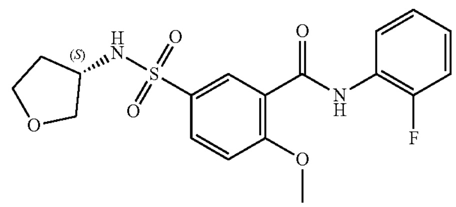 | B | / | / | M2 |
| 100 | 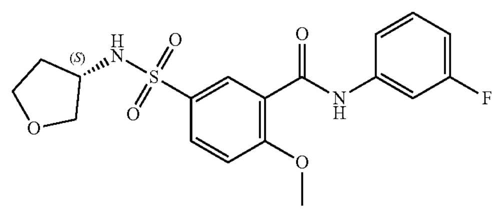 | B | / | / | M2 |
| 101 | 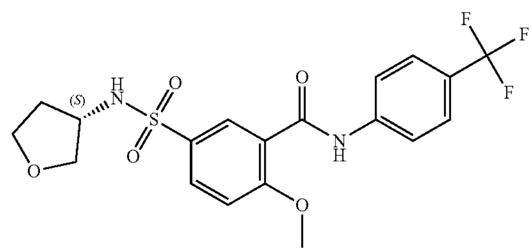 | B | / | / | M1 |
| 102 | 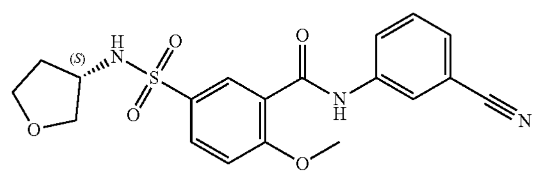 | B | / | / | M1 |
| 103 | 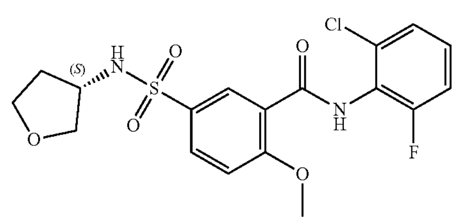 | B | / | / | M2 |
| 104 | 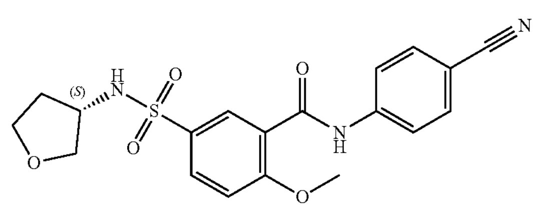 | B | / | / | M1 |
| 105 | 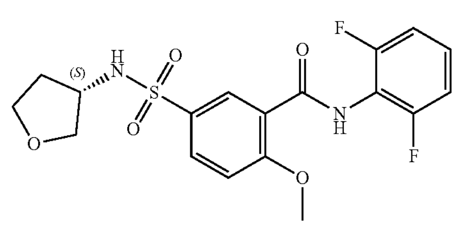 | B | / | / | M4 |

TABLE 1-continued
| # | Structure | Synthetic Method | Prep. HPLC | Prep. SFC | Analytic LC-MS |
|---|---|---|---|---|---|
| 106 | 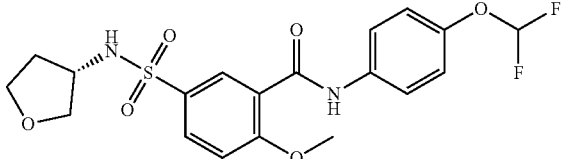 | B | / | / | M2 |
| 107 | 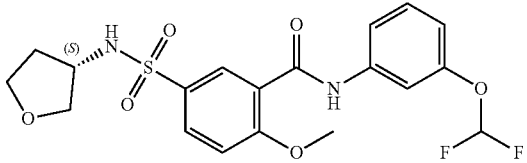 | B | / | / | M2 |
| 108 | 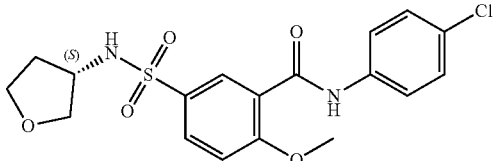 | B | / | / | M2 |
| 109 | 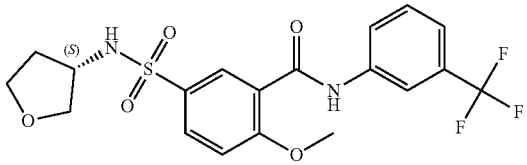 | B | / | / | M2 |
| 110 | 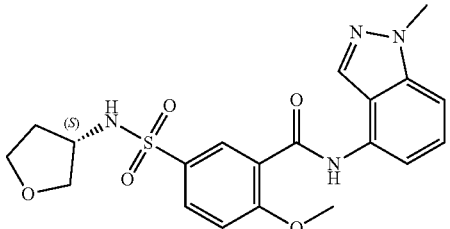 | B | / | / | M2 |
| 111 | 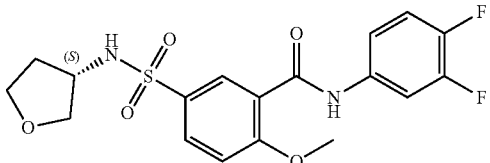 | B | / | / | M2 |
| 112 | 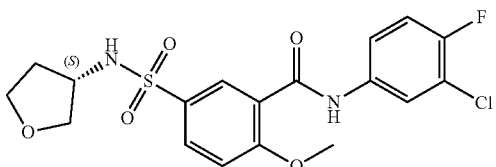 | B | / | / | M2 |
| 113 | 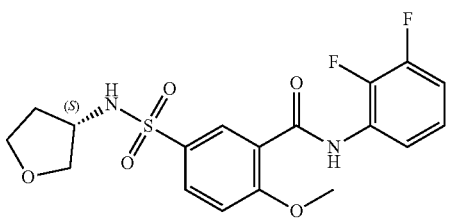 | B | / | / | M2 |

TABLE 1-continued

| # | Structure | Synthetic Method | Prep. HPLC | Prep. SFC | Analytic LC-MS |
|---|---|---|---|---|---|
| 114 | 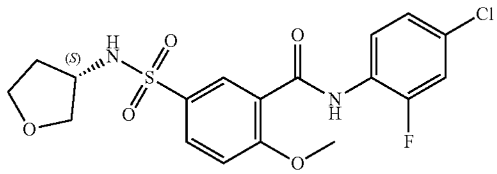 | B | / | / | M2 |
| 115 | 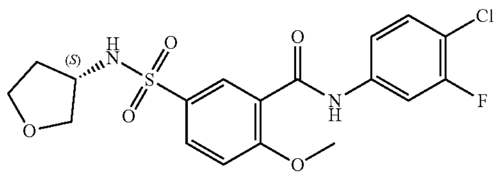 | B | / | / | M2 |
| 116 | 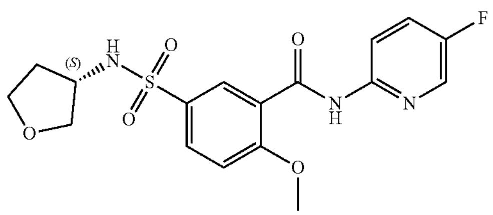 | B | / | / | M2 |
| 117 | 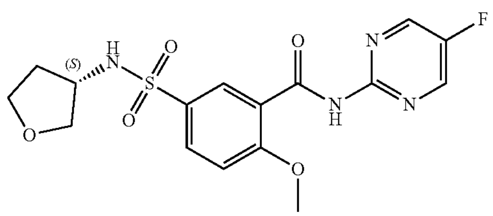 | B | / | / | M2 |
| 118 | 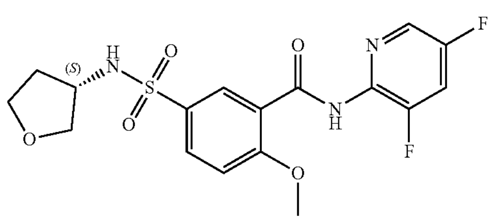 | B | HCl | / | M2 |
| 119 | 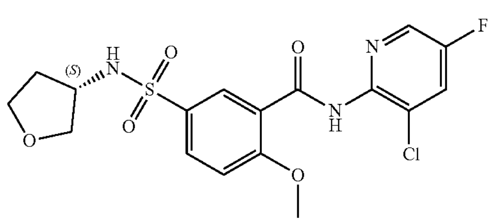 | B | / | / | M2 |
| 120 | 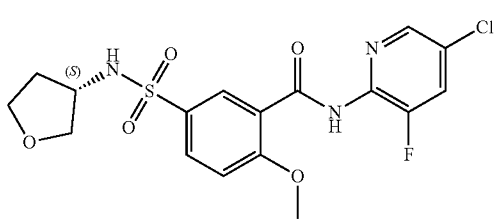 | B | / | / | M2 |

TABLE 1-continued

| # | Structure | Synthetic Method | Prep. HPLC | Prep. SFC | Analytic LC-MS |
|---|---|---|---|---|---|
| 121 | 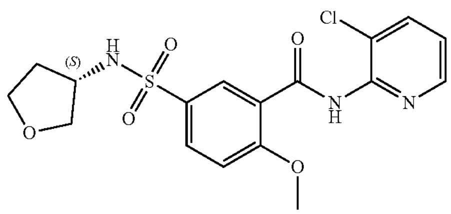 | B | / | / | M2 |
| 122 | 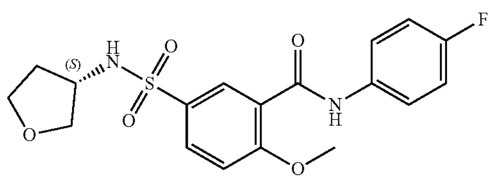 | B | HCl | / | M2 |
| 123 | 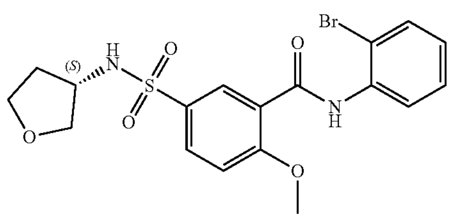 | B | / | / | M2 |
| 124 | 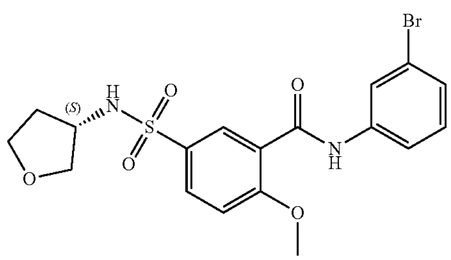 | B | / | / | M2 |
| 125 | 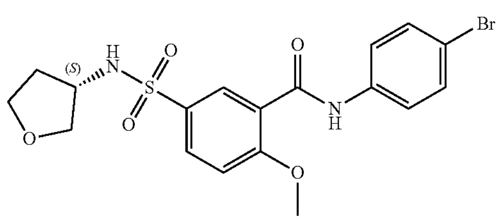 | B | / | / | M2 |
| 126 | 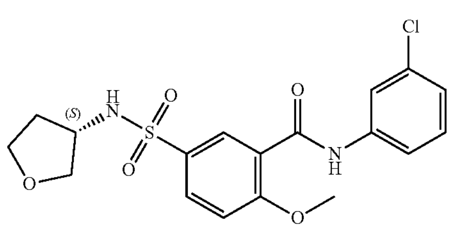 | B | / | / | M2 |
| 127 | 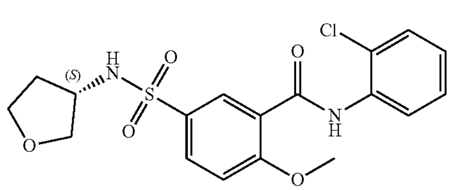 | C | / | / | M2 |

TABLE 1-continued

| # | Structure | Synthetic Method | Prep. HPLC | Prep. SFC | Analytic LC-MS |
|---|---|---|---|---|---|
| 128 | 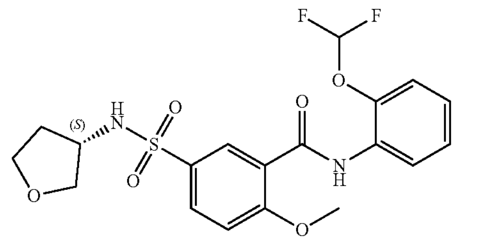 | B | / | / | M2 |
| 129 | 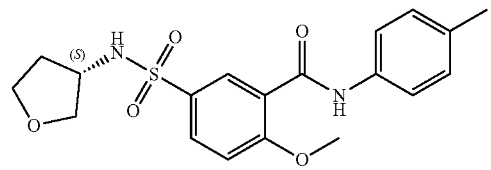 | B | / | / | M2 |
| 130 | 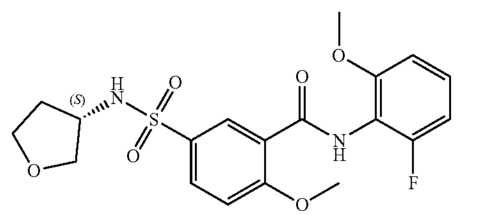 | B | NH₃H₂O | / | M2 |
| 131 | 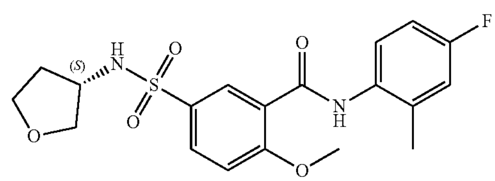 | B | / | / | M2 |
| 132 | 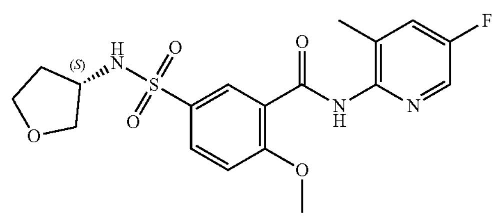 | B | NH₃H₂O | / | M4 |
| 133 | 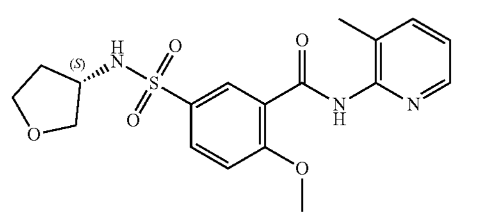 | B | NH₃H₂O | / | M2 |
| 134 | 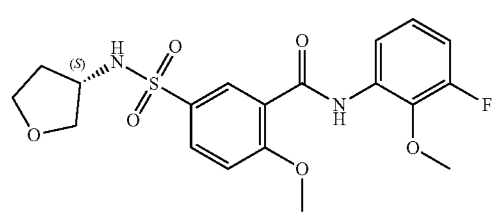 | B | NH₃H₂O | / | M2 |

TABLE 1-continued

| # | Structure | Synthetic Method | Prep. HPLC | Prep. SFC | Analytic LC-MS |
|---|---|---|---|---|---|
| 135 | 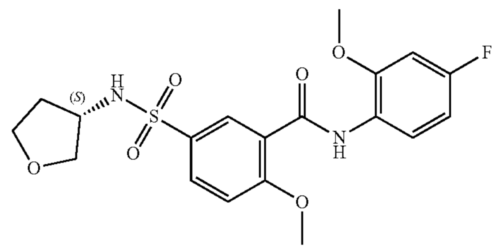 | B | NH₃H₂O | / | M2 |
| 136 | 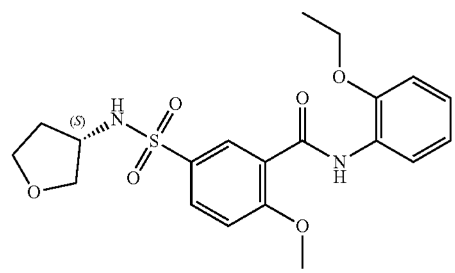 | B | NH₃H₂O | / | M2 |
| 137a | 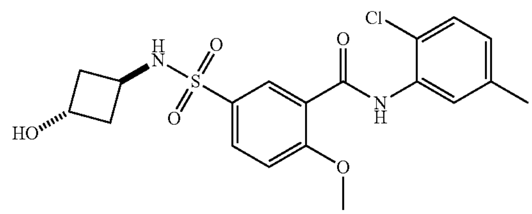 | B | HCl | / | M4 |
| 137b | 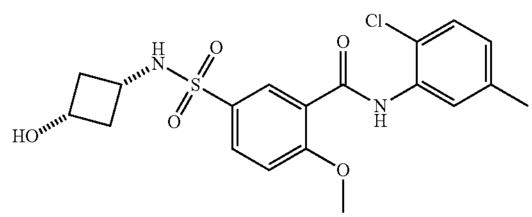 | B | HCl | / | M4 |
| 138a | 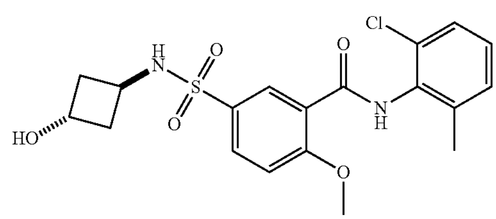 | B | HCl | Method 6 | M2 |
| 138b | 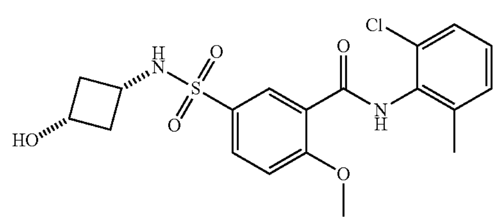 | B | HCl | Method 6 | M2 |

TABLE 1-continued

| # | Structure | Synthetic Method | Prep. HPLC | Prep. SFC | Analytic LC-MS |
|---|---|---|---|---|---|
| 139a | 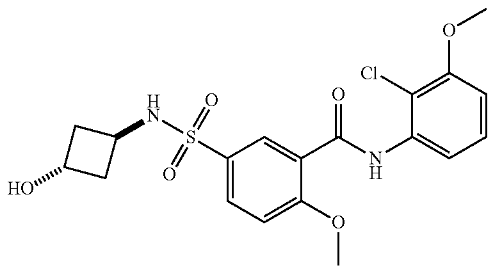 | B | HCl | Method 6 | M2 |
| 139b | 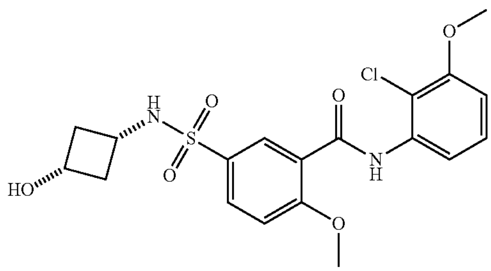 | B | HCl | Method 6 | M2 |
| 140a | 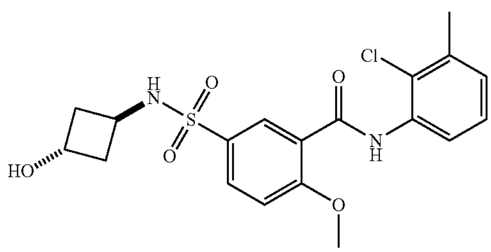 | B | HCl | Method 6 | M2 |
| 140b | 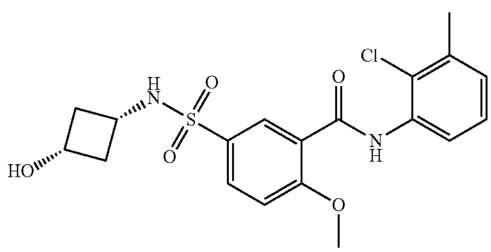 [SMILES: COc1ccc(S(=O)(=O)N[C@H]2C[C@@H](O)C2)cc1C(=O)Nc1cccc(C)c1Cl] | B | HCl | Method 6 | M4 |
| 141 | 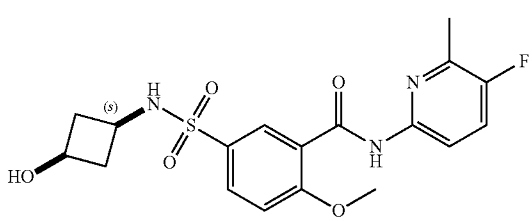 | A | NH$_3$H$_2$O | / | M2) |
| 142a | 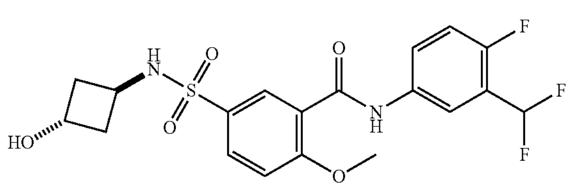 | B | HCl | Method 6 | M2 |

TABLE 1-continued

| # | Structure | Synthetic Method | Prep. HPLC | Prep. SFC | Analytic LC-MS |
|---|---|---|---|---|---|
| 142b | 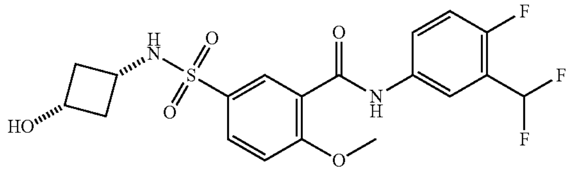 | B | HCl | Method 6 | M2 |
| 143a | 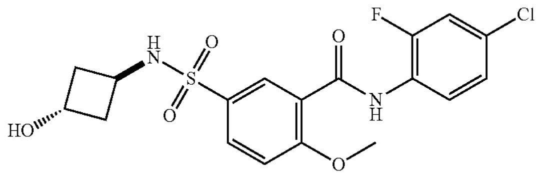 | B | HCl | Method 6 | M2 |
| 143b | 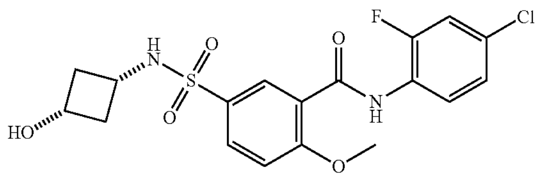 | B | HCl | Method 6 | M2 |
| 144a | 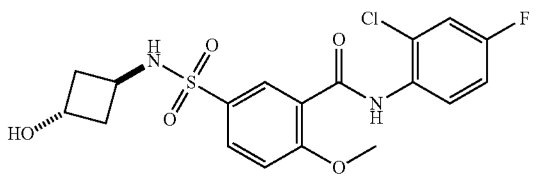 | B | HCl | Method 6 | M2 |
| 144b | 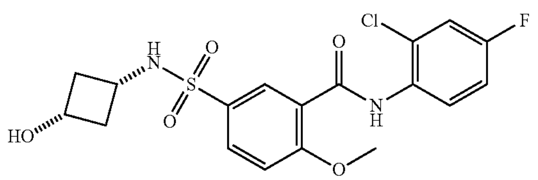 | B | HCl | Method 6 | M2 |
| 145a | 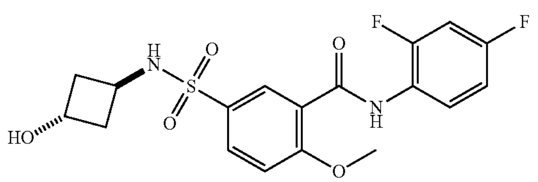 | B | HCl | Method 6 | M2 |
| 145b | 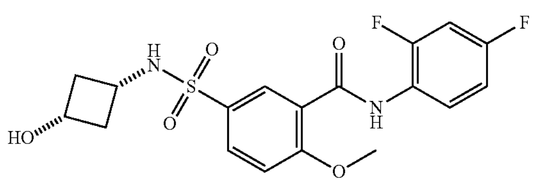 | B | HCl | Method 6 | M2 |
| 146a | 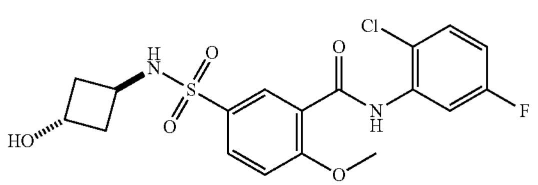 | B | HCl | Method 6 | M2 |

TABLE 1-continued

| # | Structure | Synthetic Method | Prep. HPLC | Prep. SFC | Analytic LC-MS |
|---|---|---|---|---|---|
| 146b | 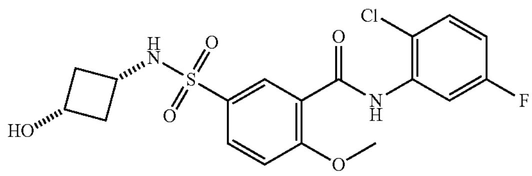 | B | HCl | Method 6 | M2 |
| 147a | 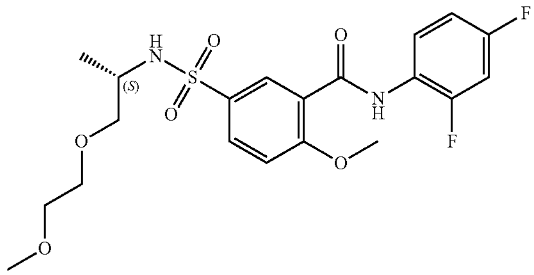 | B | / | / | M2 |
| 147b | 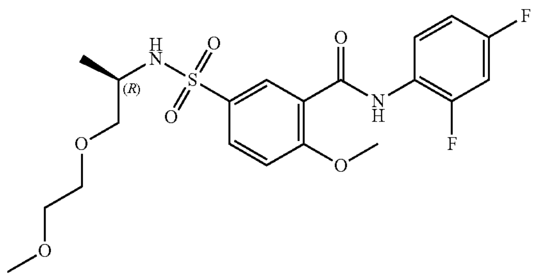 | B | / | / | M2 |
| 148 | 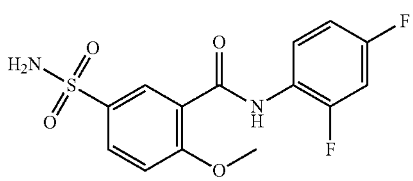 [SMILES: COc1ccc(S(N)(=O)=O)cc1C(=O)Nc1ccc(F)cc1F] | A | NH₃H₂O | / | M4 |
| 149 | 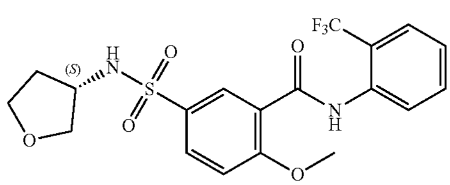 | B | / | / | M2 |
| 150 | 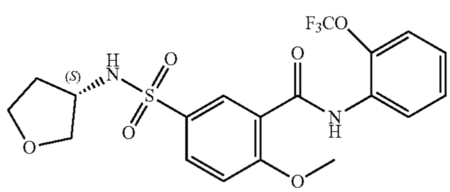 | B | / | / | M2 |
| 151 | 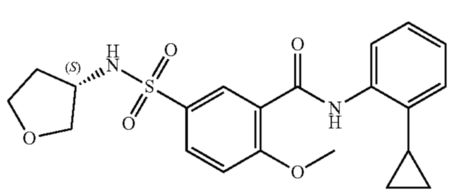 | C | / | / | M2 |

TABLE 1-continued

| # | Structure | Synthetic Method | Prep. HPLC | Prep. SFC | Analytic LC-MS |
|---|-----------|------------------|------------|-----------|----------------|
| 152 | 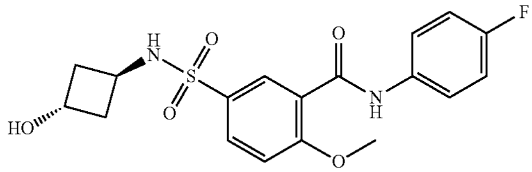 [SMILES: COc1ccc(S(=O)(=O)N[C@H]2C[C@H](O)C2)cc1C(=O)Nc1ccc(F)cc1] | B | NH₃H₂O | / | M2 |
| 153 | 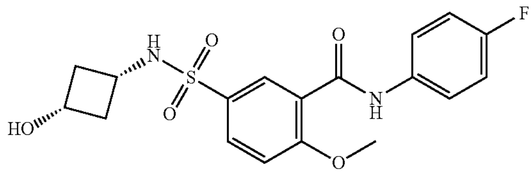 [SMILES: COc1ccc(S(=O)(=O)N[C@H]2C[C@@H](O)C2)cc1C(=O)Nc1ccc(F)cc1] | B | NH₃H₂O | / | M2 |
| 154 | 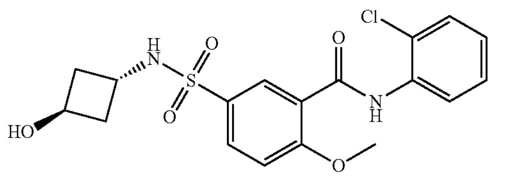 [SMILES: COc1ccc(S(=O)(=O)N[C@H]2C[C@H](O)C2)cc1C(=O)Nc1ccccc1Cl] | C | NH₄HCO₃ | Method 8 | M2 |
| 155 | 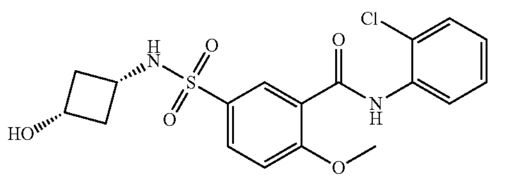 [SMILES: COc1ccc(S(=O)(=O)N[C@H]2C[C@@H](O)C2)cc1C(=O)Nc1ccccc1Cl] | C | NH₄HCO₃ | Method 8 | M2 |
| 156 | 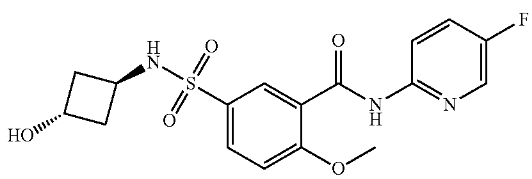 [SMILES: COc1ccc(S(=O)(=O)N[C@H]2C[C@H](O)C2)cc1C(=O)Nc1ccc(F)cn1] | B | NH₄HCO₃ | / | M2 |
| 157 | 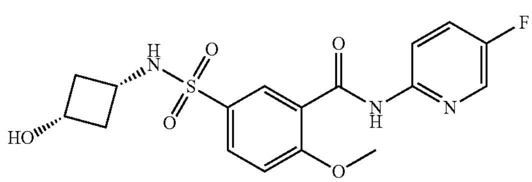 [SMILES: COc1ccc(S(=O)(=O)N[C@H]2C[C@@H](O)C2)cc1C(=O)Nc1ccc(F)cn1] | B | NH₄HCO₃ | / | M2 |
| 158 | 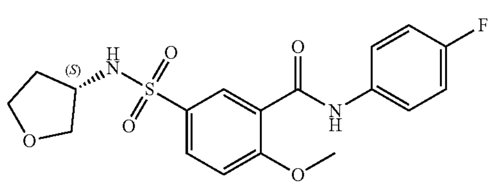 | D | NH₃H₂O | / | M2 |
| 159 | 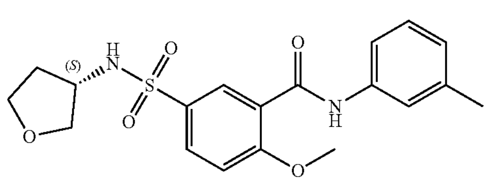 | D | NH₃H₂O | / | M2 |

TABLE 1-continued

| # | Structure | Synthetic Method | Prep. HPLC | Prep. SFC | Analytic LC-MS |
|---|---|---|---|---|---|
| 160 | 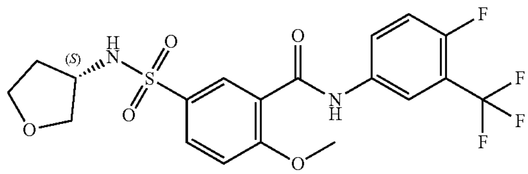 | D | / | / | M4 |
| 161 | 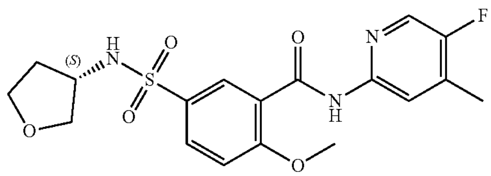 | D | / | / | M2 |
| 162 | 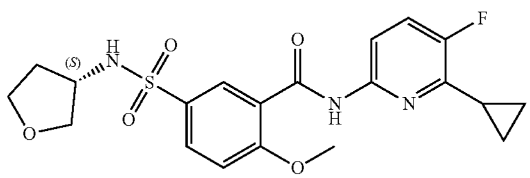 | C | NH$_3$H$_2$O | / | M1 |
| 163 | 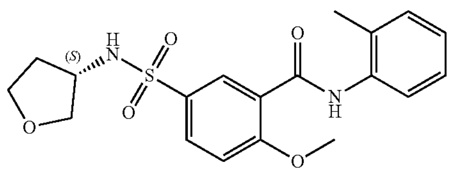 | B | / | / | M2 |
| 164 | 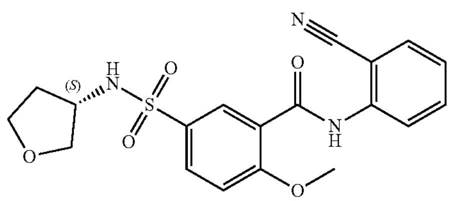 | B | / | / | M4 |
| 165 | 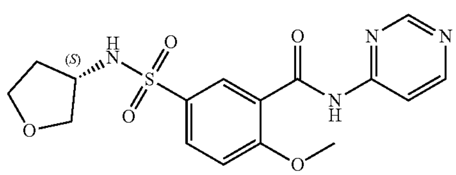 | B | / | / | M4 |
| 166 | 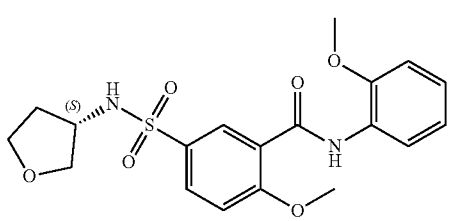 | B | / | / | M2 |
| 167 | 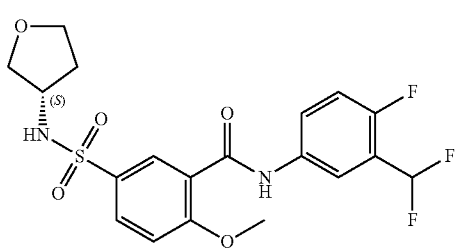 | D | / | / | M2 |

TABLE 1-continued

| # | Structure | Synthetic Method | Prep. HPLC | Prep. SFC | Analytic LC-MS |
|---|---|---|---|---|---|
| 168 | 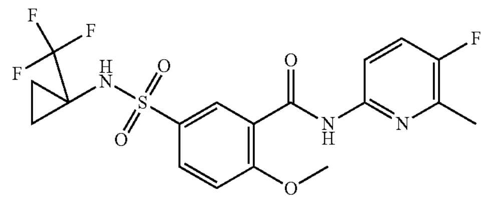 [SMILES: COc1ccc(S(=O)(=O)NC2(C(F)(F)F)CC2)cc1C(=O)Nc1ccc(F)c(C)n1] | / | / | / | M2 |
| 169 | 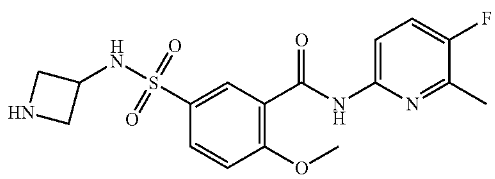 [SMILES: COc1ccc(S(=O)(=O)NC2CNC2)cc1C(=O)Nc1ccc(F)c(C)n1] | / | / | / | M4 |
| 170 | 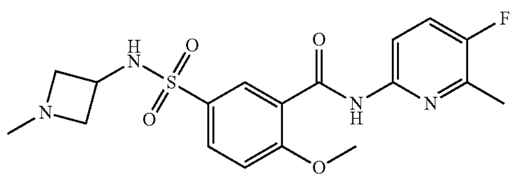 | / | NH₄HCO₃ | / | M2 |
| 171 | 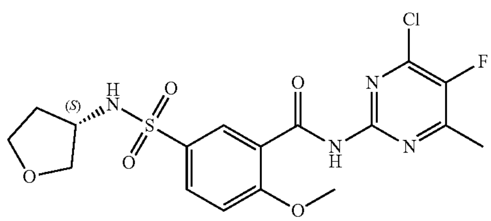 | / | / | / | M4 |
| 172 | 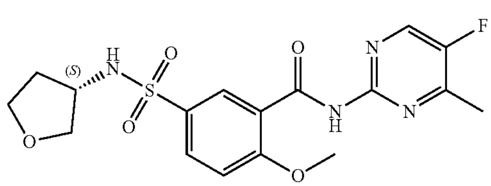 | / | / | / | M4 |
| 173 | 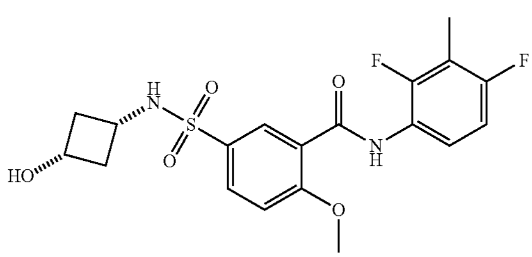 | / | HCl | / | M2 |
| 174a | 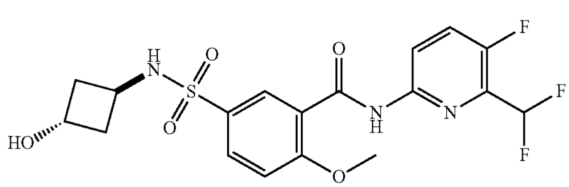 | / | NH₃H₂O | Method 6 | M4 |

TABLE 1-continued

| # | Structure | Synthetic Method | Prep. HPLC | Prep. SFC | Analytic LC-MS |
|---|---|---|---|---|---|
| 174b | 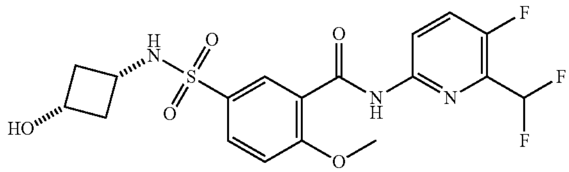 | / | NH$_3$H$_2$O | Method 6 | M2 |
| 175 | 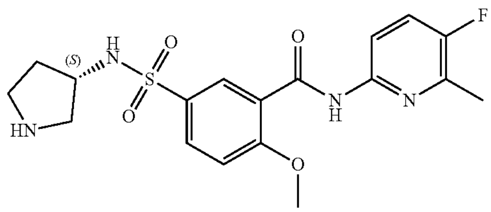 | / | / | / | M2 |
| 176 | 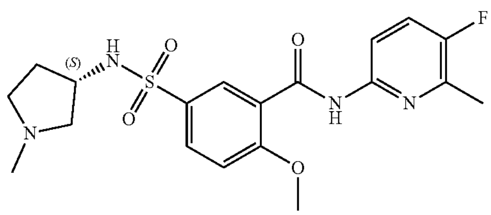 | / | TFA | / | M2 |
| 177 | 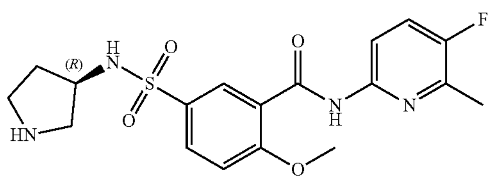 | / | / | / | M2 |
| 178 | 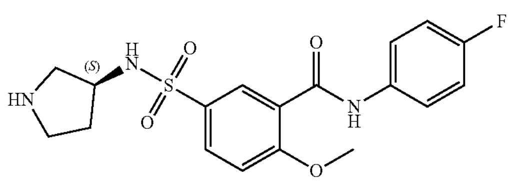 | / | NH$_4$HCO$_3$ | / | M2 |
| 179 | 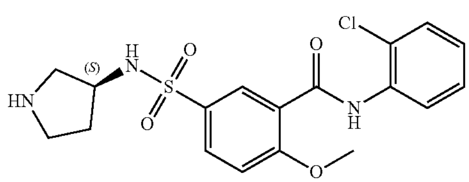 | / | / | / | M2 |
| 180 | 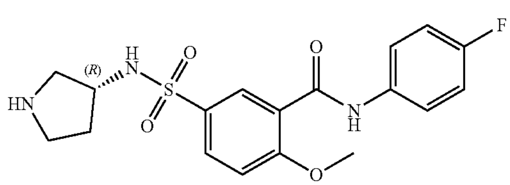 | / | / | / | M2 |
| 181 | 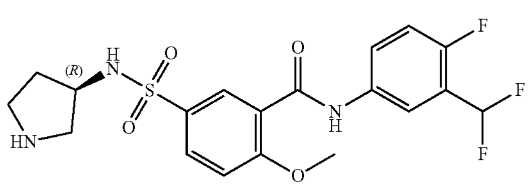 | / | / | / | M4 |

TABLE 1-continued

| # | Structure | Synthetic Method | Prep. HPLC | Prep. SFC | Analytic LC-MS |
|---|---|---|---|---|---|
| 182 | 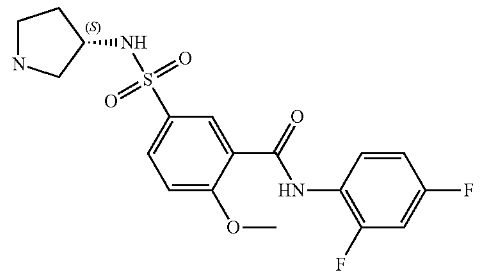 | / | NH₃H₂O | / | M4 |
| 183 | 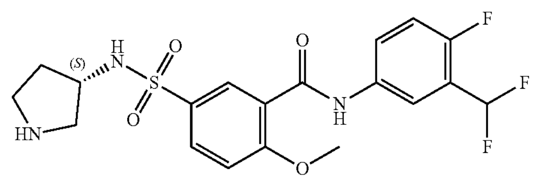 | / | / | / | M2 |
| 184 | 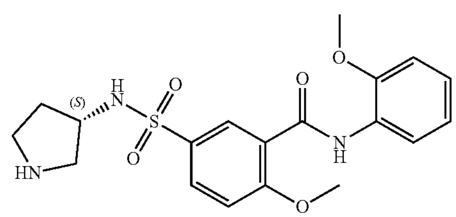 | / | / | / | M4 |
| 185 | 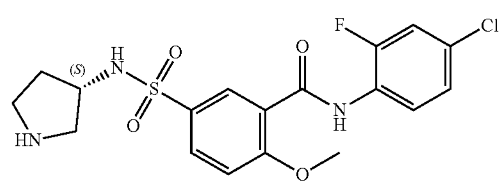 | / | NH₃H₂O | / | M2 |
| 186 | 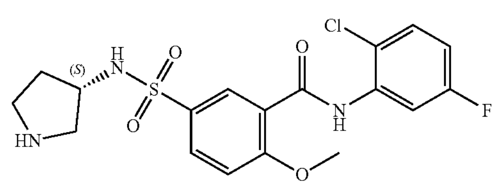 | / | NH₃H₂O | / | M2 |
| 187 | 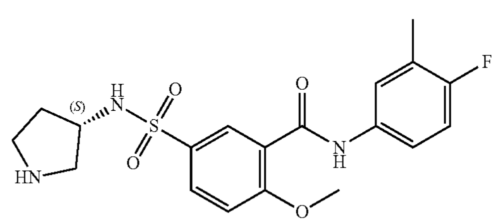 | / | NH₃H₂O | / | M4 |
| 188 | 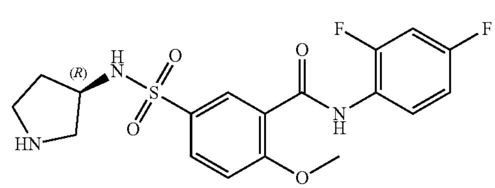 | / | / | / | M2 |

TABLE 1-continued

| # | Structure | Synthetic Method | Prep. HPLC | Prep. SFC | Analytic LC-MS |
|---|---|---|---|---|---|
| 189 | 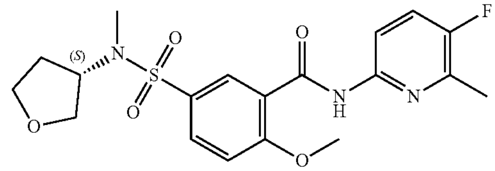 | / | / | / | M2 |
| 190 | 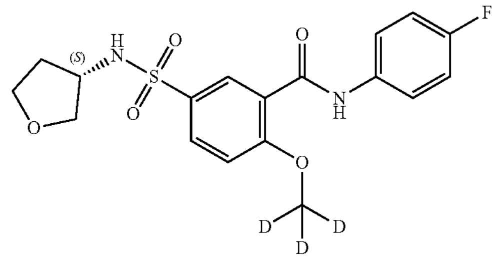 | / | / | / | M2 |
| 191 | 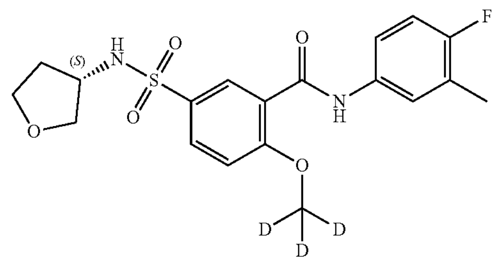 | / | / | / | M2 |
| 192 | 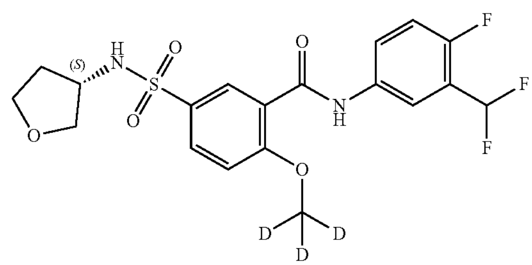 | / | / | / | M2 |
| 193 | 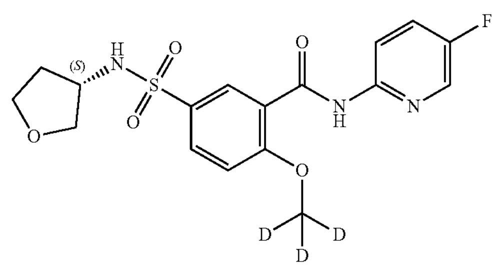 | / | / | / | M2 |
| 194 | 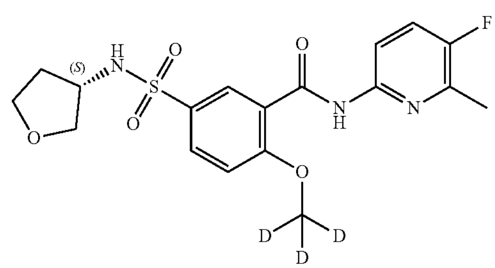 | / | / | / | M2 |

TABLE 1-continued

| # | Structure | Synthetic Method | Prep. HPLC | Prep. SFC | Analytic LC-MS |
|---|---|---|---|---|---|
| 195 | 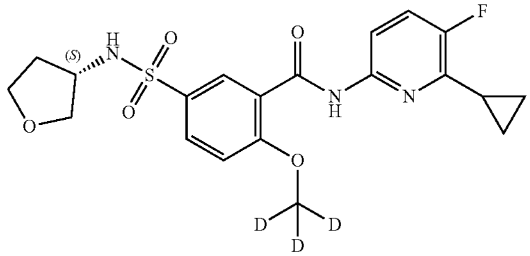 | / | / | / | M2 |
| 196 | 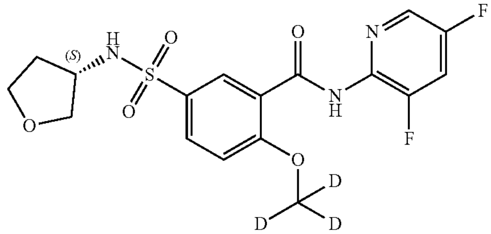 | / | / | / | M4 |
| 197 | 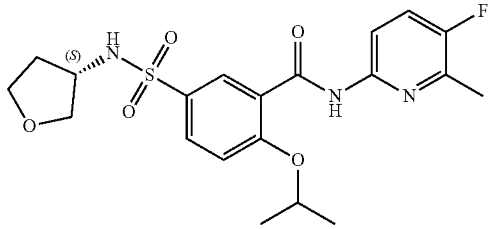 | / | NH₃H₂O | / | M2 |
| 198 | 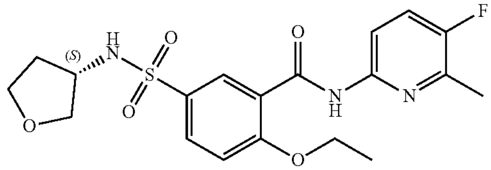 | / | NH₃H₂O | / | M2 |
| 199 | 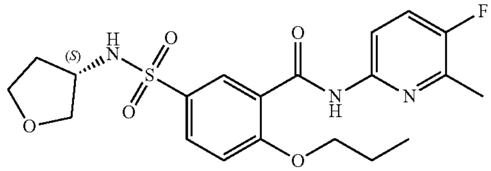 | / | / | / | M2 |
| 200 | 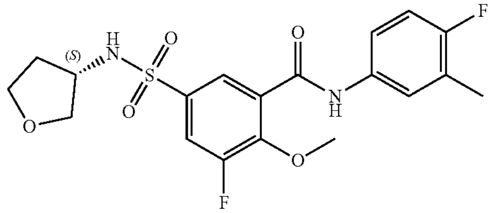 | / | NH₃H₂O | / | M2 |
| 201 | 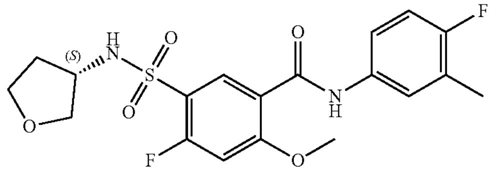 | / | NH₃H₂O | / | M2 |

| # | Structure | Synthetic Method | Prep. HPLC | Prep. SFC | Analytic LC-MS |
|---|---|---|---|---|---|
| 202a | 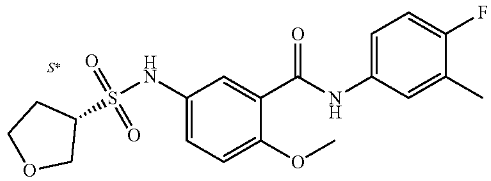 [SMILES: COc1ccc(NS(=O)(=O)[C@H]2CCOC2)cc1C(=O)Nc1ccc(F)c(C)c1] | / | NH₃H₂O | Method 8 | M2 |
| 202b | 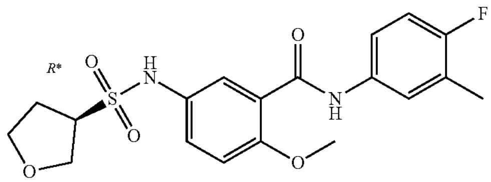 [SMILES: COc1ccc(NS(=O)(=O)[C@@H]2CCOC2)cc1C(=O)Nc1ccc(F)c(C)c1] | / | NH₃H₂O | Method 8 | M2 |
| 203 | 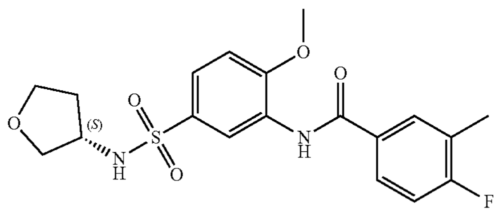 | / | NH₃H₂O | / | M2 |
| 204a | 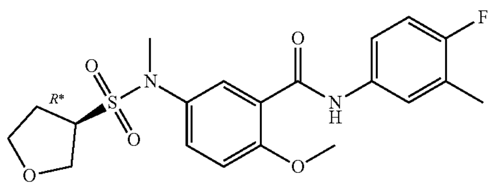 [SMILES: COc1ccc(N(C)S(=O)(=O)[C@@H]2CCOC2)cc1C(=O)Nc1ccc(F)c(C)c1] | / | NH₄HCO₃ | Method 5 | M2 |
| 204b | 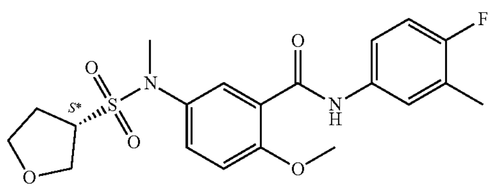 [SMILES: COc1ccc(N(C)S(=O)(=O)[C@H]2CCOC2)cc1C(=O)Nc1ccc(F)c(C)c1] | / | NH₄HCO₃ | Method 5 | M2 |

Compound 5: N-(4-Fluoro-3-methylphenyl)-2-methoxy-5-(N-(oxetan-3-yl)sulfamoyl) benzamide LC-MS (ESI): mass calcd. for $C_{18}H_{19}FN_2O_5S$ 394.10, m/z found 395.1 [M+H]⁺. ¹H NMR (400 MHz, DMSO-d₆) δ 10.21 (br.s., 1H), 8.51 (br. s., 1H), 7.95 (d, J=2.4 Hz, 1H), 7.87 (dd, J=2.4, 8.8 Hz, 1H), 7.65-7.60 (m, 1H), 7.58-7.52 (m, 1H), 7.36 (d, J=8.8 Hz, 1H), 7.13 (t, J=9.2 Hz, 1H), 4.51 (t, J=6.8 Hz, 2H), 4.41-4.32 (m, 1H), 4.25 (t, J=6.8 Hz, 2H), 3.96 (s, 3H), 2.24 (s, 3H).

Compound 6a: N-(4-Fluoro-3-methylphenyl)-5-(N-((trans)-3-hydroxycyclobutyl)sulfamoyl)-2-methoxy-benzamide LC-MS (ESI): mass calcd. for $C_{19}H_{21}FN_2O_5S$ 408.12, m/z found 409.1 [M+H]⁺. ¹H NMR (400 MHz, DMSO-d₆) δ 10.21 (br.s, 1H), 7.95 (d, J=2.4 Hz, 1H), 7.90-7.83 (m, 2H), 7.65-7.61 (m, 1H), 7.58-7.52 (m, 1H), 7.36 (d, J=8.8 Hz, 1H), 7.13 (t, J=9.6 Hz, 1H), 4.95 (d, J=5.2 Hz, 1H), 4.16-4.09 (m, 1H), 3.97 (s, 3H), 3.75-3.64 (m, 1H), 2.24 (s, 3H), 2.00-1.86 (m, 4H).

Compound 6b: N-(4-Fluoro-3-methylphenyl)-5-(N-((cis)-3-hydroxycyclobutyl)sulfamoyl)-2-methoxy-benzamide LC-MS (ESI): mass calcd. for $C_{19}H_{21}FN_2O_5S$ 408.12, m/z found 409.1 [M+H]⁺. ¹H NMR (400 MHz, DMSO-d₆) δ 10.20 (br.s, 1H), 7.97 (d, J=2.4 Hz, 1H), 7.89-7.82 (m, 2H), 7.65-7.61 (m, 1H), 7.58-7.53 (m, 1H), 7.36 (d, J=8.8 Hz, 1H), 7.13 (t, J=9.0 Hz, 1H), 5.02 (d, J=5.5 Hz, 1H), 3.97 (s, 3H), 3.69-3.62 (m, 1H), 3.14-3.03 (m, 1H), 2.27-2.29 (m, 5H), 1.61-1.53 (m, 2H).

Compound 7: N-(4-Fluoro-3-methylphenyl)-2-methoxy-5-(N-(3-methylcyclobutyl)sulfamoyl) benzamide LC-MS (ESI): mass calcd. for $C_{20}H_{23}FN_2O_4S$ 406.14, m/z found 407.1 [M+H]⁺. ¹H NMR (400 MHz, DMSO-d₆) δ 10.21 (s, 1H), 7.97 (d, J=2.21 Hz, 1H), 7.95-7.82 (m, 2H), 7.67-7.60 (m, 1H), 7.59-7.51 (m, 1H), 7.35 (d, J=9.04 Hz, 1H), 7.13 (t, J=9.26 Hz, 1H), 3.97 (s, 3H), 3.81-3.73 (m, 1H, trans), 3.47-3.42 (m, 1H, cis), 2.24 (s, 3H), 2.15-2.05 (m, 3H, cis), 1.96-1.82 (m, 3H, trans), 1.68-1.59 (m, 1H), 1.37-1.27 (m, 1H), 1.00 (d, J=1.00 Hz, 1.5H), 0.91 (d, J=6.62 Hz, 1.5H).

Compound 7a: N-(4-Fluoro-3-methylphenyl)-2-methoxy-5-(N-((cis)-3-methylcyclobutyl) sulfamoyl)benzamide LC-MS (ESI): mass calcd. for $C_{20}H_{23}FN_2O_4S$ 406.14, m/z found 407.1 [M+H]$^+$. $^1$H NMR (400 MHz, DMSO-d$_6$) δ 10.19 (s, 1H), 7.95 (d, J=2.21 Hz, 1H), 7.86 (dd, J=8.82, 2.43 Hz, 1H), 7.84-7.76 (m, 1H), 7.64-7.58 (m, 1H), 7.54 (m, 1H), 7.33 (d, J=8.82 Hz, 1H), 7.11 (t, J=9.15 Hz, 1H), 3.94 (s, 3H), 3.43-3.38 (m, 1H), 2.22 (s, 3H), 2.13-2.02 (m, 2H), 1.86-1.75 (m, 1H), 1.35-1.25 (m, 2H), 0.89 (d, J=6.39 Hz, 3H).

Compound 7b: N-(4-Fluoro-3-methylphenyl)-2-methoxy-5-(N-((trans)-3-methylcyclobutyl) sulfamoyl)benzamide LC-MS (ESI): mass calcd. for $C_{20}H_{23}FN_2O_4S$ 406.14, m/z found 407.1 [M+H]$^+$. $^1$H NMR (400 MHz, DMSO-d$_6$) δ 10.19 (s, 1H), 7.96 (d, J=2.01 Hz, 1H), 7.91 (m, J=7.50 Hz, 1H), 7.87 (dd, J=8.53, 2.51 Hz, 1H), 7.66-7.60 (m, 1H), 7.58-7.51 (m, 1H), 7.35 (d, J=9.03 Hz, 1H), 7.12 (t, J=9.03 Hz, 1H), 3.96 (s, 3H), 3.82-3.70 (m, 1H), 2.23 (s, 3H), 2.12 (m, 1H), 1.95-1.85 (m, 2H), 1.68-1.58 (m, 2H), 0.99 (d, J=7.03 Hz, 3H).

Compound 8: N-(4-Fluoro-3-methylphenyl)-5-(N-isopropylsulfamoyl)-2-methoxybenzamide LC-MS (ESI): mass calcd. for $C_{18}H_{21}FN_2O_4S$ 380.12, m/z found 381.1 [M+H]$^+$. $^1$H NMR (400 MHz, DMSO-d$_6$) δ 10.22 (s, 1H), 8.00 (d, J=2.4 Hz, 1H), 7.91 (dd, J=2.3, 8.7 Hz, 1H), 7.66-7.61 (m, 1H), 7.60-7.52 (m, 2H), 7.37 (d, J=8.8 Hz, 1H), 7.13 (t, J=9.3 Hz, 1H), 3.97 (s, 3H), 3.27-3.17 (m, 1H), 2.24 (s, 3H), 0.97 (d, J=6.4 Hz, 6H).

Compound 9: N-(4-Fluoro-3-methylphenyl)-2-methoxy-5-(N-(3-methyloxetan-3-yl)sulfamoyl)benzamide LC-MS (ESI): mass calcd. for $C_{19}H_{21}FN_2O_5S$ 408.12, m/z found 409.1 [M+H]$^+$. $^1$H NMR (400 MHz, DMSO-d$_6$) δ 10.22 (s, 1H), 8.33 (s, 1H), 8.00 (d, J=2.4 Hz, 1H), 7.92 (dd, J=2.4, 8.8 Hz, 1H), 7.63 (dd, J=2.2, 7.1 Hz, 1H), 7.59-7.52 (m, 1H), 7.37 (d, J=8.8 Hz, 1H), 7.13 (t, J=9.2 Hz, 1H), 4.54 (d, J=6.0 Hz, 2H), 4.12 (d, J=6.2 Hz, 2H), 3.97 (s, 3H), 2.24 (s, 3H), 1.43 (s, 3H).

Compound 10: N-(4-Fluoro-3-methylphenyl)-5-(N-(1-hydroxypropan-2-yl)sulfamoyl)-2-methoxybenzamide LC-MS (ESI): mass calcd. for $C_{18}H_{21}FN_2O_5S$ 396.12, m/z found 397.1 [M+H]$^+$. $^1$H NMR (400 MHz, DMSO-d) δ 10.21 (s, 1H), 8.01 (d, J=2.4 Hz, 1H), 7.92 (dd, J=2.3, 8.7 Hz, 1H), 7.67-7.60 (m, 1H), 7.59-7.49 (m, 2H), 7.36 (d, J=8.8 Hz, 1H), 7.13 (t, J=9.2 Hz, 1H), 4.73 (t, J=5.4 Hz, 1H), 3.97 (s, 3H), 3.34-3.28 (m, 1H), 3.16-3.02 (m, 2H), 2.24 (s, 3H), 0.91 (d, J=6.2 Hz, 3H).

Compound 10a: (S)—N-(4-Fluoro-3-methylphenyl)-5-(N-(1-hydroxypropan-2-yl)sulfamoyl)-2-methoxybenzamide LC-MS (ESI): mass calcd. for $C_{18}H_{21}FN_2O_5S$ 396.12, m/z found 397.1 [M+H]$^+$. $^1$H NMR (400 MHz, DMSO-d) δ 10.21 (s, 1H), 8.01 (d, J=2.2 Hz, 1H), 7.92 (dd, J=2.2, 8.8 Hz, 1H), 7.66-7.60 (m, 1H), 7.59-7.48 (m, 2H), 7.36 (d, J=9.0 Hz, 1H), 7.13 (t, J=9.2 Hz, 1H), 4.71 (t, J=5.4 Hz, 1H), 3.97 (s, 3H), 3.34-3.26 (m, 1H), 3.15-3.02 (m, 2H), 2.24 (s, 3H), 0.91 (d, J=6.0 Hz, 3H).

Compound 10b: (R)—N-(4-Fluoro-3-methylphenyl)-5-(N-(1-hydroxypropan-2-yl)sulfamoyl)-2-methoxybenzamide Compound 11a: (S*)-5-(N-(1-Cyanopropan-2-yl)sulfamoyl)-N-(4-fluoro-3-methylphenyl)-2-methoxybenzamide LC-MS (ESI): mass calcd. for $C_{19}H_{20}FN_3O_4S$ 405.12, m/z found 406.1 [M+H]$^+$. $^1$H NMR (400 MHz, DMSO-d$_6$) 10.20 (s, 1H), 8.02 (d, J=2.2 Hz, 2H), 7.94 (dd, J=2.4, 8.8 Hz, 1H), 7.63 (dd, J=2.1, 7.0 Hz, 1H), 7.58-7.52 (m, 1H), 7.38 (d, J=8.8 Hz, 1H), 7.12 (t, J=9.2 Hz, 1H), 3.97 (s, 3H), 3.46-3.38 (m, 1H), 2.76-2.66 (m, 1H), 2.66-2.57 (m, 1H), 2.24 (s, 3H), 1.00 (d, J=6.6 Hz, 3H).

Compound 11b: (R*)-5-(N-(1-Cyanopropan-2-yl)sulfamoyl)-N-(4-fluoro-3-methylphenyl-2-methoxybenzamide LC-MS (ESI): mass calcd. for $C_{19}H_{20}FN_3O_4S$ 405.12, m/z found 406.1 [M+H]$^+$. $^1$H NMR (400 MHz, DMSO-d$_6$) δ 10.20 (s, 1H), 8.03 (br. s., 1H), 8.01 (d, J=2.4 Hz, 1H), 7.94 (dd, J=2.4, 8.8 Hz, 1H), 7.66-7.60 (m, 1H), 7.59-7.50 (m, 1H), 7.38 (d, J=8.8 Hz, 1H), 7.12 (t, J=9.2 Hz, 1H), 3.97 (s, 3H), 3.47-3.39 (m, 1H), 2.75-2.66 (m, 1H), 2.66-2.57 (m, 1H), 2.24 (s, 3H), 1.00 (d, J=6.6 Hz, 3H).

Compound 12: 5-(N-(1-Amino-1-oxopropan-2-yl)sulfamoyl)-N-(4-fluoro-3-methylphenyl)-2-methoxybenzamide

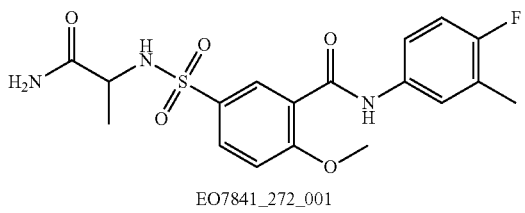 [SMILES: COc1ccc(S(=O)(=O)NC(C)C(N)=O)cc1C(=O)Nc1ccc(F)c(C)c1]

EO7841_272_001

LC-MS (ESI): mass calcd. for $C_{18}H_{20}FN_3O_5S$ 409.11, m/z found 410.1 [M+H]$^+$. $^1$H NMR (400 MHz, DMSO-d$_6$) δ 10.18 (s, 1H), 8.00 (d, J=2.2 Hz, 1H), 7.90 (dd, J=2.4, 8.8 Hz, 1H), 7.87 (br. s., 1H), 7.66-7.60 (m, 1H), 7.59-7.52 (m, J=4.0, 7.9 Hz, 1H), 7.35 (d, J=8.8 Hz, 1H), 7.29 (br. s., 1H), 7.13 (t, J=9.3 Hz, 1H), 7.00 (br. s., 1H), 3.96 (s, 3H), 3.67 (q, J=6.8 Hz, 1H), 2.24 (s, 3H), 1.07 (d, J=7.1 Hz, 3H).

Compound 12a: (S)-5-(N-(1-Amino-1-oxopropan-2-yl)sulfamoyl)-N-(4-fluoro-3-methylphenyl)-2-methoxybenzamide LC-MS (ESI): mass calcd. for $C_{18}H_{20}FN_3O_5S$ 409.11, m/z found 410.1 [M+H]$^+$. $^1$H NMR (400 MHz, DMSO-d$_6$) δ 10.18 (s, 1H), 8.01 (d, J=2.2 Hz, 1H), 7.95-7.84 (m, 2H), 7.67-7.60 (m, 1H), 7.59-7.51 (m, 1H), 7.35 (d, J=8.8 Hz, 1H), 7.29 (br. s., 1H), 7.13 (t, J=9.2 Hz, 1H), 7.00 (br. s., 1H), 3.96 (s, 3H), 3.74-3.61 (m, J=4.9 Hz, 1H), 2.24 (s, 3H), 1.08 (d, J=7.1 Hz, 3H).

Compound 12b: (R)-5-(N-(1-Amino-1-oxopropan-2-yl)sulfamoyl-N-(4-fluoro-3-methylphenyl)-2-methoxybenzamide LC-MS (ESI): mass calcd. for $C_{18}H_{20}FN_3O_5S$ 409.11, m/z found 410.1 [M+H]$^+$. $^1$H NMR (400 MHz, DMSO-d$_6$) δ 10.18 (s, 1H), 8.00 (d, J=2.2 Hz, 1H), 7.93-7.86 (m, 2H), 7.63 (dd, J=2.0, 6.8 Hz, 1H), 7.59-7.52 (m, 1H), 7.35 (d, J=9.0 Hz, 1H), 7.29 (br. s., 1H), 7.13 (t, J=9.3 Hz, 1H), 7.00 (br. s., 1H), 3.96 (s, 3H), 3.68 (q, J=6.9 Hz, 1H), 2.24 (s, 3H), 1.07 (d, J=7.1 Hz, 3H).

Compound 13: N-(4-Fluoro-3-methylphenyl)-5-(N-(3-(hydroxymethyl)oxetan-3-yl)sulfamoyl)-2-methoxybenzamide LC-MS (ESI): mass calcd. for $C_{19}H_{21}FN_2O_6S$ 424.11, m/z found 425.1 [M+H]$^+$. $^1$H NMR (400 MHz, DMSO-d$_6$) δ 10.21 (s, 1H), 8.31 (br. s., 1H), 8.02 (d, J=2.0 Hz, 1H), 7.94 (dd, J=2.3, 8.8 Hz, 1H), 7.66-7.60 (m, 1H), 7.59-7.52 (m, 1H), 7.36 (d, J=8.5 Hz, 1H), 7.13 (t, J=9.3 Hz, 1H), 5.17 (t, J=5.5 Hz, 1H), 4.47 (d, J=6.5 Hz, 2H), 4.36 (d, J=6.0 Hz, 2H), 3.97 (s, 3H), 3.52 (d, J=5.5 Hz, 2H), 2.24 (s, 3H).

Compound 14: 5-(N-(3,3-Dimethylcyclobutyl)sulfamoyl)-N-(4-fluoro-3-methylphenyl)-2-methoxybenzamide LC-MS (ESI): mass calcd. For $C_{21}H_{25}FN_2O_4S$ 420.15, m/z found 421.0 [M+H]$^+$; $^1$H NMR (400 MHz, DMSO-d$_6$) δ 10.19 (s, 1H), 7.96 (d, J=2.0 Hz, 1H), 7.88 (dd, J=2.3, 8.8 Hz, 1H), 7.84 (d, J=8.5 Hz, 1H), 7.66-7.60 (m, 1H), 7.58-7.51 (m, 1H), 7.35 (d, J=9.0 Hz, 1H), 7.12 (t, J=9.3 Hz, 1H), 3.96 (s, 3H), 3.70-3.54 (m, 1H), 2.24 (s, 3H), 1.86-1.72 (m, 2H), 1.61-1.47 (m, 2H), 0.99 (s, 3H), 0.97 (s, 3H).

Compound 15a: N-(4-Fluoro-3-methylphenyl)-5-(N-((cis)-3-hydroxycyclopentyl)sulfamoyl)-2-methoxybenzamide LC-MS (ESI): mass calcd. for $C_{20}H_{23}FN_2O_5S$ 422.13, m/z found 423.0 [M+H]$^+$; $^1$H NMR (400 MHz, DMSO-d$_6$) δ 10.20 (s, 1H), 8.00 (d, J=2.0 Hz, 1H), 7.90 (dd, J=2.0, 8.8 Hz, 1H), 7.64 (t, J=8.8 Hz, 2H), 7.59-7.51 (m, 1H), 7.36 (d, J=8.8 Hz, 1H), 7.12 (t, J=9.2 Hz, 1H), 4.57 (d, J=3.9 Hz, 1H), 3.97 (s, 3H), 3.94-3.87 (m, 1H), 2.24 (s, 3H), 1.98-1.86 (m, 1H), 1.64-1.49 (m, 2H), 1.49-1.37 (m, 2H), 1.27-1.16 (m, 1H).

Compound 15b: N-(4-Fluoro-3-methylphenyl)-5-(N-((cis)-3-hydroxycyclopentyl)sulfamoyl)-2-methoxybenzamide LC-MS (ESI): mass calcd. for $C_{20}H_{23}FN_2O_5S$ 422.13, m/z found 423.1 [M+H]$^+$; $^1$H NMR (400 MHz, DMSO-d$_6$) δ 10.20 (s, 1H), 8.01 (d, J=1.5 Hz, 1H), 7.95-7.87 (m, 1H), 7.70-7.60 (m, 2H), 7.59-7.51 (m, 1H), 7.36 (d, J=8.5 Hz, 1H), 7.13 (t, J=9.0 Hz, 1H), 4.65 (d, J=4.0 Hz, 1H), 3.97 (s, 3H), 3.95-3.88 (m, 1H), 2.24 (s, 3H), 1.98-1.88 (m, 1H), 1.64-1.38 (m, 4H), 1.28-1.17 (m, 1H).

Compound 16a: (S*)—N-(5-Fluoro-6-methylpyridin-2-yl)-2-methoxy-5-(N-(tetrahydro-2H-pyran-3-yl)sulfamoyl)benzamide LC-MS (ESI): mass calcd. for $C_{19}H_{22}FN_3O_5S$ 423.13, m/z found 424.1 [M+H]$^+$; $^1$H NMR (400 MHz, DMSO-d$_6$) δ 10.60 (s, 1H), 8.14 (d, J=2.3 Hz, 1H), 8.11-8.06 (m, 1H), 7.95 (dd, J=2.5, 8.8 Hz, 1H), 7.81 (br. s., 1H), 7.71 (t, J=8.9 Hz, 1H), 7.39 (d, J=8.8 Hz, 1H), 4.01 (s, 3H), 3.64-3.53 (m, 2H), 3.24-3.15 (m, 1H), 3.06-2.94 (m, 2H), 2.40 (d, J=2.8 Hz, 3H), 1.69-1.53 (m, 2H), 1.44-1.28 (m, 2H).

Compound 16b: (R*)—N-(5-Fluoro-6-methylpyridin-2-yl)-2-methoxy-5-(N-(tetrahydro-2H-pyran-3-yl)sulfamoyl)benzamide LC-MS (ESI): mass calcd. for $C_{19}H_{22}FN_3O_5S$ 423.13, m/z found 424.1 [M+H]$^+$; $^1$H NMR (400 MHz, DMSO-d$_6$) δ 10.60 (s, 1H), 8.14 (d, J=2.5 Hz, 1H), 8.12-8.07 (m, 1H), 7.95 (dd, J=2.5, 8.8 Hz, 1H), 7.83-7.78 (m, 1H), 7.71 (t, J=9.0 Hz, 1H), 7.39 (d, J=9.0 Hz, 1H), 4.01 (s, 3H), 3.63-3.54 (m, 2H), 3.24-3.16 (m, 1H), 3.06-2.94 (m, 2H), 2.41 (d, J=3.0 Hz, 3H), 1.70-1.53 (m, 2H), 1.42-1.27 (m, 2H).

Compound 17: N-(5-Fluoro-6-methylpyridin-2-yl)-2-methoxy-5-(N-(tetrahydro-2H-pyran-4-yl) sulfamoyl)benzamide LC-MS (ESI): mass calcd. for $C_{19}H_{22}FN_3O_5S$ 423.13, m/z found 424.1 [M+H]$^+$. $^1$H NMR (400 MHz, DMSO-d$_6$) δ 10.58 (s, 1H), 8.16 (d, J=2.3 Hz, 1H), 8.13-8.07 (m, 1H), 7.95 (dd, J=2.5, 8.8 Hz, 1H), 7.80 (d, J=7.0 Hz, 1H), 7.71 (t, J=8.9 Hz, 1H), 7.39 (d, J=8.8 Hz, 1H), 4.02 (s, 3H), 3.76-3.68 (m, 2H), 3.27-3.21 (m, 2H), 3.16 (d, J=4.8 Hz, 1H), 2.41 (d, J=2.8 Hz, 3H), 1.54 (d, J=10.8 Hz, 2H), 1.42-1.30 (m, 2H).

Compound 18: (trans)-N-(5-Fluoro-6-methylpyridin-2-yl)-5-(N-(-4-hydroxycyclohexyl) sulfamoyl)-2-methoxybenzamid LC-MS (ESI): mass calcd. for $C_{20}H_{24}FN_3O_5S$ 437.14, m/z found 438.1 [M+H]$^+$. $^1$H NMR (400 MHz, DMSO-d$_6$) δ 10.58 (s, 1H), 8.14 (d, J=2.4 Hz, 1H), 8.12-8.07 (m, 1H), 7.93 (dd, J=2.4, 8.8 Hz, 1H), 7.71 (t, J=9.0 Hz, 1H), 7.62 (d, J=7.0 Hz, 1H), 7.38 (d, J=8.8 Hz, 1H), 4.49 (d, J=4.3 Hz, 1H), 4.01 (s, 3H), 3.29-3.26 (m, 1H), 2.92-2.81 (m, 1H), 2.41 (d, J=2.8 Hz, 3H), 1.74-1.66 (m, 2H), 1.64-1.57 (m, 2H), 1.19-1.02 (m, 4H).

Compound 19: N-(5-Fluoro-6-methylpyridin-2-yl)-2-methoxy-5-(N-(1-methylpiperidin-4-yl) sulfamoyl)benzamid LC-MS (ESI): mass calcd. for $C_{20}H_{25}FN_4O_4S$ 436.16, m/z found 437.1 [M+H]$^+$. $^1$H NMR (400 MHz, DMSO-d$_6$) δ 10.55 (s, 1H), 8.16 (d, J=2.3 Hz, 1H), 8.09 (d, J=5.5 Hz, 1H), 7.94 (dd, J=2.4, 8.7 Hz, 1H), 7.74-7.64 (m, 2H), 7.39 (d, J=8.8 Hz, 1H), 4.02 (s, 3H), 2.94-2.83 (m, 1H), 2.63-2.56 (m, 2H), 2.41 (d, J=2.8 Hz, 3H), 2.08 (s, 3H), 1.86-1.76 (m, 2H), 1.58-1.49 (m, 2H), 1.44-1.32 (m, 2H).

Compound 20: 5-(N-Cyclohexylsulfamoyl)-N-(5-fluoro-6-methylpyridin-2-yl)-2-methoxy benzamide LC-MS (ESI): mass calcd. for $C_{20}H_{24}FN_3O_4S$ 421.15, m/z found 422.1 [M+H]$^+$. $^1$H NMR (400 MHz, DMSO-d$_6$)

δ 10.57 (s, 1H), 8.16 (s, 1H), 8.13-8.07 (m, 1H), 7.94 (d, J=8.5 Hz, 1H), 7.71 (t, J=8.7 Hz, 1H), 7.64 (d, J=7.3 Hz, 1H), 7.38 (d, J=8.5 Hz, 1H), 4.02 (s, 3H), 2.98-2.87 (m, 1H), 2.41 (d, J=2.3 Hz, 3H), 1.64-1.53 (m, 4H), 1.48-1.40 (m, 1H), 1.19-1.01 (m, 5H).

Compound 21: 5-(N-Cyclopropylsulfamoyl)-N-(5-fluoro-6-methylpyridin-2-yl)-2-methoxy benzamide LC-MS (ESI): mass calcd. for $C_{17}H_{18}FN_3O_4S$ 379.10, m/z found 380.0 [M+H]$^+$. $^1$H NMR (400 MHz, DMSO-d$_6$) δ 10.60 (s, 1H), 8.15 (d, J=2.0 Hz, 1H), 8.13-8.07 (m, 1H), 7.96-7.89 (m, 2H), 7.71 (t, J=9.0 Hz, 1H), 7.42 (d, J=8.8 Hz, 1H), 4.02 (s, 3H), 2.41 (d, J=2.8 Hz, 3H), 2.14-2.06 (m, 1H), 0.52-0.45 (m, 2H), 0.42-0.35 (m, 2H).

Compound 22: N-(5-Fluoro-6-methylpyridin-2-yl-2-methoxy-5-sulfamoylbenzamide

LC-MS (ESI): mass calcd. for $C_{14}H_{14}FN_3O_4S$ 339.07, m/z found 340.0 [M+H]$^+$, $^1$H NMR (400 MHz, DMSO-d$_6$) δ 10.57 (br.s, 1H), 8.21 (s, 1H), 8.11 (d, J=6.4 Hz, 1H), 7.95 (m, J=7.6 Hz, 1H), 7.71 (t, J=9.2 Hz, 1H), 7.33-7.43 (m, 3H), 4.02 (s, 3H), 2.41 (s, 3H).

Compound 23a: (R*)—N-(5-fluoro-6-methylpyridin-2-yl)-2-methoxy-5-(N-(3,3,3-trifluoro-2-hydroxypropyl)sulfamoyl)benzamide LC-MS (ESI): mass calcd. for $C_{17}H_7F_4N_3O_5S$ 451.08, m/z found 452.1 [M+H]$^+$, $^1$H NMR (400 MHz, DMSO-d) δ 10.60 (br.s, 1H), 8.07-8.15 (m, 2H), 7.91-8.00 (m, 2H), 7.72 (t, J=9.2 Hz, 1H), 7.41 (d, J=8.8 Hz, 1H), 6.63 (s, 1H), 4.01 (s, 4H), 2.98 (dd, J=13.6 Hz, J=4.0 Hz, 1H), 2.82 (dd, J=13.6 Hz, J=8.0 Hz, 1H), 2.41 (d, J=2.4 Hz, 3H).

Compound 23b: (S*)—N-(5-fluoro-6-methylpyridin-2-yl)-2-methoxy-5-(N-(3,3,3-trifluoro-2-hydroxypropyl)sulfamoyl)benzamide LC-MS (ESI): mass calcd. for $C_{17}H_{17}F_4N_3O_5S$ 451.08, m/z found 452.1 [M+H]$^{+1}$H NMR (400 MHz, DMSO-d$_6$) δ 10.61 (br.s, 1H), 8.07-8.16 (m, 2H), 7.91-8.01 (m, 2H), 7.72 (t, J=8.8 Hz, 1H), 7.41 (d, J=8.8 Hz, 1H), 6.63 (s, 1H), 4.01 (s, 4H), 2.98 (dd, J=13.6 Hz, J=4.0 Hz, 1H), 2.82 (dd, J=13.6 Hz, J=8.0 Hz, 1H), 2.41 (d, J=2.4 Hz, 3H).

Compound 24: N-(5-Fluoro-6-methylpyridin-2-yl-2-methoxy-5-(N-methylsulfamoyl)benzamide LC-MS (ESI): mass calcd. for $C_{15}H_{16}FN_3O_4S$ 353.08, m/z found 354.1 [M+H]$^+$. $^1$H NMR (400 MHz, DMSO-d6) 10.61 (br.s, 1H), 8.12-8.07 (m, 2H), 7.91 (dd, J=2.4 Hz, J=8.8 Hz, 1H), 7.71 (t, J=8.8 Hz, 1H), 7.48-7.38 (m, 2H), 4.01 (s, 3H), 2.44-2.36 (m, 6H).

Compound 25: N-(5-Fluoro-6-methylpyridin-2-yl)-5-(N-isopropylsulfamoyl)-2-methoxy benzamide LC-MS (ESI): mass calcd. for $C_{17}H_{20}FN_3O_4S$ 381.12, m/z found 382.1 [M+H]$^+$. $^1$H NMR (400 MHz, DMSO-d$_6$) 10.58 (s, 1H), 8.19-8.05 (m, 2H), 7.93 (dd, J=2.5, 8.5 Hz, 1H), 7.71 (t, J=9.0 Hz, 1H), 7.59 (d, J=7.0 Hz, 1H), 7.39 (d, J=8.5 Hz, 1H), 4.01 (s, 3H), 3.30-3.15 (m, 1H), 2.40 (d, J=2.5 Hz, 3H), 0.96 (d, J=6.5 Hz, 6H).

Compound 26: 5-(N-Ethylsulfamoyl)-N-(5-fluoro-6-methylpyridin-2-yl)-2-methoxybenzamide LC-MS (ESI): mass calcd. for $C_{16}H_{18}FN_3O_4S$ 367.10, m/z found 368.1 [M+H]$^+$. $^1$H NMR (400 MHz, DMSO-d6) 10.59 (br.s, 1H), 8.15-8.05 (m, 2H), 7.91 (dd, J=2.4 Hz, J=8.8 Hz, 1H), 7.71 (t, J=8.8 Hz, 1H), 7.55 (t, J=5.6 Hz, 1H), 7.39 (d, J=8.8 Hz, 1H), 4.01 (s, 3H), 2.80-2.70 (m, 2H), 2.40 (d, J=2.8 Hz, 3H), 0.98 (t, J=7.2 Hz, 3H).

Compound 27: N-(5-Fluoro-6-methylpyridin-2-yl)-5-(N-((cis)-4-hydroxycyclohexyl)sulfamoyl)-2-methoxybenzamide LC-MS (ESI): mass calcd. for $C_{20}H_{24}FN_3O_5S$ 437.14, m/z found 438.1 [M+H]$^+$. $^1$H NMR (400 MHz, DMSO-d$_6$) δ 10.56 (s, 1H), 8.21-8.00 (m, 2H), 7.92 (s, 1H), 7.80-7.50 (m, 2H), 7.36 (d, J=7.1 Hz, 1H), 4.40-4.25 (m, 1H), 3.99 (s, 3H), 3.60-3.50 (m, 1H), 3.00-2.90 (m, 1H), 2.39 (s, 3H), 1.60-1.40 (m, 4H), 1.40-1.20 (m, 4H).

Compound 28a: N-(5-Fluoro-6-methylpyridin-2-yl)-5-(N-((trans)-2-hydroxycyclohexyl) sulfamoyl)-2-methoxybenzamide LC-MS (ESI): mass calcd. for $C_{20}H_{24}FN_3O_5S$ 437.14, m/z found 438.2 [M+H]$^+$. $^1$H NMR (400 MHz, DMSO-d$_6$) δ 10.55 (s, 1H), 8.19 (d, J=2.4 Hz, 1H), 8.15-8.05 (m, 1H), 7.96 (dd, J=8.8, 2.5 Hz, 1H), 7.71 (t, J=9.0 Hz, 1H), 7.52-7.42 (m, 1H), 7.36 (d, J=8.9 Hz, 1H), 4.50 (d, J=4.6 Hz, 1H), 4.01 (s, 3H), 3.25-3.15 (m, 1H), 2.82-2.72 (m, 1H), 2.41 (d, J=2.8 Hz, 3H), 1.80-1.72 (m, 1H), 1.70-1.62 (m, 1H), 1.56-1.42 (m, 2H), 1.19-1.02 (m, 4H).

Compound 28b: N-(5-Fluoro-6-methylpyridin-2-yl)-5-(N-((trans)-2-hydroxycyclohexyl) sulfamoyl)-2-methoxybenzamide LC-MS (ESI): mass calcd. for $C_{20}H_{24}FN_3O_5S$ 437.14, m/z found 438.2 [M+H]$^+$. $^1$H NMR (400 MHz, DMSO-d$_6$) δ 10.55 (s, 1H), 8.19 (d, J=2.4 Hz, 1H), 8.15-8.05 (m, 1H), 7.96 (dd, J=8.8, 2.5 Hz, 1H), 7.71 (t, J=9.0 Hz, 1H), 7.52-7.42 (m, 1H), 7.36 (d, J=8.9 Hz, 1H), 4.50 (d, J=4.6 Hz, 1H), 4.01 (s, 3H), 3.25-3.15 (m, 1H), 2.82-2.72 (m, 1H), 2.41 (d, J=2.8 Hz, 3H), 1.80-1.72 (m, 1H), 1.70-1.62 (m, 1H), 1.56-1.42 (m, 2H), 1.19-1.02 (m, 4H).

Compound 29a: (S*)—N-(5-Fluoro-6-methylpyridin-2-yl)-2-methoxy-5-(N-(1,1,1-trifluoropropan-2-yl)sulfamoyl)benzamide LC-MS (ESI): mass calcd. for $C_{17}H_{17}F_4N_3O_4S$ 435.09, m/z found 436.1 [M+H]$^+$; $^1$H NMR (400 MHz, DMSO-d$_6$) δ 10.62 (s, 1H), 8.50 (d, J=8.8 Hz, 1H), 8.16 (d, J=2.0 Hz, 1H), 8.10 (d, J=6.2 Hz, 1H), 7.98 (dd, J=2.4, 8.8 Hz, 1H), 7.72 (t, J=8.9 Hz, 1H), 7.41 (d, J=9.0 Hz, 1H), 4.12-4.04 (m, 1H), 4.02 (s, 3H), 2.41 (d, J=2.4 Hz, 3H), 1.01 (d, J=7.1 Hz, 3H).

Compound 29b: (R*)—N-(5-Fluoro-6-methylpyridin-2-yl)-2-methoxy-5-(N-(1,1,1-trifluoropropan-2-yl)sulfamoyl)benzamide LC-MS (ESI): mass calcd. for $C_{17}H_{17}F_4N_3O_4S$ 435.09, m/z found 436.1 [M+H]$^+$; $^1$H NMR (400 MHz, DMSO-d$_6$) δ 10.62 (s, 1H), 8.50 (d, J=5.3 Hz, 1H), 8.16 (d, J=2.2 Hz, 1H), 8.10 (d, J=6.4 Hz, 1H), 7.98 (dd, J=2.4, 8.8 Hz, 1H), 7.72 (t, J=9.0 Hz, 1H), 7.41 (d, J=9.0 Hz, 1H), 4.13-4.04 (m, J=6.6 Hz, 1H), 4.02 (s, 3H), 2.41 (d, J=2.4 Hz, 3H), 1.01 (d, J=6.8 Hz, 3H).

Compound 30: N-(5-Fluoro-6-methylpyridin-2-yl)-2-methoxy-5-(pyrrolidin-1-ylsulfonyl) benzamide LC-MS (ESI): mass calcd. for $C_{18}H_{20}FN_3O_4S$ 393.43, m/z found 394.1 $[M+H]^+$; $^1$H NMR (400 MHz, DMSO-$d_6$) δ 10.65 (br.s, 1H), 8.09 (d, J=6.8 Hz, 1H), 8.02 (s, 1H), 7.94 (dd, J=8.8 Hz, J=2.4 Hz, 1H), 7.71 (t, J=8.8 Hz, 1H), 7.41 (d, J=4.8 Hz, 1H), 4.00 (s, 3H), 3.49-3.05 (m, 4H), 2.45-2.35 (m, 3H), 1.73-1.60 (m, 4H).

Compound 31: N-(5-fluoro-6-methylpyridin-2-yl)-5-(N-((cis)-3-hydroxy-3-methylcyclobutyl) sulfamoyl)-2-methoxybenzamide LC-MS (ESI): mass calcd. for $C_{19}H_{22}FN_3O_5S$ 423.13, m/z found 424.1 $[M+H]^+$; $^1$H NMR (400 MHz, DMSO-$d_6$) δ 10.56 (s, 1H), 8.12 (d, J=2.0 Hz, 1H), 8.11-8.05 (m, 1H), 7.89 (dd, J=2.3, 8.8 Hz, 1H), 7.85 (d, J=7.3 Hz, 1H), 7.70 (t, J=9.0 Hz, 1H), 7.37 (d, J=8.8 Hz, 1H), 4.89 (s, 1H), 4.00 (s, 3H), 3.23-3.12 (m, 1H), 2.39 (d, J=2.5 Hz, 3H), 2.01-1.93 (m, 2H), 1.81-1.72 (m, 2H), 1.09 (s, 3H).

Compound 32a: (R*)—N-(3-(Difluoromethyl)-4-fluorophenyl)-2-methoxy-5-(N-(1-methoxypropan-2-yl)sulfamoyl)benzamide LC-MS (ESI): mass calcd. for $C_{19}H_{21}F_3N_2O_5S$ 446.11, m/z found 447.1 $[M+H]^+$. $^1$H NMR (400 MHz, DMSO-$d_6$) δ 10.47 (s, 1H), 8.07 (d, J=4.4 Hz, 1H), 8.01 (d, J=2.0 Hz, 1H), 7.93 (dd, J=2.4, 8.8 Hz, 1H), 7.90-0.783 (m, 1H), 7.68 (d, J=7.6 Hz, 1H), 7.43-7.33 (m, 2H), 7.24 (t, J=54.4 Hz, 1H), 3.96 (s, 3H), 3.29-3.07 (m, 3H), 3.14 (s, 3H), 0.91 (d, J=6.8 Hz, 3H).

Compound 32b: (S*)—N-(3-(Difluoromethyl)-4-fluorophenyl)-2-methoxy-5-(N-(1-methoxypropan-2-yl)sulfamoyl)benzamide LC-MS (ESI): mass calcd. for $C_{19}H_{21}F_3N_2O_5S$ 446.11, m/z found 447.1 $[M+H]^+$. $^1$H NMR (400 MHz, DMSO-$d_6$) δ 10.47 (s, 1H), 8.07 (d, J=4.0 Hz, 1H), 8.01 (d, J=2.0 Hz, 1H), 7.93 (dd, J=2.4, 8.8 Hz, 1H), 7.83-7.89 (m, 1H), 7.68 (d, J=7.2 Hz, 1H), 7.43-7.34 (m, 2H), 7.24 (t, J=54.0 Hz, 1H), 3.96 (s, 3H), 3.22-3.07 (m, 3H), 3.14 (s, 3H), 0.92 (d, J=6.8 Hz, 3H).

Compound 33a: N-(3-(Difluoromethyl)-4-fluorophenyl)-5-(N-((cis)-3-hydroxycyclopentyl) sulfamoyl)-2-methoxybenzamide LC-MS (ESI): mass calcd. for $C_{20}H_{21}F_3N_2O_5S$ 458.11, m/z found 459.1 $[M+H]^+$. $^1$H NMR (400 MHz, DMSO-$d_6$) δ 10.48 (s, 1H), 8.11-8.05 (m, 1H), 8.00 (d, J=2.4 Hz, 1H), 7.92 (dd, J=2.4, 8.8 Hz, 1H), 7.90-7.83 (m, 1H), 7.67 (d, J=7.2 Hz, 1H), 7.43-7.35 (m, 2H), 7.24 (t, J=54.4 Hz, 1H), 4.60 (d, J=4.0 Hz, 1H), 3.97 (s, 3H), 3.91 (dd, J=4.6, 9.8 Hz, 1H), 1.96-1.88 (m, 1H), 1.60-1.41 (m, 4H), 1.28-1.18 (m, 2H).

Compound 33b: N-(3-(Difluoromethyl)-4-fluorophenyl)-5-(N-((cis)-3-hydroxycyclopentyl) sulfamoyl)-2-methoxybenzamide LC-MS (ESI): mass calcd. for $C_{20}H_{21}F_3N_2O_5S$ 458.11, m/z found 459.0 $[M+H]^+$. $^1$H NMR (400 MHz, DMSO-$d_6$) δ 10.48 (s, 1H), 8.11-8.05 (m, 1H), 8.00 (d, J=2.4 Hz, 1H), 7.92 (dd, J=2.4, 8.8 Hz, 1H), 7.89-7.84 (m, 1H), 7.67 (d, J=7.2 Hz, 1H), 7.43-7.35 (m, 2H), 7.24 (t, J=54.4 Hz, 1H), 4.60 (d, J=4.4 Hz, 1H), 3.97 (s, 3H), 3.92 (dd, J=4.4, 10.4 Hz, 1H), 1.96-1.89 (m, 1H), 1.60-1.41 (m, 4H), 1.31-1.17 (m, 2H).

Compound 34a: (S)-5-(N-(1-Amino-1-oxopropan-2-yl)sulfamoyl)-N-(3-(difluoromethyl)-4-fluorophenyl)-2-methoxybenzamide LC-MS (ESI): mass calcd. for $C_{18}H_{18}F_3N_3O_5S$ 445.09, m/z found 446.1 $[M+H]^+$. $^1$H NMR (400 MHz, DMSO-$d_6$) δ 10.49 (s, 1H), 8.09 (dd, J=2.4, 6.4 Hz, 1H), 8.00 (d, J=2.4 Hz, 1H), 7.93 (dd, J=2.4, 8.8 Hz, 1H), 7.89-7.85 (m, 1H), 7.42-7.33 (m, 3H), 7.24 (t, J=54.4 Hz, 1H), 6.99 (s, 1H), 3.96 (s, 3H), 3.68 (q, J=6.8 Hz, 1H), 1.09 (d, J=6.8 Hz, 3H).

Compound 34b: (R)-5-(N-(1-Amino-1-oxopropan-2-yl)sulfamoyl)-N-(3-(difluoromethyl)-4-fluorophenyl)-2-methoxybenzamide LC-MS (ESI): mass calcd. for $C_{18}H_{18}F_3N_3O_5S$ 445.09, m/z found 446.1 $[M+H]^+$. $^1$H NMR (400 MHz, DMSO-$d_6$) δ 10.45 (s, 1H), 8.08 (dd, J=2.4, 6.4 Hz, 1H), 8.01 (d, J=2.4 Hz, 1H), 7.92 (dd, J=2.4, 8.8 Hz, 1H), 7.89-7.85 (m, 1H), 7.41-7.35 (m, 3H), 7.24 (t, J=54.4 Hz, 1H), 6.99 (s, 1H), 3.96 (s, 3H), 3.68 (t, J=5.6, 6.8 Hz, 1H), 1.08 (d, J=7.2 Hz, 3H).

Compound 35a: (S)—N-(3-(Difluoromethyl)-4-fluorophenyl)-5-(N-(1-hydroxypropan-2-yl) sulfamoyl)-2-methoxybenzamide LC-MS (ESI): mass calcd. for $C_{18}H_{19}F_3N_2O_5S$ 432.10, m/z found 433.1 $[M+H]^+$. $^1$H NMR (400 MHz, DMSO-$d_6$) δ 10.48 (s, 1H), 8.08 (dd, J=2.4, 6.4 Hz, 1H), 8.01 (d, J=2.8 Hz, 1H), 7.93 (dd, J=2.4, 8.8 Hz, 1H), 7.89-7.84 (m, 1H), 7.53 (d, J=6.0 Hz, 1H), 7.41-7.36 (m, 2H), 7.24 (t, J=54.4 Hz, 1H), 4.71 (t, J=5.2, 6 Hz, 1H), 3.96 (s, 3H), 3.14-3.05 (m, 2H), 0.91 (d, J=6.4 Hz, 3H).

Compound 35b: (R)—N-(3-(Difluoromethyl)-4-fluorophenyl)-5-(N-(1-hydroxypropan-2-yl) sulfamoyl)-2-methoxybenzamide LC-MS (ESI): mass calcd. for $C_{18}H_{19}F_3N_2O_5S$ 432.10, m/z found 433.1 $[M+H]^+$. $^1$H NMR (400 MHz, DMSO-$d_6$) δ 10.48 (s, 1H), 8.08 (dd, J=2.4, 6.4 Hz, 1H), 8.01 (d, J=2.4 Hz, 1H), 7.93 (dd, J=2.4, 8.8 Hz, 1H), 7.88-7.84 (m, 1H), 7.53 (d, J=6.0 Hz, 1H), 7.42-7.36 (m, 2H), 7.24 (t, J=54.4 Hz, 1H), 4.71 (t, J=5.6 Hz, 1H), 3.96 (s, 3H), 3.14-3.08 (m, 2H), 0.91 (d, J=6.0 Hz, 3H).

Compound 36: N-(3-(Difluoromethyl)-4-fluorophenyl)-2-methoxy-5-(N-(3-methyloxetan-3-yl) sulfamoyl)benzamide LC-MS (ESI): mass calcd. for $C_{19}H_{19}F_3N_2O_5S$ 444.10, m/z found 445.1 $[M+H]^+$. $^1$H NMR (400 MHz, DMSO-$d_6$) δ 10.50 (s, 1H), 8.37 (s, 1H), 8.08 (dd, J=2.4, 6.2 Hz, 1H), 8.00 (d, J=2.4 Hz, 1H), 7.93 (dd, J=2.4, 8.8 Hz, 1H), 7.90-7.83 (m, 1H), 7.42-7.09 (m, 3H), 4.54 (d, J=6.0 Hz, 2H), 4.12 (d, J=6.4 Hz, 2H), 3.96 (s, 3H), 1.43 (s, 3H).

Compound 37: (S)—N-(3-(Difluoromethyl)-4-fluorophenyl)-2-methoxy-5-(N-(tetrahydro-2H-pyran-3-yl)sulfamoyl)benzamide LC-MS (ESI): mass calcd. for $C_{20}H_{21}F_3N_2O_5S$ 458.11, m/z found 459.1 [M+H]$^+$. $^1$H NMR (400 MHz, DMSO-d$_6$) δ 10.49 (s, 1H), 8.07 (d, J=4.0 Hz, 1H), 8.01 (d, J=2.0 Hz, 1H), 7.95 (dd, J=2.5, 9.0 Hz, 1H), 7.89-7.83 (m, 1H), 7.80 (d, J=7.0 Hz, 1H), 7.42-7.35 (m, 2.25H), 7.24 (s, 0.50H), 7.11 (s, 0.26H), 3.97 (s, 3H), 3.65-3.54 (m, 2H), 3.26-3.16 (m, 1H), 3.08-2.94 (m, 2H), 1.71-1.54 (m, 2H), 1.45-1.28 (m, 2H).

Compound 38: N-(3-(Difluoromethyl)-4-fluorophenyl)-5-(N-((cis)-4-hydroxycyclohexyl) sulfamoyl)-2-methoxybenzamide LC-MS (ESI): mass calcd. for $C_{21}H_{23}F_3N_2O_5S$ 472.13, m/z found 473.1 [M+H]$^+$. $^1$H NMR (400 MHz, DMSO-d$_6$) δ 10.49 (s, 1H), 8.11-8.04 (m, 1H), 8.04-7.98 (m, 1H), 7.96-7.90 (m, 1H), 7.89-7.82 (m, 1H), 7.67-7.54 (m, 1H), 7.42-7.34 (m, 1H), 7.24 (s, 1H), 7.10 (s, 1H), 3.96 (s, 3H), 3.60-3.54 (m, 2H), 3.00-2.92 (m, 1H), 1.61-1.44 (m, 4H), 1.41-1.27 (m, 4H).

Compound 39: N-(3-(Difluoromethyl)-4-fluorophenyl)-2-methoxy-5-(N-(oxetan-3-yl) sulfamoyl)benzamide LC-MS (ESI): mass calcd. for $C_{18}H_{17}F_3N_2O_5S$ 430.08, m/z found 431.1 [M+H]$^+$. $^1$H NMR (400 MHz, DMSO-d$_6$) δ 10.50 (s, 1H), 8.56 (d, J=8.0 Hz, 1H), 8.11-8.04 (m, 1H), 7.98-7.94 (m, J=2.5, 1H), 7.92-7.84 (m, 2H), 7.44-7.33 (m, 2H), 7.33-7.10 (m, 1H), 4.51 (t, J=6.5 Hz, 2H), 4.43-4.32 (m, 1H), 4.31-4.25 (m, 2H), 3.96 (s, 3H).

Compound 40a: (S*)—N-(4-Fluorophenyl)-2-methoxy-5-(N-(1-methoxypropan-2-yl)sulfamoyl)benzamide LC-MS (ESI): mass calcd. for $C_{18}H_{21}FN_2O_5S$ 396.12, m/z found 397.1 [M+H]$^+$, $^1$H NMR (400 MHz, DMSO-d$_6$) δ 10.29 (s, 1H), 8.00 (d, J=2.5 Hz, 1H), 7.92 (dd, J=2.5, 8.8 Hz, 1H), 7.77-7.72 (m, 2H), 7.68 (d, J=7.0 Hz, 1H), 7.35 (d, J=8.8 Hz, 1H), 7.20 (t, J=8.9 Hz, 2H), 3.96 (s, 3H), 3.30-3.23 (m, 1H), 3.23-3.18 (m, 1H), 3.14 (s, 3H), 3.12-3.07 (m, 1H), 0.91 (d, J=6.5 Hz, 3H).

Compound 40b: (R*)—N-(4-Fluorophenyl)-2-methoxy-5-(N-(1-methoxypropan-2-yl)sulfamoyl)benzamide LC-MS (ESI): mass calcd. for $C_{18}H_{21}FN_2O_5S$ 396.12, m/z found 397.1 [M+H]$^+$, $^1$H NMR (400 MHz, DMSO-d$_6$) δ 10.29 (s, 1H), 8.00 (d, J=2.5 Hz, 1H), 7.92 (dd, J=2.5, 8.8 Hz, 1H), 7.77-7.72 (m, 2H), 7.68 (d, J=7.3 Hz, 1H), 7.36 (d, J=8.8 Hz, 1H), 7.23-7.17 (m, 2H), 3.96 (s, 3H), 3.27 (td, J=6.4, 12.6 Hz, 1H), 3.23-3.17 (m, 1H), 3.14 (s, 3H), 3.12-3.06 (m, 1H), 0.91 (d, J=6.5 Hz, 3H).

Compound 41: (S)—N-(4-Fluorophenyl)-2-methoxy-5-(N-(tetrahydro-2H-pyran-3-yl)sulfamoyl)benzamide LC-MS (ESI): mass calcd. for $C_{19}H_{21}FN_2O_5S$ 408.12, m/z found 409.1 [M+H]$^+$. $^1$H NMR (400 MHz, DMSO-d$_6$) δ 10.31 (s, 1H), 8.00 (d, J=2.3 Hz, 1H), 7.94 (dd, J=2.5, 8.8 Hz, 1H), 7.83-7.71 (m, 3H), 7.37 (d, J=9.0 Hz, 1H), 7.20 (t, J=8.9 Hz, 2H), 3.96 (s, 3H), 3.64-3.54 (m, 2H), 3.25-3.17 (m, 1H), 3.07-2.93 (m, 2H), 1.71-1.52 (m, 2H), 1.44-1.27 (m, 2H).

Compound 42: N-(4-Fluorophenyl)-2-methoxy-5-(N-(3-methyloxetan-3-yl)sulfamoyl)benzamide LC-MS (ESI): mass calcd. for $C_{18}H_{19}FN_2O_5S$ 394.10, m/z found 395.1 [M+H]$^+$. $^1$H NMR (400 MHz, DMSO-d$_6$) δ 10.30 (s, 1H), 8.30 (br. s., 1H), 8.00 (d, J=2.4 Hz, 1H), 7.92 (dd, J=2.4, 8.8 Hz, 1H), 7.78-7.71 (m, 2H), 7.37 (d, J=8.8 Hz, 1H), 7.20 (t, J=8.8 Hz, 2H), 4.54 (d, J=6.0 Hz, 2H), 4.12 (d, J=6.4 Hz, 2H), 3.97 (s, 3H), 1.43 (s, 3H).

Compound 43: N-(4-Fluorophenyl)-2-methoxy-5-(N-(oxetan-3-yl)sulfamoyl)benzamide LC-MS (ESI): mass calcd. for $C_{17}H_{17}FN_2O_5S$ 380.08, m/z found 381.1 [M+H]$^+$. $^1$H NMR (400 MHz, DMSO-d$_6$) δ 10.29 (s, 1H), 8.51 (d, J=6.8 Hz, 1H), 7.95 (d, J=2.5 Hz, 1H), 7.88 (dd, J=2.5, 8.8 Hz, 1H), 7.77-7.71 (m, 2H), 7.36 (d, J=8.8 Hz, 1H), 7.24-7.17 (m, 2H), 4.51 (t, J=6.8 Hz, 2H), 4.42-4.32 (m, 1H), 4.30-4.24 (m, 2H), 3.96 (s, 3H).

Compound 44a (S*)—N-(4-Fluorophenyl)-2-methoxy-5-(N-(3,3,3-trifluoro-2-hydroxypropyl)sulfamoyl)benzamide LC-MS (ESI): mass calcd. for $C_{17}H_{16}F_4N_2O_5S$ 436.07, m/z found 437.0 [M+H]$^+$. $^1$H NMR (400 MHz, DMSO-d$_6$) δ 10.32 (s, 1H), 8.02-7.90 (m, 3H), 7.78-7.70 (m, 2H), 7.38 (d, J=9.0 Hz, 1H), 7.21 (t, J=8.9 Hz, 2H), 6.64 (d, J=6.0 Hz, 1H), 4.04 (br. s., 1H), 3.97 (s, 3H), 3.03-2.94 (m, 1H), 2.86-2.77 (m, 1H).

Compound 44b: (R*)—N-(4-Fluorophenyl)-2-methoxy-5-(N-(3,3,3-trifluoro-2-hydroxypropyl)sulfamoyl)benzamide LC-MS (ESI): mass calcd. for $C_{17}H_{16}F_4N_2O_5S$ 436.07, m/z found 437.0 [M+H]$^+$. $^1$H NMR (400 MHz, DMSO-d$_6$) δ 10.32 (s, 1H), 8.02-7.89 (m, 3H), 7.79-7.71 (m, 2H), 7.38 (d, J=8.8 Hz, 1H), 7.21 (t, J=8.9 Hz, 2H), 6.64 (d, J=6.3 Hz, 1H), 4.10-3.99 (m, 1H), 3.97 (s, 3H), 3.02-2.94 (m, 1H), 2.86-2.77 (m, 1H).

Compound 45a: N-(4-Fluorophenyl)-5-(N-((cis)-3-hydroxycyclopentyl)sulfamoyl)-2-methoxybenzamide LC-MS (ESI): mass calcd. for $C_{19}H_{21}FN_2O_5S$ 408.12, m/z found 409.1 [M+H]$^+$. $^1$H NMR (400 MHz, DMSO-d$_6$) 10.29 (s, 1H), 7.99 (d, J=2.0 Hz, 1H), 7.91 (dd, J=2.3, 8.8 Hz, 1H), 7.75 (dd, J=5.0, 8.5 Hz, 2H), 7.66 (d, J=7.0 Hz, 1H), 7.36 (d, J=9.0 Hz, 1H), 7.20 (t, J=8.8 Hz, 2H), 4.59 (d, J=4.0 Hz, 1H), 3.96 (s, 3H), 3.94-3.86 (m, J=4.8, 9.8 Hz, 1H), 1.96-1.86 (m, 1H), 1.64-1.37 (m, 4H), 1.25-1.17 (m, 1H).

Compound 45b: N-(4-Fluorophenyl)-5-(N-((cis)-3-hydroxycyclopentyl sulfamoyl)-2-methoxybenzamide LC-MS (ESI): mass calcd. for $C_{19}H_{21}FN_2O_5S$ 408.12, m/z found 409.1 [M+H]$^+$. $^1$H NMR (400 MHz, DMSO-d$_6$) 10.29 (s, 1H), 7.99 (d, J=2.5 Hz, 1H), 7.91 (dd, J=2.3, 8.8

Hz, 1H), 7.75 (dd, J=5.0, 9.0 Hz, 2H), 7.66 (d, J=6.5 Hz, 1H), 7.36 (d, J=8.5 Hz, 1H), 7.20 (t, J=8.8 Hz, 2H), 4.59 (d, J=4.0 Hz, 1H), 3.96 (s, 3H), 3.94-3.86 (m, 1H), 3.34-3.29 (m, 1H), 1.97-1.86 (m, 1H), 1.63-1.37 (m, 4H), 1.25-1.17 (m, 1H).

Compound 46a: (R)-5-(N-(1-Amino-1-oxopropan-2-yl)sulfamoyl)-N-(4-fluorophenyl)-2-methoxybenzamide LC-MS (ESI): mass calcd. for $C_{17}H_{18}FN_3O_5S$ 395.10, m/z found 396.1 [M+H]$^+$. $^1$H NMR (400 MHz, DMSO-d$_6$) 10.28 (s, 1H), 8.00 (d, J=2.2 Hz, 1H), 7.95-7.85 (m, 2H), 7.75 (dd, J=5.1, 8.8 Hz, 2H), 7.35 (d, J=8.8 Hz, 1H), 7.31 (br. s., 1H), 7.21 (t, J=8.8 Hz, 2H), 7.01 (br. s., 1H), 3.96 (s, 3H), 3.73-3.62 (m, 1H), 1.07 (d, J=7.1 Hz, 3H).

Compound 46b: (S)-5-(N-(1-Amino-1-oxopropan-2-yl)sulfamoyl)-N-(4-fluorophenyl)-2-methoxybenzamide LC-MS (ESI): mass calcd. for $C_{17}H_{18}FN_3O_5S$ 395.10, m/z found 396.1 [M+H]$^+$. $^1$H NMR (400 MHz, DMSO-d$_6$) 10.27 (s, 1H), 8.00 (d, J=2.0 Hz, 1H), 7.94-7.85 (m, 2H), 7.75 (dd, J=5.0, 8.5 Hz, 2H), 7.35 (d, J=9.0 Hz, 1H), 7.30 (br. s., 1H), 7.20 (t, J=8.8 Hz, 2H), 7.00 (br. s., 1H), 3.96 (s, 3H), 3.68 (q, J=7.0 Hz, 1H), 1.07 (d, J=7.0 Hz, 3H).

Compound 47: 5-(N-Cyclobutylsulfamoyl)-N-(4-fluorophenyl)-2-methoxybenzamide

LC-MS (ESI): mass calcd. for $C_{18}H_{19}FN_2O_4S$ 378.10, m/z found 379.1 [M+H]$^+$. $^1$H NMR (400 MHz, DMSO-d$_6$) 10.28 (s, 1H), 7.97 (s, 1H), 7.94 (d, J=8.5 Hz, 1H), 7.91-7.85 (m, 1H), 7.75 (dd, J=5.0, 8.5 Hz, 2H), 7.35 (d, J=8.5 Hz, 1H), 7.20 (t, J=8.8 Hz, 2H), 3.96 (s, 3H), 3.67-3.56 (m, 1H), 1.98-1.85 (m, 2H), 1.81-1.66 (m, 2H), 1.56-1.41 (m, 2H).

Compound 48: 5-(N-Cyclopropylsulfamoyl)-N-(4-fluorophenyl)-2-methoxybenzamide

LC-MS (ESI): mass calcd. for $C_{17}H_{17}FN_2O_4S$ 364.09, m/z found 365.1 [M+H]$^+$. $^1$H NMR (400 MHz, DMSO-d$_6$) 10.31 (s, 1H), 7.99 (d, J=2.0 Hz, 1H), 7.96-7.86 (m, 2H), 7.74 (dd, J=5.0, 8.5 Hz, 2H), 7.39 (d, J=8.5 Hz, 1H), 7.20 (t, J=9.0 Hz, 2H), 3.97 (s, 3H), 2.14-2.05 (m, 1H), 0.54-0.45 (m, 2H), 0.43-0.35 (m, 2H).

Compound 49a: (S)—N-(4-Fluorophenyl)-5-(N-(1-hydroxypropan-2-yl)sulfamoyl)-2-methoxybenzamide LC-MS (ESI): mass calcd. for $C_{17}H_{19}FN_2O_5S$ 382.10, m/z found 383.1 [M+H]$^+$. $^1$H NMR (400 MHz, DMSO-d$_6$) 10.29 (s, 1H), 8.01 (d, J=2.5 Hz, 1H), 7.92 (dd, J=2.3, 8.8 Hz, 1H), 7.75 (dd, J=5.0, 9.0 Hz, 2H), 7.52 (d, J=6.0 Hz, 1H), 7.37 (d, J=9.0 Hz, 1H), 7.20 (t, J=8.8 Hz, 2H), 4.75-4.68 (m, 1H), 3.97 (s, 3H), 3.33-3.27 (m, 1H), 3.16-3.03 (m, 2H), 0.91 (d, J=6.0 Hz, 3H).

Compound 49b: (R)—N-(4-Fluorophenyl)-5-(N-(1-hydroxypropan-2-yl)sulfamoyl)-2-methoxybenzamide LC-MS (ESI): mass calcd. for $C_{17}H_{19}FN_2O_5S$ 382.10, m/z found 383.1 [M+H]$^+$. $^1$H NMR (400 MHz, DMSO-d$_6$) 10.30 (s, 1H), 8.01 (d, J=2.0 Hz, 1H), 7.92 (dd, J=2.3, 8.8 Hz, 1H), 7.75 (dd, J=5.0, 9.0 Hz, 2H), 7.52 (d, J=5.0 Hz, 1H), 7.37 (d, J=9.0 Hz, 1H), 7.20 (t, J=9.0 Hz, 2H), 4.75-4.67 (m, 1H), 3.97 (s, 3H), 3.34-3.27 (m, 1a), 3.15-3.03 (m, 2H), 0.91 (d, J=6.5 Hz, 3H).

Compound 50: N-(4-Fluorophenyl)-2-methoxy-5-(N-(1-(trifluoromethyl)cyclopropyl) sulfamoyl)benzamide LC-MS (ESI): mass calcd. for $C_{18}H_{16}F_4N_2O_4S$ 432.08, m/z found 433.1 [M+H]$^+$. $^1$H NMR (400 MHz, DMSO-d$_6$) 10.31 (s, 1H), 9.13 (br. s., 1H), 7.97 (d, J=2.4 Hz, 1H), 7.89 (dd, J=2.3, 8.7 Hz, 1H), 7.78-7.72 (m, 2H), 7.37 (d, J=8.8 Hz, 1H), 7.21 (t, J=8.9 Hz, 2H), 3.97 (s, 3H), 1.22-1.16 (m, 2H), 1.08-0.98 (m, 2H).

Compound 51: 5-(N-Cyclopentylsulfamoyl)-N-(4-fluorophenyl)-2-methoxybenzamide

LC-MS (ESI): mass calcd. for $C_{19}H_{21}FN_2O_4S$ 392.12, m/z found 393.1 [M+H]$^+$. $^1$H NMR (400 MHz, DMSO-d$_6$) 10.29 (s, 1H), 7.99 (d, J=2.0 Hz, 1H), 7.91 (dd, J=2.3, 8.8 Hz, 1H), 7.79-7.70 (m, 2H), 7.62 (d, J=7.0 Hz, 1H), 7.36 (d, J=8.5 Hz, 1H), 7.20 (t, J=8.8 Hz, 2H), 3.96 (s, 3H), 3.44-3.36 (m, 1H), 1.67-1.49 (m, 4H), 1.45-1.25 (m, 4H).

Compound 52a: (S)—N-(4-fluorophenyl)-5-(N-(1-hydroxypropan-2-yl)sulfamoyl)-2-methoxybenzamide LC-MS (ESI): mass calcd. for $C_{17}H_{19}FN_2O_5S$ 382.10, m/z found 383.1 [M+H]$^+$; NMR (400 MHz, DMSO-d$_6$) δ 10.29 (s, 1H), 8.01 (d, J=2.5 Hz, 1H), 7.93 (dd, J=2.3, 8.8 Hz, 1H), 7.80-7.71 (m, 2H), 7.51 (br. s., 1H), 7.37 (d, J=9.0 Hz, 1H), 7.20 (t, J=9.0 Hz, 2H), 4.74-4.67 (m, 1H), 3.97 (s, 3H), 3.16-3.03 (m, 2H), 0.91 (d, J=6.0 Hz, 3H).

Compound 52b: (R)—N-(4-fluorophenyl)-5-(N-(1-hydroxypropan-2-yl)sulfamoyl)-2-methoxybenzamide LC-MS (ESI): mass calcd. for $C_{17}H_{19}FN_2O_5S$ 382.10, m/z found 383.1 [M+H]$^+$; NMR (400 MHz, DMSO-d$_6$) δ 10.30 (s, 1H), 8.00 (d, J=2.3 Hz, 1H), 7.92 (dd, J=2.1, 8.7 Hz, 1H), 7.75 (dd, J=5.1, 8.9 Hz, 2H), 7.51 (br. s., 1H), 7.36 (d, J=8.8 Hz, 1H), 7.20 (t, J=8.9 Hz, 2H), 4.77-4.66 (m, 1H), 3.96 (s, 3H), 3.14-3.04 (m, 2H), 0.91 (d, J=6.0 Hz, 3H).

Compound 53: N-(4-Fluorophenyl)-5-(N-((cis)-4-hydroxycyclohexyl)sulfamoyl)-2-methoxybenzamide LC-MS (ESI): mass calcd. for $C_{20}H_{23}FN_2O_5S$ 422.13, m/z found 423.1 [M+H]$^+$; $^1$H NMR (400 MHz, DMSO-d$_6$) δ 10.29 (s, 1H), 8.00 (d, J=2.5 Hz, 1H), 7.92 (dd, J=2.5, 8.8 Hz, 1H), 7.77-7.72 (m, 2H), 7.68 (d, J=7.0 Hz, 1H), 7.35 (d, J=8.8 Hz, 1H), 7.20 (t, J=8.9 Hz, 2H), 4.36 (s, 1H), 3.97 (s, 3H), 3.59 (m, 1H), 2.94 (m, 1H), 1.54 (m, 4H), 1.36 (m, 4H).

Compound 54a: (S*)—N-(2-Chlorophenyl)-2-methoxy-5-(1-methyl-2-oxopyrrolidin-3-yl) sulfamoyl)benzamide LC-MS (ESI): mass calcd. for $C_{19}H_{20}ClN_3O_5S$ 437.08, m/z found 438.1 [M+H]$^+$, $^1$H NMR (400 MHz, DMSO-d$_6$) δ 10.48 (br. s., 1H), 8.48 (br. s., 1H), 8.39 (d, J=7.8 Hz, 1H), 8.15 (d, J=8.1 Hz, 1H), 8.05 (d, J=8.6 Hz, 1H), 7.59 (d, J=7.8

Hz, 1H), 7.48 (d, J=8.8 Hz, 1H), 7.41 (t, J=7.3 Hz, 1H), 7.21 (t, J=7.5 Hz, 1H), 4.15 (br. s., 3H), 3.98-3.88 (m, 1H), 3.21-3.12 (m, 2H), 2.68 (s, 3H), 2.10-1.99 (m, 1H), 1.64-1.50 (m, 1H).

Compound 54b: (R*)—N-(2-Chlorophenyl)-2-methoxy-5-(N-(1-methyl-2-oxopyrrolidin-3-yl) sulfamoyl)benzamide LC-MS (ESI): mass calcd. for $C_{19}H_{20}ClN_3O_5S$ 437.08, m/z found 438.1 [M+H]$^+$. $^1$H NMR (400 MHz, DMSO-d$_6$) δ 10.48 (br. s., 1H), 8.48 (br. s., 1H), 8.39 (d, J=7.8 Hz, 1H), 8.15 (d, J=7.6 Hz, 1H), 8.05 (d, J=8.6 Hz, 1H), 7.59 (d, J=7.8 Hz, 1H), 7.48 (d, J=8.3 Hz, 1H), 7.42 (t, J=7.5 Hz, 1H), 7.21 (t, J=7.2 Hz, 1H), 4.15 (br. s., 3H), 3.98-3.88 (m, 1H), 3.21-3.11 (m, 2H), 2.67 (s, 3H), 2.10-1.98 (m, 1H), 1.63-1.50 (m, 1H).

Compound 55a: (S)—N-(2-Chlorophenyl)-5-(N-(1-hydroxypropan-2-yl)sulfamoyl)-2-methoxy benzamide LC-MS (ESI): mass calcd. for $C_{17}H_{19}ClN_2O_5S$ 398.07, m/z found 399.1 [M+H]$^+$. $^1$H NMR (400 MHz, DMSO-d$_6$) δ 10.49 (s, 1H), 8.47 (d, J=2.3 Hz, 1H), 8.39 (d, J=8.0 Hz, 1H), 8.01 (dd, J=2.4, 8.7 Hz, 1H), 7.65-7.56 (m, 2H), 7.49 (d, J=8.8 Hz, 1H), 7.41 (t, J=7.5 Hz, 1H), 7.21 (dt, J=1.5, 7.7 Hz, 1H), 4.70 (t, J=5.5 Hz, 1H), 4.15 (s, 3H), 3.35-3.26 (m, 1H), 3.17-3.04 (m, 2H), 0.90 (d, J=6.3 Hz, 3H).

Compound 55b: (R)—N-(2-Chlorophenyl)-5-(N-(1-hydroxypropan-2-yl)sulfamoyl)-2-methoxy benzamide LC-MS (ESI): mass calcd. for $C_{17}H_{19}ClN_2O_5S$ 398.07, m/z found 399.1 [M+H]$^+$. $^1$H NMR (400 MHz, DMSO-d$_6$) δ 10.49 (s, 1H), 8.47 (d, J=2.3 Hz, 1H), 8.39 (d, J=8.0 Hz, 1H), 8.01 (dd, J=2.3, 8.8 Hz, 1H), 7.64-7.55 (m, 2H), 7.49 (d, J=8.8 Hz, 1H), 7.41 (t, J=7.8 Hz, 1H), 7.23-7.17 (m, 1H), 4.70 (t, J=5.5 Hz, 1H), 4.15 (s, 3H), 3.34-3.27 (m, 1H), 3.15-3.05 (m, 2H), 0.90 (d, J=6.3 Hz, 3H).

Compound 56a: N-(2-Chlorophenyl)-5-(N-((cis)-4-hydroxytetrahydrofuran-3-yl)sulfamoyl)-2-methoxy-benzamide LC-MS (ESI): mass calcd. for $C_{18}H_{19}ClN_2O_6S$ 426.07, m/z found 427.0 [M+H]$^+$. $^1$H NMR (400 MHz, DMSO-d$_6$) δ 10.47 (s, 1H), 8.48 (d, J=2.0 Hz, 1H), 8.38 (d, J=8.0 Hz, 1H), 8.05-7.95 (m, 2H), 7.58 (d, J=8.0 Hz, 1H), 7.51 (d, J=8.8 Hz, 1H), 7.41 (t, J=7.8 Hz, 1H), 7.20 (t, J=7.7 Hz, 1H), 5.24 (d, J=4.0 Hz, 1H), 4.15 (s, 3H), 4.01 (br.s., 1H), 3.81-3.70 (m, 2H), 3.47-3.39 (m, 3H).

Compound 56b: N-(2-Chlorophenyl)-5-(N-((cis)-4-hydroxytetrahydrofuran-3-yl)sulfamoyl)-2-methoxy-benzamide LC-MS (ESI): mass calcd. for $C_{18}H_{19}ClN_2O_6S$ 426.07, m/z found 427.0 [M+H]$^+$. $^1$H NMR (400 MHz, DMSO-d$_6$) δ 10.48 (s, 1H), 8.48 (d, J=2.5 Hz, 1H), 8.38 (d, J=8.3 Hz, 1H), 8.05-7.97 (m, 2H), 7.58 (dd, J=1.3, 8.0 Hz, 1H), 7.51 (d, J=9.0 Hz, 1H), 7.41 (t, J=7.3 Hz, 1H), 7.21 (dt, J=1.5, 7.7 Hz, 1H), 5.24 (d, J=4.0 Hz, 1H), 4.16 (s, 3H), 4.04-3.99 (m, 1H), 3.80-3.70 (m, 2H), 3.47-3.37 (m, 3H).

Compound 57a: N-(2-Chlorophenyl)-5-(N-((cis)-3-hydroxycyclopentyl)sulfamoyl-2-methoxy benzamide LC-MS (ESI): mass calcd. for $C_{19}H_{21}ClN_2O_5S$ 424.09, m/z found 425.1 [M+H]$^+$. $^1$H NMR (400 MHz, DMSO-d$_6$) δ 10.48 (s, 1H), 8.46 (d, J=2.0 Hz, 1H), 8.39 (d, J=8.0 Hz, 1H), 8.00 (dd, J=2.0, 8.5 Hz, 1H), 7.76 (d, J=7.5 Hz, 1H), 7.58 (d, J=7.5 Hz, 1H), 7.49 (d, J=8.5 Hz, 1H), 7.41 (t, J=7.8 Hz, 1H), 7.21 (t, J=7.0 Hz, 1H), 4.57 (d, J=4.0 Hz, 1H), 4.15 (s, 3H), 3.95-3.86 (m, 1H), 3.46-3.37 (m, 1H), 1.96-1.86 (m, 1H), 1.64-1.37 (m, 4H), 1.26-1.16 (m, 1H).

Compound 57b: N-(2-Chlorophenyl)-5-(N-((cis)-3-hydroxycyclopentyl)sulfamoyl)-2-methoxy benzamide LC-MS (ESI): mass calcd. for $C_{19}H_{21}ClN_2O_5S$ 424.09, m/z found 425.1 [M+H]$^+$. $^1$H NMR (400 MHz, DMSO-d$_6$) δ 10.49 (s, 1H), 8.46 (d, J=2.0 Hz, 1H), 8.39 (d, J=8.0 Hz, 1H), 8.00 (dd, J=2.3, 8.8 Hz, 1H), 7.76 (d, J=7.5 Hz, 1H), 7.58 (d, J=8.0 Hz, 1H), 7.49 (d, J=8.5 Hz, 1H), 7.41 (t, J=7.5 Hz, 1H), 7.21 (t, J=7.0 Hz, 1H), 4.58 (d, J=4.0 Hz, 1H), 4.15 (s, 3H), 3.95-3.86 (m, 1H), 3.41-3.37 (m, 1H), 1.96-1.86 (m, 1H), 1.63-1.38 (m, 4H), 1.22-1.16 (m, 1H).

Compound 58: N-(2-Chlorophenyl)-2-methoxy-5-(N-(3-methyloxetan-3-yl)sulfamoyl) benzamide LC-MS (ESI): mass calcd. for $C_{18}H_{19}ClN_2O_5S$ 410.07, m/z found 411.0 [M+H]$^+$. 1H NMR (400 MHz, DMSO-d$_6$) δ 10.48 (br. s., 1H), 8.45 (d, J=6.2 Hz, 2H), 8.38 (d, J=7.7 Hz, 1H), 8.01 (d, J=6.8 Hz, 1H), 7.59 (d, J=7.7 Hz, 1H), 7.50 (d, J=8.6 Hz, 1H), 7.42 (t, J=7.4 Hz, 1H), 7.22 (t, J=7.1 Hz, 1H), 4.54 (d, J=5.5 Hz, 2H), 4.15 (s, 3H), 4.13 (d, J=6.0 Hz, 2H), 1.43 (s, 3H).

Compound 59a: (S)-5-(N-(1-Amino-1-oxopropan-2-ylsulfamoyl)-N-(2-chlorophenyl)-2-methoxybenzamide LC-MS (ESI): mass calcd. for $C_{17}H_{18}ClN_3O_5S$ 411.07, m/z found 412.1 [M+H]$^+$. $^1$H NMR (400 MHz, DMSO-d6) δ 10.48 (s, 1H), 8.46 (d, J=1.5 Hz, 1H), 8.40 (d, J=8.0 Hz, 1H), 8.03-7.94 (m, 2H), 7.59 (d, J=8.0 Hz, 1H), 7.48 (d, J=9.0 Hz, 1H), 7.42 (t, J=7.5 Hz, 1H), 7.29 (br. s., 1H), 7.21 (t, J=7.3 Hz, 1H), 6.98 (br. s., 1H), 4.15 (s, 3H), 3.71 (quin, J=7.0 Hz, 1H), 1.09 (d, J=7.0 Hz, 3H).

Compound 59b: (R)-5-(N-(1-amino-1-oxopropan-2-yl)sulfamoyl)-N-(2-chlorophenyl)-2-methoxy benzamide LC-MS (ESI): mass calcd. for $C_{17}H_{18}ClN_3O_5S$ 411.07, m/z found 412.1 [M+H]$^+$. $^1$H NMR (400 MHz, DMSO-d6) δ 10.47 (br. s., 1H), 8.46 (br. s., 1H), 8.39 (d, J=8.0 Hz, 1H), 8.05-7.92 (m, 2H), 7.59 (d, J=8.0 Hz, 1H), 7.48 (d, J=8.5 Hz, 1H), 7.42 (t, J=7.5 Hz, 1H), 7.29 (br. s., 1H), 7.21 (t, J=7.3 Hz, 1H), 6.98 (br. s., 1H), 4.15 (s, 3H), 3.77-3.64 (m, 1H), 1.08 (d, J=7.0 Hz, 3H).

Compound 60a: (S*)—N-(2-Chlorophenyl)-5-(N-(1-cyanopropan-2-yl)sulfamoyl)-2-methoxy benzamide LC-MS (ESI): mass calcd. for $C_{18}H_{18}ClN_3O_4S$ 407.07, m/z found 408.1 [M+H]$^+$. $^1$H NMR (400 MHz, DMSO-d6) δ 10.47 (s, 1H), 8.47 (d, J=2.2 Hz, 1H), 8.38 (d, J=7.8 Hz, 1H), 8.13 (br. s., 1H), 8.03 (dd, J=2.2, 8.8 Hz, 1H), 7.59 (d, J=7.8 Hz, 1H), 7.51 (d, J=8.8 Hz, 1H), 7.42 (t, J=7.6 Hz, 1H), 7.25-7.15 (m, 1H), 4.16 (s, 3H), 3.49-3.39 (m, 1H), 2.75-2.56 (m, 2H), 1.00 (d, J=6.6 Hz, 3H).

Compound 60b: (R*)—N-(2-chlorophenyl)-5-(N-(1-cyanopropan-2-yl)sulfamoyl)-2-methoxy benzamide LC-MS (ESI): mass calcd. for $C_{18}H_{18}ClN_3O_4S$ 407.07, m/z found 408.0 [M+H]$^+$. $^1$H NMR (400 MHz, DMSO-d6) δ 10.47 (s, 1H), 8.47 (d, J=2.0 Hz, 1H), 8.39 (d, J=8.1 Hz, 1H), 8.13 (br. s., 1H), 8.04 (dd, J=2.1, 8.7 Hz, 1H), 7.59 (d, J=8.1 Hz, 1H), 7.51 (d, J=8.8 Hz, 1H), 7.41 (t, J=7.6 Hz, 1H), 7.21 (t, J=7.3 Hz, 1H), 4.16 (s, 3H), 3.50-3.39 (m, 1H), 2.74-2.57 (m, 2H), 1.00 (d, J=6.6 Hz, 3H).

Compound 61a: N-(2-Chlorophenyl)-5-(N-((1s,2r)-2-hydroxycyclopentyl)sulfamoyl)-2-methoxy benzamide LC-MS (ESI): mass calcd. for $C_{19}H_{21}ClN_2O_5S$ 424.09, m/z found 425.1 [M+H]$^+$. $^1$H NMR (400 MHz, DMSO-d$_6$) 10.48 (s, 1H), 8.49 (d, J=2.2 Hz, 1H), 8.39 (d, J=7.9 Hz, 1H), 8.05 (dd, J=8.8, 2.3 Hz, 1H), 7.57 (d, J=8.0 Hz, 1H), 7.46 (d, J=8.8 Hz, 1H), 7.41 (t, J=6.7 Hz, 2H), 7.24-7.15 (m, 1H), 4.61 (d, J=4.0 Hz, 1H), 4.14 (s, 3H), 3.80-3.72 (m, 1H), 3.30-3.19 (m, 1H), 1.66-1.51 (m, 2H), 1.50-1.23 (m, 4H).

Compound 61b: N-(2-Chlorophenyl)-5-(N-((trans)-2-hydroxycyclopentyl)sulfamoyl)-2-methoxy benzamide LC-MS (ESI): mass calcd. for $C_{19}H_{21}ClN_2O_5S$ 424.09, m/z found 425.1 [M+H]$^+$. $^1$H NMR (400 MHz, DMSO-d$_6$) 10.48 (s, 1H), 8.47 (d, J=2.3 Hz, 1H), 8.39 (d, J=7.6 Hz, 1H), 8.01 (dd, J=8.7, 2.4 Hz, 1H), 7.63 (d, J=6.3 Hz, 1H), 7.58 (dd, J=8.0, 1.2 Hz, 1H), 7.49 (d, J=8.8 Hz, 1H), 7.41 (t, J=7.4 Hz, 1H), 7.20 (td, J=7.8, 1.5 Hz, 1H), 4.68 (d, J=4.3 Hz, 1H), 4.15 (s, 3H), 3.83-3.75 (m, 1H), 3.20-3.12 (m, 1H), 1.78-1.61 (m, 2H), 1.56-1.45 (m, 2H), 1.40-1.29 (m, 1H), 1.27-1.17 (m, 1H).

Compound 61c: N-(2-chlorophenyl)-5-(N-((trans)-2-hydroxycyclopentyl)sulfamoyl)-2-methoxy benzamide LC-MS (ESI): mass calcd. for $C_{19}H_{21}ClN_2O_5S$ 424.09, m/z found 425.1 [M+H]$^+$. $^1$H NMR (400 MHz, DMSO-d) 10.49 (s, 1H), 8.47 (d, J=2.2 Hz, 1H), 8.39 (d, J=8.0 Hz, 1H), 8.01 (dd, J=8.7, 2.3 Hz, 1H), 7.63 (d, J=6.6 Hz, 1H), 7.58 (d, J=8.0 Hz, 1H), 7.49 (d, J=8.8 Hz, 1H), 7.41 (t, J=7.8 Hz, 1H), 7.20 (dd, J=11.1, 4.3 Hz, 1H), 4.68 (d, J=4.3 Hz, 1H), 4.15 (s, 3H), 3.81-3.75 (m, 1H), 3.20-3.11 (m, 1H), 1.79-1.61 (m, 2H), 1.56-1.45 (m, 2H), 1.40-1.30 (m, 1H), 1.28-1.19 (m, 1H).

Compound 62: N-(2-Chlorophenyl)-2-methoxy-5-(N-(oxetan-3-yl)sulfamoyl)benzamide

LC-MS (ESI): mass calcd. for $C_{17}H_{17}ClN_2O_5S$ 396.05, m/z found 397.1 [M+H]$^+$. $^1$H NMR (400 MHz, DMSO-d$_6$) 10.45 (s, 1H), 8.62 (s, 1H), 8.39 (dd, J=17.0, 5.0 Hz, 2H), 7.97 (d, J=2.4 Hz, 1H), 7.57 (dd, J=8.0, 1.1 Hz, 1H), 7.47 (d, J=8.8 Hz, 1H), 7.41 (t, J=7.5 Hz, 1H), 7.20 (td, J=7.9, 1.5 Hz, 1H), 4.51 (t, J=6.7 Hz, 2H), 4.43-4.33 (m, 1H), 4.27 (t, J=6.3 Hz, 2H), 4.14 (s, 3H).

Compound 63: 5-(N-Cyclobutylsulfamoyl)-N-(4-fluoro-3-methylphenyl)-2-methoxybenzamide LC-MS (ESI): mass calcd. for $C_{19}H_{21}FN_2O_4S$ 392.12, m/z found 393.1 [M+H]$^+$. $^1$H NMR (400 MHz, DMSO-d$_6$) δ 10.20 (br. s., 1H), 8.03-7.83 (m, 3H), 7.68-7.52 (m, 2H), 7.35 (d, J=8.4 Hz, 1H), 7.13 (t, J=8.8 Hz, 1H), 3.96 (s, 3H), 3.64-3.58 (m, 1H), 2.24 (s, 3H), 1.98-1.87 (m, 2H), 1.81-1.66 (m, 2H), 1.56-1.44 (m, 2H).

Compound 64: (S)-2-Methoxy-5-(N-(tetrahydro-furan-3-yl)sulfamoyl)-N-(thiazol-2-yl) benzamide LC-MS (ESI): mass calcd. for $C_{15}H_{17}N_3O_5S_2$ 383.06, m/z found 384.0 [M+H]$^+$. $^1$H NMR (400 MHz, DMSO-d$_6$) δ 12.15 (br.s, 1H), 8.04 (d, J=2.4 Hz, 1H), 7.89-7.97 (m, 2H), 7.55 (d, J=3.2 Hz, 1H), 7.40 (d, J=8.8 Hz, 1H), 7.32 (d, J=3.6 Hz, 1H), 3.98 (s, 3H), 3.66-3.74 (m, 2H), 3.55-3.64 (m, 2H), 3.39-3.41 (m, 1H), 1.86-1.96 (m, 1H), 1.57-1.66 (m, 1H).

Compound 65: (S)—N-(2,4-Difluorophenyl)-2-methoxy-5-(N-(tetrahydrofuran-3-yl)sulfamoyl) benzamide LC-MS (ESI): mass calcd. for $C_{18}H_{18}F_2N_2O_5S$ 412.09, m/z found 413.1 [M+H]$^+$. $^1$H NMR (400 MHz, DMSO-d$_6$) δ 10.12 (br.s, 1H), 8.23 (d, J=2.4 Hz, 1H), 7.92-8.00 (m, 3H), 7.35-7.45 (m, 2H), 7.10-7.17 (m, 1H), 3.93 (s, 3H), 3.65-3.74 (m, 2H), 3.55-3.64 (m, 2H), 3.35-3.36 (m, 1H) 1.85-1.95 (m, 1H), 1.52-1.66 (m, 1H).

Compound 66: (S)—N-(2-Chloro-4-fluorophenyl)-2-methoxy-5-(N-(tetrahydrofuran-3-yl) sulfamoyl) benzamide LC-MS (ESI): mass calcd. for $C_{18}H_{18}ClFN_2O_5S$ 428.06, m/z found 429.1 [M+H]$^+$. $^1$H NMR (400 MHz, DMSO-d$_6$) δ 10.12 (br.s, 1H), 8.23 (d, J=2.4 Hz, 1H), 7.92-8.00 (m, 3H), 7.35-7.45 (m, 2H), 7.10-7.17 (m, 1H), 4.12 (s, 3H), 3.65-3.74 (m, 2H), 3.55-3.64 (m, 2H), 3.35-3.36 (m, 1H) 1.85-1.95 (m, 1H), 1.52-1.66 (m, 1H).

Compound 67: (S)—N-(3,5-Difluorophenyl)-2-methoxy-5-(N-(tetrahydrofuran-3-yl) sulfamoyl) benzamide LC-MS (ESI): mass calcd. for $C_{18}H_{18}F_2N_2O_5S$ 412.09, m/z found 413.1 [M+H]$^+$. $^1$H NMR (400 MHz, DMSO-ds) δ 10.57 (br.s, 1H), 7.83-7.89 (m, 3H), 7.44 (d, J=7.6 Hz, 1H), 7.36 (d, J=8.8 Hz, 1H), 6.90-7.00 (m, 1H), 3.93 (s, 3H), 3.62-3.70 (m, 2H), 3.52-3.61 (m, 2H), 3.30-3.34 (m, 1H), 1.82-1.92 (m, 1H), 1.54-1.64 (m, 1H).

Compound 68: (S)—N-(3-Chloro-5-fluorophenyl)-2-methoxy-5-(N-(tetrahydrofuran-3-yl) sulfamoyl) benzamide LC-MS (ESI): mass calcd. for $C_{18}H_{18}ClFN_2O_5S$ 428.06, m/z found 429.0 [M+H]$^+$. $^1$H NMR (400 MHz, DMSO-d$_6$) δ 10.59 (br.s, 1H), 8.00 (d, J=2.4 Hz, 1H), 7.91-7.97 (m, 2H), 7.68 (s, 1H), 7.60-7.65 (m, 1H), 7.40 (d, J=8.8 Hz, 1H), 7.16-7.21 (m, 1H), 3.97 (s, 3H), 3.65-3.73 (m, 2H), 3.56-3.64 (m, 2H), 3.30-3.34 (m, 1H), 1.86-1.94 (m, 1H), 1.58-1.66 (m, 1H).

Compound 69: (S)—N-(2,5-Difluorophenyl)-2-methoxy-5-(N-(tetrahydrofuran-3-yl)sulfamoyl) benzamide LC-MS (ESI): mass calcd. for $C_{18}H_{18}F_2N_2O_5S$ 412.09, m/z found 413.1 [M+H]$^+$. $^1$H NMR (400 MHz, DMSO-d6) δ 10.59 (br.s, 1H), 8.00 (d, J=2.4 Hz, 1H), 7.91-7.97 (m, 2H), 7.68 (s, 1H), 7.60-7.65 (m, 1H), 7.40 (d, J=8.8 Hz, 1H), 7.16-7.21 (m, 1H), 3.97 (s, 3H), 3.65-3.73 (m, 2H), 3.56-3.64 (m, 2H), 3.30-3.34 (m, 1H), 1.86-1.94 (m, 1H), 1.58-1.66 (m, 1H).

Compound 70: (S)—N-(2-Chloro-5-fluorophenyl)-2-methoxy-5-(N-(tetrahydrofuran-3-yl) sulfamoyl) benzamide LC-MS (ESI): mass calcd. for $C_{18}H_{18}ClFN_2O_5S$ 428.06, m/z found 429.0 [M+H]$^+$. $^1$H NMR (400 MHz, DMSO-d6) δ 10.61 (br.s, 1H), 8.48 (d, J=2.0 Hz, 1H), 8.32 (dd, J=11.2 Hz, J=2.4 Hz, 1H), 7.97-8.07 (m, 2H), 7.65 (dd, J=8.8 Hz, J=6.0 Hz, 1H), 7.52 (d, J=8.8 Hz, 1H), 7.04-7.14 (m, 1H), 4.17 (s, 3H), 3.66-3.74 (m, 2H), 3.55-3.65 (m, 2H), 3.33-3.35 (m, 1H), 1.85-1.95 (m, 1H), 1.56-1.66 (m, 1H).

Compound 71: (S)—N-(2,5-Dichlorophenyl)-2-methoxy-5-(N-(tetrahydrofuran-3-yl) sulfamoyl) benzamide LC-MS (ESI): mass calcd. for $C_{18}H_{18}Cl_2N_2O_5S$ 444.03, m/z found 445.0 [M+H]$^+$. $^1$H NMR (400 MHz, DMSO-d6) δ 10.58 (br.s, 1H), 8.50 (d, J=2.0 Hz, 1H), 8.46 (d, J=2.0 Hz, 1H), 7.98-8.10 (m, 2H), 7.64 (d, J=8.4 Hz, 1H), 7.52 (d, J=8.8 Hz, 1H), 8.00 (dd, J=8.4 Hz, J=2.4 Hz, 1H), 4.16 (s, 3H), 3.66-3.74 (m, 2H), 3.54-3.65 (m, 2H), 3.33-3.36 (m, 1H), 1.85-1.96 (m, 1H), 1.56-1.67 (m, 1H).

Compound 72: (S)—N-(3,4-Dichlorophenyl)-2-methoxy-5-(N-(tetrahydrofuran-3-yl)sulfamoyl) benzamide LC-MS (ESI): mass calcd. for $C_{18}H_{18}Cl_2N_2O_5S$ 444.03, m/z found 445.0 [M+H]$^+$. $^1$H NMR (400 MHz, DMSO-d6) δ 10.53 (br.s, 1H), 8.10 (d, J=2.0 Hz, 1H), 8.00 (d, J=2.4 Hz, 1H), 7.88-7.97 (m, 2H), 7.58-7.71 (m, 2H), 7.40 (d, J=8.8 Hz, 1H), 3.97 (s, 3H), 3.65-3.74 (m, 2H), 3.55-3.64 (m, 2H), 3.36-3.39 (m, 1H), 1.86-1.96 (m, 1H), 1.57-1.67 (m, 1H).

Compound 73: (S)—N-(4-Cyano-2-fluorophenyl)-2-methoxy-5-(N-(tetrahydrofuran-3-yl) sulfamoyl) benzamide LC-MS (ESI): mass calcd. for $C_{19}H_{18}FN_3O_5S$ 419.10, m/z found 420.1 [M+H]$^+$. $^1$H NMR (400 MHz, DMSO-d6) δ 10.53 (br. s., 1H), 8.43 (t, J=7.9 Hz, 1H), 8.27 (s, 1H), 8.00 (d, J=10.5 Hz, 3H), 7.76 (d, J=8.0 Hz, 1H), 7.47 (d, J=8.8 Hz, 1H), 4.07 (s, 3H), 3.74-3.53 (m, 4H), 3.39-3.36 (m, 1H), 1.96-1.85 (m, 1H), 1.67-1.57 (m, 1H).

Compound 74: (S)-2-Methoxy-5-(N-(tetrahydrofuran-3-yl)sulfamoyl)-N-(2,4,5-trifluorophenyl) benzamide LC-MS (ESI): mass calcd. for $C_{18}H_{17}F_3N_2O_5S$ 430.08, m/z found 431.1 [M+H]$^+$. $^1$H NMR (400 MHz, DMSO-d$_6$) δ 10.26 (br. s, 1H), 8.24 (d, J=2.3 Hz, 1H), 8.16 (td, J=8.1, 12.0 Hz, 1H), 8.01-7.94 (m, 2H), 7.74 (m, 1H), 7.45 (d, J=9.0 Hz, 1H), 4.05 (s, 3H), 3.74-3.65 (m, 2H), 3.64-3.54 (m, 2H), 3.38-3.34 (m, 1H), 1.96-1.85 (m, 1H), 1.67-1.57 (m, 1H).

Compound 75: (S)—N-(5-Chloro-2,4-difluorophenyl)-2-methoxy-5-(N-(tetrahydrofuran-3-yl) sulfamoyl)benzamide LC-MS (ESI): mass calcd. for $C_{18}H_{17}ClF_2N_2O_5S$ 446.05, m/z found 447.0 [M+H]$^+$. $^1$H NMR (400 MHz, DMSO-d6) δ 10.24 (br. s, 1H), 8.28-8.20 (m, 2H), 8.01-7.93 (m, 2H), 7.72 (t, J=9.9 Hz, 1H), 7.44 (d, J=9.0 Hz, 1H), 4.04 (s, 3H), 3.73-3.65 (m, 2H), 3.64-3.55 (m, 2H), 3.38-3.34 (m, 1H), 1.95-1.85 (m, 1H), 1.64-1.59 (m, 1H).

Compound 76: (S)-2-Methoxy-5-(N-(tetrahydrofuran-3-yl)sulfamoyl)-N-(2,4,6-trifluorophenyl) benzamide LC-MS (ESI): mass calcd. for $C_{18}H_{17}F_3N_2O_5S$ 430.08, m/z found 431.1 [M+H]$^+$. $^1$H NMR (400 MHz, DMSO-d6) δ 9.86 (br., s, 1H), 8.18 (d, J=2.5 Hz, 1H), 8.00-7.91 (m, 2H), 7.42 (d, J=8.8 Hz, 1H), 7.34 (t, J=8.5 Hz, 2H), 4.01 (s, 3H), 3.73-3.56 (m, 4H), 3.37 (s, 1H), 1.96-1.84 (m, 1H), 1.66-1.57 (m, 1H).

Compound 77: (S)—N-(3-Chloro-2,4-difluorophenyl)-2-methoxy-5-(N-(tetrahydrofuran-3-yl) sulfamoyl)benzamide LC-MS (ESI): mass calcd. for $C_{18}H_{17}ClF_2N_2O_5S$ 446.05, m/z found 447.0 [M+H]$^+$. 1H NMR (400 MHz, DMSO-d6) δ 10.23 (s, 1H), 8.22 (d, J=2.0 Hz, 1H), 8.02-7.86 (m, 3H), 7.49-7.33 (m, 2H), 4.04 (s, 3H), 3.75-3.53 (m, 4H), 3.39-3.35 (m, 1H), 1.95-1.85 (m, 1H), 1.67-1.57 (m, 1H).

Compound 78: (S)—N-(2-Chloro-4,6-difluorophenyl)-2-methoxy-5-(N-(tetrahydrofuran-3-yl) sulfamoyl)benzamide LC-MS (ESI): mass calcd. for $C_{18}H_{17}ClF_2N_2O_5S$ 446.05, m/z found 447.0 [M+H]$^+$. 1H NMR (400 MHz, DMSO-d6) δ 9.94 (br. s., 1H), 8.19 (d, J=2.5 Hz, 1H), 7.98 (dd, J=2.4, 8.7 Hz, 2H), 7.57-7.46 (m, 2H), 7.43 (d, J=9.0 Hz, 1H), 4.03 (s, 3H), 3.74-3.54 (m, 4H), 3.39-3.36 (m, 1H), 1.96-1.85 (m, 1H), 1.67-1.58 (m, 1H).

Compound 79: (S)-2-Methoxy-N-(1-methyl-1H-pyrazol-3-yl)-5-(N-(tetrahydrofuran-3-yl) sulfamoyl) benzamide LC-MS (ESI): mass calcd. for $C_{16}H_{20}N_4O_5S$ 380.12, m/z found 381.1 [M+H]$^+$. $^1$H NMR (400 MHz, DMSO-d) δ 10.45 (s, 1H), 8.09 (d, J=2.5 Hz, 1H), 7.95-7.88 (m, 2H), 7.62 (d, J=2.2 Hz, 1H), 7.38 (d, J=8.9 Hz, 1H), 6.58 (d, J=2.2 Hz, 1H), 3.99 (s, 3H), 3.77 (s, 3H), 3.71-3.55 (m, 4H), 3.35-3.31 (m, 1H), 1.93-1.86 (m, 1H), 1.65-1.58 (m, 1H).

Compound 80: (S)—N-(4-cyano-2,6-difluorophenyl)-2-methoxy-5-(N-(tetrahydrofuran-3-yl) sulfamoyl)benzamide LC-MS (ESI): mass calcd. for $C_{19}H_{17}F_2N_3O_5S$ 437.09, m/z found 438.1 [M+H]$^+$. $^1$H NMR (400 MHz, DMSO-d$_6$) 10.25 (s, 1H), 8.16 (d, J=1.5 Hz, 1H), 8.00 (dd, J=2.4, 8.8

Hz, 1H), 7.93 (m, 3H), 7.43 (d, J=8.8 Hz, 1H), 4.01 (s, 3H), 3.74-3.60 (m, 4H), 3.39-3.33 (m, 1H), 1.97-1.86 (m, 1H), 1.67-1.57 (m, 1H).

Compound 81: (S)—N-(2,6-Dichlorophenyl)-2-methoxy-5-(N-(tetrahydrofuran-3-yl)sulfamoyl) benzamide LC-MS (ESI): mass calcd. for $C_{18}H_{18}Cl_2N_2O_5S$ 444.03, m/z found 445.1 [M+H]$^+$. $^1$H NMR (400 MHz, DMSO-d$_6$) δ 10.11 (br.s, 1H), 8.18 (d, J=2.8 Hz, 1H), 7.97 (dd, J=2.4 Hz, J=8.8 Hz, 2H), 7.59 (d, J=8.0 Hz, 2H), 7.45-7.35 (m, 2H), 4.02 (s, 3H), 3.74-3.54 (m, 4H), 3.40-3.30 (m, 1H), 1.96-1.85 (m, 1H), 1.68-1.56 (m, 1H).

Compound 82: (S)-2-methoxy-N-(4-methylthiazol-2-yl)-5-(N-(tetrahydrofuran-3-yl)sulfamoyl) benzamide LC-MS (ESI): mass calcd. for $C_{16}H_{19}N_3O_5S_2$ 397.47, m/z found 398.0 [M+H]$^+$, reverse phase $^1$H NMR (400 MHz, DMSO-d$_6$) δ 12.02 (s, 1H), 8.05 (d, J=2.0 Hz, 1H), 7.89-7.98 (m, 2H), 7.40 (d, J=8.8 Hz, 1H), 6.85 (s, 1H), 3.98 (s, 3H), 3.65-3.74 (m, 2H), 3.54-3.64 (m, 2H), 3.35-3.38 (m, 1H), 2.29 (s, 3H), 1.85-1.96 (m, 1H), 1.57-1.67 (m, 1H).

Compound 83: (S)—N-(4,5-dimethylthiazol-2-yl)-2-methoxy-5-(N-(tetrahydrofuran-3-yl) sulfamoyl) benzamide LC-MS (ESI): R$_T$=4.12 min, mass calcd. for $C_{17}H_{21}N_3O_5S_2$ 411.50, m/z found 412.1 [M+H]$^+$. $^1$H NMR (400 MHz, DMSO-d$_6$) δ 11.83 (s, 1H), 8.04 (d, J=2.4 Hz, 1H), 7.88-7.98 (m, 2H), 7.39 (d, J=8.8 Hz, 1H), 3.98 (s, 3H), 3.65-3.73 (m, 2H), 3.54-3.64 (m, 2H), 3.35-3.38 (m, 1H), 2.28 (s, 3H), 2.19 (s, 3H), 1.85-1.97 (m, 1H), 1.57-1.66 (m, 1H).

Compound 84: (S)-2-methoxy-N-(5-methylthiazol-2-yl)-5-(N-(tetrahydrofuran-3-yl)sulfamoyl) benzamide LC-MS (ESI): R$^T$=3.95 min, mass calcd. for $C_{16}H_{19}N_3O_5S_2$ 397.47, m/z found 398.1 [M+H]$^+$. $^1$H NMR (400 MHz, DMSO-d$_6$) δ 11.94 (s, 1H), 8.04 (d, J=2.4 Hz, 1H), 7.89-7.98 (m, 2H), 7.40 (d, J=8.8 Hz, 1H), 7.21 (s, 1H), 3.98 (s, 3H), 3.65-3.73 (m, 2H), 3.55-3.64 (m, 2H), 3.35-3.38 (m, 1H), 2.39 (s, 3H), 1.85-1.95 (m, 1H), 1.57-1.67 (m, 1H).

Compound 85: (S)—N-(2,4-Dichlorophenyl)-2-methoxy-5-(N-(tetrahydrofuran-3-yl)sulfamoyl) benzamide LC-MS (ESI): mass calcd. for $C_{18}H_{18}Cl_2N_2O_5S$ 444.03, m/z found 445.1 [M+H]$^+$. $^1$H NMR (400 MHz, DMSO-d$_6$) δ 10.50 (br.s, 1H), 8.44 (d, J=2.4 Hz, 1H), 8.39 (d, J=8.8 Hz, 1H), 8.05-7.95 (m, 2H), 7.77 (d, J=2.4 Hz, 1H), 7.50 (dd, J=2.0 Hz, J=9.2 Hz, 2H), 4.15 (s, 3H), 3.74-3.54 (m, 4H), 3.40-3.30 (m, 1H), 1.96-1.85 (m, 1H), 1.68-1.56 (m, 1H).

Compound 86: (S)—N-(3,5-Dichlorophenyl)-2-methoxy-5-(N-(tetrahydrofuran-3-yl)sulfamoyl) benzamide LC-MS (ESI): mass calcd. for $C_{18}H_{18}Cl_2N_2O_5S$ 444.03, m/z found 445.0 [M+H]$^+$. $^1$H NMR (400 MHz, DMSO-d$_6$) δ 10.56 (br.s, 1H), 8.00 (d, J=2.4 Hz, 1H), 7.98-7.90 (m, 2H), 7.82 (d, J=1.6 Hz, 2H), 7.40 (d, J=8.8 Hz, 1H), 7.36 (t, J=1.6 Hz, 1H), 3.98 (s, 3H), 3.74-3.54 (m, 4H), 3.40-3.30 (m, 1H), 1.96-1.85 (m, 1H), 1.68-1.56 (m, 1H).

Compound 87: (S)—N-(3-Cyano-5-fluorophenyl)-2-methoxy-5-(N-(tetrahydrofuran-3-yl) sulfamoyl) benzamide LC-MS (ESI): mass calcd. for $C_{19}H_{18}FN_3O_5S$ 419.10, m/z found 420.1 [M+H]$^+$. $^1$H NMR (400 MHz, DMSO-d$_6$) δ 10.73 (br.s, 1H), 8.10-7.90 (m, 5H), 7.62 (d, J=8.4 Hz, 1H), 7.41 (d, J=8.8 Hz, 1H), 3.98 (s, 3H), 3.74-3.54 (m, 4H), 3.40-3.30 (m, 1H), 1.96-1.85 (m, 1H), 1.68-1.56 (m, 1H).

Compound 88: (S)-2-Methoxy-5-(N-(tetrahydrofuran-3-yl)sulfamoyl)-N-(2,3,4-trifluorophenyl) benzamide LC-MS (ESI): mass calcd. for $C_{18}H_{17}F_3N_2O_5S$ 430.08, m/z found 431.1 [M+H]$^+$. $^1$H NMR (400 MHz, DMSO-d$_6$) δ 10.24 (br.s, 1H), 8.20 (d, J=2.4 Hz, 1H), 8.02-7.92 (m, 2H), 7.80-7.70 (m, 1H), 7.43 (d, J=8.8 Hz, 1H), 7.42-7.32 (m, 1H), 4.04 (s, 3H), 3.74-3.54 (m, 4H), 3.40-3.30 (m, 1H), 1.96-1.85 (m, 1H), 1.68-1.56 (m, 1H).

Compound 89: (S)—N-(3-Chloro-4-cyanophenyl)-2-methoxy-5-(N-(tetrahydrofuran-3-yl) sulfamoyl) benzamide LC-MS (ESI): mass calcd. for $C_{19}H_{18}ClN_3O_5S$ 435.07, m/z found 436.0 [M+H]$^+$. $^1$H NMR (400 Hz, DMSO-d$_6$) δ 10.83 (br.s, 1H), 8.15 (d, J=2.0 Hz, 1H), 8.02-7.88 (m, 4H), 7.80 (dd, J=2.0 Hz, J=8.4 Hz, 1H), 7.41 (d, J=8.8 Hz, 1H), 3.97 (s, 3H), 3.74-3.54 (m, 4H), 3.40-3.30 (m, 1H), 1.96-1.85 (m, 1H), 1.68-1.56 (m, 1H).

Compound 90: (S)—N-(4-Cyano-3-fluorophenyl-2-methoxy-5-(N-(tetrahydrofuran-3-yl) sulfamoyl) benzamide LC-MS (ESI): mass calcd. for $C_{19}H_{18}FN_3O_5S$ 419.10, m/z found 420.1 [M+H]$^+$. $^1$H NMR (400 MHz, DMSO-d$_6$) δ 10.89 (br.s, 1H), 8.02-7.84 (m, 5H), 7.63 (d, J=8.8 Hz, 1H), 7.41 (d, J=8.8 Hz, 1H), 3.96 (s, 3H), 3.74-3.54 (m, 4H), 3.40-3.30 (m, 1H), 1.96-1.85 (m, 1H), 1.68-1.56 (m, 1H).

Compound 91: (S)—N-(4-Chloro-2,6-difluorophenyl)-2-methoxy-5-(N-(tetrahydrofuran-3-yl) sulfamoyl)benzamide LC-MS (ESI): mass calcd. for $C_{18}H_{17}ClF_2N_2O_5S$ 446.05, m/z found 447.0 [M+H]$^+$. $^1$H NMR (400 MHz, DMSO-d$_6$) δ 9.95 (br.s, 1H), 8.17 (d, J=2.4 Hz, 1H), 8.02-7.92 (m, 2H), 7.52 (d, J=7.6 Hz, 2H), 7.42 (d, J=9.2 Hz, 1H), 4.01 (s, 3H), 3.74-3.54 (m, 4H), 3.40-3.30 (m, 1H), 1.96-1.85 (m, 1H), 1.68-1.56 (m, 1H).

Compound 92: (S)—N-(3-Cyano-2-fluorophenyl)-2-methoxy-5-(N-(tetrahydrofuran-3-yl) sulfamoyl) benzamide LC-MS (ESI): mass calcd. for $C_{19}H_{18}FN_3O_5S$ 419.10, m/z found 420.1 [M+H]$^+$. $^1$H NMR (400 MHz, DMSO-d$_6$) δ 10.39 (br.s, 1H), 8.35 (t, J=7.6 Hz, 1H), 8.23 (d, J=2.0 Hz, 1H), 8.10-7.94 (m, 2H), 7.80-7.70 (m, 1H), 7.50-7.40 (m, 2H), 4.06 (s, 3H), 3.74-3.54 (m, 4H), 3.40-3.30 (m, 1H), 1.96-1.85 (m, 1H), 1.68-1.56 (m, 1H).

Compound 93: (S)—N-(3-Chloro-2,6-difluorophenyl)-2-methoxy-5-(N-(tetrahydrofuran-3-yl) sulfamoyl)benzamide LC-MS (ESI): mass calcd. for $C_{18}H_{17}ClF_2N_2O_5S$ 446.05, m/z found 447.1 [M+H]$^+$. $^1$H NMR (400 MHz, DMSO-d$_6$) δ 10.07 (br.s, 1H), 8.18 (d, J=2.4 Hz, 1H), 8.05-7.90 (m, 2H), 7.70-7.60 (m, 1H), 7.43 (d, J=8.8 Hz, 1H), 7.32 (t, J=8.4 Hz, 1H), 4.02 (s, 3H), 3.74-3.54 (m, 4H), 3.40-3.30 (m, 1H), 1.96-1.85 (m, 1H), 1.68-1.56 (m, 1H).

Compound 94: (S)—N-(3-Chloro-5-cyanophenyl)-2-methoxy-5-(N-(tetrahydrofuran-3-yl) sulfamoyl) benzamide LC-MS (ESI): mass calcd. for $C_{19}H_{18}ClN_3O_5S$ 435.07, m/z found 436.0 [M+H]$^+$. $^1$H NMR (400 MHz, DMSO-d$_6$) δ 10.69 (br.s, 1H), 8.16 (t, J=2.0 Hz, 1H), 8.11 (t, J=1.6 Hz, 1H), 8.03 (d, J=2.4 Hz, 1H), 8.00-7.90 (m, 2H), 7.79 (dd, J=1.2 Hz, J=2.0 Hz, 1H), 7.41 (d, J=8.8 Hz, 1H), 3.98 (s, 3H), 3.74-3.54 (m, 4H), 3.40-3.30 (m, 1H), 1.96-1.85 (m, 1H), 1.68-1.56 (m, 1H).

Compound 95: (S)—N-(3-Cyano-4-fluorophenyl)-2-methoxy-5-(N-(tetrahydrofuran-3-yl) sulfamoyl) benzamide LC-MS (ESI): mass calcd. for $C_{19}H_{18}FN_3O_5S$ 419.10, m/z found 420.1 [M+H]$^+$. $^1$H NMR (400 MHz, DMSO-d$_6$) δ 10.59 (br.s, 1H), 8.26-8.20 (m, 1H), 8.08-8.00 (m, 2H), 8.00-7.90 (m, 2H), 7.56 (t, J=9.2 Hz, 1H), 7.40 (d, J=8.8 Hz, 1H), 3.98 (s, 3H), 3.74-3.54 (m, 4H), 3.40-3.30 (m, 1H), 1.96-1.85 (m, 1H), 1.68-1.56 (m, 1H).

Compound 96: (S)—N-(2-Chloro-3,5-difluorophenyl)-2-methoxy-5-(N-(tetrahydrofuran-3-yl) sulfamoyl)benzamide LC-MS (ESI): mass calcd. for $C_{18}H_{17}ClF_2N_2O_5S$ 446.05, m/z found 447.1 [M+H]$^+$. $^1$H NMR (400 MHz, DMSO-d$_6$) δ 10.68 (br.s, 1H), 8.45 (d, J=2.8 Hz, 1H), 8.19 (d, J=10.8 Hz, 1H), 8.06-8.00 (m, 2H), 7.52 (d, J=9.2 Hz, 1H), 7.40-7.30 (m, 1H), 4.17 (s, 3H), 3.74-3.54 (m, 4H), 3.40-3.30 (m, 1H), 1.96-1.85 (m, 1H), 1.68-1.56 (m, 1H).

Compound 97: (S)-2-Methoxy-5-(N-(tetrahydrofuran-3-yl)sulfamoyl)-N-(3,4,5-trifluorophenyl) benzamide LC-MS (ESI): mass calcd. for $C_{18}H_{17}F_3N_2O_5S$ 430.08, m/z found 431.1 [M+H]$^+$. $^1$H NMR (400 MHz, DMSO-d$_6$) δ 10.58 (br.s, 1H), 8.02-7.88 (m, 3H), 7.66 (dd, J=6.4 Hz, J=10.4 Hz, 2H), 7.40 (d, J=8.8 Hz, 1H), 3.97 (s, 3H), 3.74-3.54 (m, 4H), 3.40-3.30 (m, 1H), 1.96-1.85 (m, 1H), 1.68-1.56 (m, 1H).

Compound 98: (S)—N-(4-Cyano-2,5-difluorophenyl)-2-methoxy-5-(N-(tetrahydrofuran-3-yl) sulfamoyl)benzamide LC-MS (ESI): mass calcd. for $C_{19}H_{17}F_2N_3O_5S$ 437.09, m/z found 438.1 [M+H]$^+$. $^1$H NMR (400 MHz, DMSO-d$_6$) δ 10.69 (br.s, 1H), 8.41 (dd, J=6.0 Hz, J=11.2 Hz, 1H), 8.25 (d, J=2.8 Hz, 1H), 8.13 (dd, J=6.0 Hz, J=10.8 Hz, 1H), 8.05-7.95 (m, 2H), 7.47 (d, J=9.2 Hz, 1H), 4.06 (s, 3H), 3.74-3.54 (m, 4H), 3.40-3.30 (m, 1H), 1.96-1.85 (m, 1H), 1.68-1.56 (m, 1H).

Compound 99: (S)—N-(2-Fluorophenyl)-2-methoxy-5-(N-(tetrahydrofuran-3-yl)sulfamoyl) benzamide LC-MS (ESI): mass calcd. for $C_{18}H_{19}FN_2O_5S$ 394.10, m/z found 395.1 [M+H]$^+$. $^1$H NMR (400 MHz, DMSO-d$_6$) δ 10.19 (s, 1H), 8.28 (d, J=2.4 Hz, 1H), 8.15-8.06 (m, 1H), 8.12-7.90 (m, 2H), 7.45 (d, J=8.8 Hz, 1H), 7.38-7.30 (m, 1H), 7.28-7.17 (m, 2H), 4.07 (s, 3H), 3.75-3.66 (m, 2H), 3.65-3.54 (m, 2H), 3.42-3.38 (m, 1H), 1.97-1.84 (m, 1H), 1.68-1.55 (m, 1H).

Compound 100: (S)—N-(3-Fluorophenyl)-2-methoxy-5-(N-(tetrahydrofuran-3-yl)sulfamoyl) benzamide LC-MS (ESI): mass calcd. for $C_{18}H_{19}FN_2O_5S$ 394.10, m/z found 395.1 [M+H]$^+$. $^1$H NMR (400 MHz, DMSO-d$_6$) δ 10.46 (s, 1H), 7.99 (d, J=2.4 Hz, 1H), 7.96-7.89 (m, 2H), 7.75-7.68 (m, 1H), 7.47 (d, J=8.7 Hz, 1H), 7.43-7.36 (m, 2H), 6.98-6.93 (m, 1H), 3.97 (s, 3H), 3.75-3.64 (m, 2H), 3.63-3.55 (m, 2H), 3.39-3.36 (m, 1H), 1.96-1.85 (m, 1H), 1.68-1.55 (m, 1H).

Compound 101: (S)-2-Methoxy-5-(N-(tetrahydrofuran-3-yl)sulfamoyl)-N-(4-(trifluoromethyl) phenyl)benzamide LC-MS (ESI): mass calcd. for $C_{19}H_{19}F_3N_2O_5S$ 444.10, m/z found 444.9 [M+H]$^+$. $^1$H NMR (400 MHz, DMSO-d$_6$) δ 10.60 (s, 1H), 8.02-7.86 (m, 5H), 7.77-7.70 (m, 2H), 7.40 (d, J=8.8 Hz, 1H), 3.97 (s, 3H), 3.74-3.66 (m, 2H), 3.64-3.55 (m, 2H), 3.41-3.38 (m, 1H), 1.96-1.86 (m, 1H), 1.68-1.58 (m, 1H).

Compound 102: (S)—N-(3-cyanophenyl)-2-methoxy-5-(N-(tetrahydrofuran-3-yl)sulfamoyl) benzamide LC-MS (ESI): mass calcd. for $C_{19}H_{19}N_3O_5S$ 401.10, m/z found 402.0 [M+H]$^+$. $^1$H NMR (400 MHz, DMSO-d$_6$) δ 10.57 (s, 1H), 8.21 (s, 1H), 8.02 (d, J=2.4 Hz, 1H), 8.01-7.89 (m, 3H), 7.59-7.57 (m, 2H), 7.40 (d, J=8.9 Hz, 1H), 3.98 (s, 3H), 3.74-3.67 (m, 2H), 3.65-3.57 (m, 2H), 3.37 (dd, J=8.7, 4.2 Hz, 1H), 1.97-1.86 (m, 1H), 1.68-1.61 (m, 1H).

Compound 103: (S)—N-(2-Chloro-6-fluorophenyl)-2-methoxy-5-(N-(tetrahydrofuran-3-yl) sulfamoyl) benzamide LC-MS (ESI): mass calcd. for $C_{18}H_{18}ClFN_2O_5S$ 428.06, m/z found 429.0 [M+H]$^+$. $^1$H NMR (400 MHz, DMSO-d$_6$) δ 9.97 (s, 1H), 8.20 (d, J=2.4 Hz, 1H), 8.01-7.96 (m, 2H), 7.49-7.30 (m, 4H), 4.03 (s, 3H), 3.73-3.66 (m, 2H), 3.65-3.54 (m, 2H), 3.40-3.37 (m, 1H), 1.96-1.87 (m, 1H), 1.68-1.57 (m, 1H).

Compound 104: (S)—N-(4-Cyanophenyl)-2-methoxy-5-(N-(tetrahydrofuran-3-yl)sulfamoyl) benzamide LC-MS (ESI): mass calcd. for $C_{19}H_{19}N_3O_5S$ 401.10, m/z found 401.9 [M+H]$^+$. $^1$H NMR (400 MHz, DMSO-d) δ

10.68 (s, 1H), 8.01-7.88 (m, 5H), 7.85-7.81 (m, 2H), 7.40 (d, J=8.8 Hz, 1H), 3.97 (s, 3H), 3.74-3.67 (m, 2H), 3.66-3.55 (m, 2H), 3.38-3.35 (m, 1H), 1.97-1.86 (m, 1H), 1.67-1.58 (m, 1H).

Compound 105: (S)—N-(2,6-Difluorophenyl)-2-methoxy-5-(N-(tetrahydrofuran-3-yl)sulfamoyl) benzamide LC-MS (ESI): mass calcd. for $C_{18}H_{18}F_2N_2O_5S$ 412.09, m/z found 413.1 [M+H]$^+$. $^1$H NMR (400 MHz, DMSO-d$_6$) δ 9.91 (s, 1H), 8.18 (d, J=2.4 Hz, 1H), 8.01-7.91 (m, 2H), 7.47-7.36 (m, 2H), 7.27-7.15 (m, 2H), 4.02 (s, 3H), 3.73-3.65 (m, 2H), 3.64-3.54 (m, 2H), 3.38-3.35 (m, 1H), 1.95-1.85 (m, 1H), 1.66-1.56 (m, 1H).

Compound 106: (S)—N-(4-(Difluoromethoxy)phenyl)-2-methoxy-5-(N-(tetrahydrofuran-3-yl) sulfamoyl)benzamide LC-MS (ESI): mass calcd. for $C_{19}H_{20}F_2N_2O_6S$ 442.10, m/z found 443.0 [M+H]$^+$. $^1$H NMR (400 MHz, DMSO-d$_6$) δ 10.34 (br.s, 1H), 8.00 (d, J=2.2 Hz, 1H), 7.95-7.90 (m, 2H), 7.78-7.73 (m, 2H), 7.41-7.35 (m, 1H), 7.21-7.16 (m, 3H), 3.97 (s, 3H), 3.73-3.66 (m, 2H), 3.64-3.56 (m, 2H), 3.50-3.44 (m, 1H), 1.96-1.87 (m, 1H), 1.66-1.58 (m, 1H).

Compound 107: (S)—N-(3-(Difluoromethoxy)phenyl)-2-methoxy-5-(N-(tetrahydrofuran-3-yl) sulfamoyl)benzamide LC-MS (ESI): mass calcd. for $C_{19}H_{20}F_2N_2O_6S$ 442.10, m/z found 442.9 [M+H]$^+$. $^1$H NMR (400 MHz, DMSO-d$_6$) δ 10.44 (br.s, 1H), 7.98 (d, J=2.4 Hz, 1H), 7.96-7.87 (m, 2H), 7.73-7.67 (m, 1H), 7.53 (d, J=8.3 Hz, 1H), 7.43-7.37 (m, 2H), 7.23 (s, 1H), 6.93 (dd, J=2.0, 8.1 Hz, 1H), 3.97 (s, 3H), 3.70-3.57 (m, 4H), 3.39-3.38 (m, 1H), 1.94-1.86 (m, 1H), 1.66-1.59 (m, 1H).

Compound 108: (S)—N-(4-Chlorophenyl)-2-methoxy-5-(N-(tetrahydrofuran-3-yl)sulfamoyl) benzamide LC-MS (ESI): mass calcd. for $C_{18}H_{19}ClN_2O_5S$ 410.07, m/z found 411.0 [M+H]$^+$. $^1$H NMR (400 MHz, DMSO-d$_6$) δ 10.38 (br.s, 1H), 7.99 (d, J=2.4 Hz, 1H), 7.95-7.89 (m, 2H), 7.79-7.73 (m, 2H), 7.44-7.36 (m, 3H), 3.96 (s, 3H), 3.73-3.66 (m, 2H), 3.62-3.55 (m, 2H), 3.38-3.38 (m, 1H), 1.95-1.85 (m, 1H), 1.66-1.59 (m, 1H).

Compound 109: (S)-2-Methoxy-5-(N-(tetrahydrofuran-3-yl)sulfamoyl)-N-(3-(trifluoromethyl) phenyl)benzamide LC-MS (ESI): mass calcd. for $C_{19}H_{19}F_3N_2O_5S$ 444.10, m/z found 445.0 [M+H]$^+$. $^1$H NMR (400 MHz, DMSO-d) δ 10.58 (br. s., 1H), 8.21 (s, 1H), 8.01 (d, J=2.2 Hz, 1H), 7.97-7.87 (m, 3H), 7.61 (t, J=7.9 Hz, 1H), 7.48 (d, J=7.6 Hz, 1H), 7.40 (d, J=8.8 Hz, 1H), 3.97 (s, 3H), 3.72-3.66 (m, 2H), 3.63-3.57 (m, 2H), 3.41 (br. s, 1H), 1.96-1.88 (m, 1H), 1.67-1.59 (m, 1H).

Compound 110: (S)-2-Methoxy-N-(1-methyl-1H-indazol-4-yl)-5-(N-(tetrahydrofuran-3-yl) sulfamoyl) benzamide LC-MS (ESI): mass calcd. for $C_{20}H_{22}N_4O_5S$ 430.13, m/z found 431.1 [M+H]$^+$. $^1$H NMR (400 MHz, DMSO-d$_6$) δ 10.43 (s, 1H), 8.21 (s, 1H), 8.12 (d, J=2.0 Hz, 1H), 7.99-7.90 (m, 2H), 7.84 (d, J=4.5 Hz, 1H), 7.46-7.34 (m, 3H), 4.04 (s, 3H), 4.04 (s, 3H), 3.74-3.66 (m, 2H), 3.66-3.55 (m, 2H), 3.42-3.39 (m, 1H), 1.98-1.85 (m, 1H), 1.70-1.59 (m, 1H).

Compound 111: (S)—N-(3,4-Difluorophenyl)-2-methoxy-5-(N-(tetrahydrofuran-3-yl)sulfamoyl) benzamide LC-MS (ESI): mass calcd. for $C_{18}H_{18}F_2N_2O_5S$ 412.09, m/z found 413.1 [M+H]$^+$. $^1$H NMR (400 MHz, DMSO-d$_6$) δ 10.46 (s, 1H), 8.00 (d, J=2.5 Hz, 1H), 7.96-7.86 (m, 3H), 7.51-7.42 (m, 2H), 7.39 (d, J=9.0 Hz, 1H), 3.97 (s, 3H), 3.74-3.65 (m, 2H), 3.65-3.55 (m, 2H), 3.42-3.39 (m, 1H), 1.96-1.85 (m, 1H), 1.68-1.57 (m, 1H).

Compound 112: (S)—N-(3-Chloro-4-fluorophenyl)-2-methoxy-5-(N-(tetrahydrofuran-3-yl) sulfamoyl) benzamide LC-MS (ESI): mass calcd. for $C_{18}H_{18}ClFN_2O_5S$ 428.06, m/z found 429.0 [M+H]$^+$. $^1$H NMR (400 MHz, DMSO-d$_6$) δ 10.45 (s, 1H), 8.04 (dd, J=2.5, 7.0 Hz, 1H), 8.00 (d, J=2.5 Hz, 1H), 7.97-7.89 (m, 2H), 7.70-7.62 (m, 1H), 7.47-7.36 (m, 2H), 3.97 (s, 3H), 3.74-3.65 (m, 2H), 3.65-3.55 (m, 2H), 3.36-3.34 (m, 1H), 1.96-1.85 (m, 1H), 1.68-1.58 (m, 1H).

Compound 113: (S)—N-(2,3-Difluorophenyl)-2-methoxy-5-(N-(tetrahydrofuran-3-yl)sulfamoyl) benzamide LC-MS (ESI): mass calcd. for $C_{18}H_{18}F_2N_2O_5S$ 412.09, m/z found 429.0 [M+H]$^+$. $^1$H NMR (400 MHz, DMSO-d$_6$) δ 10.30 (s, 1H), 8.23 (d, J=2.0 Hz, 1H), 8.03-7.91 (m, 2H), 7.87-7.77 (m, 1H), 7.44 (d, J=8.5 Hz, 1H), 7.32-7.20 (m, 2H), 4.05 (s, 3H), 3.74-3.65 (m, 2H), 3.64-3.54 (m, 2H), 3.42-3.39 (m, 1H), 1.95-1.85 (m, 1H), 1.67-1.57 (m, 1H).

Compound 114: (S)—N-(4-Chloro-2-fluorophenyl)-2-methoxy-5-(N-(tetrahydrofuran-3-yl) sulfamoyl) benzamide LC-MS (ESI): mass calcd. for $C_{18}H_{18}ClFN_2O_5S$ 428.06, m/z found 429.1 [M+H]$^+$. $^1$H NMR (400 MHz, DMSO-d$_6$) δ 10.23 (s, 1H), 8.25 (d, J=2.5 Hz, 1H), 8.10 (t, J=8.8 Hz, 1H), 8.01-7.87 (m, 2H), 7.58 (dd, J=2.0, 10.5 Hz, 1H), 7.44 (d, J=9.0 Hz, 1H), 7.34 (d, J=8.5 Hz, 1H), 4.05 (s, 3H), 3.74-3.64 (m, 2H), 3.64-3.54 (m, 2H), 3.35-3.33 (m, 1H), 1.95-1.84 (m, 1H), 1.67-1.57 (m, 1H).

Compound 115: (S)—N-(4-Chloro-3-fluorophenyl)-2-methoxy-5-(N-(tetrahydrofuran-3-yl) sulfamoyl) benzamide LC-MS (ESI): mass calcd. for $C_{18}H_{18}ClFN_2O_5S$ 428.06, m/z found 428.9 [M+H]$^+$. $^1$H NMR (400 MHz, DMSO-d$_6$) δ 10.57 (s, 1H), 7.99 (d, J=2.5 Hz, 1H), 7.97-7.86 (m, 3H), 7.60-7.54 (m, 1H), 7.54-7.49 (m, 1H), 7.39 (d, J=8.5 Hz, 1H), 3.96 (s, 3H), 3.74-3.64 (m, 2H), 3.64-3.55 (m, 2H), 3.36-3.34 (m, 1H), 1.96-1.85 (m, 1H), 1.67-1.57 (m, 1H).

Compound 116: (S)—N-(5-Fluoropyridin-2-yl)-2-methoxy-5-(N-(tetrahydrofuran-3-yl)sulfamoyl) benzamide LC-MS (ESI): mass calcd. for $C_{17}H_{18}FN_3O_5S$ 395.10, m/z found 396.1 [M+H]$^+$. $^1$H NMR (400 MHz, DMSO-d$_6$)

δ 10.70 (br.s, 1H), 8.39 (d, J=3.2 Hz, 1H), 8.28 (dd, J=4.0, 9.2 Hz, 1H), 8.16 (d, J=2.4 Hz, 1H), 8.00-7.90 (m, 2H), 7.83 (td, J=3.2, 8.8 Hz, 1H), 7.42 (d, J=8.8 Hz, 1H), 4.03 (s, 3H), 3.74-3.54 (m, 4H), 3.40-3.30 (m, 1H), 1.96-1.85 (m, 1H), 1.68-1.56 (m, 1H).

Compound 117: (S)—N-(5-Fluoropyrimidin-2-yl)-2-methoxy-5-(N-(tetrahydrofuran-3-yl) sulfamoyl) benzamide LC-MS (ESI): mass calcd. for $C_{16}H_{17}FN_4O_5S$ 396.09, m/z found 397.0 $[M+H]^+$. $^1H$ NMR (400 MHz, DMSO-$d_6$) δ 11.02 (br.s, 1H), 8.77 (s, 2H), 7.98 (d, J=2.4 Hz, 1H), 7.92 (dd, J=2.4, 8.4 Hz, 2H), 7.34 (d, J=8.8 Hz, 1H), 3.90 (s, 3H), 3.74-3.54 (m, 4H), 3.40-3.30 (m, 1H), 1.96-1.85 (m, 1H), 1.68-1.56 (m, 1H).

Compound 118: (S)—N-(3,5-Difluoropyridin-2-yl)-2-methoxy-5-(N-(tetrahydrofuran-3-yl) sulfamoyl) benzamide LC-MS (ESI): mass calcd. for $C_{17}H_{17}F_2N_3O_5S$ 413.09, m/z found 414.1 $[M+H]^+$. $^1H$ NMR (400 MHz, DMSO-$d_6$) δ 10.49 (brs, 1H), 8.40 (d, J=2.0 Hz, 1H), 8.17-8.05 (m, 2H), 8.00-7.91 (m, 2H), 7.40 (d, J=8.0, 1H), 3.98 (s, 3H), 3.74-3.55 (m, 4H), 3.40-3.30 (m, 1H), 1.96-1.85 (m, 1H), 1.67-1.57 (m, 1H).

Compound 119: ((S)—N-(3-Chloro-5-fluoropyridin-2-yl)-2-methoxy-5-(N-(tetrahydrofuran-3-yl) sulfamoyl)benzamide LC-MS (ESI): mass calcd. for $C_{17}H_{17}ClFN_3O_5S$ 429.06, m/z found 430.0 $[M+H]^+$. $^1H$ NMR (400 MHz, DMSO-$d_6$) δ 10.49 (br. s., 1H), 8.50 (d, J=2.5 Hz, 1H), 8.25 (dd, J=2.5, 8.0 Hz, 1H), 8.17 (d, J=2.5 Hz, 1H), 7.96 (dd, J=2.3, 8.8 Hz, 2H), 7.40 (d, J=8.5 Hz, 1H), 4.00 (s, 3H), 3.74-3.54 (m, 4H), 3.39-3.35 (m, 1H), 1.96-1.85 (m, 1H), 1.62 (dt, J=6.3, 12.4 Hz, 1H).

Compound 120: (S)—N-(5-Chloro-3-fluoropyridin-2-yl)-2-methoxy-5-(N-(tetrahydrofuran-3-yl) sulfamoyl)benzamide LC-MS (ESI): mass calcd. for $C_{17}H_{17}ClFN_3O_5S$ 429.06, m/z found 430.0 $[M+H]^+$. $^1H$ NMR (400 MHz, DMSO-$d_6$) δ 10.58 (br. s., 1H), 8.42-8.36 (m, 1H), 8.21 (d, J=9.5 Hz, 1H), 8.10 (br. s., 1H), 8.00-7.89 (m, 2H), 7.39 (d, J=9.0 Hz, 1H), 3.97 (br. s., 3H), 3.73-3.56 (m, 4H), 3.37 (br. s., 1H), 1.89 (d, J=5.5 Hz, 1H), 1.62 (d, J=6.0 Hz, 1H).

Compound 121: (S)—N-(3-Chloropyridin-2-yl)-2-methoxy-5-(N-(tetrahydrofuran-3-yl)sulfamoyl) benzamide LC-MS (ESI): mass calcd. for $C_{17}H_{18}ClN_3O_5S$ 411.07, m/z found 412.1 $[M+H]^+$. $^1H$ NMR (400 MHz, DMSO-$d_6$) δ 10.52 (s, 1H), 8.41 (dd, J=1.4, 4.8 Hz, 1H), 8.18 (d, J=2.4 Hz, 1H), 8.06 (dd, J=1.4, 8.0 Hz, 1H), 7.96 (dd, J=2.4, 8.8 Hz, 2H), 7.43-7.32 (m, 2H), 4.00 (s, 3H), 3.73-3.55 (m, 4H), 3.39-3.35 (m, 1H), 1.95-1.84 (m, 1H), 1.62 (dt, J=5.4, 12.4 Hz, 1H).

Compound 122: (S)—N-(4-Fluorophenyl)-2-methoxy-5-(N-(tetrahydrofuran-3-yl)sulfamoyl) benzamide LC-MS (ESI): mass calcd. for $C_{18}H_{19}FN_2O_5S$ 394.10, m/z found 395.1 $[M+H]^+$. $^1H$ NMR (400 MHz, DMSO-$d_6$) δ 10.30 (brs, 1H), 8.00 (d, J=2.3 Hz, 1H), 7.96-7.88 (m, 2H), 7.80-7.71 (m, 2H), 7.38 (d, J=8.8 Hz, 1H), 7.20 (t, J=8.9 Hz, 2H), 3.97 (s, 3H), 3.74-3.54 (m, 4H), 3.39-3.35 (m, 1H), 1.97-1.84 (m, 1H), 1.68-1.58 (m, 1H).

Compound 123: (S)—N-(2-Bromophenyl)-2-methoxy-5-(N-(tetrahydrofuran-3-yl)sulfamoyl) benzamide LC-MS (ESI): mass calcd. for $C_{18}H_{19}BrN_2O_5S$ 454.02, m/z found 454.9 $[M+H]^+$. $^1H$ NMR (400 MHz, DMSO-$d_6$) δ 10.42 (s, 1H), 8.48 (d, J=2.4 Hz, 1H), 8.37 (d, J=8.0 Hz, 1H), 8.02 (dd, J=2.4, 8.8 Hz, 1H), 7.73 (dd, J=1.4, 8.0 Hz, 1H), 7.51 (d, J=8.8 Hz, 1H), 7.44 (t, J=7.8 Hz, 1H), 7.14 (dt, J=1.4, 7.8 Hz, 1H), 4.18 (s, 3H), 3.73-3.55 (m, 4H), 3.38-3.36 (m, 1H), 1.97-1.82 (m, 1H), 1.68-1.56 (m, 1H).

Compound 124: (S)—N-(3-Bromophenyl)-2-methoxy-5-(N-(tetrahydrofuran-3-yl)sulfamoyl) benzamide LC-MS (ESI): mass calcd. for $C_{18}H_{19}BrN_2O_5S$ 454.02, m/z found 455.0 $[M+H]^+$. $^1H$ NMR (400 MHz, DMSO-$d_6$) δ 10.40 (s, 1H), 8.08-8.04 (m, 1H), 7.99 (d, J=2.4 Hz, 1H), 7.95-7.88 (m, 2H), 7.67 (td, J=2.4, 6.8 Hz, 1H), 7.39 (d, J=8.4 Hz, 1H), 7.35-7.28 (m, 2H), 3.97 (s, 3H), 3.74-3.65 (m, 2H), 3.64-3.55 (m, 2H), 3.40-3.34 (m, 1H), 1.96-1.85 (m, 1H), 1.68-1.58 (m, 1H).

Compound 125: (S)—N-(4-Bromophenyl)-2-methoxy-5-(N-(tetrahydrofuran-3-yl)sulfamoyl) benzamide LC-MS (ESI): mass calcd. for $C_{18}H_{19}BrN_2O_5S$ 454.02, m/z found 455.0 $[M+H]^+$. $^1H$ NMR (400 MHz, DMSO-$d_6$) δ 10.37 (s, 1H), 8.02-7.97 (m, 1H), 7.95-7.88 (m, 2H), 7.74-7.67 (m, 2H), 7.57-7.51 (m, 2H), 7.38 (d, J=9.0 Hz, 1H), 3.96 (s, 3H), 3.74-3.54 (m, 4H), 3.40-3.34 (m, 1H), 1.96-1.85 (m, 1H), 1.68-1.58 (m, 1H).

Compound 126: (S)—N-(3-Chlorophenyl)-2-methoxy-5-(N-(tetrahydrofuran-3-yl)sulfamoyl) benzamide LC-MS (ESI): mass calcd. for $C_{18}H_{19}ClN_2O_5S$ 410.07, m/z found 410.9 $[M+H]^+$. $^1H$ NMR (400 MHz, DMSO-$d_6$) δ 10.43 (br.s, 1H), 7.99 (d, J=2.2 Hz, 1H), 7.96-7.87 (m, 3H), 7.62 (d, J=8.3 Hz, 1H), 7.42-7.35 (m, 2H), 7.21-7.16 (m, 1H), 3.97 (s, 3H), 3.74-3.55 (m, 4H), 3.41-3.35 (m, 1H), 1.96-1.86 (m, 1H), 1.68-1.61 (m, 1H).

Compound 127: (S)—N-(2-Chlorophenyl)-2-methoxy-5-(N-(tetrahydrofuran-3-yl)sulfamoyl) benzamide LC-MS (ESI): mass calcd. for $C_{18}H_{19}ClN_2O_5S$ 410.07, m/z found 411.1 $[M+H]^+$. $^1H$ NMR (400 MHz, DMSO-$d_6$) δ 10.47 (s, 1H), 8.45 (d, J=2.5 Hz, 1H), 8.37 (d, J=7.3 Hz, 1H), 8.01 (dd, J=2.5, 8.8 Hz, 2H), 7.59 (dd, J=1.4, 8.2 Hz, 1H), 7.51 (d, J=8.8 Hz, 1H), 7.42 (t, J=7.8 Hz, 1H), 7.21 (dt, J=1.6, 7.7 Hz, 1H), 4.15 (s, 3H), 3.73-3.65 (m, 2H), 3.64-3.54 (m, 2H), 3.33-3.30 (m, 1H), 1.97-1.87 (m, 1H), 1.66-1.57 (m, 1H).

Compound 128: (S)—N-(2-(Difluoromethoxy)phenyl)-2-methoxy-5-(N-(tetrahydrofuran-3-yl) sulfamoyl)benzamide LC-MS (ESI): mass calcd. for $C_{19}H_{20}F_2N_2O_6S$ 442.10, m/z found 443.1 $[M+H]^+$. $^1H$ NMR (400 MHz, DMSO-d) δ

10.44 (s, 1H), 8.50-8.44 (m, 2H), 8.04-7.97 (m, 2H), 7.51 (d, J=8.8 Hz, 1H), 7.36 (s, 1H), 7.35-7.29 (m, 2H), 7.25-7.19 (m, 1H), 7.18 (s, 0.25H), 4.14 (s, 3H), 3.73-3.64 (m, 2H), 3.64-3.54 (m, 2H), 3.39-3.35 (m, 1H), 1.95-1.84 (m, 1H), 1.66-1.57 (m, 1H).

Compound 129: (S)-2-Methoxy-5-(N-(tetrahydrofuran-3-yl)sulfamoyl)-N-(p-tolyl)benzamide LC-MS (ESI): mass calcd. for $C_{19}H_{22}N_2O_5S$ 390.12, m/z found 391.1 [M+H]$^+$. $^1$H NMR (400 MHz, DMSO-d$_6$) δ 10.16 (s, 1H), 8.01 (d, J=2.5 Hz, 1H), 7.94-7.88 (m, 2H), 7.61 (d, J=8.3 Hz, 2H), 7.37 (d, J=9.0 Hz, 1H), 7.16 (d, J=8.3 Hz, 2H), 3.97 (s, 3H), 3.73-3.55 (m, 4H), 3.39-3.35 (m, 1H), 2.28 (s, 3H), 1.96-1.85 (m, 1H), 1.68-1.58 (m, 1H).

Compound 130: (S)—N-(2-Fluoro-6-methoxyphenyl)-2-methoxy-5-(N-(tetrahydrofuran-3-yl) sulfamoyl)benzamide LC-MS (ESI): mass calcd. for $C_{19}H_{21}FN_2O_6S$ 424.11, m/z found 425.1 [M+H]$^+$. $^1$H NMR (400 MHz, DMSO-d$_6$) δ 9.52 (s, 1H), 8.22 (d, J=2.0 Hz, 1H), 7.99-7.91 (m, 2H), 7.41 (d, J=8.8 Hz, 1H), 7.35-7.27 (m, 1H), 6.98-6.86 (m, 2H), 4.03 (s, 3H), 3.83 (s, 3H), 3.73-3.66 (m, 2H), 3.64-3.55 (m, 2H), 3.39-3.32 (m, 1H), 1.96-1.84 (m, 1H), 1.67-1.56 (m, 1H).

Compound 131: (S)—N-(4-Fluoro-2-methylphenyl)-2-methoxy-5-(N-(tetrahydrofuran-3-yl) sulfamoyl)benzamide LC-MS (ESI): mass calcd. for $C_{19}H_{21}FN_2O_5S$ 408.12, m/z found 409.1 [M+H]$^+$. $^1$H NMR (400 MHz, DMSO-d$_6$) δ 9.82 (s, 1H), 8.24 (d, J=2.3 Hz, 1H), 7.98-7.91 (m, 2H), 7.73 (dd, J=5.5, 8.8 Hz, 1H), 7.43 (d, J=9.0 Hz, 1H), 7.16 (dd, J=2.9, 9.7 Hz, 1H), 7.07 (dt, J=3.0, 8.7 Hz, 1H), 4.05 (s, 3H), 3.73-3.65 (m, 2H), 3.64-3.55 (m, 2H), 3.39-3.35 (m, 1H), 2.31 (s, 3H), 1.96-1.86 (m, 1H), 1.67-1.58 (m, 1H).

Compound 132: (S)—N-(5-fluoro-3-methylpyridin-2-yl)-2-methoxy-5-(N-(tetrahydrofuran-3-yl) sulfamoyl)benzamide LC-MS (ESI): mass calcd. for $C_{18}H_{20}FN_3O_5S$ 409.11, m/z found 410.1 [M+H]$^+$. $^1$H NMR (400 MHz, DMSO-d$_6$) δ 10.29 (br.s, 1H), 8.27 (s, 1H), 8.08 (s, 1H), 7.93 (dd, J=8.8, 2.3 Hz, 1H), 7.75 (dd, J=9.0, 2.8 Hz, 1H), 7.37 (d, J=8.5 Hz, 1H), 3.97 (s, 3H), 3.76-3.51 (m, 5H), 2.28 (s, 3H), 1.96-1.82 (m, 1H), 1.68-1.54 (m, 1H).

Compound 133: (S)-2-Methoxy-N-(3-methylpyridin-2-yl)-5-(N-(tetrahydrofuran-3-yl)sulfamoyl)benzamide LC-MS (ESI): mass calcd. for $C_{18}H_{21}N_3O_5S$ 391.12, m/z found 392.1 [M+H]$^+$. $^1$H NMR (400 MHz, DMSO-d$_6$) δ 10.27 (br.s, 1H), 8.26 (s, 1H), 8.09 (s, 1H), 7.93 (dd, J=2.0, 8.8 Hz, 1H), 7.73 (d, J=7.3 Hz, 1H), 7.36 (d, J=8.6 Hz, 1H), 7.30-7.16 (m, 1H), 3.96 (s, 3H), 3.75-3.53 (m, 5H), 2.26 (s, 3H), 1.96-1.84 (m, 1H), 1.68-1.55 (m, 1H).

Compound 134: (S)—N-(3-fluoro-2-methoxyphenyl)-2-methoxy-5-(N-(tetrahydrofuran-3-yl) sulfamoyl)benzamide LC-MS (ESI): mass calcd. for $C_{19}H_{21}FN_2O_6S$ 424.11, m/z found 425.1 [M+H]$^+$. $^1$H NMR (400 MHz, DMSO-d$_6$) δ 10.68 (s, 1H), 8.52 (d, J=2.5 Hz, 1H), 8.29 (dd, J=10.8, 3.1 Hz, 1H), 8.07-7.95 (m, 2H), 7.51 (d, J=8.9 Hz, 1H), 7.12 (dd, J=9.1, 5.1 Hz, 1H), 6.94 (td, J=8.6, 3.2 Hz, 1H), 4.17 (s, 3H), 3.96 (s, 3H), 3.75-3.52 (m, 4H), 3.40-3.35 (m, 1H), 1.96-1.83 (m, 1H), 1.65-1.55 (m, 1H).

Compound 135: (S)—N-(4-fluoro-2-methoxyphenyl)-2-methoxy-5-(N-(tetrahydrofuran-3-yl) sulfamoyl)benzamide LC-MS (ESI): mass calcd. for $C_{19}H_{21}FN_2O_6S$ 424.11, m/z found 425.1 [M+H]$^+$. $^1$H NMR (400 MHz, DMSO-d$_6$) δ 10.45 (s, 1H), 8.49 (d, J=2.4 Hz, 1H), 8.43-8.32 (m, 1H), 8.06-7.90 (m, 2H), 7.49 (d, J=8.8 Hz, 1H), 7.07 (dd, J=10.7, 2.7 Hz, 1H), 6.82 (td, J=8.7, 2.7 Hz, 1H), 4.15 (s, 3H), 3.97 (s, 3H), 3.74-3.64 (m, 2H), 3.64-3.53 (m, 2H), 3.33-3.26 (m, 1H), 1.95-1.82 (m, 1H), 1.67-1.54 (m, 1H).

Compound 136: (S)—N-(2-ethoxyphenyl)-2-methoxy-5-(N-(tetrahydrofuran-3-yl)sulfamoyl) benzamide LC-MS (ESI): mass calcd. for $C_{20}H_{24}N_2O_6S$ 420.14, m/z found 421.1 [M+H]$^+$. $^1$H NMR (400 MHz, DMSO-d$_6$) δ 10.43 (s, 1H), 8.53 (d, J=2.5 Hz, 1H), 8.48 (d, J=7.6 Hz, 1H), 8.05-7.95 (m, 2H), 7.50 (d, J=8.9 Hz, 1H), 7.15-7.04 (m, 2H), 7.00-6.90 (m, 1H), 4.23-4.17 (m, 2H), 4.16 (s, 3H), 3.73-3.64 (m, 2H), 3.64-3.53 (m, 2H), 3.33-3.30 (m, 1H), 1.93-1.83 (m, 1H), 1.65-1.57 (m, 1H), 1.47 (t, J=7.0 Hz, 3H).

Compound 137a: N-(2-chloro-5-methylphenyl)-5-(N-((trans)-3-hydroxycyclobutyl)sulfamoyl)-2-methoxybenzamide LC-MS (ESI): mass calcd. for $C_{19}H_{21}ClN_2O_5S$ 424.1, m/z found 425.0 [M+H]$^+$. $^1$H NMR (400 MHz, DMSO-d$_6$) δ 10.41 (br. s., 1H), 8.41 (br. s, 1H), 8.22 (br. s, 1H), 8.08-7.83 (m, 2H), 7.47 (dd, J=8.4, 15.0 Hz, 2H), 7.13-6.93 (m, J=7.8 Hz, 1H), 4.96 (s, 1H), 4.14 (br. s, 3H), 3.84-3.64 (m, 1H), 3.55-3.43 (m, 1H), 2.34 (br. s., 3H), 2.13-1.75 (m, 4H).

Compound 137b: N-(2-Chloro-5-methylphenyl)-5-(N-((cis)-3-hydroxycyclobutyl)sulfamoyl)-2-methoxybenzamide LC-MS (ESI): mass calcd. for $C_{19}H_{21}ClN_2O_5S$ 424.1, m/z found 425.0 [M+H]$^+$. $^1$H NMR (400 MHz, DMSO-d$_6$) δ 10.42 (s, 1H), 8.42 (s, 1H), 8.22 (s, 1H), 8.02-7.85 (m, 2H), 7.53-7.40 (m, 2H), 7.03 (dd, J=1.5, 8.1 Hz, 1H), 5.02 (d, J=5.6 Hz, 1H), 4.21-4.08 (m, 3H), 3.72-3.61 (m, 1H), 3.16-3.05 (m, 1H), 2.34 (s, 3H), 2.30-2.19 (m, 2H), 1.64-1.52 (m, 2H).

Compound 138a: N-(2-Chloro-6-methylphenyl)-5-(N-((trans)-3-hydroxycyclobutyl)sulfamoyl)-2-methoxybenzamide LC-MS (ESI): mass calcd. for $C_{19}H_{21}ClN_2O_5S$ 424.1, m/z found 425.1 [M+H]$^+$. $^1$H NMR (400 MHz, DMSO-d$_6$) δ 9.88 (s, 1H), 8.09 (br. s., 1H), 7.89 (d, J=8.6 Hz, 2H), 7.39 (d, J=8.8 Hz, 2H), 7.33-7.23 (m, 2H), 4.96 (d, J=3.9 Hz, 1H), 4.13 (m, 1H), 4.01 (s, 3H), 3.73 (m, 1H), 2.35-2.22 (m, 3H), 2.04-1.85 (m, 4H).

Compound 138b: N-(2-Chloro-6-methylphenyl)-5-(N-((cis)-3-hydroxycyclobutyl)sulfamoyl)-2-methoxybenzamide LC-MS (ESI): mass calcd. for $C_{19}H_{21}ClN_2O_5S$ 424.1, m/z found 425.1 [M+H]$^+$. $^1$H NMR (400 MHz, DMSO-d6) δ9.87 (s, 1H), 8.11 (d, J=2.5 Hz, 1H), 7.93-7.85 (m, 2H), 7.43-7.35 (m, 2H), 7.32-7.23 (m, 2H), 5.03 (d, J=6.0 Hz, 1H), 4.01 (s, 3H), 3.74-3.59 (m, 1H), 3.17-3.04 (m, 1H), 2.30-2.18 (m, 5H), 1.65-1.52 (m, 2H).

Compound 139a: N-(2-Chloro-3-methoxyphenyl)-5-(N-((trans)-3-hydroxycyclobutyl)sulfamoyl)-2-methoxybenzamide LC-MS (ESI): mass calcd. for $C_{19}H_{21}ClN_2O_6S$ 440.1, m/z found 441.0 [M+H]$^+$. $^1$H NMR (400 MHz, DMSO-d$_6$) δ 10.51 (s, 1H), 8.43 (d, J=1.7 Hz, 1H), 8.05 (d, J=8.1 Hz, 1H), 7.96 (dd, J=2.1, 8.7 Hz, 2H), 7.49 (d, J=8.8 Hz, 1H), 7.37 (t, J=8.4 Hz, 1H), 7.00 (d, J=8.3 Hz, 1H), 4.95 (d, J=4.9 Hz, 1H), 4.20-4.07 (m, 4H), 3.90 (s, 3H), 3.73 (br. s., 1H), 2.01-1.84 (m, 4H).

Compound 139b: N-(2-Chloro-3-methoxyphenyl)-5-(N-((cis-3-hydroxycyclobutyl)sulfamoyl)-2-methoxybe LC-MS (ESI): mass calcd. for $C_{19}H_{21}ClN_2O_6S$ 440.1, m/z found 441.0 [M+H]$^+$. $^1$H NMR (400 MHz, DMSO-d) δ 10.52 (s, 1H), 8.44 (d, J=2.0 Hz, 1H), 8.05 (d, J=8.5 Hz, 1H), 8.00-7.89 (m, 2H), 7.49 (d, J=8.5 Hz, 1H), 7.36 (t, J=8.3 Hz, 1H), 6.99 (d, J=8.0 Hz, 1H), 5.02 (d, J=5.5 Hz, 1H), 4.16 (s, 3H), 3.90 (s, 3H), 3.73-3.60 (m, 1H), 3.16-3.04 (m, 1H), 2.28-2.17 (m, 2H), 1.63-1.51 (m, 2H).

Compound 140a: N-(2-Chloro-3-methylphenyl)-5-(N-((trans)-3-hydroxycyclobutyl)sulfamoyl)-2-methoxybenzamide LC-MS (ESI): mass calcd. for $C_{19}H_{21}ClN_2O_5S$ 424.1, m/z found 425.1 [M+H]$^+$. $^1$H NMR (400 MHz, DMSO-d6) δ10.51 (s, 1H), 8.45-8.39 (m, 1H), 8.24 (d, J=8.0 Hz, 1H), 8.02-7.91 (m, 2H), 7.49 (d, J=9.0 Hz, 1H), 7.34-7.27 (m, 1H), 7.22-7.15 (m, 1H), 4.98 (d, J=5.0 Hz, 1H), 4.19-4.08 (m, 4H), 3.78-3.68 (m, 1H), 2.40 (s, 3H), 2.04-1.83 (m, 4H).

Compound 140b: N-(2-Chloro-3-methylphenyl)-5-(N-((cis)-3-hydroxycyclobutyl)sulfamoyl)-2-methoxybenzamide LC-MS (ESI): mass calcd. for $C_{19}H_{21}ClN_2O_5S$ 424.1, m/z found 425.1 [M+H]$^+$. $^1$H NMR (400 MHz, DMSO-d$_6$) δ 10.51 (s, 1H), 8.43 (d, J=2.5 Hz, 1H), 8.25 (d, J=8.0 Hz, 1H), 8.00-7.87 (m, 2H), 7.48 (d, J=9.0 Hz, 1H), 7.35-7.26 (m, 1H), 7.19 (d, J=7.5 Hz, 1H), 5.03 (d, J=5.5 Hz, 1H), 4.15 (s, 3H), 3.73-3.60 (m, 1H), 3.18-3.01 (m, 1H), 2.40 (s, 3H), 2.29-2.17 (m, 2H), 1.62-1.50 (m, 2H).

Compound 141: (cis-N-(5-Fluoro-6-methylpyridin-2-yl)-5-(N-(-3-hydroxycyclobutyl sulfamoyl)-2-methoxybenzamide LC-MS (ESI): mass calcd. for $C_{18}H_{20}FN_3O_5S$ 409.11, m/z found 410.1 [M+H]$^+$. $^1$H NMR (400 MHz, DMSO-d$_6$) δ 10.59 (s, 1H), 8.17-8.06 (m, 2H), 7.93-7.83 (m, 2H), 7.72 (t, J=8.9 Hz, 1H), 7.39 (d, J=9.0 Hz, 1H), 5.02 (d, J=5.6 Hz, 1H), 4.02 (s, 3H), 3.71-3.62 (m, 1H), 3.14-3.04 (m, 1H), 2.41 (d, J=2.7 Hz, 3H), 2.29-2.19 (m, 2H), 1.64-1.51 (m, 2H).

Compound 142a: N-(3-(difluoromethyl)-4-fluorophenyl)-5-(N-((trans)-3-hydroxycyclobutyl) sulfamoyl)-2-methoxybenzamide LC-MS (ESI): mass calcd. for $C_{19}H_{19}F_3N_2O_5S$ 444.10, m/z found 445.0 [M+H]$^+$. 1H NMR (400 MHz, DMSO-d$_6$) δ 10.48 (br.s, 1H), 8.07 (d, J=3.6 Hz, 1H), 7.95 (d, J=2.4 Hz, 1H), 7.92-7.82 (m, 3H), 7.43-7.10 (m, 3H), 4.96 (d, J=4.8 Hz, 1H), 4.15-4.08 (m, 1H), 3.96 (s, 3H), 3.75-3.65 (m, 1H), 2.02-1.85 (m, 4H).

Compound 142b: N-(3-(difluoromethyl)-4-fluorophenyl)-5-(N-((cis)-3-hydroxycyclobutyl) sulfamoyl)-2-methoxybenzamide LC-MS (ESI): mass calcd. for $C_{19}H_{19}F_3N_2O_5S$ 444.10, m/z found 445.1 [M+H]$^+$. 1H NMR (400 MHz, DMSO-d$_6$) δ 10.48 (br.s, 1H), 8.08 (dd, J=2.4 Hz, J=6.0 Hz, 1H), 7.96 (d, J=2.4 Hz, 1H), 7.92-7.80 (m, 3H), 7.43-7.10 (m, 3H), 5.03 (d, J=5.6 Hz, 1H), 3.96 (s, 3H), 3.70-3.60 (m, 1H), 3.15-3.05 (m, 1H), 2.30-2.18 (m, 2H), 1.62-1.50 (m, 2H).

Compound 143a: N-(4-chloro-2-fluorophenyl)-5-(N-((trans)-3-hydroxycyclobutyl)sulfamoyl)-2-methoxybenzamide LC-MS (ESI): mass calcd. for $C_{18}H_{18}ClFN_2O_5S$ 428.06, m/z found 429.0 [M+H]$^+$. 1H NMR (400 MHz, DMSO-d$_6$) δ 10.23 (br.s, 1H), 8.21 (d, J=2.8 Hz, 1H), 8.11 (t, J=8.8 Hz, 1H), 7.96-7.88 (m, 2H), 7.59 (dd, J=2.4 Hz, J=10.4 Hz, 1H), 7.43 (d, J=9.2 Hz, 1H), 7.36-7.30 (m, 1H), 4.96 (d, J=4.8 Hz, 1H), 4.15-4.09 (m, 1H), 4.05 (s, 3H), 3.76-3.65 (m, 1H), 2.00-1.85 (m, 4H).

Compound 143b: N-(4-chloro-2-fluorophenyl)-5-(N-((cis)-3-hydroxycyclobutyl)sulfamoyl)-2-methoxybenzamide LC-MS (ESI): mass calcd. for $C_{18}H_{18}ClFN_2O_5S$ 428.06, m/z found 429.1 [M+H]$^+$. 1H NMR (400 MHz, DMSO-d$_6$) δ 10.24 (br.s, 1H), 8.23 (d, J=2.0 Hz, 1H), 8.11 (t, J=8.8 Hz, 1H), 7.96-7.88 (m, 2H), 7.59 (dd, J=2.0 Hz, J=10.4 Hz, 1H), 7.43 (d, J=8.8 Hz, 1H), 7.36-7.30 (m, 1H), 5.03 (d, J=5.2 Hz, 1H), 4.05 (s, 3H), 3.70-3.60 (m, 1H), 3.15-3.05 (m, 1H), 2.30-2.18 (m, 2H), 1.62-1.50 (m, 2H).

Compound 144a: N-(2-chloro-4-fluorophenyl)-5-(N-((trans)-3-hydroxycyclobutyl)sulfamoyl)-2-methoxybenzamide LC-MS (ESI): mass calcd. for $C_{18}H_{18}ClFN_2O_5S$ 428.06, m/z found 429.1 [M+H]$^+$. 1H NMR (400 MHz, DMSO-d$_6$) 10.38 (br.s, 1H), 8.37 (d, J=2.8 Hz, 1H), 8.29 (dd, J=5.6, J=8.8 Hz, 1H), 8.00-7.90 (m, 2H), 7.62 (dd, J=2.8 Hz, J=8.4 Hz, 1H), 7.48 (d, J=8.8 Hz, 1), 7.31 (td, J=2.8 Hz, J=8.8 Hz, 1H), 4.94 (d, J=4.8 Hz, 1H), 4.13 (s, 3H), 4.16-4.06 (m, 1H), 3.76-3.65 (m, 1H), 2.00-1.85 (m, 4H).

Compound 144b: N-(2-chloro-4-fluorophenyl)-5-(N-((cis)-3-hydroxycyclobutyl)sulfamoyl)-2-methoxybenzamide LC-MS (ESI): mass calcd. for $C_{18}H_{18}ClFN_2O_5S$ 428.06, m/z found 429.0 [M+H]$^+$. 1H NMR (400 MHz, DMSO-d$_6$)

10.38 (br.s, 1H), 8.39 (d, J=2.8 Hz, 1H), 8.29 (dd, J=2.0 Hz, J=9.2 Hz, 1H), 8.00-7.85 (m, 2H), 7.62 (dd, J=2.8 Hz, J=8.4 Hz, 1H), 7.47 (d, J=8.8 Hz, 1H), 7.31 (td, J=2.8 Hz, J=8.8 Hz, 1H), 5.02 (d, J=5.6 Hz, 1H), 4.13 (s, 3H), 3.70-3.60 (m, 1H), 3.16-3.06 (m, 1H), 2.30-2.18 (m, 2H), 1.62-1.50 (m, 2H).

Compound 145a: N-(2,4-difluorophenyl)-5-(N-((trans)-3-hydroxycyclobutyl)sulfamoyl)-2-methoxy-benzamide LC-MS (ESI): mass calcd. for $C_{18}H_{18}F_2N_2O_5S$ 412.09, m/z found 413.1 [M+H]$^+$. 1H NMR (400 MHz, DMSO-d$_6$) δ 10.12 (br.s, 1H), 8.19 (d, J=2.4 Hz, 1H), 8.04-7.86 (m, 3H), 7.45-7.35 (m, 2H), 7.19-7.10 (m, 1H), 4.95 (d, J=4.8 Hz, 1H), 4.16-4.06 (m, 1H), 4.04 (s, 3H), 3.75-3.65 (m, 1H), 2.00-1.82 (m, 4H).

Compound 145b: N-(2,4-difluorophenyl)-5-(N-((cis)-3-hydroxycyclobutyl)sulfamoyl)-2-methoxy-benzamide LC-MS (ESI): mass calcd. for $C_{18}H_{18}F_2N_2O_5S$ 412.09, m/z found 413.1 [M+H]$^+$. 1H NMR (400 MHz, DMSO-d$_6$) δ 10.12 (br.s, 1H), 8.22 (d, J=2.8 Hz, 1H), 8.04-7.86 (m, 3H), 7.45-7.35 (m, 2H), 7.19-7.10 (m, 1H), 5.03 (d, J=5.6 Hz, 1H), 4.04 (s, 3H), 3.70-3.60 (m, 1H), 3.15-3.05 (m, 1H), 2.30-2.18 (m, 2H), 1.62-1.50 (m, 2H).

Compound 146a: N-(2-chloro-5-fluorophenyl)-5-(N-((trans)-3-hydroxycyclobutyl)sulfamoyl)-2-methoxy-benzamide LC-MS (ESI): mass calcd. for $C_{18}H_{18}ClFN_2O_5S$ 428.06, m/z found 429.1 [M+H]$^+$. 1H NMR (400 MHz, DMSO-d$_6$) δ 10.62 (br.s, 1H), 8.44 (d, J=2.4 Hz, 1H), 8.33 (dd, J=3.2 Hz, J=11.2 Hz, 1H), 8.04-7.94 (m, 2H), 7.68-7.60 (m, 1H), 7.51 (d, J=8.8 Hz, 1H), 7.15-7.05 (m, 1H), 4.95 (d, J=5.2 Hz, 1H), 4.16 (s, 3H), 4.15-4.05 (m, 1H), 3.78-3.65 (m, 1H), 2.00-1.85 (m, 4H).

Compound 146b: N-(2-chloro-5-fluorophenyl)-5-(N-((cis)-3-hydroxycyclobutyl)sulfamoyl)-2-methoxybenzamide LC-MS (ESI): mass calcd. for $C_{18}H_{18}ClFN_2O_5S$ 428.06, m/z found 429.1 [M+H]$^+$. 1H NMR (400 MHz, DMSO-d$_6$) δ 10.63 (br.s, 1H), 8.45 (d, J=2.4 Hz, 1H), 8.33 (dd, J=2.8 Hz, J=11.2 Hz, 1H), 8.02-7.92 (m, 2H), 7.70-7.62 (m, 1H), 7.50 (d, J=8.8 Hz, 1H), 7.15-7.05 (m, 1H), 5.03 (d, J=5.6 Hz, 1H), 4.17 (s, 3H), 3.70-3.60 (m, 1H), 3.15-3.05 (m, 1H), 2.30-2.18 (m, 2H), 1.62-1.50 (m, 2H).

Compound 147a: (S)—N-(2,4-Difluorophenyl)-2-methoxy-5-(N-(1-(2-methoxyethoxy)propan-2-yl)sulfamoyl)benzamide LC-MS (ESI): RT=5.06 min, mass calcd. for $C_{20}H_{24}F_2N_2O_6S$ 458.13, m/z found 459.1 [M+H]$^+$, 1H NMR (400 MHz, DMSO-d$_6$) δ 10.12 (s, 1H), 8.26 (d, J=2.0 Hz, 1H), 8.04-7.94 (m, 2H), 7.72 (s, 1H), 7.47-7.35 (m, 2H), 7.15 (t, J=8.3 Hz, 1H), 4.05 (s, 3H), 3.41-3.38 (m, 2H), 3.36-3.31 (m, 2H), 3.31-3.23 (m, 2H), 3.20 (s, 3H), 3.18-3.13 (m, 1H), 0.93 (d, J=6.0 Hz, 3H).

Compound 147b: (R)—N-(2,4-Difluorophenyl)-2-methoxy-5-(N-(1-(2-methoxyethoxy)propan-2-yl)sulfamoyl)benzamide LC-MS (ESI): mass calcd. for $C_{20}H_{24}F_2N_2O_6S$ 458.13, m/z found 459.1 [M+H]$^+$; 1H NMR (400 MHz, DMSO-d$_6$) δ 10.12 (s, 1H), 8.26 (d, J=2.4 Hz, 1H), 8.05-7.93 (m, 2H), 7.71 (d, J=6.8 Hz, 1H), 7.46-7.34 (m, 2H), 7.14 (t, J=8.2 Hz, 1H), 4.04 (s, 3H), 3.39-3.36 (m, 2H), 3.36-3.31 (m, 2H), 3.31-3.22 (m, 2H), 3.20 (s, 3H), 3.18-3.13 (m, 1H), 0.92 (d, J=6.4 Hz, 3H).

Compound 148: N-(2,4-Difluorophenyl)-2-methoxy-5-sulfamoylbenzamide

LC-MS (ESI): $R_T$=4.23 min, mass calcd. for $C_{14}H_{12}F_2N_2O_4S$ 342.05, m/z found 343.0 [M+H]$^+$, 1H NMR (400 MHz, DMSO-d$_6$) δ 10.12 (s, 1H), 8.28 (d, J=2.5 Hz, 1H), 8.03-7.93 (m, 2H), 7.45-7.35 (m, 4H), 7.18-7.10 (m, 1H), 4.03 (s, 3H).

Compound 149: (S)-2-Methoxy-5-(N-(tetrahydrofuran-3-yl)sulfamoyl)-N-(2-(trifluoromethyl) phenyl)benzamide LC-MS (ESI): mass calcd. for $C_{19}H_{19}F_3N_2O_5S$ 444.10, m/z found 445.1 [M+H]$^+$. 1H NMR (400 MHz, DMSO-d$_6$) δ 10.24 (br.s, 1H), 8.40 (d, J=2.0 Hz, 1H), 8.11 (d, J=8.0 Hz, 1H), 8.01 (dd, J=8.0 Hz, J=2.0 Hz, 2H), 7.80 (d, J=8.0 Hz, 1H), 7.75 (t, J=8.0 Hz, 1H), 7.53-7.40 (m, 2H), 4.08 (s, 3H), 3.75-3.64 (m, 2H), 3.63-2.53 (m, 2H), 3.43-3.35 (m, 1H), 1.94-1.84 (m, 1H), 1.65-1.54 (m, 1H).

Compound 150: (S)-2-Methoxy-5-(N-(tetrahydrofuran-3-yl)sulfamoyl)-N-(2-(trifluoromethoxy) phenyl)benzamide LC-MS (ESI): mass calcd. for $C_{19}H_{19}F_3N_2O_6S$ 460.09, m/z found 461.1 [M+H]$^+$. 1H NMR (400 MHz, DMSO-d$_6$) δ 10.31 (br.s, 1H), 8.43-8.30 (m, 2H), 8.06-7.96 (m, 2H), 7.50 (d, J=8.0 Hz, 2H), 7.45 (d, J=8.0 Hz, 1H), 7.30 (t, J=8.0 Hz, 1H), 4.10 (s, 3H), 3.75-3.64 (m, 2H), 3.63-2.53 (m, 2H), 3.43-3.35 (m, 1H), 1.94-1.84 (m, 1H), 1.65-1.54 (m, 1H).

Compound 151: (S)—N-(2-Cyclopropylphenyl)-2-methoxy-5-(N-(tetrahydrofuran-3-yl)sulfamoyl) benzamide LC-MS (ESI): mass calcd. for $C_{21}H_{24}N_2O_5S$ 416.14, m/z found 417.1 [M+H]$^+$. 1H NMR (400 MHz, DMSO-d$_6$) δ 10.12 (s, 1H), 8.40 (d, J=2.5 Hz, 1H), 8.06 (d, J=8.0 Hz, 1H), 8.01-7.95 (m, 2H), 7.47 (d, J=9.0 Hz, 1H), 7.28-7.21 (m, 1H), 7.17-7.08 (m, 2H), 4.08 (s, 3H), 3.74-3.55 (m, 4H), 3.40-3.37 (m, 1H), 2.05-1.85 (m, 2H), 1.71-1.57 (m, 1H), 1.04-0.96 (m, 2H), 0.72-0.62 (m, 2H).

Compound 152: N-(4-Fluorophenyl)-5-(N-((trans)-3-hydroxycyclobutyl)sulfamoyl)-2-methoxybenzamide LC-MS (ESI): mass calcd. for $C_{18}H_{19}FN_2O_5S$ 394.10, m/z found 395.1 [M+H]$^+$. 1H NMR (400 MHz, DMSO-d$_6$) δ 10.29 (br.s, 1H), 7.95 (d, J=2.0 Hz, 1H), 7.91-7.82 (m, 2H), 7.78-7.70 (m, 2H), 7.36 (d, J=8.8 Hz, 1H), 7.20 (t, J=8.8 Hz, 2H), 4.95 (d, J=5.2 Hz, 1H), 4.17-4.09 (m, 1H), 3.96 (s, 3H), 3.74-3.66 (m, 1H), 2.02-1.84 (m, 4H).

Compound 153: N-(4-Fluorophenyl)-5-(N-((cis)-3-hydroxycyclobutyl)sulfamoyl)-2-methoxy benzamide LC-MS (ESI): mass calcd. for $C_{18}H_{19}FN_2O_5S$ 394.10, m/z found 395.1 [M+H]$^+$. $^1$H NMR (400 MHz, DMSO-d$_6$) δ 10.29 (br.s, 1H), 7.97 (d, J=2.4 Hz, 1H), 7.91-7.81 (m, 2H), 7.78-7.71 (m, 2H), 7.36 (d, J=9.2 Hz, 1H), 7.20 (t, J=8.8 Hz, 2H), 5.03 (d, J=5.6 Hz, 1H), 3.97 (s, 3H), 3.70-3.61 (m, 1H), 3.14-3.04 (m, 1H), 2.28-2.18 (m, 2H), 1.63-1.52 (m, 2H).

Compound 154: N-(2-Chlorophenyl)-5-(N-((trans)-3-hydroxycyclobutyl)sulfamoyl-2-methoxy benzamide LC-MS (ESI): mass calcd. for $C_{18}H_{19}ClN_2O_5S$ 410.07, m/z found 411.0 [M+H]$^+$. $^1$H NMR (400 MHz, DMSO-d$_6$) δ 10.49 (br.s, 1H), 8.43 (d, J=2.0 Hz, 1H), 8.39 (d, J=8.4 Hz, 1H), 8.00-7.93 (m, 2H), 7.60 (dd, J=8.0 Hz, J=1.6 Hz, 1H), 7.50 (d, J=9.2 Hz, 1H), 7.42 (t, J=7.6 Hz, 1H), 7.25-7.19 (m, 1H), 4.96 (d, J=5.2 Hz, 1H), 4.16 (s, 3H), 4.14-4.09 (m, 1H), 3.78-3.69 (m, 1H), 2.01-1.93 (m, 2H), 1.93-1.85 (m, 2H).

Compound 155: N-(2-Chlorophenyl)-5-(N-((cis)-3-hydroxycyclobutyl)sulfamoyl)-2-methoxy benzamide LC-MS (ESI): mass calcd. for $C_{18}H_{19}ClN_2O_5S$ 410.07, m/z found 411.1 [M+H]$^+$. $^1$H NMR (400 MHz, DMSO-d$_6$) δ 10.49 (br.s, 1H), 8.45 (d, J=2.4 Hz, 1H), 8.40 (d, J=8.0 Hz, 1H), 8.01-7.90 (m, 2H), 7.60 (dd, J=8.0 Hz, J=1.2 Hz, 1H), 7.49 (d, J=9.2 Hz, 1H), 7.42 (t, J=7.6 Hz, 1H), 7.25-7.19 (m, 1H), 5.02 (d, J=5.2 Hz, 1H), 4.16 (s, 3H), 3.72-3.61 (m, 1H), 3.19-3.03 (m, 1H), 2.29-2.19 (m, 2H), 1.64-1.52 (m, 2H).

Compound 156: N-(5-Fluoropyridin-2-yl)-5-(N-((trans)-3-hydroxycyclobutyl sulfamoyl)-2-methoxybenzamide LC-MS (ESI): mass calcd. for $C_{17}H_{18}FN_3O_5S$ 395.10, m/z found 396.1 [M+H]$^+$, $^1$H NMR (400 MHz, DMSO-d$_6$) δ 10.68 (br.s, 1H), 8.39 (d, J=2.8 Hz, 1H), 8.32-8.24 (m, 1H), 8.13 (d, J=2.4 Hz, 1H), 7.93-7.87 (m, 2H), 7.86-7.80 (m, 1H), 7.41 (d, J=8.8 Hz, 1H), 4.95 (d, J=4.8 Hz, 1H), 4.16-4.09 (m, 1H), 4.02 (s, 3H), 3.75-3.67 (m, 1H), 2.01-1.93 (m, 2H), 1.92-1.85 (m, 2H).

Compound 157: N-(5-Fluoropyridin-2-yl)-5-(N-((cis)-3-hydroxycyclobutyl)sulfamoyl)-2-methoxy-benzamide LC-MS (ESI): mass calcd. for $C_{17}H18FN_3O_5S$ 395.10, m/z found 396.1 [M+H]$^+$, $^1$H NMR (400 MHz, DMSO-d$_6$) δ 10.68 (br.s, 1H), 8.39 (d, J=2.8 Hz, 1H), 8.32-8.25 (m, 1H), 8.15 (d, J=2.4 Hz, 1H), 7.95-7.79 (m, 3H), 7.40 (d, J=8.8 Hz, 1H), 5.02 (d, J=5.6 Hz, 1H), 4.03 (s, 3H), 3.71-3.59 (m, 1H), 3.15-3.04 (m, 1H), 2.28-2.18 (m, 2H), 1.63-1.52 (m, 2H).

Compound 158: (S)—N-(4-Fluorophenyl)-2-methoxy-5-(N-(tetrahydrofuran-3-yl)sulfamoyl) benzamide LC-MS (ESI): mass calcd. for $C_{18}H19FN_2O_5S$ 394.10, m/z found 395.1 [M+H]$^+$, $^1$H NMR (400 MHz, DMSO-d$_6$) δ 10.30 (br.s, 1H), 8.00 (d, J=2.5 Hz, 1H), 7.96-7.84 (m, 2H), 7.80-7.70 (m, 2H), 7.38 (d, J=8.8 Hz, 1H), 7.20 (t, J=9.0 Hz, 2H), 3.97 (s, 3H), 3.74-3.65 (m, 2H), 3.64-3.55 (m, 2H), 3.39-3.37 (m, 1H), 1.96-1.85 (m, 1H), 1.68-1.57 (m, 1H).

Compound 159: (S)-2-Methoxy-5-(N-(tetrahydrofuran-3-yl)sulfamoyl-N-(m-tolyl)benzamide LC-MS (ESI): mass calcd. for $C_{19}H_{22}N_2O_5S$ 390.12, m/z found 391.1 [M+H]$^+$, $^1$H NMR (400 MHz, DMSO-d$_6$) δ 10.17 (br.s, 1H), 8.00 (d, J=2.3 Hz, 1H), 7.95-7.88 (m, 2H), 7.55-7.53 (m, 2H), 7.38 (d, J=8.8 Hz, 1H), 7.23 (t, J=7.8 Hz, 1H), 6.94 (d, J=7.5 Hz, 1H), 3.97 (s, 3H), 3.74-3.66 (m, 2H), 3.65-3.56 (m, 2H), 3.40-3.35 (m, 1H), 2.31 (s, 3H), 1.97-1.83 (m, 1H), 1.72-1.54 (m, 1H).

Compound 160: (S)—N-(4-Fluoro-3-(trifluoromethyl)phenyl)-2-methoxy-5-(N-(tetrahydrofuran-3-yl)sulfamoyl)benzamide LC-MS (ESI): mass calcd. for $C_{19}H_{18}F_4N_2O_5S$ 462.09, m/z found 463.1 [M+H]$^+$. $^1$H NMR (400 MHz, DMSO-d$_6$) δ 10.60 (br.s, 1H), 8.26-8.20 (m, 1H), 8.04-7.90 (m, 4H), 7.54 (t, J=9.8 Hz, 1H), 7.40 (d, J=8.8 Hz, 1H), 3.97 (s, 3H), 3.74-3.66 (m, 2H), 3.65-3.55 (m, 2H), 3.39-3.36 (m, 1H), 1.96-1.85 (m, 1H), 1.69-1.57 (m, 1H).

Compound 161 (S)—N-(5-Fluoro-4-methylpyridin-2-yl)-2-methoxy-5-(N-(tetrahydrofuran-3-yl) sulfamoyl)benzamide LC-MS (ESI): mass calcd. for $C_{18}H_{20}FN_3O_5S$ 409.11, m/z found 410.1 [M+H]$^+$, $^1$H NMR (400 MHz, DMSO-d$_6$) δ 10.60 (br.s, 1H), 8.27 (s, 1H), 8.19 (d, J=4.8 Hz, 1H), 8.15 (d, J=2.0 Hz, 1H), 7.96 (d, J=2.0 Hz, 1H), 7.94 (d, J=2.4 Hz, 1H), 7.42 (d, J=8.4 Hz, 1H), 4.02 (s, 3H), 3.73-3.64 (m, 2H), 3.64-3.55 (m, 2H), 3.39-3.38 (m, 1H), 2.34 (s, 3H), 1.96-1.85 (m, 1H), 1.67-1.59 (m, 1H).

Compound 162: (S)—N-(6-Cyclopropyl-5-fluoropyridin-2-yl)-2-methoxy-5-(N-(tetrahydrofuran-3-yl) sulfamoyl)benzamide LC-MS (ESI): mass calcd. for $C_{20}H_{22}FN_3O_5S$ 435.13, m/z found 436.0 [M+H]$^+$, $^1$H NMR (400 MHz, DMSO-d$_6$) δ 10.50 (br.s, 1H), 8.11 (s, 1H), 8.02-7.87 (m, 3H), 7.68 (t, J=9.2 Hz, 1H), 7.40 (d, J=8.8 Hz, 1H), 4.00 (s, 3H), 3.73-3.64 (m, 2H), 3.64-3.54 (m, 2H), 3.42-3.38 (m, 1H), 2.25-2.23 (m, 1H), 1.96-1.83 (m, 1H), 1.67-1.55 (m, 1H), 1.07-0.97 (m, 4H).

Compound 163: (S)-2-Methoxy-5-(N-(tetrahydrofuran-3-yl)sulfamoyl)-N-(o-tolyl)benzamide LC-MS (ESI): mass calcd. for $C_{19}H_{22}N_2O_5S$ 390.12, m/z found 391.1 [M+H]$^+$, $^1$H NMR (400 MHz, DMSO-d$_6$) δ 9.87 (br.s, 1H), 8.29 (s, 1H), 8.02-7.92 (m, 2H), 7.84 (d, J=7.6 Hz, 1H), 7.46 (d, J=8.8 Hz, 1H), 7.33-7.21 (m, 2H), 7.14 (t, J=7.2 Hz, 1H), 4.09 (s, 3H), 3.75-3.55 (m, 4H), 3.38-3.30 (m, 1H), 2.33 (s, 3H), 1.97-1.85 (m, 1H), 1.69-1.59 (m, 1H).

Compound 164: (S)—N-(2-Cyanophenyl)-2-methoxy-5-(N-(tetrahydrofuran-3-ylsulfamoyl) benzamide LC-MS (ESI): mass calcd. for $C_{19}H_{19}N_3O_5S$ 401.10, m/z found 402.1 [M+H]$^+$, $^1$H NMR (400 MHz, DMSO-d$_6$) δ 10.61 (br.s, 1H), 8.37 (br.s, 1H), 8.21 (d, J=8.4 Hz, 1H), 8.06-7.97 (m, 2H), 7.89 (d, J=7.2 Hz, 1H), 7.77 (t, J=7.6 Hz, 1H), 7.49 (d, J=8.8 Hz, 1H), 7.38 (t, J=7.6 Hz, 1H), 4.12 (s, 3H), 3.74-3.56 (m, 4H), 3.39-3.35 (m, 1H), 1.95-1.85 (m, 1H), 1.68-1.58 (m, 1H).

Compound 165: (S)-2-Methoxy-N-(pyrimidin-4-yl)-5-(N-(tetrahydrofuran-3-yl)sulfamoyl) benzamide LC-MS (ESI): mass calcd. for $C_{16}H_{18}N_4O_5S$ 378.10, m/z found 379.1 [M+H]$^+$, $^1$H NMR (400 MHz, DMSO-d$_6$) δ 10.97 (br.s, 1H), 8.94 (br.s, 1H), 8.75 (d, J=5.6 Hz, 1H), 8.21 (d, J=5.6 Hz, 1H), 8.10 (d, J=1.6 Hz, 1H), 8.01-7.91 (m, 2H), 7.42 (d, J=8.8 Hz, 1H), 4.01 (s, 3H), 3.74-3.66 (m, 2H), 3.65-3.56 (m, 2H), 3.39-3.36 (m, 1H), 1.97-1.85 (m, 1H), 1.69-1.57 (m, 1H).

Compound 166: (S)-2-Methoxy-N-(2-methoxyphenyl)-5-(N-(tetrahydrofuran-3-yl)sulfamoyl) benzamide LC-MS (ESI): mass calcd. for $C_{19}H_{22}N_2O_6S$ 406.12, m/z found 407.1 [M+H]$^+$, $^1$H NMR (400 MHz, DMSO-d$_6$) δ 10.58 (br.s, 1H), 8.52 (d, J=2.4 Hz, 1H), 8.44 (d, J=8.0 Hz, 1H), 8.04-7.96 (m, 2H), 7.50 (d, J=8.8 Hz, 1H), 7.12 (d, J=3.6 Hz, 2H), 7.03-6.96 (m, 1H), 4.18 (s, 3H), 3.97 (s, 3H), 3.73-3.65 (m, 2H), 3.64-3.54 (m, 2H), 3.38-3.35 (m, 1H), 1.94-1.84 (m, 1H), 1.66-1.57 (m, 1H).

Compound 167: (S)—N-(3-(Difluoromethyl)-4-fluorophenyl)-2-methoxy-5-(N-(tetrahydrofuran-3-yl)sulfamoyl)benzamide LC-MS (ESI): mass calcd. for $C_{19}H_{19}F_3N_2O_5S$ 444.10, m/z found 445.1 [M+H]$^+$. $^1$H NMR (400 MHz, DMSO-d$_6$) δ 10.48 (br.s, 1H), 8.07 (d, J=2.0 Hz, 1H), 8.03-7.97 (m, 1H), 7.96-7.88 (m, 2H), 7.86-7.82 (m, 1H), 7.43-7.35 (m, 2H), 7.40-7.07 (m, 1H), 3.97 (s, 3H), 3.75-3.65 (m, 2H), 3.65-3.55 (m, 2H), 3.40-3.35 (m, 1H), 1.95-1.85 (m, 1H), 1.70-1.55 (m, 1H).

Compound 168: N-(5-fluoro-6-methylpyridin-2-yl)-2-methoxy-5-(N-(1-(trifluoromethyl) cyclopropyl)sulfamoyl)benzamide

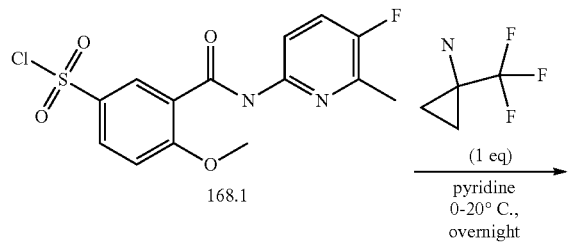

3-((5-fluoro-6-methylpyridin-2-yl)carbamoyl)-4-methoxybenzene-1-sulfonyl chloride (200 mg, 0.557 mmol) was added to a solution consisting of 1-(trifluoromethyl)cyclopropan-1-amine and pyridine (2 mL) at 0° C. The mixture was stirred overnight at 20° C. The mixture was concentrated to dryness to give a residue which was purified by flash column chromatography over silica gel (eluent: petroleum ether:ethyl acetate from 100:0 to 50:50) to give the title compound (100 mg, purity 99.99%, 40% yield). LC-MS (ESI): RT=4.89 min, mass calcd. for $C_{18}H_{17}F_4N_3O_4S$ 447.09, m/z found 448.1 [M+H]$^+$. $^1$H NMR (400 MHz, DMSO-d$_6$) δ 10.60 (s, 1H), 9.14 (br. s., 1H), 8.18-8.03 (m, 2H), 7.90 (dd, J=2.0, 8.5 Hz, 1H), 7.72 (t, J=9.0 Hz, 1H), 7.40 (d, J=9.0 Hz, 1H), 4.02 (s, 3H), 2.41 (d, J=2.0 Hz, 3H), 1.21-1.12 (m, 2H), 1.07-0.96 (m, 2H).

Synthetic Routes for Compound 168-170

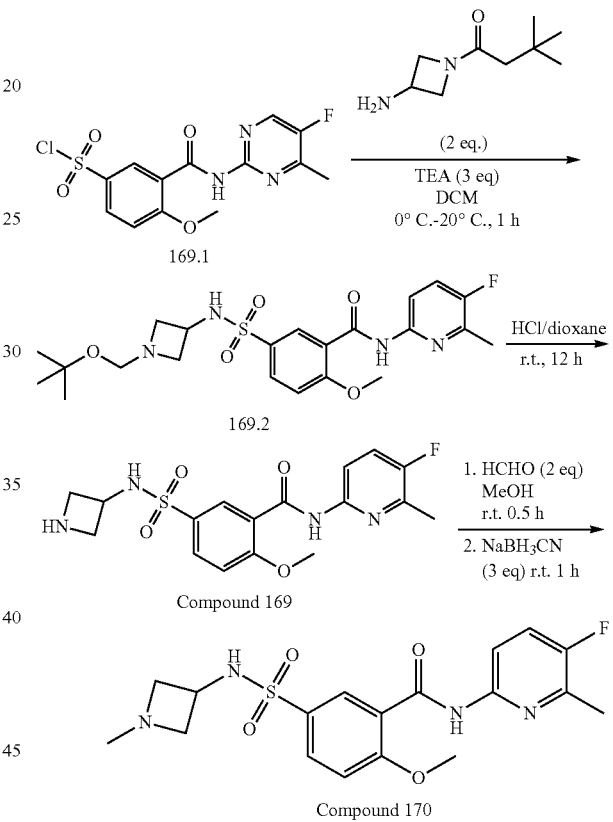

Intermediate 169.2: (tert-Butyl 3-(3-((5-fluoro-6-methylpyridin-2-yl)carbamoyl)-4-methoxy phenylsulfonamido)azetidine-1-carboxylate 3-((5-Fluoro-6-methylpyridin-2-yl)carbamoyl)-4-methoxybenzene-1-sulfonyl chloride (600 mg, 1.34 mmol, purity 80%) was dissolved in dry DCM (5 mL). tert-Butyl 3-aminoazetidine-1-carboxylate (461 mg, 2.68 mmol) and TEA (406 mg, 4.01 mmol) were added to the above mixture at 20° C. The mixture was stirred at 20° C. for 1 h. The resultant mixture was extracted with ethyl acetate (5 mL×3). The combined organic layers were concentrated to dryness. The residue was purified by flash column chromatography over silica gel (eluent: petroleum ether:ethyl acetate from 100:0 to 0:100) to afford the title compound (500 mg, 64% yield, purity 85%). LC-MS (ESI): RT=0.78 min, mass calcd. for $C_{22}H_{27}FN_4O_6S$ 494.16, m/z found 495.0 [M+H]$^+$.

Compound 169: 5-(N-(Azetidin-3-yl)sulfamoyl)-N-(5-fluoro-6-methylpyridin-2-yl)-2-Methoxy benzamide tert-Butyl-3-(3-((5-fluoro-6-methylpyridin-2-yl)carbamoyl)-4-methoxyphenylsulfonamido)azetidine-1-carboxylate was dissolved in HCl/dioxane (4N, 10 mL). The reaction was stirred at 20° C. for 12 h before concentrating it to dryness. The mixture was adjusted to pH 7~8 with saturated aq. $Na_2CO_3$. Water (10 mL) was added. The precipitate was collected, dried and then recrystallized from DMF (20 mL) to afford the title compound (300 mg, 85% yield).

LC-MS (ESI): RT=4.05 min, mass calcd. for $C_{17}H_{19}FN_4O_4S$ 394.11, m/z found 395.1 [M+H]$^+$. $^1$H NMR (400 MHz, DMSO-d$_6$) δ 10.63 (s, 1H), 9.38 (br. s., 1H), 8.87 (br. s., 1H), 8.12-8.05 (m, 2H), 7.94 (dd, J=2.5, 8.8 Hz, 1H), 7.71 (t, J=9.0 Hz, 1H), 7.41 (d, J=8.8 Hz, 1H), 4.13 (d, J=7.0 Hz, 1H), 4.00 (s, 3H), 3.88-3.81 (m, 2H), 3.79-3.71 (m, 2H), 2.40 (d, J=2.8 Hz, 3H).

Compound 170: N-(5-Fluoro-6-methylpyridin-2-yl)-2-methoxy-5-(N-(1-methylazetidin-3-yl) sulfamoyl)benzamide 5-(N-(Azetidin-3-yl)sulfamoyl)-N-(5-fluoro-6-methylpyridin-2-yl)-2-methoxybenzamide (120 mg, 0.304 mmol) was dissolved in methanol (2 mL) in a 50 mL round-bottomed flask and then treated with formaldehyde (49.3 mg, 0.608 mmol, w/w 37%). The mixture was stirred at 20° C. for 30 minutes before NaBH$_3$CN (57.3 mg, 0.912 mmol) was added. The reaction mixture was stirred at room temperature for 1 h and then concentrated to dryness under reduced pressure. Ethyl acetate (20 mL) was added. The resultant mixture was washed with water (20 mL), brine (20 mL), dried over Na$_2$SO$_4$ and filtered. The filtrate was concentrated to dryness to give a residue which was further purified by prep.HPLC (Waters Xbridge Prep OBD C18 150 mm*30 mm, 5 um (eluent: CH$_3$CN/H$_2$O (10 mM NH$_4$HCO$_3$-ACN) from 25% to 55%, flow rate: 30 ml/min) to afford the title compound (14.2 mg, 11% yield).

LC-MS (ESI): RT=3.89 min, mass calcd. for $C_{18}H_{21}FN_4O_4S$ 408.13, m/z found 409.1 [M+H]$^+$. $^1$H NMR (400 MHz, DMSO-d) δ 10.61 (s, 1H), 8.18 (br. s., 1H), 8.09 (d, J=2.3 Hz, 2H), 7.90 (dd, J=2.5, 8.8 Hz, 1H), 7.72 (t, J=9.0 Hz, 1H), 7.38 (d, J=9.0 Hz, 1H), 4.01 (s, 3H), 3.69 (br. s., 1H), 3.33-3.30 (m, 2H), 2.65 (t, J=7.5 Hz, 2H), 2.41 (d, J=2.8 Hz, 3H), 2.13 (s, 3H).

Compound 171: (S)—N-(4-chloro-5-fluoro-6-methylpyrimidin-2-yl)-2-methoxy-5-(N-(tetrahydrofuran-3-yl)sulfamoyl)benzamide

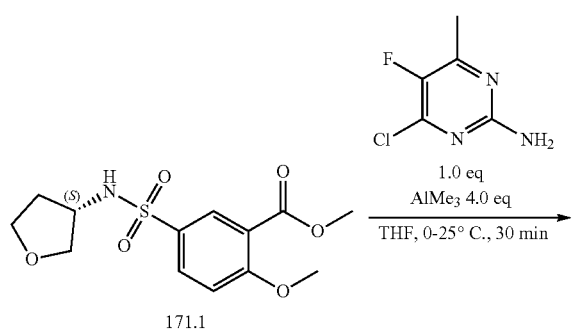

171.1

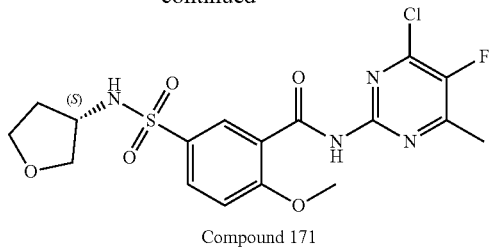

Compound 171

(S)-Methyl 2-methoxy-5-(N-(tetrahydrofuran-3-yl)sulfamoyl)benzoate (300 mg, 0.95 mmol) and 4-chloro-5-fluoro-6-methylpyrimidin-2-amine (207 mg, 1.05 mmol) were dissolved in dry THF (5 mL) followed by the addition of trimethylaluminum (1.90 mL) drop-wise at 0° C. The reaction mixture was stirred at room temperature for 30 min and then quenched with saturated NH$_4$Cl (5 mL). The organic phase was separated, dried over Na$_2$SO$_4$ and filtered. The filtrate was concentrated under reduced pressure to give a residue which was purified by prep.TLC to give the title compound (39.10 mg, yield: 9.25%) as a pale-yellow solid.

LC-MS (ESI): R$_T$=4.18 min, mass calcd. for $C_{17}H_{18}ClFN_4O_5S$ 444.07, m/z found 445.1 [M+H]$^+$. $^1$H NMR (400 MHz, DMSO-d) δ 11.15 (br.s, 1H), 8.07-7.73 (m, 3H), 7.32 (d, J=7.2 Hz, 1H), 3.88 (s, 3H), 3.75-3.64 (m, 2H), 3.63-2.53 (m, 2H), 3.40-3.35 (m, 1H), 2.46-2.36 (m, 3H), 1.94-1.84 (m, 1H), 1.65-1.54 (m, 1H).

Compound 172: (S)—N-(5-fluoro-4-methylpyrimidin-2-yl)-2-methoxy-5-(N-(tetrahydrofuran-3-yl)sulfamoyl)benzamide

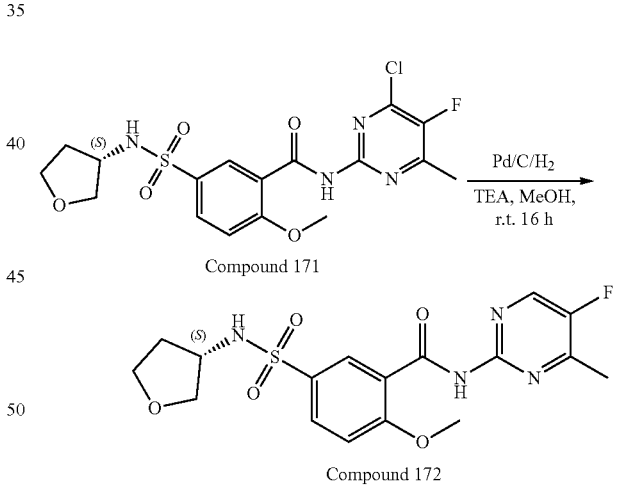

Compound 171

Compound 172

(S)—N-(4-chloro-5-fluoro-6-methylpyrimidin-2-yl)-2-methoxy-5-(N-(tetrahydrofuran-3-yl)sulfamoyl)benzamide (300 mg, 0.67 mmol) and TEA (1 mL) were dissolved in MeOH (5 mL) followed by the addition of Pd/C (50 mg, 10% w/w). The reaction mixture was stirred at room temperature for 16 hours under H$_2$ (30 psi) and then filtered. The filtrate was concentrated under reduced pressure to give a residue which was triturated with DCM (2-3 mL). The solid was filtered and then dried in vacuum to give the title compound (47.50 mg, yield: 17.06%) as a brown solid.

LC-MS (ESI): R$_T$=3.67 min, mass calcd. for $C_{17}H_{19}FN_4O_5S$ 410.11, m/z found 411.1 [M+H]$^+$. $^1$H NMR (400 MHz, DMSO-d$_6$) δ 10.92 (br.s, 1H), 8.59 (br.s, 1H), 7.95 (d, J=2.0 Hz, 1H), 7.91 (dd, J=8.8 Hz, J=2.4 Hz, 2H), 7.32 (d, J=8.8 Hz, 1H), 3.88 (s, 3H), 3.75-3.64 (m, 2H), 3.63-2.53 (m, 2H), 3.40-3.35 (m, 1H), 2.46-2.36 (m, 3H), 1.94-1.84 (m, 1H), 1.65-1.54 (m, 1H).

Compound 173: N-(2,4-Difluoro-3-methylphenyl)-5-(N-((cis)-3-hydroxycyclobutyl)sulfamoyl)-2-methoxybenzamide

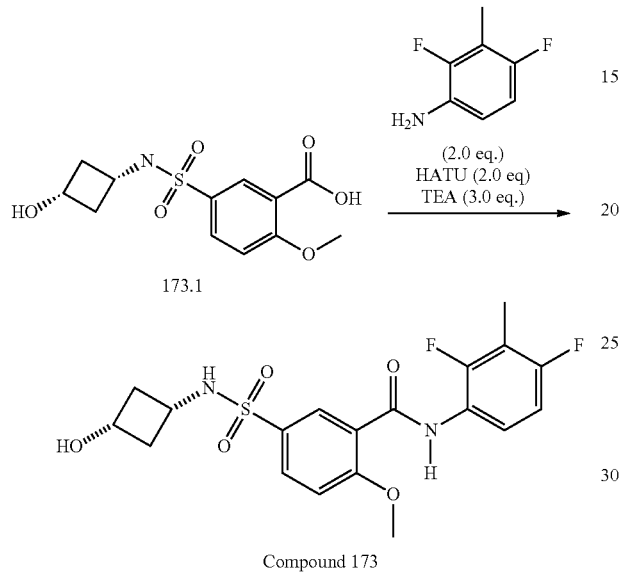

Compound 173

To a solution consisting of 2,4-difluoro-3-methylaniline (95 mg, 0.664 mmol), triethylamine (0.14 mL, 1.00 mmol), HATU (252 mg, 0.664 mmol) and DCM (2 mL) was added 5-(N-((cis)-3-hydroxycyclobutyl)sulfamoyl)-2-methoxybenzoic acid (106 mg, 0.332 mmol) under 0° C. The reaction mixture was stirred at 25° C. for 3 h. The resulting mixture was concentrated. The residue was purified by prep.HPLC (eluent: CH$_3$CN/H$_2$O (0.05% HCl) from 37% to 77%, v/v). The pure fractions were collected and the solvent was evaporated under vacuum. The aqueous layer was lyophilized to dryness to give title compound as a white powder (15.60 mg, 97.62% purity, 10.84% yield).

LC-MS (ESI): R$_T$=4.84 min, mass calcd. for C$_{19}$H$_{20}$F$_2$N$_2$O$_5$S 426.1, m/z found 427.1 [M+H]$^+$. $^1$H NMR (400 MHz, DMSO-d$_6$) δ 10.10 (s, 1H), 8.23 (d, J=2.0 Hz, 1H), 7.98-7.79 (m, 3H), 7.42 (d, J=9.0 Hz, 1H), 7.10 (t, J=9.3 Hz, 1H), 5.03 (d, J=5.5 Hz, 1H), 4.05 (s, 3H), 3.72-3.59 (m, 1H), 3.16-3.03 (m, 1H), 2.28-2.16 (m, 5H), 1.65-1.49 (m, 2H).

Compound 174a-174b

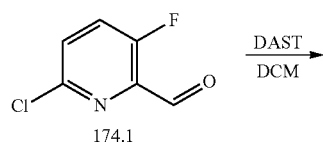

174.1

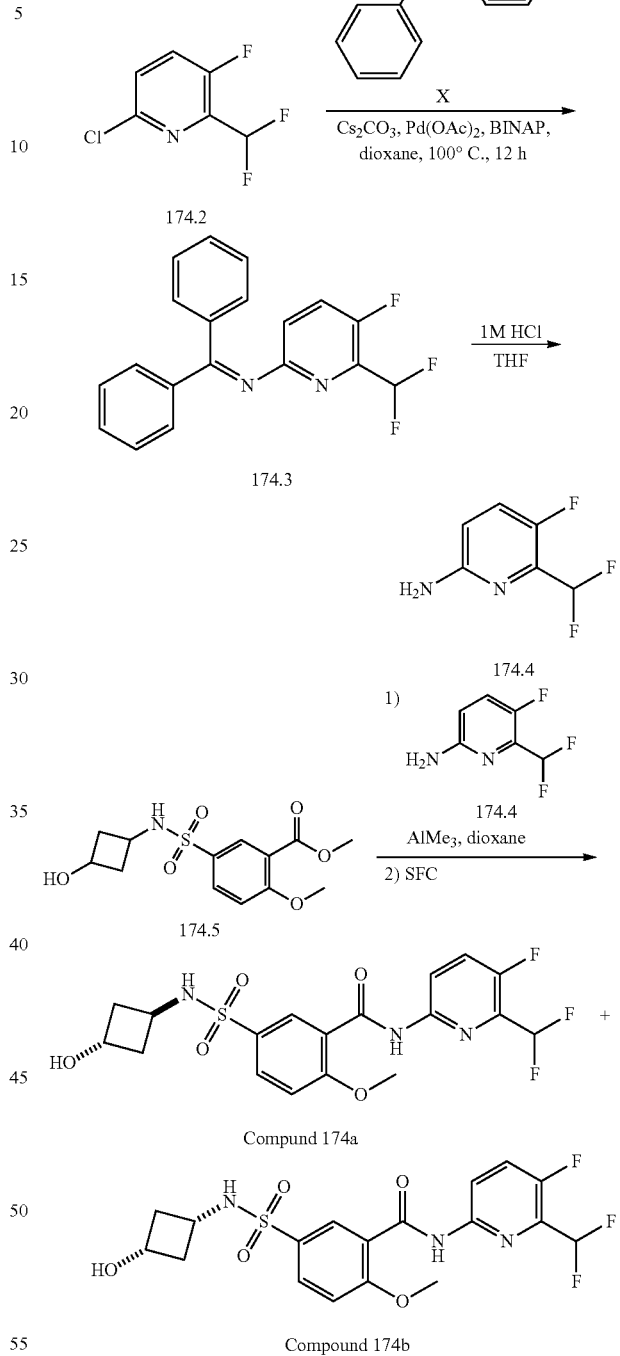

Intermediate 174.2: 6-Chloro-2-(difluoromethyl)-3-fluoropyridine

To a solution consisting of 6-chloro-3-fluoropicolinaldehyde (1.0 g, 6.27 mmol) and DCM (20 mL) was added DAST (1.5 g, 9.32 mmol) at 0° C. The reaction was stirred at room temperature overnight. The reaction mixture was diluted with DCM (20 mL) and then quenched with sat. NaHCO$_3$ (20 mL). The organic layer was separated, washed with brine (20 mL), dried over Na$_2$SO$_4$ and filtered. The filtrate was concentrated to dryness to give compound the title compound (1 g, 88% yield). $^1$H NMR (400 MHz, CDCl$_3$) δ 7.56-7.46 (m, 2H), 6.71 (t, J=53.2 Hz, 1H).

Intermediate 174.3: 6-(Difluoromethyl)-N-(diphenylmethylene)-5-fluoropyridin-2-amine 6-Chloro-2-(difluoromethyl)-3-fluoropyridine (700 mg, 3.86 mmol), diphenylmethanimine (1.40 g, 7.73 mmol), Cs$_2$CO$_3$ (2.51 g, 7.70 mmol), Pd(OAc)$_2$ (86 mg, 0.38 mmol) and BINAP (240 mg, 0.38 mmol) was suspended in dry dioxane (15 mL). The resultant reaction mixture was stirred at 100° C. overnight under N$_2$. The mixture was then concentrated in vacuum. The residue was diluted with DCM (40 mL) and then filtered. The filtrate was concentrated to give the title compound (2.5 g, crude) as brown oil, which was used directly for next step.

Preparation of Compound 174.4: 6-(Difluoromethyl)-5-fluoropyridin-2-amine

HCl (1 M, 20 mL, 20 mmol) was added to a solution consisting of 6-(difluoromethyl)-N-(diphenylmethylene)-5-fluoropyridin-2-amine (2.5 g, crude) and THF (20 mL). The mixture was stirred at 25° C. for 1 h before concentrating it to dryness. The residue was purified by prep-HPLC to give the title compound (600 mg) as a light yellow solid.

Compound 174a: N-(6-(Difluoromethyl)-5-fluoropyridin-2-yl)-5-(N-((trans)-3-hydroxycyclobutyl) sulfamoyl)-2-methoxybenzamide Compound 174b: N-(6-(Difluoromethyl)-5-fluoropyridin-2-yl)-5-(N-((cis)-3-hydroxycyclobutyl) sulfamoyl)-2-methoxybenzamide To a solution consisting of methyl 5-(N-(3-hydroxycyclobutyl)sulfamoyl)-2-methoxybenzoate (200 mg, 0.634 mmol), 6-(difluoromethyl)-5-fluoropyridin-2-amine (525 mg, 1.901 mmol) and dry dioxane (6 mL) was added Me$_3$Al (2 M solution, 1.9 mL, 3.8 mmol) drop-wise at 25° C. The mixture was stirred at 50° C. for 2 hrs. After cooling to room temperature, the mixture was quenched with water (0.5 mL), then diluted with MeOH (20 mL) and filtered. The filtrate was concentrated to dryness. The residue was purified by prep-HPLC (NH$_3$·H$_2$O as additive) to give the racemic mixture as a white solid. The racemic mixture was separated by SFC (separation condition: Column: ChiralPak AD, Daicel Chemical Industries, Ltd, 250×30 mm I.D., 10 µm; Mobile phase: A: Supercritical CO$_2$, B: ethanol (0.1% NH$_3$·H$_2$O), A:B=75:25 at 80 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to give 174a (16.20 mg purity 96.8%, yield: 5.52%) and 174b (77.10 mg purity 99.9%, yield: 27.29%).

Analytic data of 174a: LC-MS (ESI): R$_t$=4.33 min, mass calcd. for C$_{18}$H$_{18}$F$_3$N$_3$O$_5$S 445.09, m/z found 446.1 [M+H]$^+$. 1H NMR (400 MHz, DMSO-d$_6$) δ 10.95 (br.s, 1H), 8.47-8.40 (m, 1H), 8.08-8.00 (m, 2H), 7.90-7.85 (m, 2H), 7.38 (d, J=8.8 Hz, 1H), 7.11 (t, J=52.8 Hz, 1H), 4.95 (d, J=5.2 Hz, 1H), 4.16-4.08 (m, 1H), 3.99 (s, 3H), 3.75-3.65 (m, 1H), 2.02-1.85 (m, 4H);

Analytic data of 174b: LC-MS (ESI): R$_t$=4.54 min, mass calcd. for C$_{18}$H$_{18}$F$_3$N$_3$O$_5$S 445.09, m/z found 446.1 [M+H]$^+$. 1H NMR (400 MHz, DMSO-d$_6$) δ 10.95 (br.s, 1H), 8.47-8.40 (m, 1H), 8.08-8.00 (m, 2H), 7.93-7.82 (m, 2H), 7.38 (d, J=8.8 Hz, 1H), 7.11 (t, J=53.2 Hz, 1H), 5.02 (d, J=5.6 Hz, 1H), 3.99 (s, 3H), 3.70-3.60 (m, 1H), 3.16-3.04 (m, 1H), 2.30-2.20 (m, 2H), 1.64-1.52 (m, 2H).

Compound 175

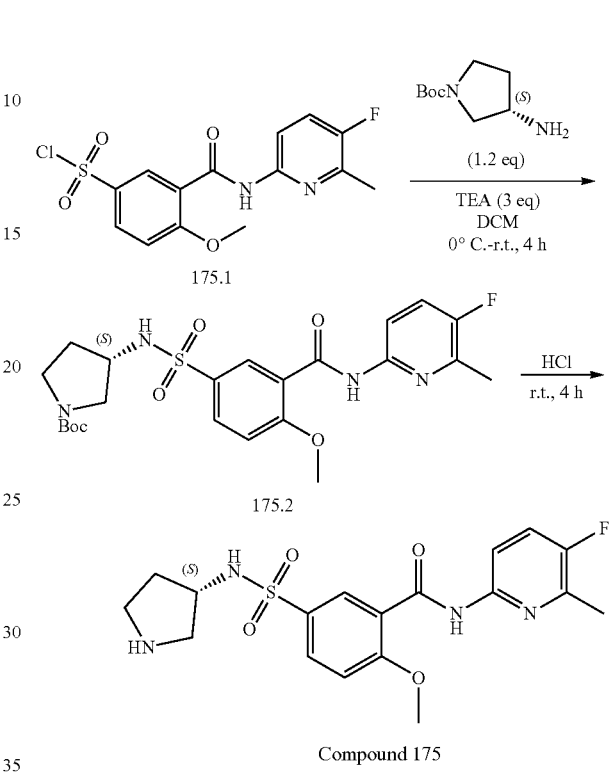

Compound 175

Intermediate 175.2: (S)-tert-Butyl 3-(3-((5-fluoro-6-methylpyridin-2-yl)carbamoyl)-4-methoxyphenylsulfonamido)pyrrolidine-1-carboxylate 3-((5-Fluoro-6-methylpyridin-2-yl)carbamoyl)-4-methoxybenzene-1-sulfonyl chloride (1.0 g, 2.23 mmol) was dissolved in dry DCM (10 mL). (S)-tert-Butyl 3-aminopyrrolidine-1-carboxylate (498 mg, 2.68 mmol) and TEA (677 mg, 6.69 mmol) were added to the above mixture at 0° C. The mixture was stirred at 20° C. for 4 h. The mixture was washed with H$_2$O (20 mL), dried over sodium sulfate, filtered and concentrated. The residue was purified by flash column over silica gel (gradient eluent: petroleum ether: ethyl acetate from 100:0 to 0:100). The residue was crystallized from ethyl acetate to afford the title compound (600 mg, 50% yield).

LC-MS (ESI): RT=0.76 min, mass calcd. for C$_{23}$H$_{29}$FN$_4$O$_6$S 508.2, m/z found 509.2 [M+H]$^+$.

Compound 175: (S)—N-(5-Fluoro-6-methylpyridin-2-yl)-2-methoxy-5-(N-(pyrrolidin-3-yl) sulfamoyl) benzamide (S)-tert-Butyl-3-(3-((5-fluoro-6-methylpyridin-2-yl)carbamoyl)-4-methoxyphenylsulfonamido) pyrrolidine-1-carboxylate was dissolved in HCl/dioxane (10 mL). The reaction was stirred at 20° C. for 4 h, the solvent was concentrated in vacuum. The residue was dissolved in DMSO (10 mL). Aqueous Na$_2$CO$_3$ (1N) was added drop-wise with stirring till PH=7 at 20° C. Then a white precipitate formed. The precipitate was filtered off and dried to afford the title compound (400 mg, 85% yield).

LC-MS (ESI): RT=3.60 min, mass calcd. for $C_{18}H_{21}FN_4O_4S$ 408.1, m/z found 409.1 [M+H]$^+$. $^1$H NMR (400 MHz, DMSO-d$_6$) δ 10.60 (s, 1H), 8.16-8.07 (m, 2H), 7.93 (dd, J=2.5, 8.8 Hz, 1H), 7.72 (t, J=9.0 Hz, 1H), 7.40 (d, J=9.0 Hz, 1H), 4.02 (s, 3H), 3.50-3.42 (m, 1H), 2.76-2.66 (m, 2H), 2.64-2.55 (m, 2H), 2.41 (d, J=2.8 Hz, 3H), 2.39-2.31 (m, 2H), 1.74-1.64 (m, 1H), 1.42-1.34 (m, 1H).

Compound 176: (S)—N-(5-Fluoro-6-methylpyridin-2-yl)-2-methoxy-5-(N-(1-methylpyrrolidin-3-yl)sulfamoyl)benzamide

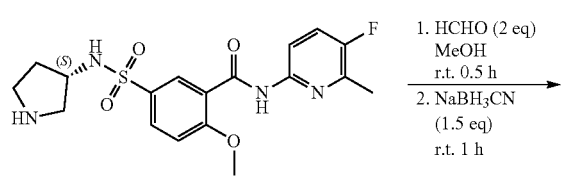

Compound 175

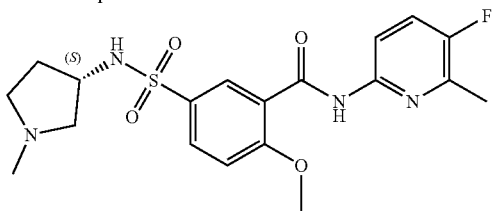

Compound 176

(S)—N-(5-Fluoro-6-methylpyridin-2-yl)-2-methoxy-5-(N-(pyrrolidin-3-yl)sulfamoyl)benzamide (150 mg, 0.367 mmol) was dissolved in methanol (5 mL) in a 50 mL round-bottomed flask and then treated with formaldehyde (59.6 mg, 0.74 mmol, purity 37%). The mixture was stirred at 20° C. for 30 minutes. Sodium cyanotrihydroborate (34.6 mg, 0.55 mmol) was added to the mixture. The reaction mixture was stirred at room temperature for 1 h and concentrated to dryness under reduced pressure. The crude was crystallized from a mixture of DMSO:water=1:2. The residue was purified by prep.HPLC (column: Synergi Max-RP 200 mm*25 mm, 4 µm; mobile phase: CH$_3$CN in water (0.075% TFA water) from 18% to 48%, flow rate: 30 ml/min). The pure fractions were collected and the volatiles were removed under vacuum. The aqueous phase was basified with IM aqueous Na$_2$CO$_3$ till pH=7. Ethyl acetate (50 mL) was added. The organic layer was separate and filtered. The filtrate was evaporated to dryness under vacuum to afford the title compound (79.8 mg, 52% yield).

LC-MS (ESI): RT=3.65 min, mass calcd. for $C_{19}H_{23}FN_4O_4S$ 422.1, m/z found 423.1 [M+H]$^+$. $^1$H NMR (400 MHz, DMSO-d$_6$) δ 10.56 (s, 1H), 8.14-8.02 (m, 2H), 7.94-7.82 (m, 2H), 7.68 (t, J=8.9 Hz, 1H), 7.37 (d, J=8.8 Hz, 1H), 3.98 (s, 3H), 3.65-3.56 (m, 1H), 2.68-2.59 (m, 1H), 2.54-2.49 (m, 1H), 2.45-2.40 (m, 1H), 2.37 (d, J=2.4 Hz, 3H), 2.33-2.26 (m, 1H), 2.22 (s, 3H), 1.94-1.83 (m, 1H), 1.53-1.42 (m, 1H).

Compound 177 to 181 were Synthesized as Similar Procedure to Compound 175

Compound 177: (R)—N-(5-Fluoro-6-methylpyridin-2-yl)-2-methoxy-5-(N-(pyrrolidin-3-yl) sulfamoyl)benzamide LC-MS (ESI): mass calcd. for $C_{18}H_{21}FN_4O_4S$ 408.13, m/z found 409.1 [M+H]$^+$; $^1$H NMR (400 MHz, DMSO-d$_6$) δ 10.61 (s, 1H), 8.14 (d, J=2.5 Hz, 1H), 8.09 (d, J=8.3 Hz, 1H), 7.96 (dd, J=2.5, 8.8 Hz, 1H), 7.72 (t, J=9.0 Hz, 1H), 7.43 (d, J=9.0 Hz, 1H), 4.02 (s, 3H), 3.73-3.65 (m, 2H), 3.13-3.02 (m, 4H), 2.91-2.84 (m, 1H), 2.41 (d, J=2.8 Hz, 3H), 1.95-1.84 (m, 1H), 1.74-1.64 (m, 1H).

Compound 178: (S)—N-(4-Fluorophenyl)-2-methoxy-5-(N-(pyrrolidin-3-yl)sulfamoyl)benzamide LC-MS (ESI): mass calcd. for $C_{18}H_{20}FN_3O_4S$ 393.12, m/z found 394.1 [M+H]$^+$; $^1$H NMR (400 MHz, DMSO-d$_6$) δ 10.30 (s, 1H), 7.99 (s, 1H), 7.91 (d, J=8.8 Hz, 1H), 7.74 (dd, J=5.3, 8.5 Hz, 2H), 7.37 (d, J=8.8 Hz, 1H), 7.20 (t, J=8.8 Hz, 2H), 3.96 (s, 3H), 2.79-2.70 (m, 2H), 2.69-2.59 (m, 1H), 2.47-2.37 (m, 2H), 1.76-1.65 (m, 1H), 1.48-1.35 (m, 1H).

Compound 179: (S)—N-(2-Chlorophenyl)-2-methoxy-5-(N-(pyrrolidin-3-yl)sulfamoyl)benzamide LC-MS (ESI): mass calcd. for $C_{18}H_{20}ClN_3O_4S$ 409.09, m/z found 410.1 [M+H]$^+$; $^1$H NMR (400 MHz, DMSO-d$_6$) δ 10.48 (s, 1H), 8.45 (br. s., 1H), 8.38 (d, J=7.8 Hz, 1H), 8.00 (d, J=8.3 Hz, 1H), 7.59 (d, J=8.0 Hz, 1H), 7.50 (d, J=8.5 Hz, 1H), 7.41 (t, J=7.7 Hz, 1H), 7.21 (t, J=7.7 Hz, 1H), 4.15 (s, 3H), 3.55-3.47 (m, 2H), 2.82-2.72 (m, 2H), 2.70-2.65 (m, 1H), 1.78-1.64 (m, 1H), 1.47-1.37 (m, 1H).

Compound 180: (R)—N-(4-Fluorophenyl)-2-methoxy-5-(N-(pyrrolidin-3-yl)sulfamoyl)benzamide LC-MS (ESI): mass calcd. for $C_{18}H_{20}FN_3O_4S$ 393.12, m/z found 394.1 [M+H]$^+$; $^1$H NMR (400 MHz, DMSO-d$_6$) δ 10.39 (s, 1H), 8.06 (d, J=1.8 Hz, 1H), 7.99 (d, J=8.8 Hz, 1H), 7.81 (dd, J=5.0, 8.8 Hz, 2H), 7.44 (d, J=8.8 Hz, 1H), 7.26 (t, J=8.8 Hz, 2H), 4.03 (s, 3H), 3.66-3.58 (m, 1H), 2.97-2.86 (m, 2H), 2.86-2.77 (m, 1H), 2.66-2.57 (m, 1H), 1.89-1.78 (m, 1H), 1.61-1.51 (m, 1H).

Compound 181: (R)—N-(3-(Difluoromethyl-4-fluorophenyl)-2-methoxy-5-(N-(pyrrolidin-3-yl) sulfamoyl)benzamide LC-MS (ESI): mass calcd. for $C_{19}H_{20}F_3N_3O_4S$ 443.11, m/z found 444.11 [M+H]$^+$; $^1$H NMR (400 MHz, DMSO-d$_6$) δ 10.48 (s, 1H), 8.11-8.05 (m, 1H), 8.03-7.98 (m, 1H), 7.97-7.82 (m, 2H), 7.43-7.33 (m, 1), 7.10 (s, 1H), 3.97 (s, 3H), 3.56-3.49 (m, 3H), 2.84-2.75 (m, 2H), 2.73-2.65 (m, 1H), 1.80-1.65 (m, 1H), 1.51-1.39 (m, 1H).

Compound 182-188

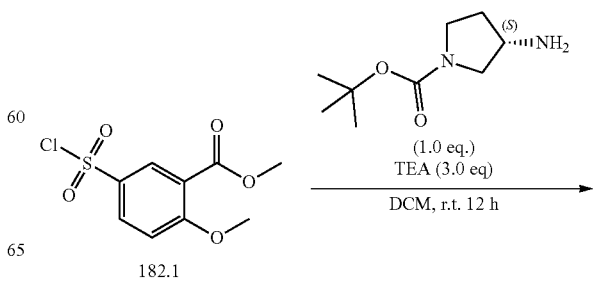

182.1

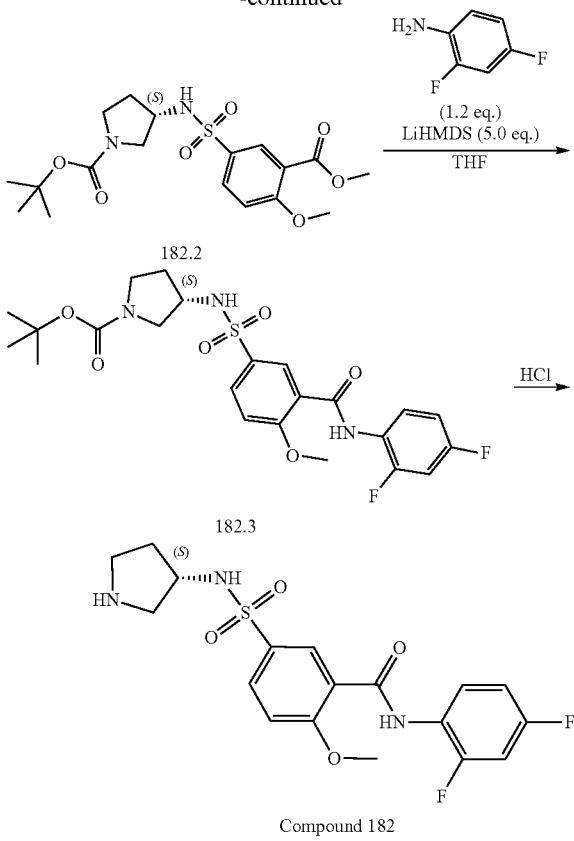

Compound 182

Intermediate 182.2: (S)-tert-butyl 3-(4-methoxy-3-(methoxycarbonyl) phenylsulfonamido) pyrrolidine-1-carboxylate To a solution consisting of(S)-tert-butyl 3-aminopyrrolidine-1-carboxylate (10.0 g, 53.7 mmol), TEA (22.5 mL, 161 mmol) and DCM (100 mL) was added methyl 5-(chlorosulfonyl)-2-methoxybenzoate (14.2 g, 53.7 mmol) at 0° C. The mixture was stirred at room temperature for 12 hours. Water (60 mL) was added. The aqueous layer was extracted with dichloromethane (80 mL*2). The combined organic layers were washed with brine, dried over $Na_2SO_4$ and filtered. The filtrate was concentrated under reduced pressure to give a residue which was purified by silica gel chromatography (elute: petroleum ether:ethyl acetate=3:1) to give title compound (14.5 g, 58.6% yield).

Intermediate 182.3: (S)-tert-butyl 3-(3-((2,4-difluorophenyl)carbamoyl)-4-methoxyphenyl sulfonamido)pyrrolidine-1-carboxylate To a solution consisting of (S)-tert-butyl 3-(4-methoxy-3-(methoxycarbonyl) phenylsulfonamido)pyrrolidine-1-carboxylate (200 mg, 0.483 mmol)), 2,4-difluoroaniline (74.9 mg, 0.580 mmol) and THF (3 mL) was added LiHMDS (2.42 mL, 2.42 mmol). The mixture was stirred at room temperature for 12 hours and then quenched with saturated ammonium chloride. The organic layer was separated and dried over $Na_2SO_4$ and filtered. The filtrate was concentrated under reduced pressure to give the title compound (250 mg, 78.1% yield).

Compound 182: (S)—N-(2,4-difluorophenyl-2-methoxy-5-(N-(pyrrolidin-3-yl)sulfamoyl) benzamide To a solution consisting of (S)-tert-butyl 3-(3-((2,4-difluorophenyl)carbamoyl)-4-methoxyphenylsulfonamido) pyrrolidine-1-carboxylate (250 mg, 0.489 mmol) and ethyl acetate (3 mL) was added HCl/ethyl acetate (3 mL, 4N). The mixture was stirred at room temperature for 12 hours and then adjusted to pH 7 with saturated sodium bicarbonate. The aqueous layer was extracted with ethyl acetate (30 mL*2). The combined organic layers were washed with brine, dried over $Na_2SO_4$ and filtered. The filtrate was concentrated under reduced pressure to give a residue which was purified by prep.HPLC (Column: Phenomenex Gemini C18 200*25 mm*10 um, Flow rate: 25 ml/min, Mobile Phase A: Base water (containing 0.05% $NH_3.H_2O$), Mobile Phase B: Acetonitrile.). The desired fraction was collected and the volatile was removed under reduced pressure. The water phase was lyophilized to give the title compound (26.10 mg, 12.3% yield).

LC-MS (ESI): $R_T$=4.74 min, mass calcd. for $C_{18}H_{19}F_2N_3O_4S$ 411.42, m/z found 412.1 [M+H]$^+$. $^1$H NMR (400 MHz, DMSO-d$_6$) δ 10.12 (br.s, 1H), 8.23 (d, J=2.0 Hz, 1H), 7.94-8.02 (m, 2H), 7.37-7.45 (m, 2H), 7.14 (t, J=8.0 Hz, 1H), 4.04 (s, 3H), 2.61-2.77 (m, 4H), 2.38-2.43 (m, 1H), 1.65-1.74 (m, 1H), 1.35-1.43 (m, 1H).

Compound 183-188 were Synthesized as Similar Procedure to Compound 182

Compound 183: (S)—N-(3-(difluoromethyl)-4-fluorophenyl)-2-methoxy-5-(N-(pyrrolidin-3-yl) sulfamoyl)benzamide LC-MS (ESI): mass calcd. for $C_{19}H_{20}F_3N_3O_4S$ 443.44, m/z found 444.0 [M+H]$^+$, $^1$H NMR (400 MHz, DMSO-d$_6$) δ 10.51 (br.s, 2H), 8.06-8.10 (m, 1H), 8.00 (d, J=2.0 Hz, 1H), 7.94 (dd, J=8.8 Hz, J=2.4 Hz, 1H), 7.84-7.90 (m, 1H), 7.36-7.42 (m, 2H), 7.24-7.21 (m, 1H), 3.97 (s, 3H), 2.74-2.94 (m, 4H), 2.57-2.63 (m, 1H), 1.74-1.83 (m, 1H), 1.48-1.56 (m, 1H).

Compound 184: (S)-2-methoxy-N-(2-methoxyphenyl)-5-(N-(pyrrolidin-3-yl)sulfamoyl) benzamide LC-MS (ESI): mass calcd. for $C_{19}H_{23}N_3O_5S$ 405.47, m/z found 406.2 [M+H]$^+$, $^1$H NMR (400 MHz, DMSO-d$_6$) δ 10.59 (br.s, 2H), 8.52 (s, 1H), 8.43 (d, J=8.0 Hz, 1H), 7.95-8.02 (m, 1H), 7.50 (d, J=8.8 Hz, 1K), 7.13 (d, J=3.6 Hz, 2H), 6.96-7.03 (m, 1H), 4.17 (s, 3H), 3.97 (s, 3H), 2.57-2.80 (m, 4H), 2.38-2.44 (m, 1H), 1.65-1.76 (m, 1H), 1.34-1.44 (m, 1H).

Compound 185: (S)—N-(4-chloro-2-fluorophenyl)-2-methoxy-5-(N-(pyrrolidin-3-yl)sulfamoyl) benzamide LC-MS (ESI): mass calcd. for $C_{18}H_{19}ClFN_3O_4S$ 427.88, m/z found 428.1 [M+H]$^+$, $^1$H NMR (400 MHz, DMSO-d$_6$) δ 10.24 (br.s, 2H), 8.24 (s, 1H), 8.11 (t, J=8.4 Hz, 1H), 7.94-7.99 (m, 1H), 7.57 (d, J=10.4 Hz, 1H), 7.44 (d, J=8.8 Hz, 1H), 7.34 (d, J=8.8 Hz, 1H), 4.05 (s, 3H), 2.58-2.78 (m, 4H), 2.38-2.42 (m, 1H), 1.64-1.73 (m, 1H), 1.32-1.43 (m, 1H).

Compound 186: (S)—N-(2-chloro-5-fluorophenyl)-2-methoxy-5-(N-(pyrrolidin-3-yl)sulfamoyl) benzamide LC-MS (ESI): mass calcd. for $C_{18}H_{19}ClFN_3O_4S$ 427.88, m/z found 428.1 $[M+H]^+$, $^1H$ NMR (400 MHz, DMSO-$d_6$) δ 10.63 (br.s, 2H), 8.47 (s, 1H), 8.32 (d, J=10.4 Hz, 1H), 8.02 (d, J=10.8 Hz, 1H), 7.61-7.67 (m, 1H), 7.51 (d, J=8.8 Hz, 1H), 7.13 (t, J=6.4 Hz, 1H), 4.16 (s, 3H), 2.60-2.89 (m, 4H), 1.65-1.85 (m, 2H).

Compound 187: (S)—N-(4-fluoro-3-methylphenyl)-2-methoxy-5-(N-(pyrrolidin-3-yl)sulfamoyl) benzamide LC-MS (ESI): mass calcd. for $C_{19}H_{22}FN_3O_4S$ 407.46, m/z found 408.1 $[M+H]^+$, $^1H$ NMR (400 MHz, DMSO-$d_6$) δ 10.23 (br.s, 1H), 7.97-8.02 (m, 1H), 7.87-7.95 (m, 1H), 7.61-7.65 (m, 1H), 7.52-7.58 (m, 1H), 7.34-7.41 (m, 1H), 7.13 (t, J=9.2 Hz, 1H), 3.97 (s, 3H), 2.58-2.80 (m, 4H), 2.39-2.45 (m, 1H), 2.24 (s, 3H), 1.66-1.75 (m, 1H), 1.36-1.45 (m, 1H).

Compound 188: (R)—N-(2,4-difluorophenyl)-2-methoxy-5-(N-(pyrrolidin-3-yl)sulfamoyl) benzamide LC-MS (ESI): mass calcd. for $C_{18}H_{19}F_2N_3O_4S$ 411.11, m/z found 412.1 $[M+H]^+$, $^1H$ NMR (400 MHz, DMSO-$d_6$) δ 10.12 (br. s., 1H), 8.24 (d, J=2.0 Hz, 1H), 8.05-7.90 (m, 2H), 7.49-7.30 (m, 2H), 7.14 (t, J=7.8 Hz, 1H), 4.04 (s, 3H), 2.82-2.71 (m, 2H), 2.70-2.61 (m, 2H), 2.44 (m, 1H), 1.78-1.65 (m, 1H), 1.41 (m, J=5.8, 13.2 Hz, 1H).

Compound 189

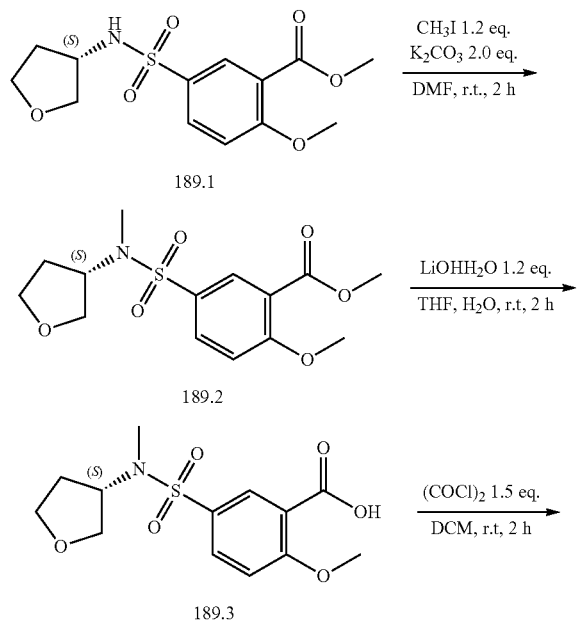

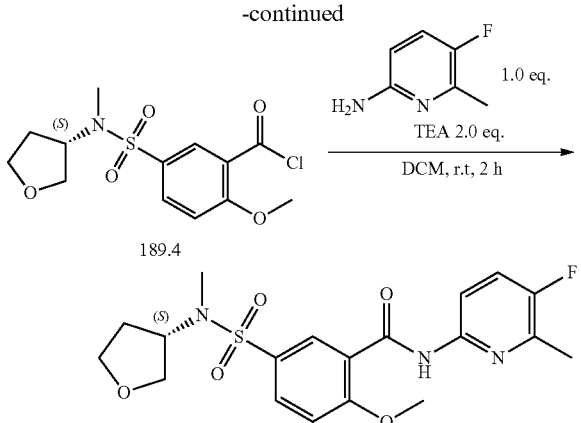

Compound 189

Intermediate 189.2: (S)-Methyl 2-methoxy-5-(N-methyl-N-(tetrahydrofuran-3-yl) sulfamoyl) benzoate (S)-Methyl 2-methoxy-5-(N-(tetrahydrofuran-3-yl) sulfamoyl) benzoate (1.00 g, 3.17 mmol) and potassium carbonate (893 mg, 6.46 mmol) were dissolved in DMF (5 mL) at 0° C. Then iodomethane (539 mg, 3.80 mmol) was added into the mixture and the mixture was stirred at room temperature for 2 hours. The mixture was poured into ice water and precipitation formed. The precipitation was collected. The crude product (1.00 g crude) was used directly for next step without further purification.

Intermediate 189.3: (3S)-2-Methoxy-5-(N-methyl-N-(tetrahydrofuran-3-yl) sulfamoyl) benzoic acid To a solution consisting of (S)-methyl 2-methoxy-5-(N-methyl-N-(tetrahydrofuran-3-yl) sulfamoyl) benzoate (1.00 g, 3.04 mmol) in THF (4 mL) and $H_2O$ (1 mL) was added lithium hydroxide hydrate (151 mg, 3.60 mmol). The mixture was stirred at room temperature for 2 hours and the resultant solution was concentrated under reduced pressure. The residue was adjusted to pH=5~6 (1 N HCl) and precipitation formed. The precipitation was collected. The crude product (800 mg crude) was used directly for next step without further purification.

Intermediate 189.4: (S)-2-Methoxy-5-(N-methyl-N-(tetrahydrofuran-3-yl) sulfamoyl) benzoyl chloride To a solution of (S)-2-methoxy-5-(N-methyl-N-(tetrahydrofuran-3-yl) sulfamoyl)benzoic acid (300 mg, 0.95 mmol) in DCM (3 mL) was added oxalyl dichloride (150 mg, 1.18 mmol). The mixture was stirred at room temperature for 2 hours and the resultant solution was concentrated under reduced pressure. The crude product (310 mg crude) was used directly for next step without further purification.

Compound 189: (S)—N-(5-fluoro-6-methylpyridin-2-yl)-2-methoxy-5-(N-methyl-N-(tetrahydrofuran-3-yl)sulfamoyl) benzamide (S)-2-Methoxy-5-(N-methyl-N-(tetrahydrofuran-3-yl) sulfamoyl)benzoyl chloride (310 mg, 0.93 mmol) was added into a solution consisting of 5-fluoro-6-methylpyridin-2- amine (117 mg, 0.93 mmol), triethylamine (202 mg, 2.00 mmol) and DCM (3 mL). The reaction was stirred at 25° C. for 2 hours. The mixture was concentrated under reduced pressure. The residue was purified by prep. TLC to give the title compound as a pale-yellow solid (154.80 mg, 37.4% yield, purity: 95.0%).

LC-MS (ESI): $R_T$=4.71 min, mass calcd. for $C_{19}H_{22}FN_3O_5S$ 423.5, m/z found 424.1 [M+H]$^+$. $^1$H NMR (400 MHz, DMSO-d$_6$) δ 10.65 (br.s, 1H), 8.06 (d, J=6.4 Hz, 1H), 7.97 (s, 1H), 7.90 (dd, J=8.8 Hz, J=2.4 Hz, 1H), 7.69 (t, J=8.8 Hz, 1H), 7.36 (d, J=4.8 Hz, 1H), 4.59-4.49 (m, 2H), 3.98 (s, 3H), 3.81-3.69 (m, 2H), 3.55-3.45 (m, 1H), 2.62 (s, 3H), 2.42-2.32 (m, 3H), 1.94-1.84 (m, 1H), 1.56-1.45 (m, 1H).

Compound 190-196

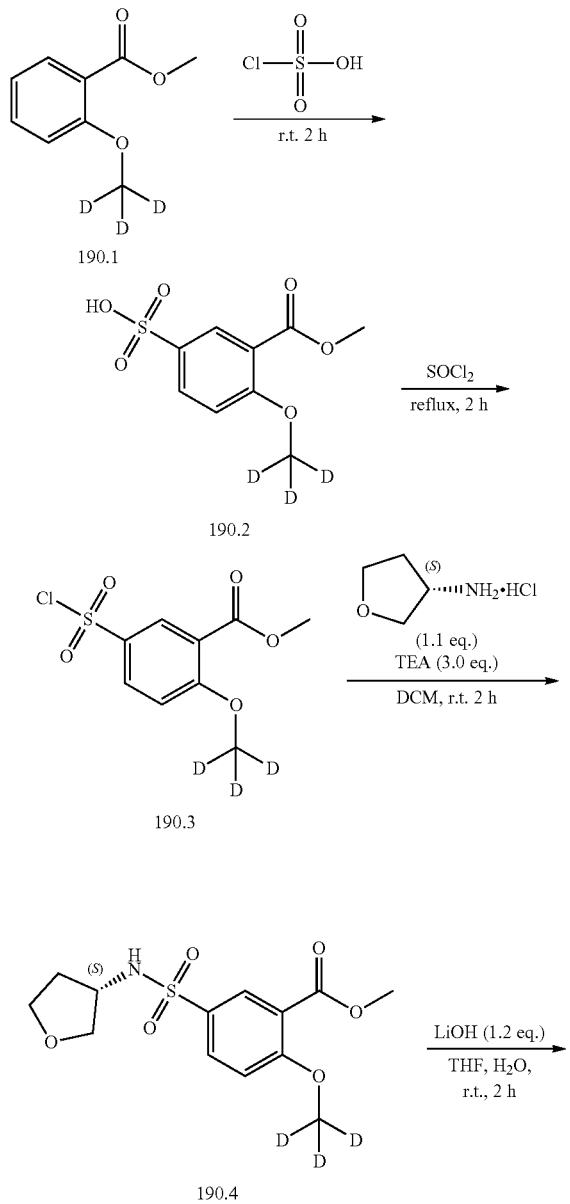

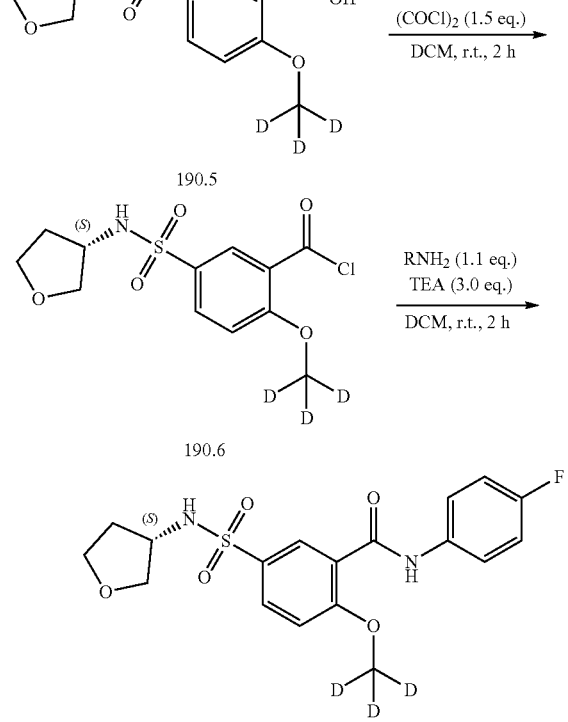

Compound 190

Intermediate 190.2: 4-(Methoxy-d3)-3-(methoxycarbonyl)benzenesulfonic acid

Chlorosulfonic acid (20 mL) was added to methyl 2-(methoxy-d3) benzoate (3.00 g, 17.7 mmol) drop-wise at room temperature. The mixture was stirred at that temperature for 2 hours and then concentrated under reduced pressure to give the crude product (2.20 g). The residue was used for next step without further purification.

Intermediate 190.3: Methyl 5-(chlorosulfonyl)-2-(methoxy-d3)benzoate

Sulfurous dichloride (10 mL) was added to 4-(methoxy-d3)-3-(methoxycarbonyl) benzenesulfonic acid (2.20 g, 8.83 mmol) drop-wise at room temperature. The mixture was stirred at that temperature for 2 hours and then concentrated under reduced pressure to give the crude product (2.00 g). The residue was used for next step without further purification.

Intermediate 190.4: (S)-Methyl 2-(methoxy-d3)-5-(N-(tetrahydrofuran-3-yl)sulfamoyl)benzoate To a solution consisting of (S)-3-aminotetrahydrofuran hydrochloride (1.01 g, 8.17 mmol, Shanghai Nuohey Chemical Technology CO., LTD.), TEA (2.23 g, 22.04 mmol) and DCM (20 mL) was added methyl 5-(chlorosulfonyl)-2-(methoxy-d3) benzoate (2.00 g, 7.47 mmol). The mixture was stirred at room temperature for 2 hours and the resultant solution was concentrated under reduced pressure. Water and ethyl acetate were added. The organic layer was separated and the water phase was extracted twice with ethyl acetate. The combined organic layers were washed with brine, dried over $Na_2SO_4$ and filtered. The filtrate was concentrated under reduced pressure to give the title compound (2.00 g, 84.09% yield).

Intermediate 190.5: (S)-2-(methoxy-d3)-5-(N-(tetrahydrofuran-3-yl)sulfamoyl)benzoic acid Lithium hydroxide (158 mg, 3.77 mmol) was added into a solution consisting of (S)-methyl 2-(methoxy-d3)-5-(N-(tetrahydrofuran-3-yl) sulfamoyl) benzoate (2.00 g, 6.28 mmol), THF (4 mL) and $H_2O$ (1 mL). The reaction mixture was stirred at room temperature for 2 hours before concentrating it under reduced pressure to remove volatiles. The resultant aqueous phase was adjusted to pH=5-6 with aq. HCl solution and the precipitation was collected and dried to give the product (1.40 g, 73.22% yield).

Intermediate 190.6: (S)-2-(methoxy-d3)-5-(N-(tetrahydrofuran-3-yl)sulfamoyl)benzoyl chloride Oxalyl dichloride (876 mg, 6.90 mmol) was added into a solution consisting of (S)-2-(methoxy-d3)-5-(N-(tetrahydrofuran-3-yl) sulfamoyl) benzoic acid (1.40 g, 4.60 mmol) and DCM (20 mL). The reaction was stirred at room temperature for 2 hours. The resultant mixture was concentrated under reduced pressure to give the title compound (1.50 g crude), which was used for the next step directly.

Compound 190: (S)—N-(4-fluorophenyl)-2-(methoxy-d3)-5-(N-(tetrahydrofuran-3-yl)sulfamoyl)benzamide (S)-2-(Methoxy-d3)-5-(N-(tetrahydrofuran-3-yl)sulfamoyl)benzoylchloride (200 mg, 0.62 mmol) was dissolved in dry DCM (2 mL) and the resultant solution was added drop-wise to a well stirred solution consisting of 4-fluoroaniline (76.0 mg, 0.68 mmol), TEA (182 mg, 1.80 mmol) and DCM (3 mL) at room temperature. The reaction mixture was stirred at room temperature for 2 hours and then diluted with DCM (5 mL). Water (5 mL) was added. The organic phase was separated, dried over $Na_2SO_4$ and filtered. The filtrate was concentrated under reduced pressure to give a residue which was purified by prep-TLC.

LC-MS (ESI): $R_T$=4.21 min, mass calcd. for $C_{18}H_{16}D_3FN_2O_5S$ 397.44, m/z found 398.1 $[M+H]^+$. $^1H$ NMR (400 MHz, DMSO-$d_6$) δ 10.30 (br.s, 1H), 8.00 (d, J=4.0 Hz, 1H), 7.98-7.86 (m, 2H), 7.81-7.68 (m, 2H), 7.38 (d, J=8.8 Hz, 1H), 7.20 (t, J=8.8 Hz, 2H), 3.74-3.54 (m, 4H), 3.30-3.20 (m, 1H), 1.96-1.85 (m, 1H), 1.68-1.58 (m, 1H).

Compound 191-196 were Synthesized as Similar Procedure to Compound 190

Compound 191: (S)—N-(4-fluoro-3-methylphenyl)-2-(methoxy-d3)-5-(N-(tetrahydrofuran-3-yl) sulfamoyl)benzamide LC-MS (ESI): mass calcd. for $C_{19}H_{18}D_3FN_2O_5S$ 411.46, m/z found 412.1 $[M+H]^+$. $^1H$ NMR (400 MHz, DMSO-$d_6$) δ 10.23 (br.s, 1H), 8.00 (d, J=4.0 Hz, 1H), 7.98-7.86 (m, 2H), 7.68-7.51 (m, 2H), 7.38 (d, J=8.8 Hz, 1H), 7.13 (t, J=8.8 Hz, 1H), 3.74-3.54 (m, 4H), 3.30-3.20 (m, 1H), 2.24 (s, 3H), 1.96-1.85 (m, 1H), 1.68-1.58 (m, 1H).

Compound 192: (S)—N-(3-(Difluoromethyl)-4-fluorophenyl)-2-(methoxy-d3)-5-(N-(tetrahydrofuran-3-yl)sulfamoyl)benzamide LC-MS (ESI): mass calcd. for $C_{19}H_{16}D_3F_3N_2S$ 447.44, m/z found 448.1 $[M+H]^+$. $^1H$ NMR (400 MHz, DMSO-$d_6$) δ 10.50 (br.s, 1H), 8.15-7.77 (m, 5H), 7.47-7.32 (m, 2H), 7.25 (t, J=56.0 Hz, 1H), 3.74-3.54 (m, 4H), 3.30-3.20 (m, 1H), 1.96-1.85 (m, 1H), 1.68-1.58 (m, 1H).

Compound 193: (S)—N-(5-fluoropyridin-2-yl)-2-(methoxy-d3)-5-(N-(tetrahydrofuran-3-yl) sulfamoyl)benzamide LC-MS (ESI): mass calcd. for $C_{17}H_{15}D_3FN_3O_5S$ 398.42, m/z found 399.1 $[M+H]^+$. $^1H$ NMR (400 MHz, DMSO-$d_6$) δ 10.69 (br.s, 1H), 8.44-8.10 (m, 3H), 8.03-7.76 (m, 3H), 7.42 (d, J=8.8 Hz, 1H), 3.74-3.54 (m, 4H), 3.30-3.20 (m, 1H), 1.96-1.85 (m, 1H), 1.68-1.58 (m, 1H).

Compound 194: (S)—N-(5-fluoro-6-methylpyridin-2-yl)-2-(methoxy-d3)-5-(N-(tetrahydrofuran-3-yl) sulfamoyl)benzamide LC-MS (ESI): mass calcd. for $C_{18}H_{17}D_3FN_3O_5S$ 412.45, m/z found 413.1 $[M+H]^+$. $^1H$ NMR (400 MHz, DMSO-$d_6$) δ 10.61 (br.s, 1H), 8.14 (d, J=4.0 Hz, 1H), 8.10 (d, J=8.8 Hz, 1H), 7.94 (dd, J=8.8 Hz, J=4.0 Hz, 2H), 7.72 (t, J=8.8 Hz, 1H), 7.40 (d, J=8.8 Hz, 1H), 3.74-3.54 (m, 4H), 3.30-3.20 (m, 1H), 2.47-2.24 (m, 3H), 1.96-1.85 (m, 1H), 1.68-1.58 (m, 1H).

Compound 195: (S)—N-(6-cyclopropyl-5-fluoropyridin-2-yl)-2-(methoxy-d3)-5-(N-(tetrahydrofuran-3-yl)sulfamoyl)benzamide LC-MS (ESI): mass calcd. for $C_{20}H_{19}D_3FN_3O_5S$ 438.49, m/z found 439.2 $[M+H]^+$. $^1H$ NMR (400 MHz, DMSO-$d_6$) δ 10.47 (br.s, 1H), 8.10 (s, 1H), 7.93 (d, J=8.8 Hz, 2H), 7.66 (t, J=9.2 Hz, 1H), 7.37 (d, J=8.4 Hz, 1H), 3.74-3.54 (m, 4H), 3.30-3.20 (m, 1H), 2.32-2.18 (m, 1H), 1.96-1.85 (m, 1H), 1.68-1.58 (m, 1H), 1.17-0.76 (m, 4H).

Compound 196: (S)—N-(3,5-difluoropyridin-2-yl)-2-(methoxy-d3)-5-(N-(tetrahydrofuran-3-yl) sulfamoyl)benzamide LC-MS (ESI): mass calcd. for $C_{17}H_{14}D_3F_2N_3O_5S$ 416.41, m/z found 417.1 $[M+H]^+$. $^1H$ NMR (400 MHz, DMSO-$d_6$) δ 10.49 (br.s, 1H), 8.40 (s, 1H), 8.16-8.04 (m, 2H), 8.02-7.92 (m, 1H), 7.39 (d, J=8.8 Hz, 1H), 3.75-3.53 (m, 4H), 3.40-3.35 (m, 1H), 1.96-1.85 (m, 1H), 1.68-1.58 (m, 1H).

Compound 197

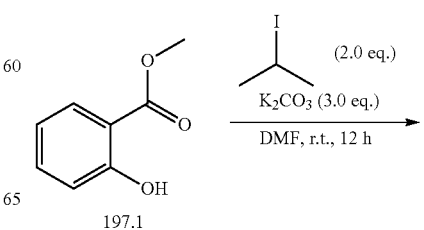

197.1

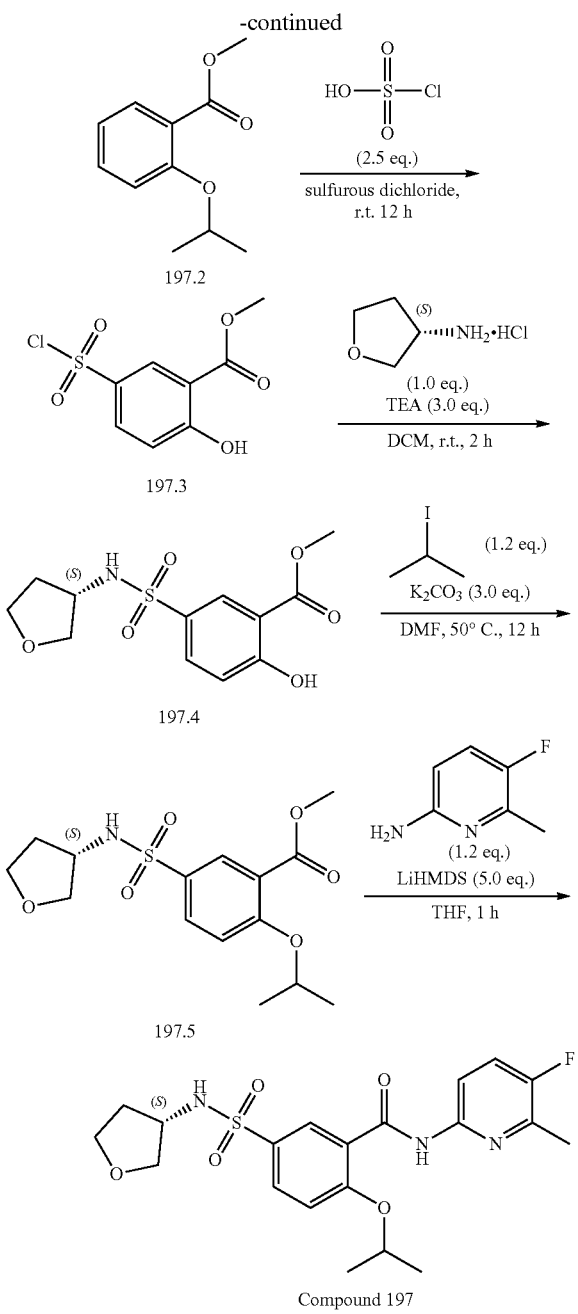

Intermediate 197.3: Methyl 5-(chlorosulfonyl)-2-hydroxybenzoate

To a solution consisting of methyl 2-isopropoxybenzoate (1.00 g, 5.15 mmol) and sulfurous dichloride (8 mL) was added sulfurochloridic acid (0.847 mL, 12.9 mmol) at 0° C. The mixture was stirred at room temperature for 12 hours. The reaction mixture was poured into ice water. The title compound was precipitated and filtered. (1.00 g, 77.5% yield) $^1$H NMR (400 MHz, DMSO-$d_6$) δ 8.02 (d, J=2.4 Hz, 1H), 7.70 (dd, J=2.4, 8.8 Hz, 1H), 6.94 (d, J=8.4 Hz, 1H), 3.89 (s, 3H).

Intermediate 197.4; (S)-Methyl 2-hydroxy-5-(N-(tetrahydrofuran-3-yl)sulfamoyl)benzoate To a solution consisting of (S)-3-aminotetrahydrofuran hydrochloride (172 mg, 1.40 mmol, Shanghai Nuohey Chemical Technology CO., LTD.), TEA (0.584 mL, 4.19 mmol) and DCM (5 mL) was added methyl 5-(chlorosulfonyl)-2-hydroxybenzoate (350 mg, 1.40 mmol). The mixture was stirred at room temperature for 2 hours and the resultant solution was concentrated under reduced pressure. Water and ethyl acetate were added. The organic layer was separated and the water phase was extracted with ethyl acetate (20 mL×2). The combined organic layers were washed with brine, dried over $Na_2SO_4$ and filtered. The filtrate was concentrated under reduced pressure to give the title compound (250 mg, 59.5% yield).

Intermediate 197.5: (S)-Methyl 2-isopropoxy-5-(N-(tetrahydrofuran-3-yl)sulfamoyl)benzoate To a solution consisting of (S)-methyl 2-hydroxy-5-(N-(tetrahydrofuran-3-yl) sulfamoyl) benzoate (250 mg, 0.830 mmol), $K_2CO_3$ (344 mg, 2.49 mmol) and DMF (4 mL) was added 2-iodopropane (169 mg, 0.996 mmol). The mixture was stirred at 50° C. for 12 hours. Water (20 mL) was added into the mixture. The aqueous layer was extracted with ethyl acetate (40 mL×2). The combined organic layers were washed with brine (20 mL×2) and dried over $Na_2SO_4$. The organic layer was filtered and concentrated under reduced pressure to give the title compound (200 mg, 70.1% yield).

Compound 197: (S)—N-(5-fluoro-6-methylpyridin-2-yl)-2-isopropoxy-5-(N-(tetrahydrofuran-3-yl) sulfamoyl)benzamide To a solution consisting of (S)-methyl 2-isopropoxy-5-(N-(tetrahydrofuran-3-yl) sulfamoyl) benzoate (200 mg, 0.582 mmol)), 5-fluoro-6-methylpyridin-2-amine (87.8 mg, 0.696 mmol) and THF (4 mL) was added LiHMDS (2.91 mL, 2.91 mmol). The mixture was stirred at room temperature for 1 hour. The mixture was quenched with saturated ammonium chloride. The organic layer was separated, dried over $Na_2SO_4$ and filtered. The filtrate was concentrated under reduced pressure. The residue was purified by prep.H-PLC (Column: Phenomenex Gemini 150*25 mm*5 um, Flow rate: 25 ml/min, Mobile Phase A: Base water (containing 0.05% $NH_3.H_2O$), Mobile Phase B: Acetonitrile.) to give the title compound (17.20 mg, 6.70% yield).

LC-MS (ESI): $R_T$=5.38 min, mass calcd. for $C_{20}H_{24}FN_3O_5S$ 437.14, m/z found 438.1 [M+H]$^+$. $^1$H NMR (400 MHz, DMSO-$d_6$) δ 10.74 (br.s, 1H), 8.33 (s, 1H), 8.11 (d, J=6.4 Hz, 1H), 7.90-7.99 (m, 2H), 7.72 (t, J=9.2 Hz, 1H), 7.47 (d, J=8.8 Hz, 1H), 4.97-5.04 (m, 1a), 3.66-3.73 (m, 2H), 3.56-3.64 (m, 2H), 2.41 (s, 3H), 1.85-1.95 (m, 1H), 1.58-1.67 (m, 1H), 1.45 (d, J=6.0 Hz, 6H).

Compound 198

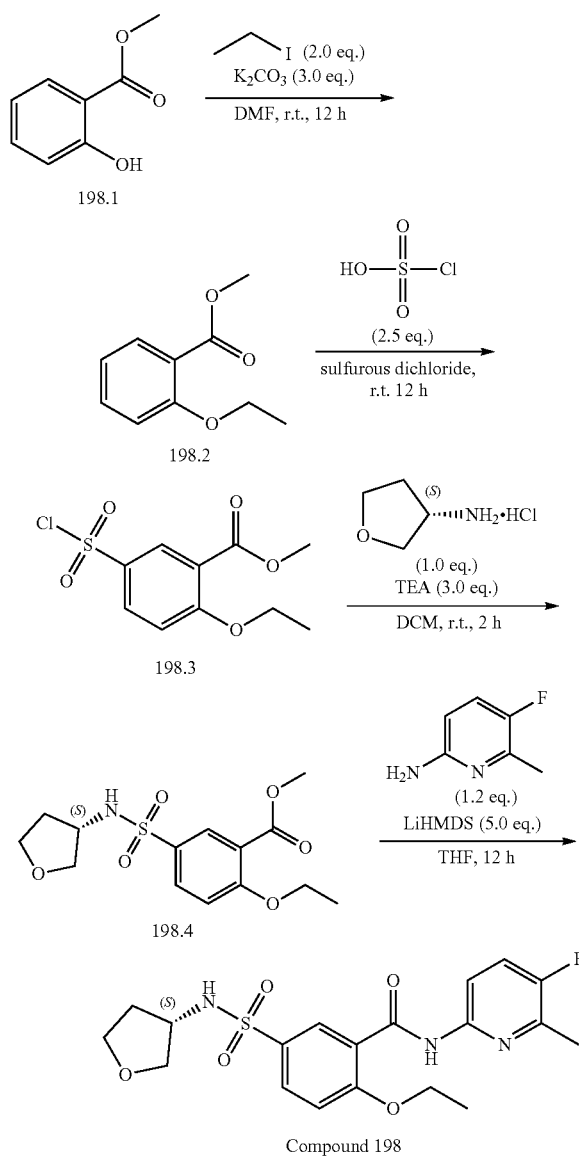

Intermediate 198.2: Methyl 2-ethoxybenzoate

To a solution consisting of methyl 2-hydroxybenzoate (2.00 g, 13.1 mmol), K₂CO₃ (5.45 g, 39.4 mmol) and DMF (20 mL) was added iodoethane (4.10 g, 26.3 mmol). The mixture was stirred at room temperature for 12 hours. Water (20 mL) was added into the mixture. The aqueous layer was extracted with ethyl acetate (40 mL×2). The combined organic layers were washed with brine (20 mL×2) and dried over Na₂SO₄. The organic layer was filtered and concentrated under reduced pressure to give the title compound (2.00 g, 84.4% yield).

Intermediate 198.3: Methyl 5-(chlorosulfonyl)-2-ethoxybenzoate

To a solution consisting of methyl 2-ethoxybenzoate (1.00 g, 5.55 mmol) and sulfurous dichloride (8 mL) was added sulfurochloridic acid (0.913 mL, 13.9 mmol) at 0° C. The mixture was stirred at room temperature for 12 hours. The reaction mixture was poured into ice water. Title compound was precipitated and filtered (500 mg, 32.3% yield). ¹H NMR (400 MHz, DMSO-d₆) δ 7.87 (d, J=1.6 Hz, 1H), 7.71-7.68 (m, 1H), 7.08 (d, J=8.8 Hz, 1H), 4.08 (q, J=6.8 Hz, 2H), 3.77 (s, 3H), 1.30 (t, J=7.2 Hz, 3H).

Intermediate 198.4: (S)-methyl 2-ethoxy-5-(N-(tetrahydrofuran-3-yl)sulfamoyl)benzoate To a solution consisting of (S)-3-aminotetrahydrofuran hydrochloride (155 mg, 1.26 mmol, Shanghai Nuohey Chemical Technology CO., LTD.), TEA (0.527 mL, 3.78 mmol) and DCM (5 mL) was added methyl 5-(chlorosulfonyl)-2-ethoxybenzoate (350 mg, 1.26 mmol). The mixture was stirred at room temperature for 2 hours and the resultant solution was concentrated under reduced pressure. Water and ethyl acetate were added. The organic layer was separated and the water phase was extracted with ethyl acetate (20 mL×2). The combined organic layers were washed with brine, dried over Na₂SO₄ and filtered. The filtrate was concentrated under reduced pressure to give the title compound (300 mg, 72.5% yield).

Compound 198: (S)-2-ethoxy-N-(5-fluoro-6-methylpyridin-2-yl)-5-(N-(tetrahydrofuran-3-yl) sulfamoyl) benzamide To a solution consisting of(S)-methyl 2-ethoxy-5-(N-(tetrahydrofuran-3-yl) sulfamoyl) benzoate (300 mg, 0.911 mmol)), 5-fluoro-6-methylpyridin-2-amine (138 mg, 1.09 mmol) and THF (4 mL) was added LiHMDS (4.56 mL, 4.56 mmol). The mixture was stirred at room temperature for 12 hours. The mixture was quenched with saturated ammonium chloride. The organic layer was separated, dried over Na₂SO₄ and filtered. The filtered was concentrated under reduced pressure. The residue was purified by prep. HPLC (Column: Xtimate C18 150*25 mm*5 um, Flow rate: 25 ml/min, Mobile Phase A: Base water (containing 0.05% NH₃.H₂O), Mobile Phase B: Acetonitrile.) to give the title compound (138.30 mg, 35.89% yield).

LC-MS (ESI): R$_T$=5.11 min, mass calcd. for C₁₉H₂₂FN₃O₅S 423.13, m/z found 424.1 [M+H]⁺. ¹H NMR (400 MHz, DMSO-d₆) δ 10.69 (br.s, 1H), 8.25 (d, J=1.6 Hz, 1H), 8.11 (d, J=6.4 Hz, 1H), 7.91-7.97 (m, 2H), 7.72 (t, J=9.2 Hz, 1H), 7.41 (d, J=8.8 Hz, 1H), 4.34 (q, J=6.8 Hz, 2H), 3.66-3.73 (m, 2H), 3.55-3.64 (m, 2H), 3.34-3.37 (m, 1H), 2.40 (d, J=2.4 Hz, 3H), 1.85-1.95 (m, 1H), 1.57-1.67 (m, 1H) 1.48 (t, J=6.8 Hz, 3H).

Compound 199

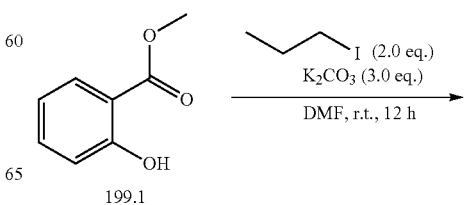

-continued

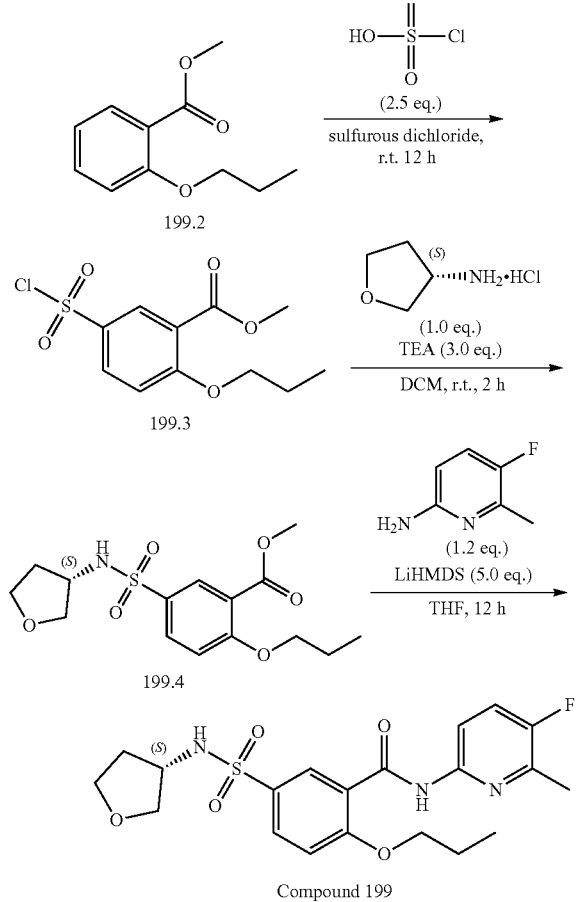

Intermediate 199.2: Methyl 2-propoxybenzoate

To a solution consisting of methyl 2-hydroxybenzoate (2.00 g, 13.1 mmol), $K_2CO_3$ (5.45 g, 39.4 mmol) and DMF (20 mL) was added 1-iodopropane (4.47 g, 26.3 mmol). The mixture was stirred at room temperature for 12 hours. Water (20 mL) was added into the mixture. The aqueous layer was extracted with ethyl acetate (40 mL×2). The combined organic layers were washed with brine (20 mL×2) and dried over $Na_2SO_4$. The organic layer was filtered and concentrated under reduced pressure to give the title compound (2.00 g, 78.33% yield).

Intermediate 199.3: Methyl 5-(chlorosulfonyl)-2-propoxybenzoate

To a solution consisting of methyl 2-propoxybenzoate (1.00 g, 5.15 mmol) and sulfurous dichloride (8 mL) was added sulfurochloridic acid (0.847 mL, 12.9 mmol) at 0° C. The mixture was stirred at room temperature for 12 hours. The reaction mixture was poured into ice water. The aqueous layer was extracted with ethyl acetate (20 mL×2). The combined organic layers were washed with brine (15 mL×2) and dried over $Na_2SO_4$. The organic layer was filtered and concentrated under reduced pressure. The crude product was purified by silica gel chromatography (eluent: petroleum ether:ethyl acetate=10:1) to give the title compound (350 mg, 23.2% yield).

$^1$H NMR (400 MHz, DMSO-$d_6$) δ 7.89 (d, J=2.0 Hz, 1H), 7.71 (dd, J=1.6, 8.4 Hz, 1H), 7.09 (d, J=8.4 Hz, 1H), 4.01 (t, J=6.4 Hz, 2H), 3.79 (s, 3H), 1.75-1.70 (m, 2H), 0.99 (t, J=7.6 Hz, 3H).

Intermediate 199.4: (S)-methyl 2-propoxy-5-(N-(tetrahydrofuran-3-yl)sulfamoyl)benzoate To a solution consisting of (S)-3-aminotetrahydrofuran hydrochloride (148 mg, 1.20 mmol, Shanghai Nuohey Chemical Technology CO., LTD.), TEA (0.500 mL, 3.59 mmol) and DCM (5 mL) was added methyl 5-(chlorosulfonyl)-2-propoxybenzoate (350 mg, 1.20 mmol). The mixture was stirred at room temperature for 2 hours and the resultant solution was concentrated under reduced pressure. Water and ethyl acetate were added. The organic layer was separated and the water phase was extracted with ethyl acetate (20 mL×2). The combined organic layers were washed with brine, dried over $Na_2SO_4$ and filtered. The filtrate was concentrated under reduced pressure to give the title compound (300 mg, 73.1% yield).

Compound 199: (S)—N-(5-fluoro-6-methylpyridin-2-yl)-2-propoxy-5-(N-(tetrahydrofuran-3-yl) sulfamoyl) benzamide To a solution consisting of (S)-methyl 2-propoxy-5-(N-(tetrahydrofuran-3-yl) sulfamoyl) benzoate (300 mg, 0.874 mmol)), 5-fluoro-6-methylpyridin-2-amine (132 mg, 1.05 mmol) and THF (3 mL) was added LiHMDS (4.37 mL, 4.37 mmol). The mixture was stirred at room temperature for 12 hours. The mixture was quenched with saturated ammonium chloride. The organic layer was separated, dried over $Na_2SO_4$ and filtered. The filtrate was concentrated under reduced pressure. The residue was purified by silica gel chromatography to give the title compound (187.80 mg, 47.60% yield).

LC-MS (ESI): $R_1$=5.48 min, mass calcd. for $C_{20}H_{24}FN_3O_5S$ 437.14, m/z found 438.1 [M+H]$^+$. Total run time was 9.5 minutes. $^1$H NMR (400 MHz, DMSO-$d_6$) δ 10.67 (br.s, 1H), 8.28 (s, 1H), 8.11 (d, J=6.4 Hz, 1H), 7.91-7.98 (m, 2H), 7.72 (t, J=9.2 Hz, 1H), 7.42 (d, J=8.8 Hz, 1H), 4.25 (t, J=6.0 Hz, 2H), 3.66-3.73 (m, 2H), 3.56-3.64 (m, 2H), 2.40 (d, J=1.2 Hz, 3H), 1.85-1.94 (m, 3H), 1.58-1.66 (m, 1H) 1.10 (t, J=7.2 Hz, 3H).

Compound 200

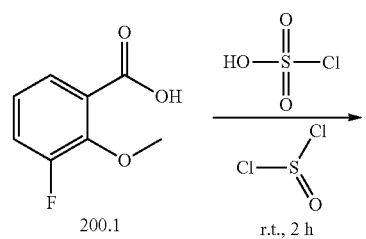

-continued

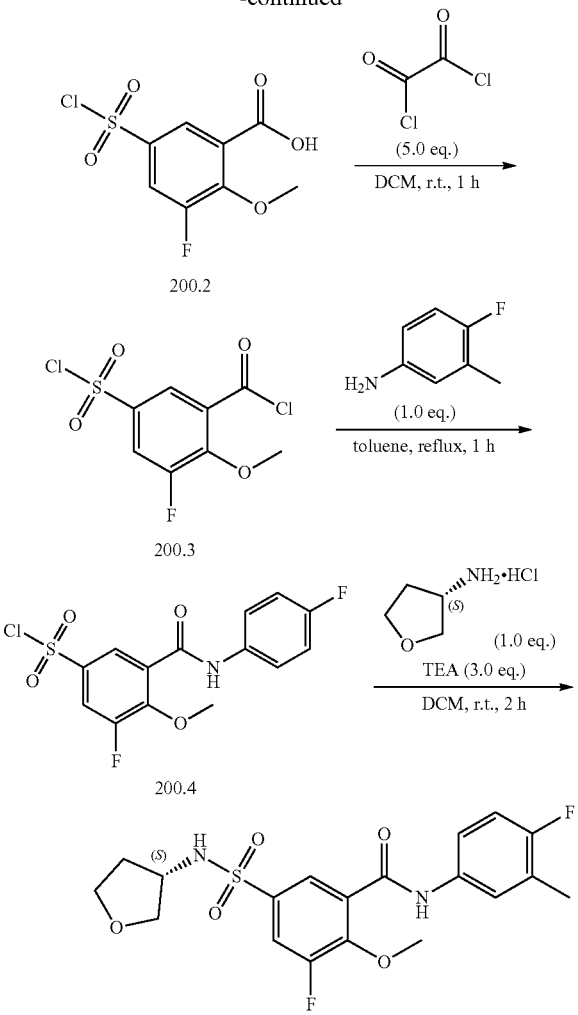

Intermediate 200.2:
5-(Chlorosulfonyl)-3-fluoro-2-methoxybenzoic acid

Sulfurochloridic acid (0.484 mL, 7.35 mmol) was added into a solution consisting of 3-fluoro-2-methoxybenzoic acid (500 mg, 2.94 mmol) and sulfurous dichloride (5 mL) at 0° C. The mixture was stirred at room temperature for 2 hours. The mixture was poured into ice water. The aqueous layer was extracted with ethyl acetate (50 mL×2). The combined organic layers were washed with brine and dried over $Na_2SO_4$. The organic layer was filtered and concentrated under reduced pressure. The crude product was purified by silica gel chromatography (eluent: petroleum ether: ethyl acetate=10:1) to give title compound (200 mg, 23% yield). $^1$H NMR (400 MHz, DMSO-$d_6$) δ 7.67 (s, 1H), 7.48 (d, J=10.8 Hz, 2H), 3.82 (s, 3H).

Intermediate 200.3:
5-(Chlorosulfonyl)-3-fluoro-2-methoxybenzoyl chloride

Oxalyl dichloride (0.315 mL, 3.72 mmol) was added into a solution consisting of 5-(chlorosulfonyl)-3-fluoro-2-methoxybenzoic acid (200 mg, 0.744 mmol) and DCM (4 mL) at 0° C. The reaction was stirred at room temperature for 1 hour. The mixture reaction was concentrated under reduced pressure to give the crude product (200 mg, 75% yield).

Intermediate 200.4: 3-Fluoro-5-((4-fluoro-3-methyl-phenyl)carbamoyl)-4-methoxybenzene-1-sulfonyl chloride 4-Fluoro-3-methylaniline (87.2 mg, 0.697 mmol) was added into a solution consisting of 5-(chlorosulfonyl)-3-fluoro-2-methoxybenzoyl chloride (200 mg, 0.697 mmol) and toluene (5 mL). The reaction was refluxed for 1 hour. The mixture reaction was concentrated under reduced pressure to give the crude product (250 mg, 76% yield).

Compound 200: (S)-3-fluoro-N-(4-fluoro-3-methyl-phenyl)-2-methoxy-5-(N-(tetrahydrofuran-3-yl) sulfamoyl)benzamide 3-Fluoro-5-((4-fluoro-3-methylphenyl) carbamoyl)-4-methoxybenzene-1-sulfonyl chloride (250 mg, 0.665 mmol) was added into a solution consisting of (S)-3-aminotetrahydrofuran hydrochloride (82.2 mg, 0.665 mmol, Shanghai Nuohey Chemical Technology CO., LTD.), TEA (0.278 mL, 2.00 mmol) and DCM (5 mL). The reaction was stirred at room temperature for 2 hours. The mixture reaction was concentrated under reduced pressure. The residue was purified by prep.HPLC: (Column: Phenomenex Gemini C18 200×25 mm×10 μm, Flow rate: 25 mL/min, Mobile Phase A: Base water (containing 0.05% $NH_3.H_2O$), Mobile Phase B: Acetonitrile.). The desired fraction was collected and evaporated to remove off $CH_3CN$ in vacuum. The residue was lyophilized to dryness to give the title compound (102.90 mg, 36% yield, purity 99.99%).

LC-MS (ESI): $R_T$=4.68 min, mass calcd. for $C_{19}H_{20}F_2N_2O_5S$ 426.43, m/z found 427.1 [M+H]$^+$. $^1$H NMR (400 MHz, DMSO-$d_6$) δ 10.45 (br.s, 1H), 8.08 (s, 1H), 7.83 (dd, J=11.2 Hz, J=2.0 Hz, 1H), 7.76 (s, 1H), 7.63 (dd, J=7.2 Hz, J=2.0 Hz, 1H), 7.47-7.55 (m, 1H), 7.14 (t, J=9.6 Hz, 1H), 4.02 (d, J=2.0 Hz, 3H), 3.57-3.80 (m, 4H), 3.37-3.42 (m, 1H), 2.25 (s, 3H), 1.90-2.01 (m, 1H), 1.60-1.70 (m, 1H).

Compound 201

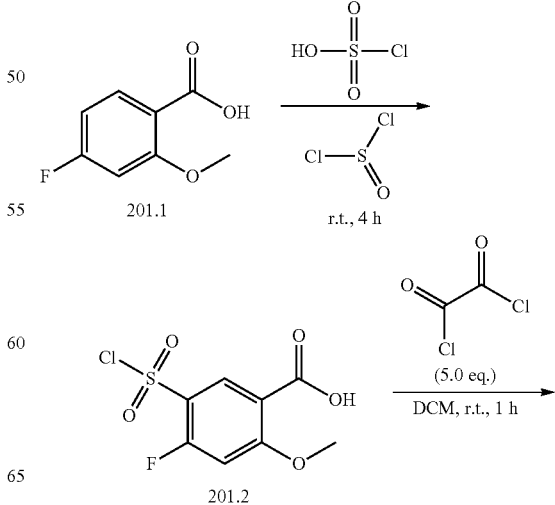

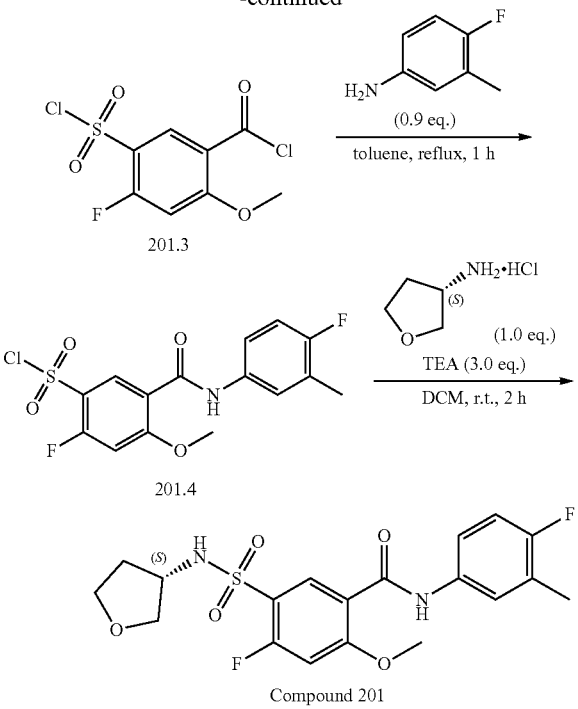

Intermediate 201.2:
5-(Chlorosulfonyl)-4-fluoro-2-methoxybenzoic acid

Sulfurochloridic acid (0.894 mL, 13.6 mmol) was added into a solution consisting of 4-fluoro-2-methoxybenzoic acid (1.00 g, 5.43 mmol) and sulfurous dichloride (4 mL) at 0° C. The mixture was stirred at room temperature for 4 hours. The mixture was stirred at 80° C. for 4 hours. The mixture was poured into ice water. The aqueous layer was extracted with ethyl acetate (80 mL×2). The combined organic layers were washed with brine and dried over Na₂SO₄. The organic layer was filtered and concentrated under reduced pressure. The crude product was purified by silica gel chromatography (eluent: petroleum ether:ethyl acetate=1:1) to give the title compound (600 mg, 37% yield). $^1$H NMR (400 MHz, DMSO-$d_6$) δ 8.00 (d, J=8.8 Hz, 1H), 6.93 (d, J=12.4 Hz, 2H), 3.78 (s, 3H).

Intermediate 201.3:
5-(Chlorosulfonyl)-4-fluoro-2-methoxybenzoyl chloride

Oxalyl dichloride (0.473 mL, 5.59 mmol) was added into a solution consisting of 5-(chlorosulfonyl)-4-fluoro-2-methoxybenzoic acid (300 mg, 1.12 mmol) and DCM (4 mL) at 0° C. The reaction was stirred at room temperature for 1 hour. The mixture reaction was concentrated under reduced pressure to give the crude product (320 mg, 90% yield).

Intermediate 201.4: 4-Fluoro-5-((4-fluoro-3-methylphenyl)carbamoyl)-4-methoxybenzene-1-sulfonyl chloride 4-Fluoro-3-methylaniline (126 mg, 1.00 mmol) was added into a solution consisting of 5-(chlorosulfonyl)-4-fluoro-2-methoxybenzoyl chloride (320 mg, 1.12 mmol) and toluene (5 mL). The reaction was refluxed for 1 hour. The mixture reaction was concentrated under reduced pressure to give the crude product (419 mg, 80% yield).

Compound 201: (S)-4-fluoro-N-(4-fluoro-3-methylphenyl)-2-methoxy-5-(N-(tetrahydrofuran-3-yl) sulfamoyl)benzamide 4-Fluoro-5-((4-fluoro-3-methylphenyl) carbamoyl)-4-methoxybenzene-1-sulfonyl chloride (400 mg, 1.06 mmol) was added into a solution consisting of (S)-3-aminotetrahydrofuran hydrochloride (131 mg, 1.06 mmol, Shanghai Nuohey Chemical Technology CO., LTD.), TEA (0.445 mL, 3.19 mmol) and DCM (5 mL). The reaction was stirred at room temperature for 2 hours. The mixture reaction was concentrated under reduced pressure. The residue was purified by high performance liquid chromatography. HPLC condition: (Column: Phenomenex Gemini C18 200×25 mm×10 μm, Flow rate: 25 mL/min, Mobile Phase A: Base water (containing 0.05% NH₃.H₂O), Mobile Phase B: Acetonitrile.). The desired fraction was collected and evaporated to remove off CH₃CN in vacuum. The residue was lyophilized to dryness to give the title compound (33.80 mg, 7.33% yield, purity 99.01%).

LC-MS (ESI): $R_T$=4.60 min, mass calcd. for $C_{19}H_{20}F_2N_2O_5S$ 426.43, m/z found 427.1 [M+H]⁺. $^1$H NMR (400 MHz, DMSO-$d_6$) δ 10.65 (br.s, 1H), 8.22 (s, 1H), 7.85 (t, J=8.8 Hz, 1H), 7.61 (dd, J=6.8 Hz, J=2.4 Hz, 1H), 7.45-7.50 (m, 1H), 7.10-7.17 (m, 2H), 3.91 (s, 3H), 3.58-3.77 (m, 4H), 3.40-3.41 (m, 1H), 2.24 (s, 3H), 1.93-2.00 (m, 1H), 1.68-1.75 (m, 1H).

Compound 202a-202b

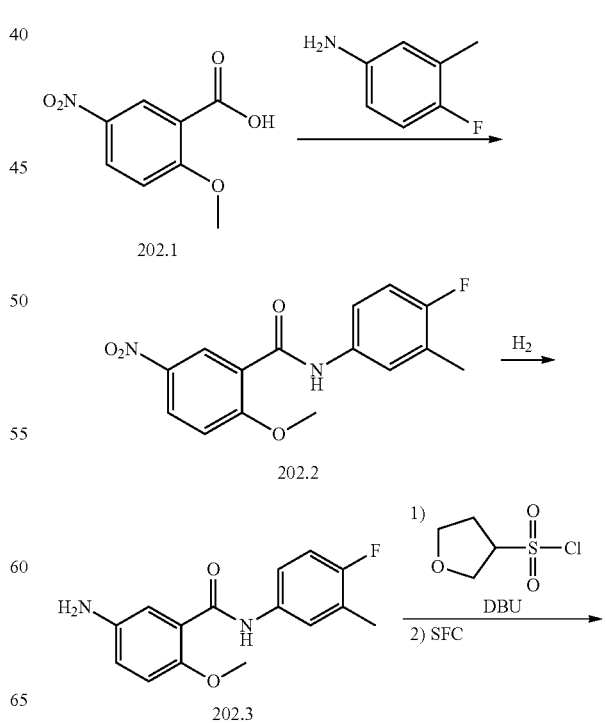

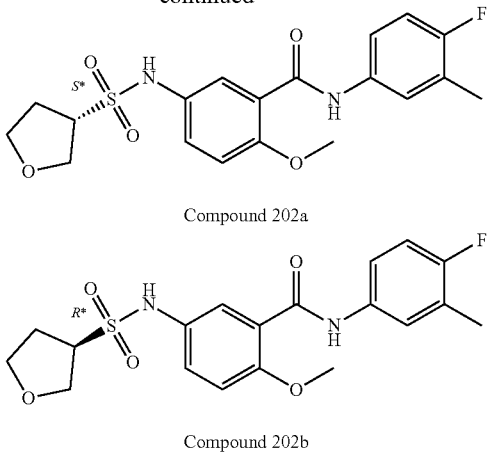

Compound 202a

Compound 202b

Intermediate 202.2: N-(4-Fluoro-3-methylphenyl)-2-methoxy-5-nitrobenzamide

2-Methoxy-5-nitrobenzoic acid (2.0 g, 10 mmol) was dissolved in dry DMF (20 mL). 4-Fluoro-3-methylaniline (1.9 g, 15 mmol), HATU (5.7 g, 15 mmol) and DIEA (3.9 g, 30 mmol) were added to the above mixture. The mixture was stirred at 25° C. for 3 h. The mixture was poured into water (100 mL) and extracted with DCM (100 mL×3). The combined organic extracts were washed with saturated aq. NaHCO₃ (50 mL), brine (50 mL), dried over Na₂SO₄ and filtered. The filtrate was concentrated under reduced pressure to give a residue which was purified by column chromatography over silica gel (petroleum ether:ethyl acetate=5:1) to afford the title compound (3 g, 97.2% yield).

Intermediate 202.3: 5-Amino-N-(4-fluoro-3-methylphenyl)-2-methoxybenzamide

N-(4-Fluoro-3-methylphenyl)-2-methoxy-5-nitrobenzamide (2.8 g, 9.2 mmol) was dissolved in dry MeOH (50 mL). Pd/C (280 mg, 10%) was added to the above mixture. The mixture was stirred at 25° C. under H₂ (50 psi) for 5 h. The reaction mixture was filtered and the filtrate was concentrated under reduced pressure to afford the title compound (2.5 g, 99% yield).

Compound 202a (S*)N-4-fluoro-3-methylphenyl)-2-methoxy-5-(tetrahydrofuran-3-sulfonamido)benzamide Compound 202b (R*)N-4-fluoro-3-methylphenyl)-2-methoxy-5-(tetrahydrofuran-3-sulfonamido)benzamide To a solution consisting of 5-amino-N-(4-fluoro-3-methylphenyl)-2-methoxybenzamide (300 mg, 1.09 mmol), DBU (500 mg, 3.28 mmol) and THF (6 mL) were added tetrahydrofuran-3-sulfonyl chloride (373 mg, 2.19 mmol). The reaction mixture was refluxed for 12 hours. Water (10 mL) was added into the mixture. The resultant mixture was extracted with ethyl acetate (20 mL×2). The combined organic extracts were washed with brine, dried over Na₂SO₄ and filtered. The filtrate was concentrated under reduced pressure. The residue was purified by prep. HPLC (Column: OJ (250×30 mm 5 μm), Flow rate: 25 ml/min, Mobile Phase A: 40% MeOH+NH₃.H₂O 50 mL/min 220 nm water, Mobile Phase B: Acetonitrile) to give the crude compound which was further purified by prep.SFC (separation condition: Column: ChiralPak OJ-H, Daicel Chemical Industries, Ltd, 250*30 mm I.D., 5 μm; Mobile phase: A: Supercritical CO₂, B: Methanol (0.1% NH₃.H₂O), A:B=65:35 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to afford Compound 202a (58.5 mg, 13.08% yield, purity 100%) and Compound 202b (55.8 mg, 12.53% yield, purity 100%). Compound 202a:

LC-MS (ESI): $R_T$=4.65 min, mass calcd. for $C_{19}H_{21}FN_2O_5S$ 408.12, m/z found 409.0 [M+H]⁺. ¹H NMR (400 MHz, DMSO-d₆) δ 10.10 (br.s, 1H), 7.63 (dd, J=6.8 Hz, J=2.4 Hz 1H), 7.52-7.58 (m, 1H), 7.49 (d, J=2.8 Hz, 1H), 7.35 (dd, J=8.8 Hz, J=2.8 Hz 1H), 7.07-7.20 (m, 2H), 3.91-3.97 (m, 1H), 3.88 (s, 3H), 3.77-3.85 (m, 3H), 3.60-3.67 (m, 1H), 2.23 (d, J=1.6 Hz, 3H), 2.10-2.16 (m, 2H). Compound 202b: LC-MS (ESI): $R_T$=4.65 min, mass calcd. for $C_{19}H_{21}FN_2O_5S$ 408.12, m/z found 409.0 [M+H]⁺. ¹H NMR (400 MHz, DMSO-d₆) δ 10.10 (br.s, 1H), 7.63 (dd, J=6.8 Hz, J=2.4 Hz 1H), 7.52-7.58 (m, 1H), 7.49 (d, J=2.8 Hz, 1H), 7.35 (dd, J=8.8 Hz, J=2.8 Hz 1H), 7.07-7.20 (m, 2H), 3.91-3.97 (m, 1H), 3.88 (s, 3H), 3.76-3.85 (m, 3H), 3.60-3.67 (m, 1H), 2.23 (d, J=1.6 Hz, 3H), 2.10-2.16 (m, 2H).

Compound 203

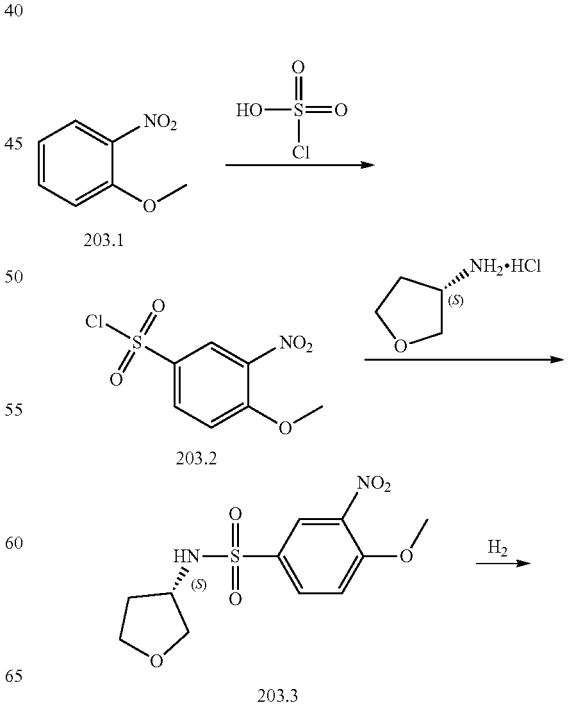

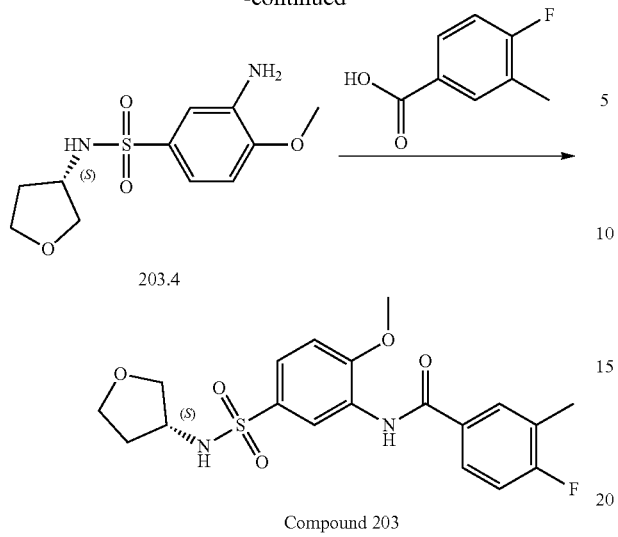

Compound 203

Intermediate 203.2: 4-Methoxy-3-nitrobenzene-1-sulfonyl chloride

1-Methoxy-2-nitrobenzene (3.00 g, 19.6 mmol) was dissolved in sulfurochloridic acid (30.0 g, 257 mmol) at 0° C. and then stirred at room temperature for 1 h. The mixture was poured into ice water. The title compound was precipitated and filtered. (4.15 g, 75.76% yield). $^1$H NMR (400 MHz, DMSO-$d_6$) δ 7.94 (s, 1H), 7.80 (d, J=8.4 Hz, 1H), 7.29 (d, J=8.4 Hz, 1H), 3.89 (s, 3H).

Intermediate 203.3: (S)-4-Methoxy-3-nitro-N-(tetrahydrofuran-3-yl)benzenesulfonamide To a solution consisting of (S)-3-aminotetrahydrofuran hydrochloride (589 mg, 4.77 mmol), TEA (1.66 mL, 11.9 mmol) and DCM (10 mL) was added 4-methoxy-3-nitrobenzene-1-sulfonyl chloride (1.00 g, 3.97 mmol) at 0° C. The mixture was stirred at room temperature for 4 h. The resultant solution was concentrated under reduced pressure to give the title compound (1.00 g, 67% yield).

Intermediate 203.4: (S)-3-Amino-4-methoxy-N-(tetrahydrofuran-3-yl) benzenesulfonamide To a solution consisting of (S)-4-Methoxy-3-nitro-N-(tetrahydrofuran-3-yl)benzenesulfonamide (1 g, 3.31 mmol) and methanol (30 mL) was added Pd(OH)$_2$/C (20% w/w, 100 mg). The mixture was hydrogenated at room temperature (30 psi) for 2 hrs. The catalyst was filtered off and the filtrate was concentrated to dryness to give the title compound (800 mg, 67% yield).

Compound 203: (S)-4-Fluoro-N-(2-methoxy-5-(N-(tetrahydrofuran-3-yl)sulfamoyl)phenyl)-3-methylbenzamide To a solution consisting of 4-fluoro-3-methylbenzoic acid (226 mg, 1.47 mmol), (S)-3-amino-4-methoxy-N-(tetrahydrofuran-3-yl)benzenesulfonamide (400 mg, 1.47 mmol), TEA (0.614 mL, 4.41 mmol) and DMF (5 mL) was added HATU (670 mg, 1.76 mmol). The reaction mixture was stirred at room temperature for 12 hrs. Water was added into the mixture. The aqueous layer was extracted with ethyl acetate (25 mL×2). The organic layers were combined, washed with brine, dried over Na$_2$SO$_4$ and filtered. The filtrate was concentrated to dryness under reduced pressure. The residue was purified by prep.HPLC (Column: YMC-Actus.Triart C18 150×30×5 um, Flow rate: 30 mL/min, Mobile Phase A: Base water (containing 0.05% NH$_3$.H$_2$O), Mobile Phase B: Acetonitrile, Gradient: 25-55% (% B)) to give the title compound (191.00 mg, purity 99.99%, 31.86% yield). LC-MS (ESI): R$_T$=4.63 min, mass calcd. for C$_{19}$H$_{21}$FN$_2$O$_5$S 408.12, m/z found 409.1 [M+H]$^+$, $^1$H NMR (400 MHz, DMSO-$d_6$) δ 9.63 (br.s, 1H), 8.25 (d, J=2.5 Hz, 1H), 7.94 (dd, J=1.9, 7.4 Hz, 1H), 7.89-7.83 (m, 1H), 7.65 (dd, J=2.3, 8.8 Hz, 1H), 7.33-7.28 (m, 2H), 3.93 (s, 3H) 3.73-3.54 (m, 4H), 3.38-3.36 (m, 1H), 2.32 (d, J=1.8 Hz, 3H), 1.97-1.86 (m, 1H), 1.69-1.58 (m, 1H).

Compound 204a-204b

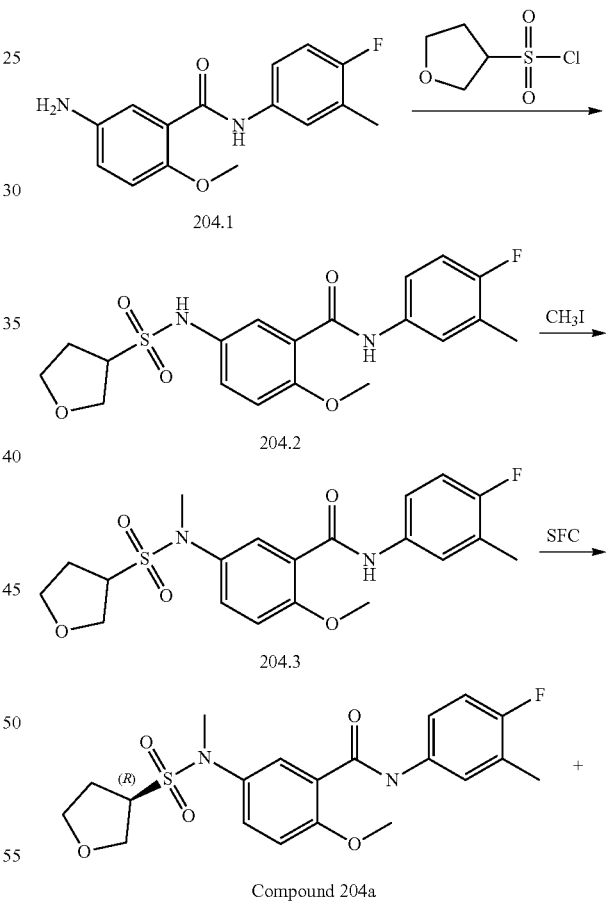

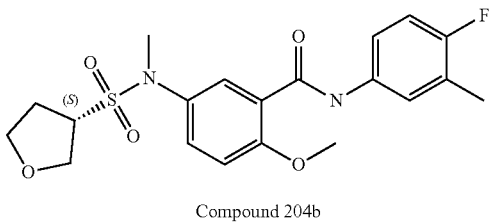

Compound 204b

Intermediate 204.2: N-(4-Fluoro-3-methylphenyl)-2-methoxy-5-(tetrahydrofuran-3-sulfonamido) benzamide 5-Amino-N-(4-fluoro-3-methylphenyl)-2-methoxybenzamide (300 mg, 1.094 mmol) and DBU (426 mg, 2.798 mmol) were dissolved in THF (10 mL) followed by the addition of tetrahydrofuran-3-sulfonyl chloride (313 mg, 1.835 mmol). The mixture was stirred at 90° C. for 16 hours before concentrating it to dryness. The residue was purified by prep.TLC (petroleum ether:ethyl acetate=3:1) and prep.HPLC (formic acid as additive) to give the title compound (80 mg, 17.92% yield).

Compound 204a: (R*)—N-(4-Fluoro-3-methylphenyl)-2-methoxy-5-(N-methyltetrahydrofuran-3-sulfonamido)benzamide

Compound 204b: (S*)—N-(4-Fluoro-3-methylphenyl)-2-methoxy-5-(N-methyltetrahydrofuran-3-sulfonamido)benzamide

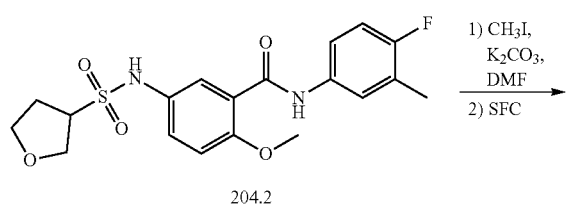

204.2

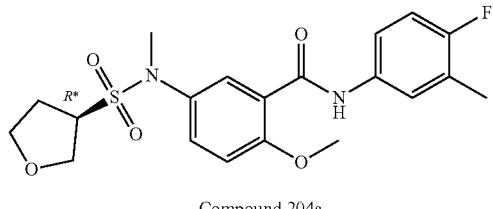

Compound 204a

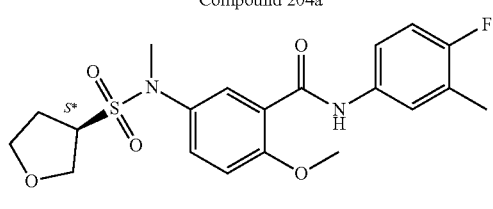

Compound 204b

N-(4-Fluoro-3-methylphenyl)-2-methoxy-5-(tetrahydrofuran-3-sulfonamido)benzamide (80 mg, 0.196 mmol) and $K_2CO_3$ (59 mg, 0.427 mmol) were dissolved in DMF (3 mL) followed by the addition of iodomethane (34 mg, 0.24 mmol). The mixture was stirred at 90° C. for 16 hours before concentrating it to dryness. The residue was purified by prep.TLC (petroleum ether:ethyl acetate=3:1), prep-HPLC (RP-18 ($NH_4HCO_3$ as additive) and SFC to obtain the title two compounds. Compound 204a (9.11 mg, 11.22% yield).

LC-MS (ESI): mass calcd. for $C_{20}H_{23}FN_2O_5S$ 422.13, m/z found 423.1 [M+H]$^+$. $^1$H NMR (400 MHz, DMSO-$d_6$) 10.14 (br.s, 1H), 7.69-7.60 (m, 2H), 7.59-7.50 (m, 2H), 7.20 (d, J=8.0 Hz, 1H), 7.11 (t, J=8.0 Hz, 1H), 4.18-4.08 (m, 1H), 3.95-3.91 (m, 1H), 3.90 (s, 3H), 3.79-3.72 (m, 2H), 3.66-3.59 (m, 1H), 3.27 (s, 3H), 2.23 (s, 3H), 2.21-2.15 (m, 1H). Compound 204b (24.60 mg, 29.59% yield). LC-MS (ESI): mass calcd. for $C_{20}H_{23}FN_2O_5S$ 422.13, m/z found 423.1 [M+H]$^+$. $^1$H NMR (400 MHz, DMSO-$d_6$) 10.14 (br.s, 1H), 7.69-7.60 (m, 2H), 7.59-7.50 (m, 2H), 7.20 (d, J=8.0 Hz, 1H), 7.11 (t, J=8.0 Hz, 1H), 4.18-4.08 (m, 1H), 3.95-3.91 (m, 1H), 3.90 (s, 3H), 3.79-3.72 (m, 2H), 3.66-3.59 (m, 1H), 3.27 (s, 3H), 2.23 (s, 3H), 2.21-2.15 (m, 1H), 2.04-1.95 (m, 1H).

Biological Examples—5HTR2b Antagonist Activity of Compounds

The 5HTR2B antagonist activity was measured using human Maverick/293 cells in a calcium mobilization assay. The measurement starting with plating human Maverick/293 cells (log phase) onto 96-well black and incubate at 37° C. overnight, Followed by starving cells for 2 h by changing complete medium to DMEM without FBS, removing the medium from the 96-well plate. Loading staining calcium buffer into each well and incubated the plate at 37° C. for 50 min. After removal of staining calcium buffer, diluted antagonist were added into the well, incubate 15 to 30 minutes. Dispense serotonin as the 5HTR2B agonists into each well. Intracellular calcium concentration is recorded for 80 seconds by monitoring an emission at a wavelength of 525 nm with an excitation wavelength of 485 nm. Inhibition efficiency of the cell line was determined following the equation: % Inhibition=100%−(D−B)/(S−B)*100%. (S: The peak value in the presence of agonist serotonin; D: The peak value in the presence of different dilution compound or serotonin; B: The peak value in the presence of calcium HBSS buffer only). Finally the data was displayed graphically using GraphPad Prism 5.0. A dose response curve was fitted using nonlinear regression model with a sigmoidal dose response. The IC50 was automatically produced by GraphPad Prism 5.0. Results are displayed in Table 3.

TABLE 3

| Co. No. | Ca assay IC50 (nM) |
|---|---|
| 1 | 2.3 |
| 2 | 0.6 |
| 3 | 1.7 |
| 4 | 0.7 |
| 5 | 4.2 |
| 6a | 18 |
| 6b | 1.9 |
| 7 | 5.4 |
| 7a | 3.8 |
| 7b | 6.9 |
| 8 | 2.5 |
| 9 | 2.2 |
| 10 | 4.5 |
| 10a | 4.5 |
| 10b | 12 |
| 11a | 68 |
| 11b | 5.1 |
| 12 | 9.3 |
| 12a | 1.8 |
| 12b | 122 |
| 13 | 66.3 |
| 14 | 14.6 |
| 15a | 2 |
| 15b | 1.0 |
| 16a | 1.1 |
| 16b | 9.1 |
| 17 | 7.2 |
| 18 | 222 |
| 19 | 173 |
| 20 | 4.4 |
| 21 | 1.6 |

TABLE 3-continued

| Co. No. | Ca assay IC50 (nM) |
|---|---|
| 22 | 610 |
| 23a | 4.7 |
| 23b | 5 |
| 24 | 47 |
| 25 | 1.4 |
| 26 | 1.3 |
| 27 | 1.1 |
| 28a | 19 |
| 28b | 119 |
| 29a | 3.0 |
| 29b | 4.6 |
| 30 | 24 |
| 31 | 55 |
| 32a | 1.8 |
| 32b | 8.5 |
| 33a | 0.4 |
| 33b | 0.4 |
| 34a | 1.4 |
| 34b | 167 |
| 35a | 0.7 |
| 35b | 4.3 |
| 36 | 2.7 |
| 37 | 0.8 |
| 38 | 0.6 |
| 39 | 3.6 |
| 40a | 1.7 |
| 40b | 9.5 |
| 41 | 0.7 |
| 42 | 2.2 |
| 43 | 7.2 |
| 44a | 2.4 |
| 44b | 3.2 |
| 45a | 1.3 |
| 45b | 1.9 |
| 46a | 1.5 |
| 46b | 1.8 |
| 47 | 0.5 |
| 48 | 2.7 |
| 49a | 3.4 |
| 49b | 9.0 |
| 50 | 7.6 |
| 51 | 1.0 |
| 52a | 50 |
| 52b | 4.5 |
| 53 | 0.3 |
| 54a | 1.1 |
| 54b | 1.2 |
| 55a | 0.3 |
| 55b | 0.1 |
| 56a | 0.1 |
| 56b | 0.2 |
| 57a | 0.2 |
| 57b | 0.2 |
| 58 | 0.2 |
| 59a | 0.2 |
| 59b | 0.2 |
| 60a | 0.4 |
| 60b | 0.4 |
| 61a | 0.1 |
| 61b | 0.2 |
| 61c | 0.2 |
| 62 | 0.1 |
| 63 | 1.3 |
| 64 | 65 |
| 65 | 0.34 |
| 66 | 0.2 |
| 67 | 8.8 |
| 68 | 2.9 |
| 69 | 1.5 |
| 70 | 0.3 |
| 71 | 1.6 |
| 72 | 5.1 |
| 73 | 5.5 |
| 74 | 0.8 |
| 75 | 9.1 |
| 76 | 3.1 |
| 77 | 5.3 |
| 78 | 2.4 |
| 79 | 98 |
| 80 | 574 |
| 81 | 32 |
| 82 | 1.1 |
| 83 | 126 |
| 84 | 716 |
| 85 | 1.5 |
| 86 | 1.8 |
| 87 | 29 |
| 88 | 28 |
| 89 | 1947 |
| 90 | 1361 |
| 91 | 92 |
| 97 | 136 |
| 93 | 1063 |
| 94 | 12 |
| 95 | 648 |
| 96 | 84 |
| 97 | 186 |
| 98 | 37 |
| 99 | 1.6 |
| 100 | 4.6 |
| 101 | 219 |
| 102 | 435 |
| 103 | 8.4 |
| 104 | 201 |
| 105 | 12 |
| 106 | 596 |
| 107 | 27 |
| 108 | 5.5 |
| 109 | 231 |
| 110 | 10 |
| 111 | 1.3 |
| 112 | 2.9 |
| 113 | 17 |
| 114 | 0.4 |
| 115 | 0.8 |
| 116 | 5.4 |
| 117 | 64 |
| 118 | 6.7 |
| 119 | 1.4 |
| 120 | 50 |
| 121 | 3.8 |
| 122 | 0.6 |
| 123 | 0.2 |
| 124 | 6.3 |
| 125 | 28 |
| 126 | 12 |
| 127 | 0.1 |
| 128 | 1.2 |
| 129 | 12 |
| 130 | 2.1 |
| 131 | 1.3 |
| 132 | 163 |
| 133 | 405 |
| 134 | 0.5 |
| 135 | 0.1 |
| 136 | 0.4 |
| 137a | 17.1 |
| 137b | 39 |
| 138a | 159 |
| 138b | 329 |
| 139a | 11 |
| 139b | 3.9 |
| 140a | 3.9 |
| 140b | 0.9 |
| 141 | 2.8 |
| 142a | 2.2 |
| 142b | 1.1 |
| 143a | 0.7 |
| 143b | 5.9 |
| 144a | 0.5 |
| 144b | 0.3 |
| 145a | 2.5 |

TABLE 3-continued

| Co. No. | Ca assay IC50 (nM) |
|---|---|
| 145b | 1.0 |
| 146a | 0.8 |
| 146b | 1.0 |
| 147a | 3.4 |
| 147b | 2.1 |
| 148 | 161 |
| 149 | 8.4 |
| 150 | 9.9 |
| 151 | 39 |
| 152 | 11 |
| 153 | 1.0 |
| 154 | 0.6 |
| 155 | 0.2 |
| 156 | 159 |
| 157 | 53 |
| 158 | 0.17 |
| 159 | 0.7 |
| 160 | 4.6 |
| 161 | 79 |
| 162 | 0.5 |
| 163 | 0.9 |
| 164 | 1.1 |
| 165 | 511 |
| 166 | 0.16 |
| 167 | 0.32 |
| 168 | 3.9 |
| 169 | 65 |
| 170 | 58 |
| 171 | 106 |
| 172 | 33 |
| 173 | 0.8 |
| 174a | 3.9 |
| 174b | 1.7 |
| 175 | 1.6 |
| 176 | 5.0 |
| 177 | 4.2 |
| 178 | 0.3 |
| 179 | 0.1 |
| 180 | 3.3 |
| 181 | 4.5 |
| 182 | 0.3 |
| 183 | 0.5 |
| 184 | 0.3 |
| 185 | 0.8 |
| 186 | 0.3 |
| 187 | 0.7 |
| 188 | 1.6 |
| 189 | 14 |
| 190 | 0.9 |
| 191 | 1.1 |
| 192 | 0.4 |
| 193 | 3.2 |
| 194 | 1.1 |
| 195 | 0.9 |
| 196 | 19 |
| 197 | 5.3 |
| 198 | 0.7 |
| 199 | 3.7 |
| 200 | 3.3 |
| 201 | 8.6 |
| 202a | 1.0 |
| 202b | 2.8 |
| 203 | 13 |
| 204a | 50 |
| 204b | 56 |

The invention claimed is:

1. A compound of Formula (I)

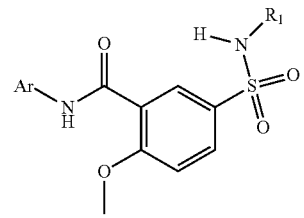

or a stereoisomer or tautomeric form thereof, wherein:

Ar represents a monocyclic or bicyclic aromatic ring, optionally containing one or more heteroatoms each independently selected from the group consisting of O, S and N, such aromatic ring optionally being substituted with one or more substituents each independently selected from the group consisting of halogen, —CN, —OR$^6$, $C_1$-$C_3$ alkyl, $C_3$-$C_7$cycloalkyl, $CHF_2$, $CH_2F$ and $CF_3$;

$R^1$ represents a 3-7 membered saturated ring optionally containing one or more heteroatoms each independently selected from the group consisting of O, S and N, such 3-7 membered saturated ring optionally being substituted with one or more substituents each independently selected from the group consisting of Fluor, —OH, oxo and $C_1$-$C_3$ alkyl optionally substituted with one or more Fluor and/or OH;

$R^6$ represents hydrogen, $C_1$-$C_3$ alkyl optionally substituted with one or more Fluor, or —$C_1$-$C_3$ alkyl-O(R$^5$);

$R^5$ represents hydrogen or $C_1$-$C_3$ alkyl;

or a pharmaceutically acceptable salt or a solvate thereof.

2. The compound according to claim 1, wherein Ar is phenyl, pyridine or benzimidazole optionally substituted with one or more substituents each independently selected from the group consisting of —CN, halogen, $C_1$-$C_3$ alkyl, $C_1$-$C_3$cycloalkyl, $CHF_2$, $CH_2F$ and $CF_3$.

3. The compound according to claim 1 wherein $R^1$ represents a 4-7 membered saturated ring containing carbon atoms and optionally one oxygen atom, such 4-7 membered saturated ring optionally substituted with one or more of $C_1$-$C_3$alkyl and/or OH.

4. The compound according to claim 1, wherein $R^1$ represents a 5 membered saturated ring containing carbon atoms and one oxygen atom.

5. A compound according to claim 1, wherein Ar is phenyl or pyridine, optionally substituted with one or more substituents each independently selected from halogen, —OH, $C_1$-$C_3$ alkyl, $C_1$-$C_3$cycloalkyl, $CHF_2$, $CH_2F$ and $CF_3$.

6. A method of preventing or treating liver fibrosis and/or cirrhosis in a mammal comprising administering a therapeutically effective amount of at least one compound according to Formula A

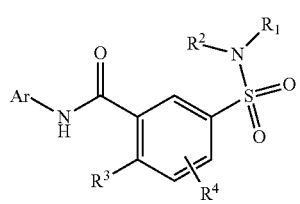

or a stereoisomer or tautomeric form, and/or a salt or solvate thereof, wherein

Ar represents a monocyclic or bicyclic aromatic ring, optionally containing one or more heteroatoms each independently selected from the group consisting of O, S and N, such aromatic ring optionally being substituted with one or more substituents each independently selected from the group consisting of hydrogen, halogen, —CN, —OH, $C_1$-$C_3$ alkyl, $C_3$-$C_7$cycloalkyl, —O($R^6$), $CHF_2$, $CH_2F$ and $CF_3$;

$R^1$ represents hydrogen, a 3-7 membered saturated ring optionally containing one or more heteroatoms each independently selected from the group consisting of O, S and N, or $C_1$-$C_6$ alkyl, such 3-7 membered saturated ring or $C_1$-$C_6$alkyl optionally being substituted with one or more substituents each independently selected from the group consisting of $C_1$-$C_3$ alkyl, halogen, $CHF_2$, $CH_2F$ and $CF_3$, —CN, —C(=O)$R^5$, oxo-C(=O) N($R^6$)$_2$, —N($R^6$)$_2$ and —O$R^6$;

$R^2$ represents hydrogen, or $C_1$-$C_3$ alkyl;

$R^3$ represents Fluor or —O$C_1$-$C_3$ alkyl optionally substituted with one or more Fluor;

$R^4$ represents hydrogen, Fluor or —O$C_1$-$C_3$ alkyl;

$R^6$ represents hydrogen, $C_1$-$C_3$ alkyl optionally substituted with one or more Fluor, or —$C_1$-$C_3$ alkyl-O($R^5$);

$R^5$ represents hydrogen or $C_1$-$C_3$ alkyl.

7. The method according to claim 6, wherein $R^3$ represents Fluor or —O$C_1$-$C_3$ alkyl and $R^2$ and $R^4$ represent hydrogen.

8. The method according to claim 6, wherein Ar is phenyl, pyridine or benzimidazole optionally substituted with one or more substituents each independently selected from the group consisting of halogen, $C_1$-$C_3$ alkyl, $C_1$-$C_3$cycloalkyl, $CHF_2$, $CH_2F$ and $CF_3$.

9. The method according to claim 6, wherein $R^1$ represents a 5 membered saturated ring containing carbon atoms and one oxygen atom.

10. The method according to claim 6, wherein Ar is phenyl optionally substituted with one or more substituents each independently selected from —CN, $C_1$-$C_3$ alkyl, $C_1$-$C_3$cycloalkyl, $CHF_2$, $CH_2F$ and $CF_3$.

11. A pharmaceutical composition comprising a compound according to claim 1, and a pharmaceutically acceptable carrier.

12. A product containing (a) a compound of formula (I) as defined in claim 1, and (b) another liver fibrosis and/or cirrhosis inhibitor, as a combined preparation for simultaneous, separate or sequential use in the treatment of liver fibrosis and/or cirrhosis.

* * * * *